US012371507B2

(12) United States Patent
Cantley et al.

(10) Patent No.: US 12,371,507 B2
(45) Date of Patent: Jul. 29, 2025

(54) CDCP1 ANTIBODIES AND ANTIBODY DRUG CONJUGATES

(71) Applicants: Beth Israel Deaconess Medical Center, Boston, MA (US); Pfizer Inc., New York, NY (US); Cornell University, Ithaca, NY (US)

(72) Inventors: Lewis C. Cantley, New York, NY (US); Stephen P. Soltoff, Waban, MA (US); Brooke M. Emerling, San Diego, CA (US); Georgios Poulogiannis, Boston, MA (US); Cindy M. Hodakoski, New York, NY (US); Hui Liu, Wayland, MA (US); Irina Apostolou, Norwell, MA (US); Brian Gaither Bates, Chelmsford, MA (US); Kimberly Ann Marquette, Somerville, MA (US); Eric M. Bennett, Arlington, MA (US); Lidia Mosyak, Newton, MA (US); Lioudmila G. Tchistiakova, Stoneham, MA (US); Edward Christian Rosfjord, Oakland, NJ (US); Isaac J. Rondon, San Francisco, CA (US); Chao Bai Huang, San Leandro, CA (US)

(73) Assignees: Beth Israel Deaconess Medical Center, Boston, MA (US); Pfizer Inc, New York, NY (US); Cornell University, New York, NY (US)

( * ) Notice: Subject to any disclaimer, the term of this patent is extended or adjusted under 35 U.S.C. 154(b) by 1009 days.

(21) Appl. No.: 17/292,257

(22) PCT Filed: Nov. 7, 2019

(86) PCT No.: PCT/US2019/060276
§ 371 (c)(1),
(2) Date: May 7, 2021

(87) PCT Pub. No.: WO2020/097336
PCT Pub. Date: May 14, 2020

(65) Prior Publication Data
US 2022/0119545 A1    Apr. 21, 2022

Related U.S. Application Data

(60) Provisional application No. 62/758,442, filed on Nov. 9, 2018.

(51) Int. Cl.
*A61K 39/395* (2006.01)
*A61P 35/00* (2006.01)
*C07K 16/28* (2006.01)
*A61K 39/00* (2006.01)

(52) U.S. Cl.
CPC .......... *C07K 16/2896* (2013.01); *A61P 35/00* (2018.01); *A61K 2039/505* (2013.01); *C07K 2317/21* (2013.01); *C07K 2317/33* (2013.01); *C07K 2317/34* (2013.01); *C07K 2317/41* (2013.01); *C07K 2317/522* (2013.01); *C07K 2317/524* (2013.01); *C07K 2317/55* (2013.01); *C07K 2317/565* (2013.01); *C07K 2317/567* (2013.01); *C07K 2317/71* (2013.01); *C07K 2317/732* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | |
|---|---|---|
| 2004/0191260 A1 | 9/2004 | Reiter et al. |
| 2005/0048070 A1 | 3/2005 | Ditzel et al. |
| 2007/0020624 A1 | 1/2007 | Rubenfield et al. |
| 2008/0008719 A1 | 1/2008 | Bowdish et al. |
| 2008/0138335 A1 | 6/2008 | Takahashi et al. |
| 2009/0214560 A1 | 8/2009 | Min et al. |
| 2009/0232823 A1 | 9/2009 | Balderes et al. |
| 2011/0052582 A1 | 3/2011 | Auer et al. |
| 2013/0330335 A1 | 12/2013 | Bremel et al. |
| 2014/0271646 A1 | 9/2014 | Dimitrov et al. |
| 2017/0043033 A1 | 2/2017 | Strop et al. |
| 2017/0226225 A1 | 8/2017 | Chen et al. |
| 2017/0240633 A1 | 8/2017 | Wang et al. |

FOREIGN PATENT DOCUMENTS

| | | |
|---|---|---|
| WO | WO 2007/005502 A2 | 1/2007 |
| WO | WO 2011/023390 A1 | 3/2011 |
| WO | WO 2018/112334 A1 | 6/2018 |

OTHER PUBLICATIONS

International Search Report & Written Opinion, PCT Application No. PCT/US19/60276, dated Apr. 1, 2020, 18 pages.
Martinko, et al., "Targeting RAS-driven human cancer cells with antibodies to upregulated and essential cell-surface proteins," eLife, Jan. 23, 2018, pp. 1-26.
Emerling, et al., "Identification of CDCP1 as a hypoxia-inducible factor 2α (HIF-2α) target gene that is associated with survival in clear cell renal cell carcinoma patients", PNAS, 2013, vol. 110, No. 9, pp. 3483-3488.
Fukuchi, et al., "Inhibition of tumor metastasis: Functional Immune modulation of the CUB Domain Containing Protein 1", Molecular Pharm., 2010, vol. 7, No. 1, 17 pages.
Kollmorgen, et al., "Antibody mediated CDCP1 degradation as mode of action for cancer targeted therapy", Molecular Oncology, 2013, vol. 7, pp. 1142-1151.

(Continued)

*Primary Examiner* — Christine J Saoud
*Assistant Examiner* — Jon M Lockard
(74) *Attorney, Agent, or Firm* — Morgan, Lewis & Bockius LLP

(57) ABSTRACT

The present disclosure provides materials and methods for CUB domain-containing protein 1 (CDCP1)-targeted therapy.

8 Claims, 33 Drawing Sheets

Specification includes a Sequence Listing.

(56) References Cited

OTHER PUBLICATIONS

Siva, et al., "Targeting CUB Domain-Containing Protein 1 with a Monoclonal Antibody Inhibits Metastasis in a Prostate Cancer Model", Cancer Research, 2008, vol. 68, No. 10, pp. 3759-3766.

FIG. 3

Incorporation of Y(H100)H, W(H100C)H, Y(H100H)H into CP13E10 antibody significantly decreases hydrophobicity FIG. 4: Elution time for CDCP1 variants from TSKgel Butyl-NPR chromatography column in minutes

| Antibody | Analytical HIC Elution Time (min) |
|---|---|
| CP13E10-WT | 48.63 |
| CP13E10-34 | 28.42 |
| CP13E10-54HC-89LC | 25.38 |

FIG. 5: Incorporation of the CDRH3 point mutation V(H97)E into the CP13E10-34 variant restored CDCP1 binding properties to that of CP13E10-WT (parental) antibody FIG. 6: Binding Kinetics of anti-CDCP1 Antibodies Determined for Recombinant Human, Cynomologus Monkey and Mouse CDCP1-ECD Protein

| Antibody | Human CDCP1 ECD KD [nM] (SPR) | Cyno CDCP1 ECD KD [nM] (SPR) | Mouse CDCP1 ECD KD [nM] (SPR) |
|---|---|---|---|
| CP13E10-WT | 219.30 | 232.13 | 323.10 |
| CP13E10-34 | 607.06 | ND | 3920.62 |
| CP13E10-291 | 2.90 | 3.12 | 286.44 |
| CP13E10-54HC-89LC | 52.88 | 79.89 | 195.54 |
| CP13E10-54HC-89LC (experiment 2) | 41.99 | 63.44 | 175.91 |
| CP13E10-54HC-89LCv1 (experiment 2) | 44.50 | 69.50 | 158.00 |

FIG. 7: IGKV146 germline substitutions incorporated into CP13E10-54HC-89LCv1 do not alter CDCP1 binding properties
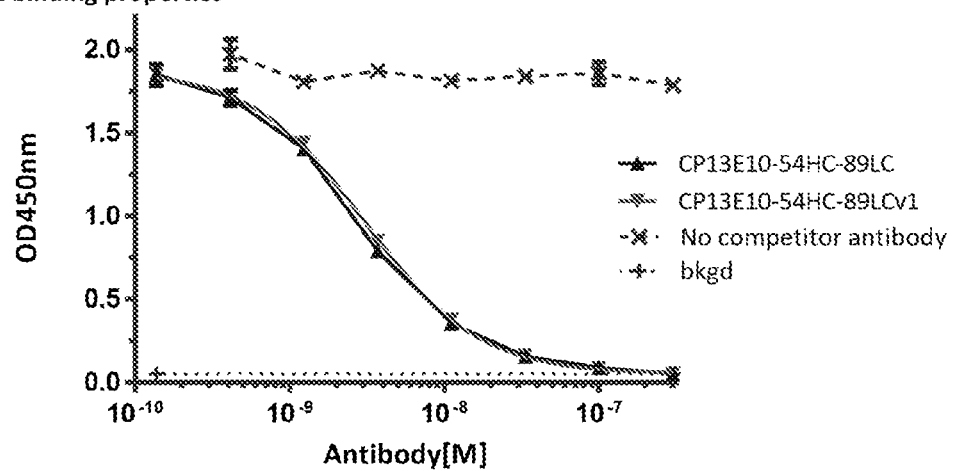

FIG. 8: Germlined CP13E10-54HC-89LCv1 binding to CDCP1 expressed on the surface of PC3 prostate cancer cells was identical to CP13E10-54HC-89LC
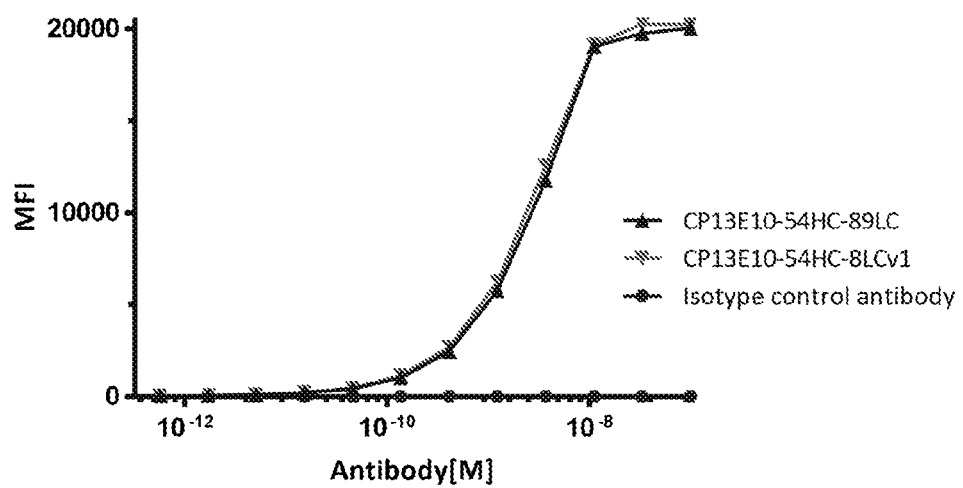

FIG. 9: CP13E10-54HCv13-89LCv1 harboring the G(H96)A mutation to remove putative isomerization site in CDRH3 completely retains CDCP1 binding properties relative to CP13E10-54HC-89LCv1

FIG. 26B
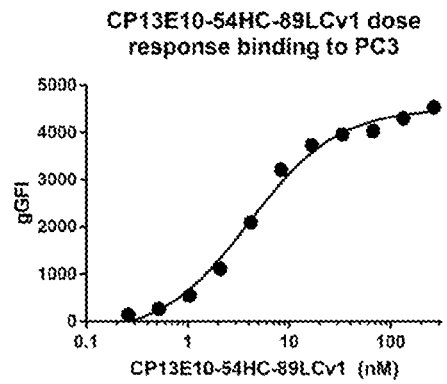
FIG. 27
| Antibody or ADC | Human CDCP1 ECD $K_D$ [nM] pH7.4 | Human CDCP1 ECD $K_D$ [nM] pH6.8 |
|---|---|---|
| CP13E10-54HC-89LCv1-183/290 antibody | 47.38 | 68.88 |
| CP13E10-54HC-89LCv1-183/290-vc0101 ADC | 45.63 | 66.55 |
FIG. 28A
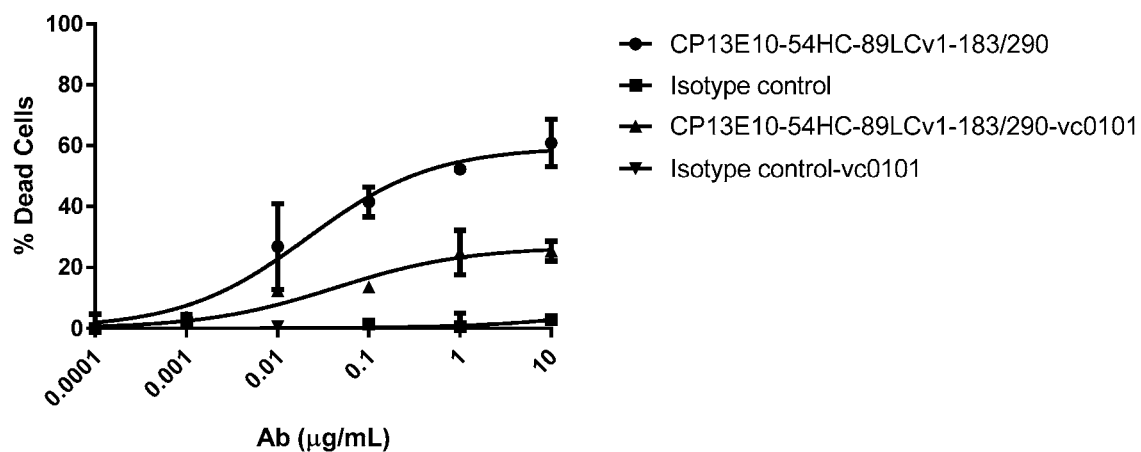

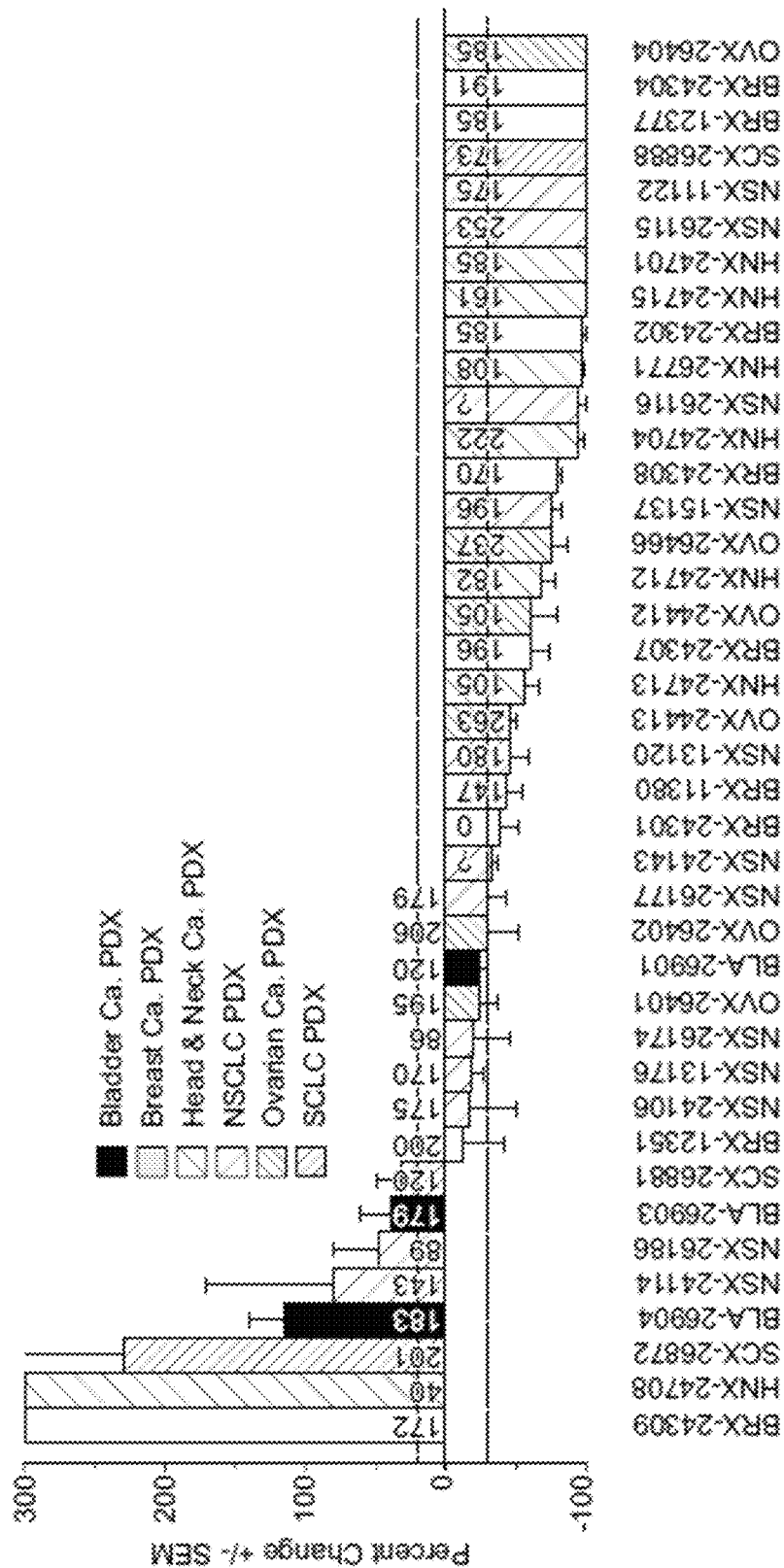

CDCP1 ANTIBODIES AND ANTIBODY DRUG CONJUGATES

CROSS-REFERENCE TO RELATED APPLICATIONS

This application is a 371 National Stage Entry of International Application No. PCT/US2019/060276 filed Nov. 7, 2019, which claims the benefit of, and claims priority to U.S. Provisional Application No. 62/758,442, filed on Nov. 9, 2018, the entire contents of which are incorporated herein.

FIELD OF THE DISCLOSURE

The disclosure is directed to materials and methods for CUB domain-containing protein 1 (CDCP1)-targeted therapy.

PARTIES TO A JOINT RESEARCH STATEMENT

The presently claimed invention was made, in part, by or on behalf of the below listed parties to a joint research agreement. The joint research agreement was in effect on or before the date the claimed invention was made and the claimed invention was made, in part, as a result of activities undertaken within the scope of the joint research agreement. The parties to the joint research agreement are BETH ISRAEL DEACONESS MEDICAL CENTER and PFIZER INC.

DESCRIPTION OF THE TEXT FILE SUBMITTED ELECTRONICALLY

The instant application contains a Sequence Listing which has been submitted in ASCII format via EFS-Web and is hereby incorporated by reference in its entirety. Said ASCII copy, created about Oct. 30, 2019, is named "BID-009US_SL_ST25.txt" and is about 120,159 bytes in size.

BACKGROUND

Although many chemotherapeutic agents have been developed they often demonstrate unacceptable toxicity and or lack of specificity for cancer cells over non-cancer tissues. To avoid the non-specific cytotoxic effects of chemotherapeutic agents, targeted antibody therapy has revolutionized cancer treatment with several monoclonal antibodies demonstrating clinical potential. Because antibodies against tumor-specific antigens often lack therapeutic activities, they have been conjugated to cytotoxic agents in order to combine the effectiveness of chemotherapy with the targeting of antibodies. In principle, selective delivery of cytotoxic agents to specific tumor tissues by antibody binding should reduce the systemic toxicity of traditional small-molecule chemotherapeutics. Since a successful antibody drug conjugate (ADC) approach must successfully bind to a target antigen in order to deliver a toxic payload to a target cell without significant binding to non-target cells, it is crucial that ADC be able to deliver a toxic payload to a target cell, be internalized thereby, and then release the payload once inside the appropriate compartment within the cell.

SUMMARY

The present disclosure satisfies the aforementioned needs, among others. CDCP1 is a target for therapeutic intervention in patients with a variety of cancers, especially those addicted to CDCP1 expression. Interestingly, the present inventors have discovered, inter alia, that CDCP1 is internalized by cells in a regulated manner and, accordingly, this property can be exploited for the development of anti-cancer therapies. Further, the inventors have discovered that CDCP1 is impacted by, or impacts, various markers linked to cancers, including without limitation, LKB1, KRAS, and AKT, providing for new treatment modalities using CDCP1 agents including, but not limited to, antibodies that specifically bind CDCP1 expressed on a cell. Further still, the present inventors have discovered interactions of CDCP1 with cancer markers, inclusive of Src, PPP4R2 and PARG1, such interactions being activation state dependent and allowing for specific cancer treatments.

In one aspect, the disclosure provides a method for treating cancer in a patient in need thereof comprising: (a) evaluating a tumor sample for an amount of a mutant LKB1 and/or KRAS; and (b) administering an agent which binds to CUB domain-containing protein 1 (CDCP1) to the cancer patient if the amount of mutant LKB1 and/or KRAS is higher than a reference sample.

In some embodiments, the tumor sample is a biopsy selected from a frozen tumor tissue specimen, cultured cells, circulating tumor cells, and a formalin-fixed paraffin-embedded tumor tissue specimen.

In some embodiments, the mutant KRAS is selected from G12C; G12A; G12D; G12R; G12S; G12V; G13C; and G13D mutants. In some embodiments, evaluating is conducted by amplifying LKB1 and/or KRAS nucleic acid from the tumor sample, or a fragment thereof suspected of containing a mutation, and sequencing said amplified nucleic acid. In some embodiments, evaluating is conducted by contacting an antibody or format thereof directed to LKB1 and/or KRAS with the tumor sample and quantifying antibody or format thereof binding.

In one aspect, the disclosure provides a method of treating a lung cancer in a patient in need thereof, comprising administering an agent which binds to CDCP1 to the patient, wherein the lung cancer is characterized by AKT activation and the agent which binds to CDCP1 is a CDCP1 activating agent.

In some embodiments, the lung cancer is Non-Small Cell Lung Cancer (NSCLC). In some embodiments, the method further comprises evaluating a sample of the lung cancer for AKT activation.

In one aspect, the disclosure provides a method of treating a prostate cancer in a patient in need thereof, comprising administering an agent which binds to CDCP1 to the patient, wherein the prostate cancer is characterized by AKT activation and the agent which binds to CDCP1 is a CDCP1 activating agent. In some embodiments, the method further comprises evaluating a sample of the prostate cancer for AKT activation.

In some embodiments, the method further comprises administering a AKT inhibitor. In some embodiments, the patient is undergoing treatment with an AKT inhibitor. In some embodiments, the AKT inhibitor is selected from Afuresertib, ARQ 751, ARQ 092, AZD5363, BAY1125976, GSK2141795, GSK690693, Ipatasertib, LY2780301, MK2206, and Perifosine.

In one aspect, the disclosure provides a method for treating cancer in a patient in need thereof comprising: (a) selecting an agent which binds to CDCP1 on a target cell and is internalized when it contacts CDCP1 on the target cell; and (b) administering the agent to the cancer patient.

In one aspect, the disclosure provides a method for treating cancer in a patient in need thereof comprising: (a)

selecting an agent which binds to CDCP1 on a target cell and is internalized when it contacts CDCP1 on the target cell; and (b) administering the agent to the cancer patient, wherein the agent which binds to CDCP1 is an antibody which activates CDCP1 and is conjugated to a serine/threonine-protein phosphatase 4 regulatory subunit 2 (PPP4R2) modulating agent.

In one aspect, the disclosure provides a method for treating cancer in a patient in need thereof comprising: (a) administering an agent which binds to CDCP1, wherein the agent which binds to CDCP1 is an antibody which does not activate CDCP1; and (b) administering an agent which modulates Poly (ADP-ribose) glycohydrolase (PARG). In some embodiments, the agent which modulates PARG is a PARG inhibitor. In some embodiments, the PARG inhibitor is selected from Olaparib, Talazoparib, Veliparib, Rucaparib, Iniparib, niraparib E7016, CEP9722, BGB-290 and 3-aminobenzamide.

In some embodiments, the agent which binds to CDCP1 is an antibody or antigen-binding portion thereof that is specific for CDCP1.

In some embodiments, the antibody or antigen-binding portion thereof that is specific for CDCP1 is selected from one or more of a monoclonal antibody, polyclonal antibody, antibody fragment, Fab, Fab', Fab'-SH, F(ab')2, Fv, single chain Fv, diabody, linear antibody, bispecific antibody, multispecific antibody, chimeric antibody, humanized antibody, human antibody, and fusion protein comprising the antigen-binding portion of an antibody.

In some embodiments, the antibody or antigen-binding portion thereof that is specific for CDCP1 is conjugated with a cytotoxic agent or cytostatic agent. In some embodiments, the method further comprises administering the cytotoxic agent or cytostatic agent. In some embodiments, the administration is sequential or simultaneous.

In some embodiments, the cytotoxic agent is selected from paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, and mixtures thereof.

In some embodiments, the cytotoxic agent is an anti-tumor agent selected from methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin, doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine, and mixtures thereof. In some embodiments, the method further comprises administering the anti-tumor agent. In some embodiments, the administration is sequential or simultaneous. In some embodiments, the anti-tumor agent is a chemotherapeutic agent.

In some embodiments, the anti-tumor agent is a checkpoint inhibitor. In some embodiments, the checkpoint inhibitor is an agent that targets one of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2. In some embodiments, the agent that targets PD-1 is an antibody or antigen-binding portion thereof that is specific for PD-1, optionally selected from nivolumab, pembrolizumab, and pidilizumab. In some embodiments, the agent that targets wherein the agent that targets PD-L1 is an antibody or antigen-binding portion thereof that is specific for PD-L1, optionally selected from atezolizumab, avelumab, durvalumab, and BMS-936559. In some embodiments, the agent that targets CTLA-4 is an antibody or antigen-binding portion thereof that is specific for CTLA-4, optionally selected from ipilimumab and tremelimumab.

In some embodiments, the anti-tumor agent is a hypoxia-inducible factor-2 (HIF-2) inhibitor. In some embodiments, the HIF-2 inhibitor is selected from PT2385 and PT2977. In some embodiments, the anti-tumor agent is not a Src inhibitor, optionally selected from KX2-391, bosutinib, saracatinib, and dasatinib.

In some embodiments, the cancer is a tumor characterized by hypoxia.

In some embodiments, the cancer is selected from one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g., that associated with brain tumors), and Meigs' syndrome.

In some embodiments, the cancer is cancer of the head and neck.

In one aspect, the disclosure provides a method of determining whether a tumor will respond to treatment with an agent which binds to CDCP1, comprising determining in a sample of said tumor the presence, absence, or amount of mutant LKB1 and/or KRAS protein or gene, whereby the presence of mutant LKB1 and/or KRAS or an increased amount of mutant LKB1 and/or KRAS protein or gene relative to a reference sample is indicative of a likelihood of responding to treatment with an agent which binds to CDCP1.

In some aspects, the invention provides antibodies, and antigen-binding fragments thereof, that specifically bind to CDCP1, antibody drug conjugates comprising such antibodies, as well as uses, and associated methods therefor. Those skilled in the art will recognize, or be able to ascertain using no more than routine experimentation, many equivalents to the specific embodiments of the invention described herein. Such equivalents are intended to encompass the following embodiments (E).

E1. An isolated antibody, or antigen-binding fragment thereof, that specifically binds CDCP1, comprising:
(i) a heavy chain variable region (VH) that comprises:
   (a) a VH complementarity determining region 1 (CDRH1) comprising the amino acid sequence of SEQ ID NO: 2,
   (b) a VH complementarity determining region 2 (CDRH2) comprising the amino acid sequence of SEQ ID NO: 3, and
   (c) a VH complementarity determining region 3 (CDRH3) comprising the amino acid sequence selected from the group consisting of SEQ ID NO: 4, SEQ ID NO: 27, SEQ ID NO: 40 and SEQ ID NO: 45,
and (ii) a light chain variable region (VL) that comprises:
   (a) a VL complementarity determining region 1 (CDRL1) comprising the amino acid sequence of SEQ ID NO: 12,
   (b) a VL complementarity determining region 2 (CDRL2) comprising the amino acid sequence of SEQ ID NO: 13, and
   (c) a VL complementarity determining region 3 (CDRL3) comprising the amino acid sequence selected from the group consisting of SEQ ID NO:14 and SEQ ID NO:31.

E2. An isolated antibody, or antigen-binding fragment thereof, that specifically binds CDCP1, comprising:
(i) a VH that comprises:
   (a) a CDRH1 comprising the amino acid sequence of SEQ ID NO:2,
   (b) a CDRH2 comprising the amino acid sequence of SEQ ID NO:3; and
   (c) a CDRH3 comprising the amino acid sequence of SEQ ID NO:27;
and (ii) a VL that comprises:
   (a) a CDRL1 comprising the amino acid sequence of SEQ ID NO:12,
   (b) a CDRL2 comprising the amino acid sequence of SEQ ID NO:13; and
   (c) a CDRL3 comprising the amino acid sequence of SEQ ID NO:31.

E3. The isolated antibody, or antigen-binding fragment thereof, of any one of E1-E2, comprising a VH that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 1, SEQ ID NO: 26, SEQ ID NO: 39 or SEQ ID NO: 44.

E4. The isolated antibody, or antigen-binding fragment thereof, of any one of E1-E3, comprising a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 11, SEQ ID NO: 30, SEQ ID NO: 36 or SEQ ID NO: 11.

E5. The isolated antibody, or antigen-binding fragment thereof, of any one of E1-E4, comprising a VH that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 26, and a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 30 or SEQ ID NO: 36.

E6. The isolated antibody, or antigen-binding fragment thereof, of any one of E1-E5, comprising a VH that comprises the amino acid sequence of SEQ ID NO:33 and a VL that comprises the amino acid sequence of SEQ ID NO:38.

E7. The isolated antibody, or antigen-binding fragment thereof, of any one of E1-E5, comprising a VH that comprises the amino acid sequence of SEQ ID NO: 26 and a VL that comprises the amino acid sequence of SEQ ID NO: 36.

E8. The isolated antibody, or antigen-binding fragment thereof, of any one of E1-E5, comprising a VH that comprises the amino acid sequence of SEQ ID NO: 26 and a VL that comprises the amino acid sequence of SEQ ID NO: 30.

E9. The isolated antibody, or antigen-binding fragment thereof, of any one of E1-E4, comprising a VH that comprises the amino acid sequence of SEQ ID NO: 39 and a VL that comprises the amino acid sequence of SEQ ID NO: 36.

E10. The isolated antibody, or antigen-binding fragment thereof, of any one of E1-E4, comprising a VH that comprises the amino acid sequence of SEQ ID NO: 44 and a VL that comprises the amino acid sequence of SEQ ID NO: 11.

E11. The isolated antibody, or antigen-binding fragment thereof, of any one of E1-E4, comprising a VH that comprises the amino acid sequence of SEQ ID NO: 1 and a VL that comprises the amino acid sequence of SEQ ID NO: 11.

E12. The antibody, or antigen-binding fragment thereof, of any one of E1-E11, comprising an Fc domain.

E13. The antibody, or antigen-binding fragment thereof, of E12, wherein the Fc domain is the Fc domain of an IgA, IgD, IgE, IgM, or IgG.

E14. The antibody, or antigen-binding fragment thereof, of E13 wherein the Fc domain is an IgG Fc domain.

E15. The antibody, or antigen-binding fragment thereof, of E14, wherein the IgG is selected from the group consisting of $IgG_1$, $IgG_2$, $IgG_3$, or $IgG_4$.

E16. The antibody, or antigen-binding fragment thereof, of E15, wherein the IgG is $IgG_1$.

E17. The isolated antibody, or antigen-binding fragment thereof, of any one of E1-E16, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 10, 29, 41 or 46.

E18. The isolated antibody, or antigen-binding fragment thereof, of any one of E1-E17, comprising a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 17, 32, or 37

E19. The isolated antibody, or antigen-binding fragment thereof, of any one of E1-E18, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 29 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 32 or SEQ ID NO: 37.

E20. The isolated antibody, or antigen-binding fragment thereof, of any one of E1-E19, comprising a heavy chain that comprises the amino acid sequence of SEQ ID NO: 29 and a light chain that comprises the amino acid sequence of SEQ ID NO: 37.

E21. The isolated antibody, or antigen-binding fragment thereof, of any one of E1-E19, comprising a heavy chain that comprises the amino acid sequence of SEQ ID NO: 29 and a light chain that comprises the amino acid sequence of SEQ ID NO: 32.

E22. The isolated antibody, or antigen-binding fragment thereof, of any one of E1-E18, comprising a heavy chain that comprises the amino acid sequence of SEQ ID NO: 41 and a light chain that comprises the amino acid sequence of SEQ ID NO: 37.

E23. The isolated antibody, or antigen-binding fragment thereof, of any one of E1-E18, comprising a heavy chain that comprises the amino acid sequence of SEQ ID NO: 46 and a light chain that comprises the amino acid sequence of SEQ ID NO: 17.

E24. The isolated antibody, or antigen-binding fragment thereof, of any one of E1-E18, comprising a heavy chain that comprises the amino acid sequence of SEQ ID NO: 10 and a light chain that comprises the amino acid sequence of SEQ ID NO: 17.

E25. An isolated antibody, or antigen-binding fragment thereof, that binds an epitope on CDCP1, wherein the epitope comprises at least one amino acid residue selected from the group consisting of Thr124, Thr160, Ser162, Ala195, Leu196, and His197, according to the numbering of SEQ ID NO: 90.

E26. The isolated antibody, or antigen-binding fragment thereof, of E25, wherein the epitope further comprises at least one amino acid residue selected from the group consisting of Lys45, Leu46, Gly47, Thr48, Pro49, Thr50, Ala53, Pro55, Glu92, Arg173, and Glu242, according to the numbering of SEQ ID NO: 90.

E27. The isolated antibody, or antigen-binding fragment thereof, of any one of E24-E25, wherein the epitope further comprises at least one amino acid residue selected from the group consisting of Thr56, Tyr57, Thr66, Met67, Ile126, Val171, Arg173, according to the numbering of SEQ ID NO: 90.

E28. The isolated antibody, or antigen-binding fragment thereof of any one of E25-E27, wherein the epitope further comprises a glycan attached to Asn122, according to the numbering of SEQ ID NO: 90.

E29. The isolated antibody, or antigen-binding fragment thereof, of any one of E25-E28, wherein the antibody, or antigen-binding fragment thereof, comprises:
  (i) a VH that comprises:
    (a) a CDRH1 comprising the amino acid sequence of SEQ ID NO: 2
    (b) a CDRH2 comprising the amino acid sequence of SEQ ID NO: 3; and
    (c) a CDRH3 comprising the amino acid sequence selected from the group consisting of SEQ ID NO: 4, SEQ ID NO: 27, SEQ ID NO: 40 and SEQ ID NO: 45.
  and (ii) a VL that comprises:
    (a) a CDRL1 comprising the amino acid sequence of SEQ ID NO: 12,
    (b) a CDRL2 comprising the amino acid sequence of SEQ ID NO: 13; and
    (c) a CDRL3 comprising the amino acid sequence selected from the group consisting of SEQ ID NO:14 and SEQ ID NO:31.

E30. The isolated antibody, or antigen-binding fragment thereof, of any one of E25-E29, wherein the antibody, or antigen-binding fragment thereof, comprises a VH that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 26, and a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 30 or SEQ ID NO: 36.

E31. The isolated antibody, or antigen-binding fragment thereof, of any one of E25-E30, wherein the antibody, or antigen-binding fragment thereof, comprises a VH that comprises the amino acid sequence of SEQ ID NO: 26 and a VL that comprises the amino acid sequence of SEQ ID NO: 36.

E32. The isolated antibody, or antigen-binding fragment thereof, of any one of E25-E31, wherein the antibody, or antigen-binding fragment thereof, comprises a heavy chain comprising an amino acid at least 90%, at least 91%, at least 92%, at least 93%, at least 94%, at least 95%, at least 96%, at least 97%, at least 98%, at least 99%, or 100% identical to the amino acid sequence of SEQ ID No: 29 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 32 or SEQ ID NO: 37.

E33. The isolated antibody, or antigen-binding fragment thereof, of any one of E25-E32, wherein the antibody, or antigen-binding fragment thereof, comprises a heavy chain that comprises the amino acid sequence of SEQ ID NO: 29 and a light chain that comprises the amino acid sequence of SEQ ID NO: 37.

E34. An isolated antibody, or antigen-binding fragment thereof, that competes for binding to CDCP1 with an antibody, or antigen-binding fragment thereof, of any one of E1-E33.

E35. An isolated antibody, or antigen-binding fragment thereof, that competes for binding to CDCP1 with an antibody, or antigen-binding fragment thereof, selected from the group consisting of: CP13E10, CP13E10-183/290, CP13E10-H7C-K222R-N297A, CP13E10-54HC-89LC, CP13E10-54HC-89LC-183/290, CP13E10-54HC-89LC-H7C-K222R-N297A, CP13E10-54HC-89LCv1, CP13E10-54HC-89LCv1-183/290, CP13E10-54HC-89LCv1-H7C-K222R-N297A, CP13E10-54HCv13-89LCv1, CP13E10-54HCv13-89LCv1-183/290, CP13E10-54HCv13-89LCv1-H7C-K222R-N297A, CP13E10-291, antibody 23, antibody 24 and antibody 76.

E36. An isolated antibody, or antigen-binding fragment thereof, that specifically binds CDCP1, wherein the antibody, or antigen-binding fragment thereof, binds substantially the same epitope as an antibody, or antigen-binding fragment thereof, of any one of E1-E35.

E37. An isolated antibody, or antigen-binding fragment thereof, that specifically binds CDCP1, wherein the antibody, or antigen-binding fragment thereof, binds substantially the same epitope as an antibody, or antigen-binding fragment thereof, selected from the group consisting of: CP13E10, CP13E10-183/290, CP13E10-H7C-K222R-N297A, CP13E10-54HC-89LC, CP13E10-54HC-89LC-183/290, CP13E10-54HC-89LC-H7C-K222R-N297A, CP13E10-54HC-89LCv1, CP13E10-54HC-89LCv1-183/290, CP13E10-54HC-89LCv1-H7C-K222R-N297A, CP13E10-54HCv13-89LCv1, CP13E10-54HCv13-89LCv1-183/290, CP13E10-54HCv13-89LCv1-H7C-K222R-N297A, CP13E10-291, antibody 23, antibody 24 and antibody 76.

E38. The isolated antibody, or antigen-binding fragment thereof, of any one of the preceding embodiments, wherein the antibody, or antigen-binding fragment thereof, binds CDCP1 with a binding affinity ($K_D$) value of or less than about 350 nM, about 325 nM, about 323.10 nM, about 300 nM, about 286.44 nM, about 275 nM, about 250 nM, about 232.13 nM, about 225 nM, about 219.13 nM, about 200 nM, about 195.54 nM, about 175 nM, about 158 nM, about 150 nM, about 125 nM, or about 100 nM.

E39. The isolated antibody, or antigen-binding fragment thereof, of any one of the preceding embodiments, wherein the antibody, or antigen-binding fragment thereof, binds CDCP1 with a $K_D$ value of or less than about 95 nM, about 90 nM, about 80 nM, about 79.89 nM, about 75 nM, about 70 nM, about 69.50 nM, about 65 nM, about 63.44 nM, about 60 nM, about 55 nM, about 52.88 nM, about 50 nM, about 45 nM, about 44.50 nM, about 41.99 nM, about 40 nM, about 35 nM, about 30 nM, about 25 nM, about 20 nM, about 10 nM, about 5 nM, or about 1 nM.

E40. The isolated antibody, or antigen-binding fragment thereof, of any one of the preceding embodiments, wherein the antibody, or antigen-binding fragment thereof, binds CDCP1 with a $K_D$ value of or less than about 5 nM, about 4.5 nM, about 4 nM, about 3.5 nM, about 3.12 nM, about 3 nM, about 2.90 nM, about 2.5 nM, about 2 nM, about 1.5 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

E41. The isolated antibody, or antigen-binding fragment thereof, of any one of E38-E40, wherein said $K_D$ value is measured by surface plasmon resonance (SPR), optionally using a Biacore T200 instrument.

E42. The antibody, or antigen-binding fragment thereof, of any one of E38-E40, wherein said $K_D$ value is measured by bio-layer interferometry (BLI), optionally using a ForteBio Octet instrument.

E43. The antibody, or antigen-binding fragment thereof, of any one of E38-E42, wherein said CDCP1 is a human CDCP1, a cyno CDCP1 or a mouse CDCP1.

E44. The antibody, or antigen-binding fragment thereof, of any one of E38-E42, wherein said CDCP1 is a human CDCP1 and the $K_D$ value is about 40 nM, about 45 nM or about 50 nM.

E45. The antibody, or antigen-binding fragment thereof, of any one of E38-E42, wherein said CDCP1 is a cyno CDCP1 and the $K_D$ value is about 62 nM, about 64 nM, about 66 nm, about 68 nM, or about 70 nM.

E46. The antibody, or antigen-binding fragment thereof, of any one of the preceding embodiments, wherein the antibody, or antigen-binding fragment thereof, internalizes upon binding to CDCP1 on a mammalian cell.

E47. The antibody, or antigen-binding fragment thereof, of any one of the preceding embodiments, wherein the antibody, or antigen-binding fragment thereof, comprises an antibody heavy chain constant domain comprising an engineered cysteine residue at position 290 according to the numbering of the Eu index of Kabat.

E48. The antibody, or antigen-binding fragment thereof, of E47, wherein the constant domain comprises an IgG, IgA, IgD, IgE, or IgM heavy chain domain.

E49. The antibody, or antigen-binding fragment thereof, of E48, wherein the constant domain comprises an $IgG_1$, $IgG_2$, $IgG_3$, or $IgG_4$ heavy chain domain.

E50. The antibody, or antigen-binding fragment thereof, of E48, wherein the constant domain comprises an $IgA_1$ or $IgA_2$ heavy chain domain.

E51. The antibody, or antigen-binding fragment thereof, of any one of E47-E50, wherein the constant domain is a human antibody constant domain.

E52. The antibody, or antigen-binding fragment thereof, of any one of E47-E51, wherein the constant domain comprises an IgG1 heavy chain $CH_2$ domain and an IgG1 heavy chain $CH_3$ domain.

E53. The antibody, or antigen-binding fragment thereof, of any one of E47-E52, wherein the antibody, or antigen-binding fragment thereof, further comprises an antibody light chain constant domain comprising an engineered cysteine residue at position 183 according to the numbering of Kabat.

E54. The antibody, or antigen-binding fragment thereof, of E53, wherein the light chain constant domain comprises a kappa light chain constant domain (CLκ).

E55. The antibody, or antigen-binding fragment thereof, of E53, wherein the light chain constant domain comprises a lambda light chain constant domain (CLλ).

E56. The isolated antibody, or antigen-binding fragment thereof, of any one of E46-E54, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 19, 33, or 42.

E57. The isolated antibody, or antigen-binding fragment thereof, of any one of E47-E56, comprising a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 21, 34, or 38.

E58. The isolated antibody, or antigen-binding fragment thereof, of any one of E47-E57, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 33 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO:34 or SEQ ID NO:38.

E59. The isolated antibody, or antigen-binding fragment thereof, of any one of E47-E58, comprising a heavy chain that comprises the amino acid sequence of SEQ ID NO: 33 and a light chain that comprises the amino acid sequence of SEQ ID NO: 38.

E60. The isolated antibody, or antigen-binding fragment thereof, of any one of E47-E58, comprising a heavy chain that comprises the amino acid sequence of SEQ ID NO: 33 and a light chain that comprises the amino acid sequence of SEQ ID NO: 34.

E61. The isolated antibody, or antigen-binding fragment thereof, of any one of E47-E57, comprising a heavy chain that comprises the amino acid sequence of SEQ ID NO: 42 and a light chain that comprises the amino acid sequence of SEQ ID NO: 38.

E62. The isolated antibody, or antigen-binding fragment thereof, of any one of E47-E57, comprising a heavy chain that comprises the amino acid sequence of SEQ ID NO: 19 and a light chain that comprises the amino acid sequence of SEQ ID NO: 21.

E63. The antibody, or antigen-binding fragment thereof, of any one of E1-E46, wherein the antibody, or antigen-binding fragment thereof, comprises an acyl donor glutamine-containing tag sequence engineered at a specific site in the Fc region of said antibody.

E64. The antibody, or antigen-binding fragment thereof, of E63, wherein the glutamine-containing tag sequence comprises LLQG (SEQ ID NO: 91).

E65. The antibody, or antigen-binding fragment thereof, of any one of E63-E64, wherein the glutamine-containing tag is engineered after amino acid residue number 135 and before amino acid residue number 136 according to the numbering of the Eu index of Kabat.

E66. The antibody, or antigen-binding fragment thereof, of any one of E63-E65, wherein the Fc domain of the antibody, or antigen-binding fragment thereof, comprises one or more amino acid substitutions selected from the group consisting of: N297A and K222R, according to the numbering of the Eu index of Kabat.

E67. The isolated antibody, or antigen-binding fragment thereof, of any one of E63-E66, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 25, 35, or 43.

E68. The isolated antibody, or antigen-binding fragment thereof, of any one of E63-E67, comprising a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 17, 32, or 37.

E69. The isolated antibody, or antigen-binding fragment thereof, of any one of E63-E68, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 35 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 32 or SEQ ID NO: 37.

E70. The isolated antibody, or antigen-binding fragment thereof, of any one of E63-E69, comprising a heavy chain that comprises the amino acid sequence of SEQ ID NO: 35 and a light chain that comprises the amino acid sequence of SEQ ID NO: 37.

E71. The isolated antibody, or antigen-binding fragment thereof, of any one of E63-E69, comprising a heavy chain that comprises the amino acid sequence of SEQ ID NO: 35 and a light chain that comprises the amino acid sequence of SEQ ID NO: 32.

E72. The isolated antibody, or antigen-binding fragment thereof, of any one of E63-E68, comprising a heavy chain that comprises the amino acid sequence of SEQ ID NO: 43 and a light chain that comprises the amino acid sequence of SEQ ID NO: 37.

E73. The isolated antibody, or antigen-binding fragment thereof, of any one of E63-E68, comprising a heavy chain that comprises the amino acid sequence of SEQ ID NO: 25 and a light chain that comprises the amino acid sequence of SEQ ID NO: 17.

E74. An isolated nucleic acid molecule, comprising one or more nucleic acid sequences encoding the antibody, or antigen-binding fragment thereof, of any one of E1-E73.

E75. An isolated nucleic acid comprising the nucleotide sequence of SEQ ID NO: 75.

E76. An isolated nucleic acid comprising the nucleotide sequence of SEQ ID NO: 76.

E77. An isolated nucleic acid comprising the nucleotide sequence of SEQ ID NO: 77.

E78. An isolated nucleic acid comprising the nucleotide sequence of SEQ ID NO: 78.

E79. An isolated nucleic acid comprising the nucleotide sequence of SEQ ID NO: 79.

E80. An isolated nucleic acid comprising the nucleotide sequence of SEQ ID NO: 80.

E81. An isolated nucleic acid comprising the nucleotide sequence of SEQ ID NO: 81.

E82. An isolated nucleic acid comprising the nucleotide sequence of SEQ ID NO: 82.

E83. An isolated nucleic acid comprising the nucleotide sequence of SEQ ID NO: 83.

E84. An isolated nucleic acid comprising the nucleotide sequence of SEQ ID NO: 84.

E85. A vector comprising the nucleic acid of any one of E74-E84.

E86. A host cell comprising at least one nucleic acid of any one of E74-84.

E87. A host cell comprising the nucleic acid of SEQ ID NO: 85 and the nucleic acid comprising the nucleotide sequence of SEQ ID NO: 86.

E88. The host cell of any one of E86-E87, wherein said cell is a mammalian cell.

E89. The host cell of E88, wherein said host cell is a CHO cell, a HEK-293 cell, or an Sp2.0 cell.

E90. A method of making an antibody, or antigen binding fragment thereof, comprising culturing the host cell of E86-89, under a condition wherein said antibody, or antigen binding fragment thereof, is expressed by said host cell.

E91. An antibody drug conjugate comprising the antibody, or antigen-binding fragment thereof, of any one of E1-E46, wherein the antibody is conjugated to a drug moiety.

E92. The antibody drug conjugate of E80, wherein the antibody is conjugated to the drug moiety via a linker.

E93. The antibody drug conjugate of any one of E91-E92, wherein the antibody is conjugated to the linker-drug moiety via one or more engineered cysteine residues on the antibody.

E94. The antibody drug conjugate of E93, wherein the antibody, or antigen-binding fragment thereof, comprises the antibody, or antigen-binding fragment thereof, of any one of E47-62.

E95. The antibody drug conjugate of any one of E91-E94, wherein the linker is selected from the group consisting of: valine-citrulline (val-cit), 6-maleimidocaproyl (mc), methoxy-polyethylene glycol maleimide 6 (MalPeg6), p-aminobenzylcarbamate (PABC), dimethylaminoethanol (DMAE), maleimidopropanoyl (MP), hydrolyzed Peg-maleimides, alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1carboxylate (SMCC), N-Succinimidyl (4-iodo-acetyl) aminobenzoate (SIAB), 6-maleimido-caproyl-valine-citrulline-p-aminobenzyloxycarbonyl (mc-val-cit-PAB), and 6-maleimidocaproyl-valine-citrulline-p-aminobenzylcarbamate (mc-val-cit-PABC).

E96. The antibody drug conjugate of any one of E91-E92, wherein the antibody is conjugated to the linker using an acyl donor glutamine-containing tag sequence engineered on the antibody.

E97. The antibody drug conjugate of E96, wherein the tag sequence is LLQG (SEQ ID NO: 91).

E98. The antibody drug conjugate of any one of E96-E97, wherein the antibody, or antigen-binding fragment thereof, comprises the antibody, or antigen-binding fragment thereof, of any one of E63-73.

E99. The antibody drug conjugate of any one of E96-E98, wherein the linker is selected from the group consisting of: Ac-Lys-Gly (acetyl-lysine-glycine), aminocaproic acid, Ac-Lys-p-Ala (acetyl-lysine-p-alanine), amino-PEG2 (polyethylene glycol)-C2, amino-PEG3-C2, amino-PEG6-C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine.

E100. The antibody drug conjugate of any one of E91-E99, wherein the drug moiety is a cytotoxic agent, an immunomodulating agent, an imaging agent, a chemotherapeutic agent, or a therapeutic protein.

E101. The antibody drug conjugate of E100, wherein the cytotoxic agent is selected from the group consisting of an anthracycline, an auristatin, CC-1065, a dolastatin, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof.

E102. The antibody drug conjugate of E101, wherein the cytotoxic agent is an auristatin selected from the group consisting of:
MMAD (Monomethyl Auristatin D), p-aminobenzylcarbamate (PABC), dimethylaminoethanol (DMAE), maleimidopropanoyl (MP), hydrolyzed Peg-maleimides, alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1carboxylate (SMCC), N-Succinimidyl (4-iodo-acetyl) aminobenzoate (SIAB), 6-maleimidocaproyl-valine-citrulline-p-aminobenzyloxycarbonyl (mc-val-cit-PAB), and 6-maleimidocaproyl-valine-citrulline-p-aminobenzylcarbamate (mc-val-cit-PABC), and the drug moiety is an auristatin.

E104. The antibody drug conjugate of E103, wherein the linker is mc-val-cit-PABC and the drug moiety is 0101 or 0131.

E105. An antibody drug conjugate comprising an antibody, or antigen-binding fragment thereof, conjugated to a linker-drug moiety via one or more engineered cysteine residues on the antibody, wherein the antibody, or antigen-binding fragment thereof, comprises a heavy chain that comprises the amino acid sequence of SEQ ID NO: 33 and a light chain that comprises the amino acid sequence of SEQ ID NO: 38, and wherein the linker-drug moiety is mc-val-cit-PABC-0101.

E106. An antibody drug conjugate comprising an antibody, or antigen-binding fragment thereof, conjugated to a linker-drug moiety via one or more engineered cysteine residues on the antibody, wherein the antibody, or antigen-binding fragment thereof, comprises a heavy chain that comprises the amino acid sequence of SEQ ID NO: 33 and a light chain that comprises the amino acid sequence of SEQ ID NO: 34, and wherein the linker-drug moiety is mc-val-cit-PABC-0101.

E107. The antibody drug conjugate of any one of E91-E102, wherein the linker is selected from the group consisting of: Ac-Lys-Gly (acetyl-lysine-glycine), aminocaproic acid, Ac-Lys-p-Ala (acetyl-lysine-p-alanine), amino-PEG2 (polyethylene glycol)-C2, amino-PEG3-C2, amino-PEG6-

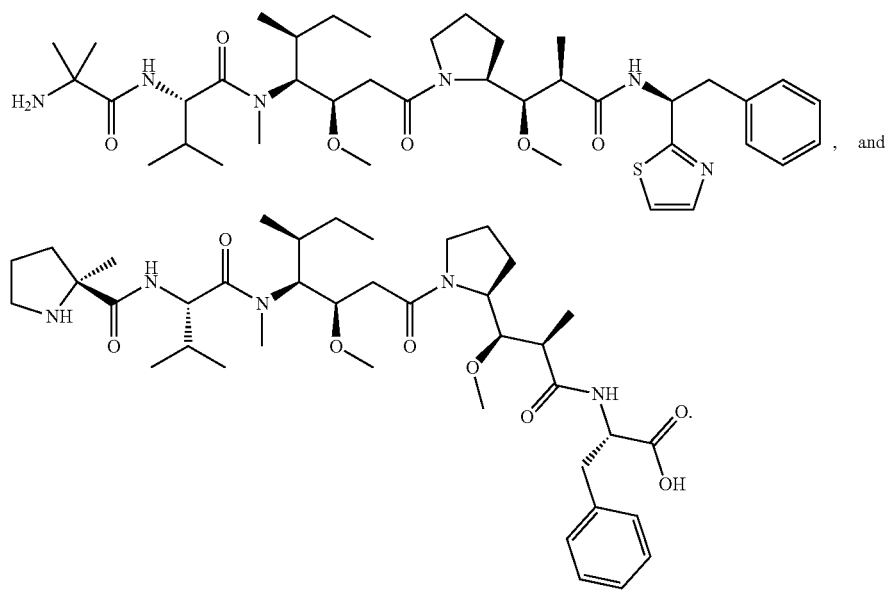

E103. The antibody drug conjugate of any one of E91-E102, wherein the linker is selected from the group consisting of: valine-citrulline (val-cit), 6-maleimidocaproyl (mc), methoxy-polyethylene glycol maleimide 6 (MalPeg6), C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]

propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine, and the drug moiety is an auristatin.

E108. The antibody drug conjugate of E107, wherein the linker is amino PEG6-propionyl (i.e., amino-PEG6-C2 or AMPeg6C2), and the drug moiety is 0101 or 0131.

E109. An antibody drug conjugate comprising an antibody, or antigen-binding fragment thereof, conjugated to a linker-drug moiety using an acyl donor glutamine-containing tag engineered at a specific site on the antibody, wherein the antibody, or antigen-binding fragment thereof, comprises a heavy chain that comprises the amino acid sequence of SEQ ID NO: 35 and a light chain that comprises the amino acid sequence of SEQ ID NO: 37, and wherein the linker-drug moiety is amino PEG6-propionyl-0131 (AmPeg6C2-0131).

E110. An antibody drug conjugate comprising an antibody, or antigen-binding fragment thereof, conjugated to a linker-drug moiety using an acyl donor glutamine-containing tag engineered at a specific site on the antibody, wherein the antibody, or antigen-binding fragment thereof, comprises a heavy chain that comprises the amino acid sequence of SEQ ID NO: 35 and a light chain that comprises the amino acid sequence of SEQ ID NO: 32, and wherein the linker-drug moiety is amino PEG6-propionyl-0131 (i.e., AmPeg6C2-0131).

E111. The antibody drug conjugate of any one of E91-E110, wherein said antibody drug conjugate has a melting transition temperature greater than at least 60° C., at least 65° C., at least 70° C., at least 75° C., at least 80° C., at least 85° C. or at least 90° C.

E112. The antibody drug conjugate of E111, wherein said antibody drug conjugate has a first melting transition temperature greater than about 65° C.

E113. The antibody drug conjugate of any one of E91-E112, wherein the antibody drug conjugate binds CDCP1 at pH 7.4 with a $K_D$ value of or less than about 50 nM, about 48 nM, about 46 nM, about 45 nM, about 44 nM, about 42 nM, or about 40 nM.

E114. The antibody drug conjugate of any one of E91-E113, wherein the antibody drug conjugate binds CDCP1 at pH 6.8 with a $K_D$ value of or less than about 70 nM, about 68 nM, about 66 nM, about 65 nM, about 64 nM, about 62 nM, or about 60 nM.

E115. The antibody drug conjugate of any one of E91-E114, wherein said antibody drug conjugate has a half maximal inhibitory concentration ($IC_{50}$) value of no more than about 20000 pM, about 15000 pM, about 10000 pM, about 9500 pM, 8000 pM, 7000 pM, 6000 pM, 5000 pM, 4000 pM, 3000 pM, 2000 pM, 1000 pM, 900 pM, 800 pM, 700 pM, 650 pM, 600 pM, 500 pM, 400 pM, 300 pM, 250 pM, 200 pM, or 100 pM.

E116. The antibody drug conjugate of any one of E91-E114, wherein said antibody drug conjugate has an IC50 value of no more than about 100 pM, about 90 pM, about 80 pM, about 70 pM, about 60 pM, about 50 pM, about 40 μm, about 30 pM, about 20 pM, about 10 pM, about 9 pM, about 8 pM, about 7 pM, about 6 pM, about 5 pM, about 4 pM, about 3 pM, about 2 pM, or about 1 pM.

E117. The antibody drug conjugate of E115 or E116, wherein IC50 values are determined using CDCP1 expressing cells.

E118. The antibody drug conjugate of any one of E91-E117, wherein said antibody drug conjugate reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% compared with mean tumor volume in otherwise identical untreated tumors using a non-small cell lung cancer (NSCLC) patient derived xenograft model.

E119. The antibody drug conjugate of any one of E91-E118, wherein said antibody drug conjugate reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% in treated tumors compared with mean tumor volume in otherwise identical untreated tumors in a head and neck cancer patient derived xenograft model.

E120. A pharmaceutical composition comprising the antibody drug conjugate of any one of E91-E119 and a pharmaceutically acceptable carrier.

E121. A method of treating cancer, an autoimmune disease, an inflammatory disease, or an infectious disease mediated by or associated with expression of CDCP1 on a cell, comprising administering to a subject in need thereof a therapeutically effective amount of the antibody drug conjugate of any one of E91-E119, or the composition of E120.

E122. The antibody drug conjugate of any one of E91-E119, or the composition of E120, for use in treating a cancer, an autoimmune disease, an inflammatory disease, or an infectious disease mediated by or associated with expression of CDCP1 on a cell.

E123. Use of the antibody drug conjugate of any one of E89-E112, or the composition of E113, for treating a cancer, an autoimmune disease, an inflammatory disease, or an infectious disease mediated by or associated with expression of CDCP1 on a cell.

E124. Use of the antibody drug conjugate of any one of E89-E112, or the composition of E113, in the manufacture of a medicament for treating a cancer, an autoimmune disease, an inflammatory disease, or an infectious disease mediated by or associated with expression of CDCP1 on a cell.

E125. The cancer of any one of E121-E124, wherein the cancer is selected from the group consisting of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g., that associated with brain tumors), and Meigs' syndrome.

BRIEF DESCRIPTION OF THE DRAWINGS

FIG. 3 is a graph showing relative hydrophobicity of anti-CDCP1 antibodies based on elution time as detected by an analytical Hydrophic Interaction Chromatography (HIC) method. Incorporation of three point mutations (Y(H100)H, W(H100C)H, Y(H100H)H) into CP13E10 CDRH3 (CP13E10-34 variant) significantly reduced hydrophobicity as demonstrated by the reduction in elution time.

FIG. 4 shows the elution time for anti-CDCP1 variants as detected by an analytical Hydrophic Interaction Chromatography (HIC) method. Incorporation of three point mutations (Y(H100)H, W(H100C)H, Y(H100H)H) into CP13E10 CDRH3 (CP13E10-34 variant) significantly reduced hydrophobicity as demonstrated by the reduction in elution time.

FIG. 5 is a line graph demonstrating that incorporation of V(H97)E into heavy chain CDR3 restored CDCP1 binding properties of variant CP13E10-54 to that of the parental wild-type CP13E10 antibody.

FIG. 6 shows the binding kinetics of anti-CDCP1 antibodies determined for recombinant human, cynomologus monkey and mouse CDCP1-ECD Protein.

FIG. 7 depicts a line graph demonstrating that IGKV146 germline substitutions incorporated into CP13E10-54HC-89LCv1 do not alter CDCP1 binding properties.

FIG. 8 shows a line graph demonstrating that germline CP13E10-54HC-89LCv1 binding to CDCP1 expressed on the surface of PC3 prostate cancer cells was identical to CP13E10-54HC-89LC.

FIG. 9 depicts a line graph demonstrating that CP13E10-54HCv13-89LCv1 comprising a G(H96)A mutation to remove putative isomerization site in CDRH3 retains CDCP1 binding properties relative to CP13E10-54HC-89LCv1.

Figure 22A:
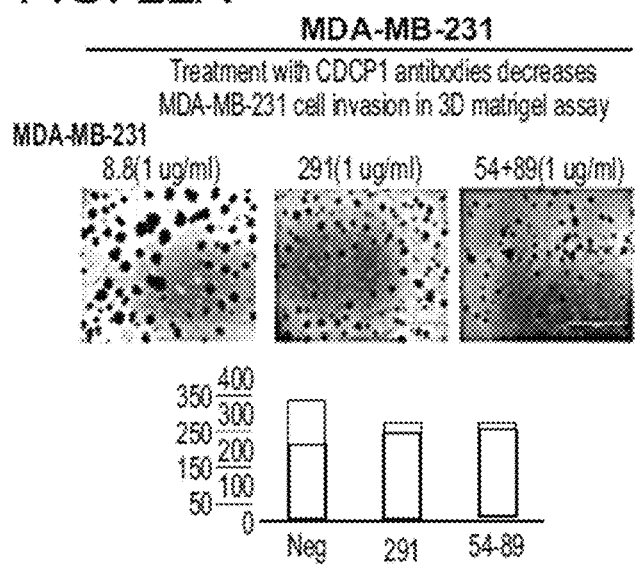
Figure 22B:
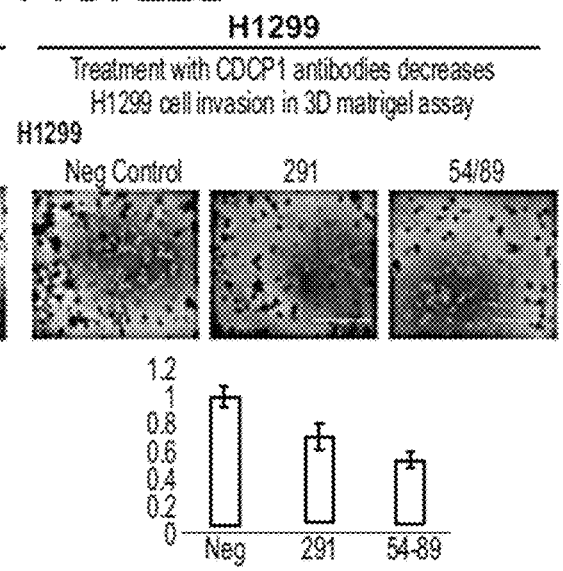

FIG. 22A-22B show images and bar graphs showing that CDCP1 antibodies CP13E10-291 and CPE10-54HC-89LC decrease MDA-MB-231 cells (FIG. 22A) and H1299 cells (FIG. 22B) invasion in a 3D Matrigel assay.

Figure 23A:
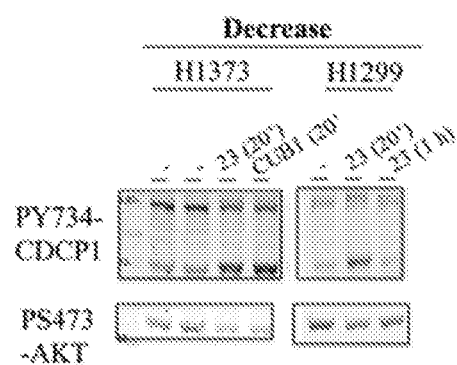
Figure 23B:
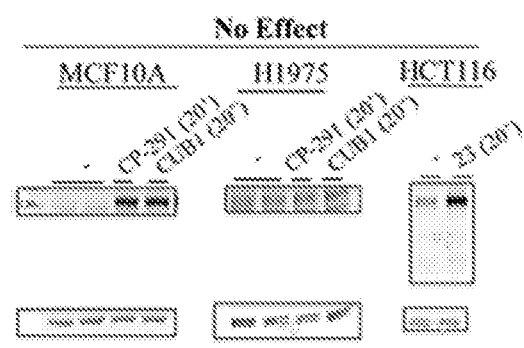

FIG. 23A-23B depicts western blot images showing that CDCP1-activating abs (CP13E10-291, CUB1 and antibody 23) decrease basal AKT activity in only some cells. FIG. 23A shows a decrease in H1373 and H1299 cells, while FIG. 23B shows no effect in MCF10A, H1975 and HCT116 cells.

Figure 24A:
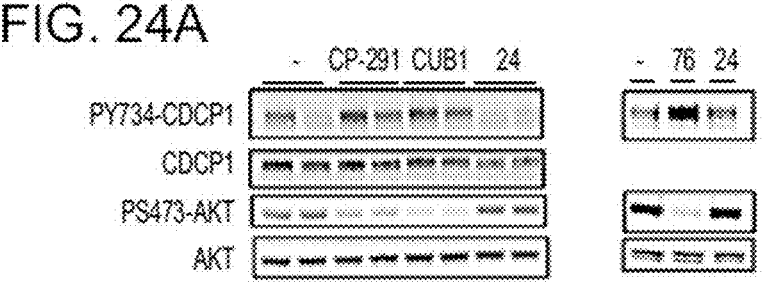
Figure 24B:
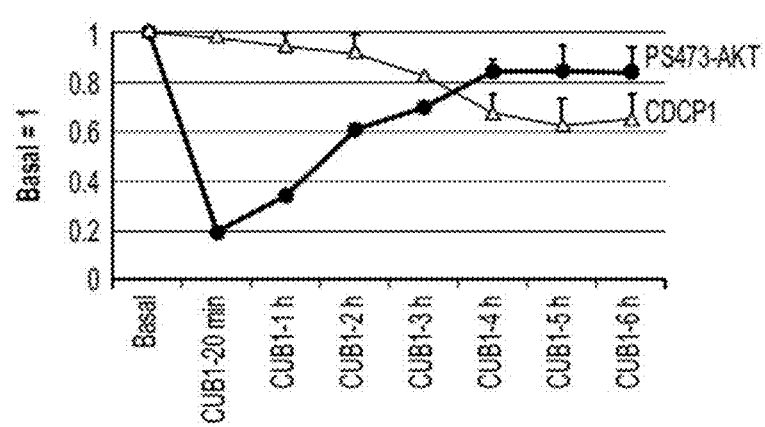
Figure 24C:
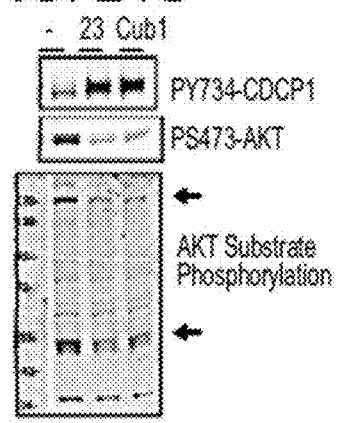

FIG. 24A-24C shows that antibodies that activate CDCP1 also reduce basal AKT activity and AKT substrate phosphorylation in PC3 Cells. FIG. 24A shows activating Abs including 291, 76, 23, CUB1 and non-activating Ab 24 which does not affect P-AKT. FIGS. 24B and 24C show the inhibition was transient after an 80% reduction within 20 min, moreover during prolonged antibody exposure the AKT phosphorylation returned towards the initial levels coincident with a reduction in the expression of CDCP1 protein expression.

Figure 25:
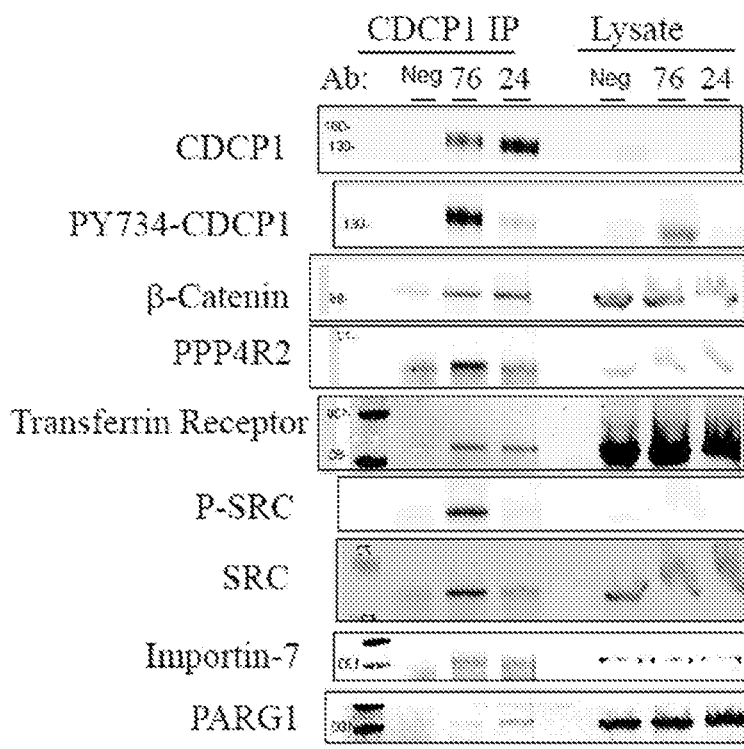

FIG. 25 shows experiments which identify new CDCP1 binding partners by using activating ("76") and ("24") anti-CDCP1 antibodies bound to intact PC3 cells.

Figure 26A:
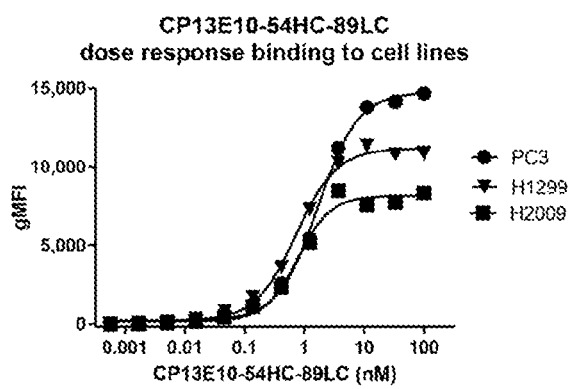

FIGS. 26A and 26B show the dose-dependent binding of anti-CDCP1 antibodies to CDCP1 expressing cells as determined by flow cytometry.

FIG. 27 shows the binding kinetics of anti-CDCP1 CP13E10-54HC-89LCv1-183/290 Antibody and CP13E10-54HC-89LCv1-183/290-vc0101 ADC determined for Recombinant Human CDCP1-ECD Protein.

Figure 28B:
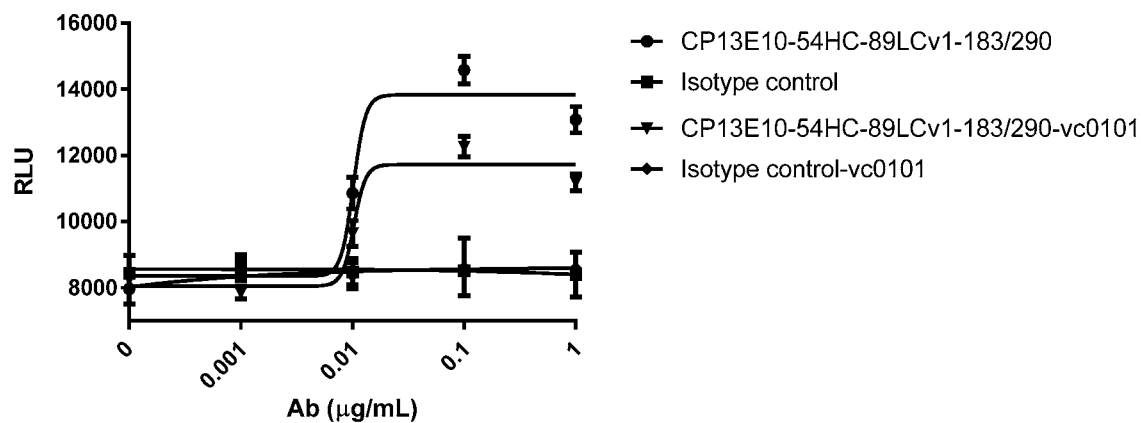

FIG. 28A demonstrate that incubation of PC3 cells with antibody CP13E10-54HC-89LCv1-183/290 or ADC CP13E10-54HC-89LCv1-183/290-vc0101 mediates cell killing (% Dead cells) in a dose-dependent fashion by co-incubated NK cells. Note that isotype control antibodies that fail to bind PC3 cells do not induce killing by NK cells. FIG. 28B demonstrates that incubation of PC3 cells with antibody CP13E10-54HC-89LCv1-183/290 or ADC CP13E10-54HC-89LCv1-183/290-vc0101 mediates induction of luciferase (measured as relative luminometer units (RLU)) in a dose-dependent fashion in reporter Jurkat Bioassay Effector Cells. Luciferase induction is indicative of engagement of the FcγRIII receptor on reporter cells by antibody bound to PC3 cells. Note that isotype control antibodies that fail to bind PC3 cells do not induce luciferase activity.

Figure 29A:
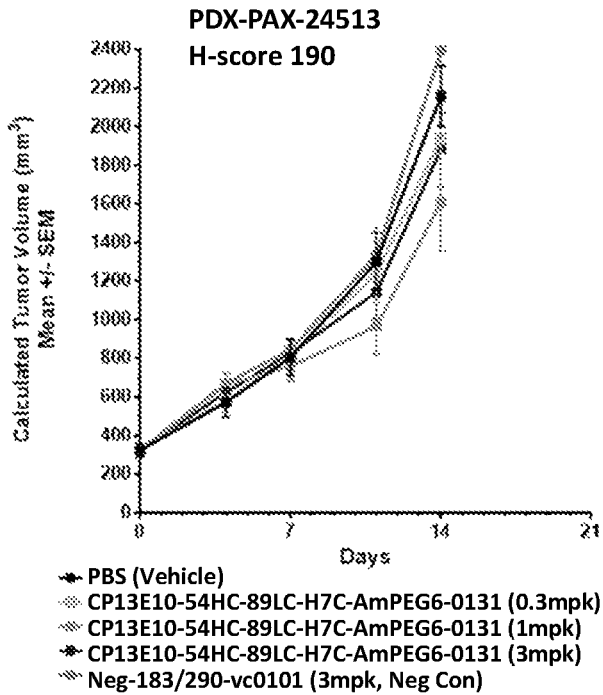
Figure 29B:
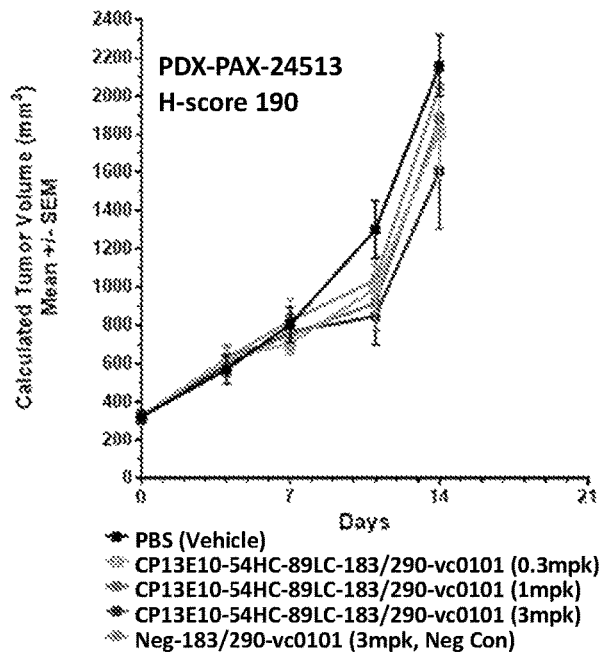

FIG. 29A-29B shows tumor growth in pancreatic cancer patient derived xenografts (PDX) models treated with CDCP1 antibody drug conjugates (ADCs). Pancreatic cancer PDX models PDX-PAX-24513 expresses substantial amounts of CDCP1 (H-score as indicated). Mouse cohorts were implanted with tumor cells and randomized to treatment when average tumor size reached approximately 200 mm$^3$ (n=10 per treatment group). Each group received intravenous (i.v.) injection of the indicated compound at the indicated concentration. Four total i.v. injections were given at four day intervals. Tumor growth was followed as described over the indicated time course.

Figure 30A:
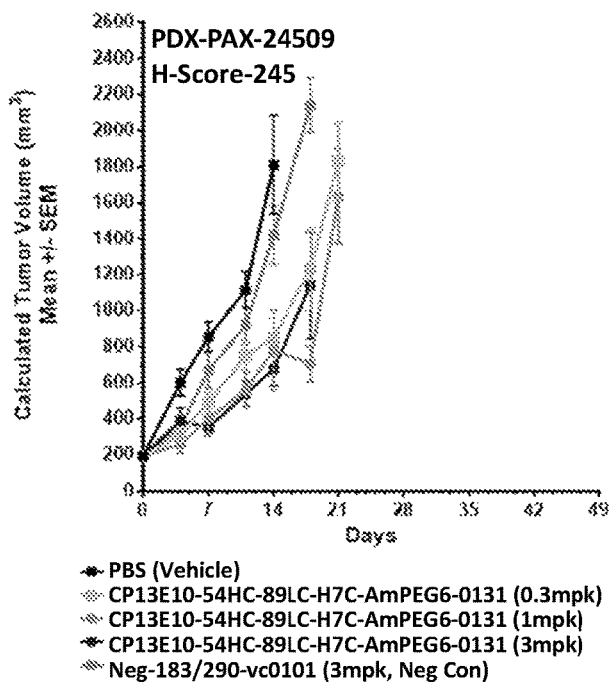
Figure 30B:
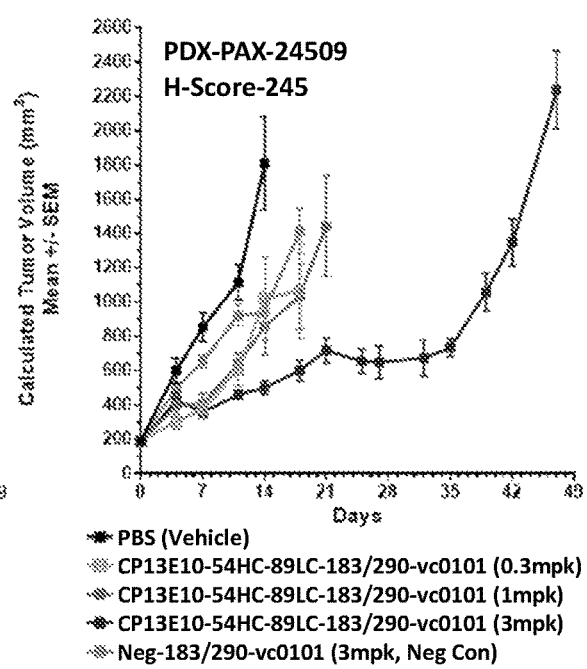

FIG. 30A-30B shows tumor growth in pancreatic cancer PDX models treated with CDCP1 antibody drug conjugates (ADCs). Pancreatic cancer PDX models PDX-PAX-24509 expresses substantial amounts of CDCP1 (H-score as indicated). Cohorts were implanted with tumor cells and randomized to treatment when average tumor size reached approximately 200 mm$^3$ (n=10 per treatment group). Each group received intravenous (i.v.) injection of the indicated compound at the indicated concentration. Four total i.v. injections were given at four day intervals. Tumor growth was assessed as described over the indicated time course.

Figure 31:
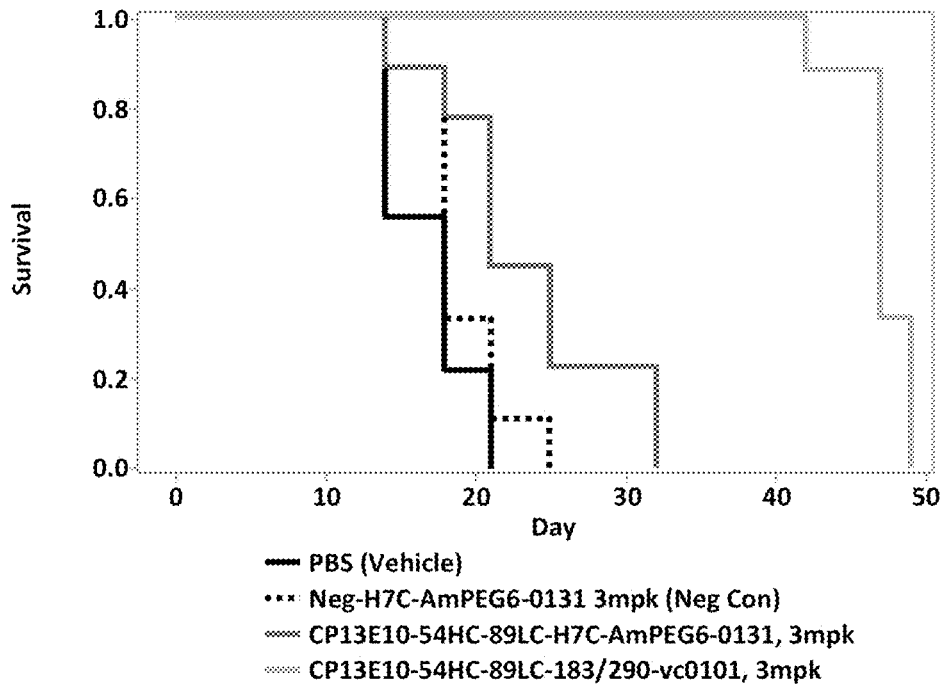

FIG. 31 shows the survival of pancreatic cancer model PDX-PAX-24509 cohorts from FIG. 30 dosed with ADCs at 3 mg/kg (milligrams per kilogram) or untreated negative controls to which phosphate buffered saline without the ADC (PBS) was administered. A statistically significant survival benefit was associated with CP13E10-54HC-89LC-183/290-vc0101 (mean±SE, 47.1±0.72 days) compared to untreated controls which received PBS (mean±SE, 16.9±0.99 days; log-rank, p<0.0001) or 3 mg/kg of CP13E10-54HC-89LC-H7C-AmPEG6-0131 (mean±SE, 20.8±0.68 days; log-rank, p<0.0001).

Figure 32A:
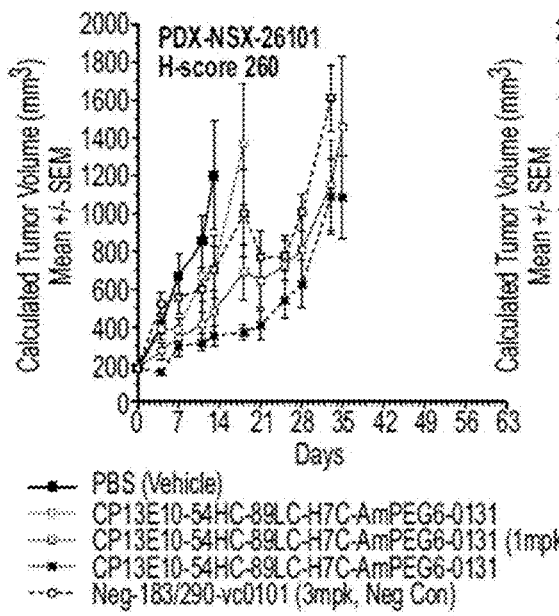
Figure 32B:
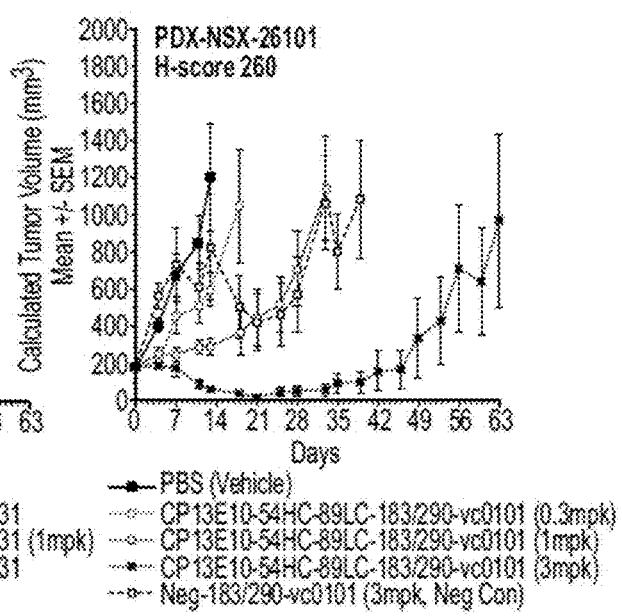

FIG. 32A shows tumor growth in non-small cell lung cancer (NSCLC) model PDX-NSX-26101. All doses of CP13E10-54HC-89LC-H7C-AmPEG6-0131 lead to progressive disease (PD). FIG. 32B shows tumor growth in NSCLC model PDX-NSX-26101. CP13E10-54HC-89LC-183/290-vc0101 also lead to progressive disease (PD) when dosed at 0.3 and 1 mg/kg. However, dosing of CP13E10-54HC-89LC-183/290-vc0101 at 3 mg/kg caused transient tumor regression leading to a partial response (PR) at least two weeks beyond the final dose (FIG. 32B).

Figure 33A:
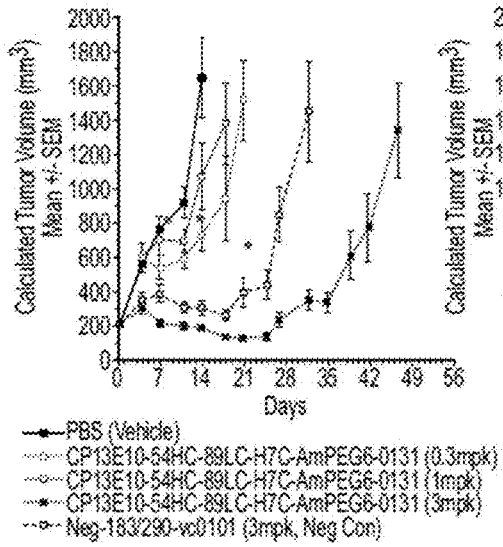
Figure 33B:
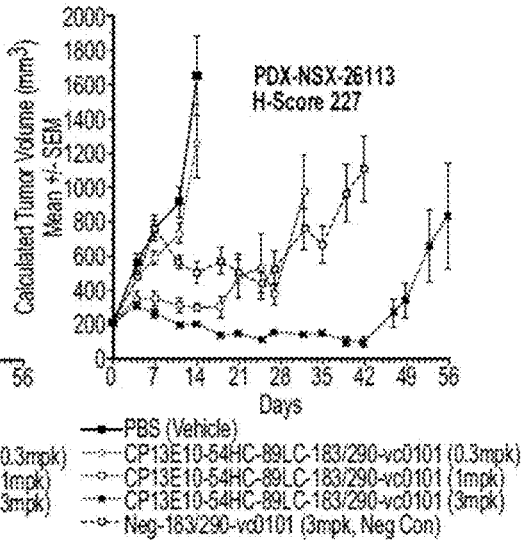

FIG. 33A shows tumor growth in NSCLC model PDX-NSX-26113. Doses of 0.3 and 1 mg/kg of CP13E10-54HC-89LC-H7C-AmPEG6-0131 lead to PD while, at 3 mg/kg, transient regression and a PR is seen until day 25 (13-days post last dose). FIG. 33B shows tumor growth in NSCLC model PDX-NSX-26113. Both 0.3 and 1 mg/kg doses of CP13E10-54HC-89LC-183/290-vc0101 lead to PD. Dosing of CP13E10-54HC-89LC-183/290-vc0101 at 3 mg/kg caused transient tumor regression leading to a PR seen at least until day 42 (29-days post last dose).

Figure 34A:
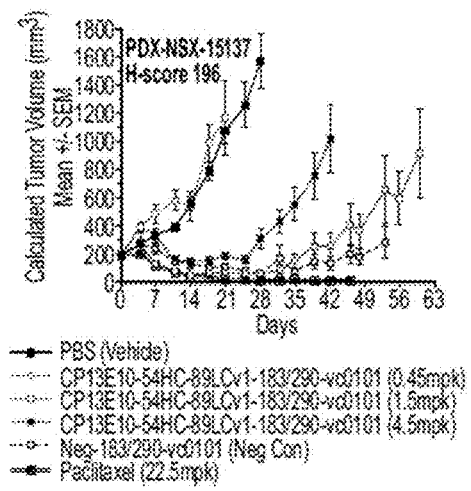
Figure 34B:
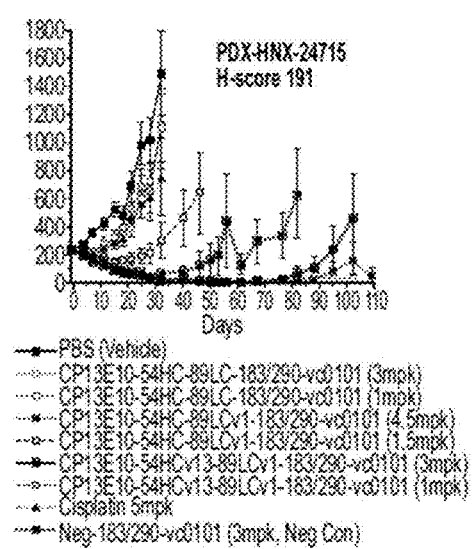

FIG. 34A shows tumor growth in NSCLC model PDX-NSX-15137. 1.5 mg/kg and 4.5 mg/kg doses of CP13E10-54HC-89LCv1-183/290-vc0101 lead to PR. By day 35, a PR was still seen at the 4.5 mg/kg dose at which time tumors in the paclitaxel treated cohort had increased in size beyond the starting volume. FIG. 34B shows tumor growth in head and neck cancer model PDX-HNX-24715. Both CP13E10-54HC-89LCv1-183/290-vc0101 at 4.5 mg/kg and CP13E10-54HC-89LC-183/290-vc0101 at 3 mg/kg were superior to treatment with cisplatin.

Figure 35A:
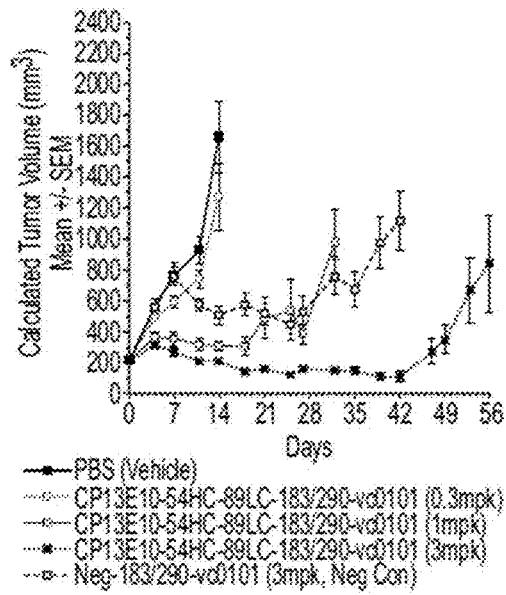
Figure 35B:
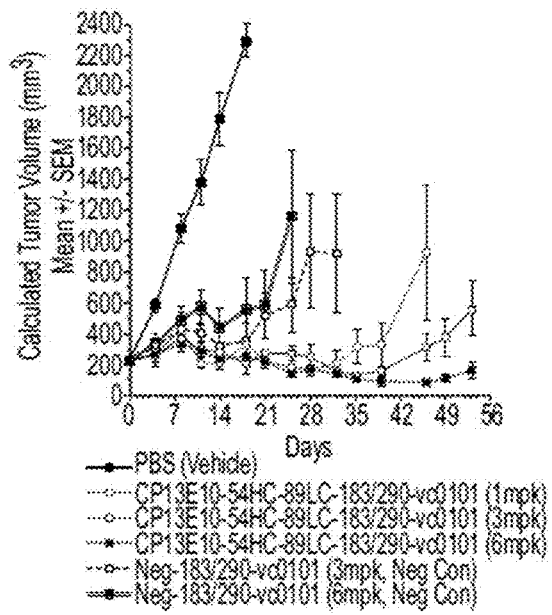

FIG. 35A shows tumor growth in PDX tumor model PDX-NSX-26113 (H-score 227). The tumor model was established and dosed four times each at four day intervals (q4d×4) at 0.3, 1, and 3 mg/kg with CP13E10-54HC-89LC-183/290-vc0101. A Partial Response was seen with 3 mg/kg dose at day 42. After this, tumors began sustained growth and were harvested on day 56 for re-implant into a naïve cohort of NOD/SCID mice. FIG. 35B shows naïve cohort implanted with tumor cells collected from 3 mg/kg cohort in FIG. 35A. Mice were randomized to treatment when average tumor size reached 200 mm$^3$. A Partial Response was seen in 3 and 6 mg/kg cohorts indicating that tumors remained sensitive to the ADC and that regrowth seen in FIG. 35A was not a consequence of development of resistance to CP13E10-54HC-89LC-183/290-vc0101.

Figure 36:
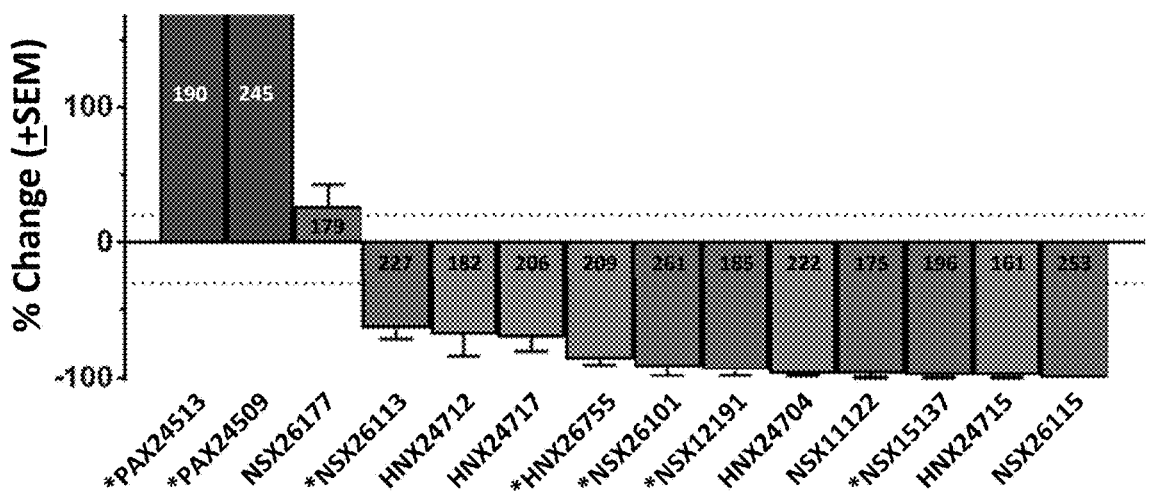

FIG. 36 shows the maximum average change in tumor size observed in Pancreatic (PAX), head and neck (HNX) or non-small cell lung cancer (NSX) patient derived xenograft (PDX) tumor model. These models were established in cohorts of mice (*n=10; n=4-5 for others). Treatment with CP13E10-54HC-89LC-183/290-vc0101 q4d×4 at 3 mg/kg began when average tumor size reached 200 mm$^3$. Percent change from starting volume was determined as described in the text. H-scores indicating CDCP1 expression levels are given within each bar. Recist Criteria: Complete Response 1/14; Partial Response 10/14; Progressive Disease 3/14; Objective Response Rate 79% (11/14).

FIG. 37 shows the maximum average change in tumor size observed in PAX, HNX, NSX, ovarian (OVX), breast (BRX), bladder (BLA), and small cell lung cancer (SCX) PDX tumor models. These models were established in cohorts of mice (n=4-5). Treatment with CP13E10-54HC-89LCv1-183/290-vc0101 q4dx4 at 3 mg/kg began when average tumor size reached 200 mm$^3$. H-scores for CDCP1 expression, where determined, are given within or above individual bars. Recist Criteria: Complete Response 8/40; Partial Response 17/40; Stable Disease 7/40; Progressive Disease 8/40; Objective Response Rate 63% (25/40).

DETAILED DESCRIPTION OF THE DISCLOSURE

The present invention is based, in part, on the surprising discovery that CDCP1 displays interesting biological activities in the setting of various cancers, which allows for specific treatment methods and patient selections. In addition, the present invention provides novel antibodies, and antibody drug conjugated based thereon, that specifically bind CDCP1 and exhibit characteristics demonstrating that they are potential novel human therapeutics for diseases and conditions mediated by or associated with expression of CDCP1 on a cell.

CDCP1 has the ability to internalize certain agents into cells and such internalization provides utility in the treatment of cancer. This internalization is mediated, without wishing to be bound by theory, by phosphorylation of CDCP1 by, for instance, Src, e.g., at tyrosine 734 of CDCP1. It has been previously suggested that this phosphorylation of CDCP1 is linked with its cancer promoting effects. Surprisingly, the present inventors have discovered that anti-tumor efficacy required that CDCP1 be phosphorylated and therefore competent for internalization. Further, targeting of CDCP1 for internalization provided targeted anti-tumor effects despite a widespread expression of CDCP1. Accordingly, inter alia, the present invention exploits the discovery of an internalization of CDCP1 in certain cells, e.g., cells that express Tyr734-phosphorylated CDCP1, to allow for drug delivery in a manner that mitigates off-target effects. Further still, the present inventors have shown that certain CDCP1-targeting agents require prolonged exposure to decrease CDCP1, presumably, without wishing to be bound by theory, by being internalized. Accordingly, such pacing of biological effects supports regimens and combination therapies as described herein. Also, the present inventors have shown that internalization of CDCP1 is favored in a hypoxic environment, like that of a tumor (e.g., as characterized by expression of HIF-2), providing a selection of oncology indications of interest.

In various aspects, the present invention relates a method for treating cancer in a patient in need thereof comprising: (a) evaluating a tumor sample for expression of CDCP1, e.g., Tyr-734-phosphorylated CDCP1, on the surface of tumor cells; and (b) administering an agent which binds to CDCP1 to the cancer patient.

Accordingly, in various aspects, the present invention relates a method for treating cancer in a patient in need thereof comprising: (a) evaluating a tumor sample for an amount of a mutant LKB1 and/or KRAS; and (b) administering an agent which binds to CDCP1 to the cancer patient if the amount of mutant LKB1 and/or KRAS is higher than a reference sample. In some embodiments, the tumor sample is a biopsy selected from a frozen tumor tissue specimen, cultured cells, circulating tumor cells, and a formalin-fixed paraffin-embedded tumor tissue specimen. In some embodiments, the mutant KRAS is selected from selected from G12C; G12A; G12D; G12R; G12S; G12V; G13C; and G13D mutants. In some embodiments, evaluating is conducted by amplifying LKB1 and/or KRAS nucleic acid from the tumor sample, or a fragment thereof suspected of containing a mutation, and sequencing said amplified nucleic acid. In some embodiments, evaluating is conducted by contacting an antibody or format thereof directed to LKB1 and/or KRAS with the tumor sample and quantifying antibody or format thereof binding.

In one aspect, the disclosure provides a method of treating a lung cancer in a patient in need thereof, comprising administering an agent which binds to CDCP1 to the patient, wherein the lung cancer is characterized by AKT activation and the agent which binds to CDCP1 is a CDCP1 activating agent. In some embodiments, the lung cancer is NSCLC. In some embodiments, the method further comprises evaluating a sample of the lung cancer for AKT activation.

In one aspect, the disclosure provides a method of treating a prostate cancer in a patient in need thereof, comprising administering an agent which binds to CDCP1 to the patient, wherein the prostate cancer is characterized by AKT activation and the agent which binds to CDCP1 is a CDCP1 activating agent. In some embodiments, the method further comprises evaluating a sample of the prostate cancer for AKT activation. In some embodiments, the method further comprises administering a AKT inhibitor. In some embodiments, the patient is undergoing treatment with an AKT inhibitor. In some embodiments, the AKT inhibitor is selected from Afuresertib, ARQ 751, ARQ 092, AZD5363, BAY1125976, GSK2141795, GSK690693, Ipatasertib, LY2780301, MK2206, and Perifosine.

In some embodiments, the patient is not undergoing treatment with a Src inhibitor, optionally selected from KX2-391, bosutinib, saracatinib, and dasatinib. In some embodiments, the patient has not previously undergone treatment with a Src inhibitor, optionally selected from KX2-391, bosutinib, saracatinib, and dasatinib.

In one aspect, the disclosure provides a method for treating cancer in a patient in need thereof comprising: (a) selecting an agent which binds to CDCP1 on a target cell and is internalized when it contacts CDCP1 on the target cell; and (b) administering the agent to the cancer patient, wherein the agent which binds to CDCP1 is an antibody which activates CDCP1 and is conjugated to a PPP4R2 modulating agent. In some embodiments, CDCP1 activating antibodies include, but are not limited to, CP13E10 and its variants including CP13E10-54HC-89LCv1-183/290 and CP13E10-291, CUB1, antibody 23 and antibody 76.

In one aspect, the disclosure provides a method for treating cancer in a patient in need thereof comprising: (a) administering an agent which binds to CDCP1, wherein the agent which binds to CDCP1 is an antibody which does not activate CDCP1; and (b) administering an agent which modulates PARG. In some embodiments, non-activating CDCP1 antibodies include, but are not limited to, antibody 24.

In one aspect, the disclosure provides a method of determining whether a tumor will respond to treatment with an agent which binds to CDCP1, comprising determining in a sample of said tumor the presence, absence, or amount of mutant LKB1 and/or KRAS protein or gene, whereby the presence of mutant LKB1 and/or KRAS or an increased amount of mutant LKB1 and/or KRAS protein or gene relative to a reference sample is indicative of a likelihood of responding to treatment with an agent which binds to CDCP1.

In some embodiments, the agent which binds to CDCP1 is an antibody or antigen-binding portion thereof that is specific for CDCP1.

In some embodiments, the disclosure provides a method for treating cancer in a patient in which an agent is selected for an ability to bind to CDCP1 on a target cell and an ability to be internalized when it contacts CDCP1 on the target cell and administering the agent to the cancer patient. In some embodiments, the internalization is mediated by phosphorylation of CDCP1 by, for instance, Src, e.g., at tyrosine 734 of CDCP1.

In various embodiments the present invention relates to a method for treating cancer in a patient with a combination therapy of a checkpoint inhibitor and an agent selected for an ability to bind to CDCP1 on a target cell, e.g., Tyr-734 phosphorylated CDCP1, and be internalized when it contacts CDCP1 on the target cell. In various embodiments, the agent selected for an ability to bind to CDCP1, e.g., Tyr-734 phosphorylated CDCP1, on a target cell and be internalized when it contacts CDCP1 on the target cell potentiates the immune system for response to the checkpoint inhibitor. In various embodiments, the agent selected for an ability to bind to CDCP1, e.g., Tyr-734 phosphorylated CDCP1, on a target cell and be internalized when it contacts CDCP1 on the target cell improves patient response to the checkpoint inhibitor (e.g., without limitation, by increasing a therapeutic effect of the checkpoint inhibitor, reducing a side effect of the checkpoint inhibitor, and/or converting a non-responder or poor responder to a responder to the checkpoint inhibitor).

CUB Domain-Containing Protein 1 (CDCPJ)

CDCP1 has a large extracellular domain (665 amino acids in size) that contains three CUB domains in the extracellular part that mediate protein-protein interactions and are recognized to be involved in cell adhesion and interaction with the extracellular matrix. CDCP1 gene has been found as a gene strongly expressed in cancer, for example, lung cancer and head and neck cancer.

Transmembrane protein CDCP1 associates with Src and PKCδ and all three proteins display increases in tyrosine phosphorylation when CDCP1 is activated. Src phosphorylates and binds to CDCP1, followed by the binding of CDCP1 to the C2 domain which is part of the regulatory domain of PKCδ. Tyr-734 was identified as the site that is phosphorylated by Src and Src Family Kinases, and as such, P-Tyr-734 is a biomarker of CDCP1 activation. The full length CDCP1 protein is 135 kDa, but in some cells the extracellular domain is proteolytically cleaved to a ~75 kDa transmembrane protein. CDCP1 antibody or antibody-drug conjugate was developed to knock down CDCP1 or otherwise target tumor cells expressing CDCP1. In some embodiments, the antibody or ADC must internalize to be an effective drug. CDCP1 was validated as a therapeutic target for cancer, and new signaling pathways that were affected by the activation of CDCP1 by target antibodies binding to its extracellular domain were also discovered.

In some aspects, the CDCP1 is human CDCP1. In some aspects, the CDCP1 is cynomologus monkey (cyno) CDCP1. In some aspects, the CDCP1 is mouse CDCP1. In some aspects, the CDCP1 is primate CDCP1. An exemplary CDCP1 sequence is provided in Table 10.

CDCP1 Antibodies

The term antibody herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989 Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al., Science 242:423-426 (1988) and Huston et al., 1988, Proc. Natl. Acad. Sci. USA 85:5879-5883. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al., 1993, Proc. Natl. Acad. Sci. USA 90:6444-6448; Poljak et al., 1994, Structure 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three complementarity determining regions (CDRs), and contribute to the formation of the antigen-binding site of antibodies.

"Complementarity Determining Regions" (CDRs) can be identified according to the definitions of the Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). The identity of the amino acid residues in a particular antibody that make up a CDR can be determined using methods well known in the art. AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, J. Biol. Chem., 283: 1156-1166). North has identified canonical CDR conformations using a different preferred set of CDR definitions (North et al., 2011, J. Mol. Biol. 406: 228-256). In another approach, referred to herein as the "conformational definition" of CDRs, the positions of the CDRs may be identified as the residues that make enthalpic contributions to antigen binding (Makabe et al., 2008, J Biol. Chem. 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

Residues in a variable domain are numbered according Kabat, which is a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, MD. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the version 2.3.3 release of Abysis (www.abysis.org) is used herein to assign Kabat numbering to variable regions CDRL1, CDRL2, CDRL3, CDRH1, CDRH2, and CDRH3.

Specific amino acid residue positions in an antibody may also be numbered according to Kabat.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

An "epitope" refers to the area or region of an antigen to which an antibody specifically binds, e.g., an area or region comprising residues that interacts with the antibody. Epitopes can be linear or conformational.

The term "paratope" is derived from the above definition of "epitope" by reversing the perspective, and refers to the area or region of an antibody molecule which is involved in binding of an antigen, e.g., an area or region comprising residues that interacts with the antigen. A paratope may be linear or conformational (such as discontinuous residues in CDRs).

The epitope/paratope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen/deuterium exchange Mass Spectrometry (HX-MS) and various competition binding methods.

At its most detailed level, the epitope/paratope for the interaction between an antibody (Ab) and antigen (Ag) can be defined by the spatial coordinates defining the atomic contacts present in the Ag-Ab interaction, as well as information about their relative contributions to the binding thermodynamics. At one level, an epitope/paratope residue can be characterized by the spatial coordinates defining the atomic contacts between the Ag and Ab. In one aspect, the epitope/paratope residue can be defined by a specific criterion, e.g., distance between atoms in the Ab and the Ag (e.g., a distance of equal to or less than about 4 Å from a heavy atom of the cognate antibody and a heavy atom of the antigen). In another aspect, an epitope/paratope residue can be characterized as participating in a hydrogen bond interaction with the cognate antibody/antigen, or with a water molecule that is also hydrogen bonded to the cognate antibody/antigen (water-mediated hydrogen bonding). In another aspect, an epitope/paratope residue can be characterized as forming a salt bridge with a residue of the cognate antibody/antigen. In yet another aspect, an epitope/paratope residue can be characterized as a residue having a non-zero change in buried surface area (BSA) due to interaction with the cognate antibody/antigen. At a less detailed level, epitope/paratope can be characterized through function, e.g., by competition binding with other Abs. The epitope/paratope can also be defined more generically as comprising amino acid residues for which substitution by another amino acid will alter the characteristics of the interaction between the Ab and Ag (e.g., alanine scanning).

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CDCP1 epitope is an antibody that binds this epitope with greater affinity, avidity, more readily, and/or with greater duration than it binds to other CDCP1 epitopes or non-CDCP1 epitopes. It is also understood by reading this definition that, for example, an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody which recognizes and binds to its cognate antigen in a sample, but does not substantially recognize or bind other molecules in the sample, specifically binds to that cognate antigen. Thus, under designated assay conditions, the specified binding moiety (e.g., an antibody or an antigen-binding portion thereof) binds preferentially to a particular target molecule and does not bind in a significant amount to other components present in a test sample.

A variety of assays may be used to select an antibody or peptide that specifically binds a molecule of interest. For example, solid-phase ELISA immunoassay, immunoprecipitation, BIAcore™ (GE Healthcare, Piscataway, NJ), fluorescence-activated cell sorting (FACS), Octet™ (FortéBio, Inc., Menlo Park, CA) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant ($K_D$) value is ≤1 µM, such as ≤100 nM, ≤10 nM, ≤100 µM, ≤10 µM, or ≤1 µM.

The term "compete", as used herein with regard to an antibody, means that binding of a first antibody, or an antigen-binding portion thereof, to an antigen reduces the subsequent binding of the same antigen by a second antibody or an antigen-binding portion thereof. In general, the binding a first antibody creates steric hindrance, conformational change, or binding to a common epitope (or portion thereof), such that the binding of the second antibody to the same antigen is reduced. Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to CDCP1. For example, a sequential binding competition assay may be used, with different antibodies being added sequentially. The first antibody may be added to reach binding that is close to saturation. Then, the second antibody is added. If the binding of second antibody to ROBO2 is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other.

"Antigen-binding portion" comprise a portion of a full length antibody, generally the antigen binding or variable region thereof. Examples of antigen-binding portions include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments. In some embodiments, the antibody or antigen-binding portion thereof is selected from a monoclonal antibody, polyclonal antibody, antibody fragment, Fab, Fab', Fab'-SH, F(ab')2, Fv, single chain Fv, diabody, linear antibody, bispecific antibody, multispecific antibody, chimeric antibody, humanized antibody, human antibody, and fusion protein comprising the antigen-binding portion of an antibody.

The term monoclonal antibody as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature 256:495, or may be made by recombinant DNA methods.

Fv is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The light chains of antibodies from any vertebrate species can be assigned to one of two clearly distinct types, called kappa (κ) and lambda (λ), based on the amino acid sequences of their constant domains.

Single-chain Fv or scFv mean single chain variable region antibody fragments which comprise the VH and VL domains of antibody, wherein these domains are present in a single polypeptide chain. The Fv polypeptide may further comprise a polypeptide linker between the VH and VL domains which enables the scFv to form the desired structure for antigen binding.

The term diabodies refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites.

Humanized forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence.

An isolated antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The antibody may be purified (1) to greater than 95% by weight of antibody as determined by the Lowry method, or more than 99% by weight, (2) to a degree sufficient to obtain at least 15 residues of N-terminal or internal amino acid sequence by use of a spinning cup protein sequencer, or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

In some aspects, the invention provides antibodies, and antigen-binding fragments thereof, that specifically bind CDCP1. Sequences of exemplary antibodies are shown in Table 10. As shown in the Examples (see, for example, Examples 11 and 19), in some embodiments, the antibody of the invention internalizes upon binding to CDCP1 on mammalian cells.

In some embodiments, the isolated antibody, or antigen-binding fragment thereof, that specifically binds CDCP1 comprises: (i) a VH that comprises: (a) a CDRH1 comprising the amino acid sequence of SEQ ID NO: 2, (b) a CDRH2 comprising the amino acid sequence of SEQ ID NO: 3, and (c) a CDRH3 comprising an amino acid sequence selected from the group consisting of SEQ ID NO: 4, SEQ ID NO: 27, SEQ ID NO: 40 and SEQ ID NO: 45, and (ii) a VL that comprises: (a) a CDRL1) comprising the amino acid sequence of SEQ ID NO: 12, (b) a CDRL2 comprising the amino acid sequence of SEQ ID NO: 13, and (c) a CDRL3 comprising an amino acid sequence selected from the group consisting of SEQ ID NO:14 and SEQ ID NO:31.

In some embodiments, the isolated antibody, or antigen-binding fragment thereof, that specifically bindsCDCP1, comprises: (i) a VH that comprises: (a) a CDRH1 comprising the amino acid sequence of SEQ ID NO:2, (b) a CDRH2 comprising the amino acid sequence of SEQ ID NO:3; and (c) a CDRH3 comprising the amino acid sequence of SEQ ID NO:27; and (ii) a VL that comprises: (a) a CDRL1 comprising the amino acid sequence of SEQ ID NO: 12, (b) a CDRL2 comprising the amino acid sequence of SEQ ID NO:13; and (c) a CDRL3 comprising the amino acid sequence of SEQ ID NO:31.

In some embodiments, the isolated antibody, or antigen-binding fragment thereof, that specifically binds CDCP1, comprises: (i) a VH that comprises: (a) a CDRH1 comprising the amino acid sequence of SEQ ID NO:2, (b) a CDRH2 comprising the amino acid sequence of SEQ ID NO:3; and (c) a CDRH3 comprising the amino acid sequence of SEQ ID NO: 40; and (ii) a VL that comprises: (a) a CDRL1 comprising the amino acid sequence of SEQ ID NO:12, (b) a CDRL2 comprising the amino acid sequence of SEQ ID NO:13; and (c) a CDRL3 comprising the amino acid sequence of SEQ ID NO:31.

In some embodiments, the isolated antibody, or antigen-binding fragment thereof, that specifically binds CDCP1 comprises: (i) a VH that comprises: (a) a CDRH1 comprising the amino acid sequence of SEQ ID NO:2, (b) a CDRH2 comprising the amino acid sequence of SEQ ID NO:3; and (c) a CDRH3 comprising the amino acid sequence of SEQ ID NO: 45; and (ii) a VL that comprises: (a) a CDRL1 comprising the amino acid sequence of SEQ ID NO:12, (b) a CDRL2 comprising the amino acid sequence of SEQ ID NO:13; and (c) a CDRL3 comprising the amino acid sequence of SEQ ID NO:14.

The antibody, or antigen-binding fragment thereof, may comprise a VH framework comprising a human germline VH framework sequence. The VH framework sequence can be derived from a human a VH1 germline, VH3 germline, a VH5 germline, or a VH4 germline. For example, VH frameworks from the following germlines may be used: IGHV1-46, IGHV3-23, IGHV3-7, or IGHV1-69 (germline names are based on IMGT germline definition). In some embodiments, the VH framework is entirely IGHV1-46*01 (DP-7) with the exclusion of CDRH3.

Preferred human germline light chain frameworks are frameworks derived from Vκ or Vλ germlines. For example, VL frameworks from the following germlines may be used: IGKV3D-7, IGKV1-39 or IGKV3-20 (germline names are based on IMGT germline definition). In some embodiments, the VL framework is IGKV3D-7*01 (DPK23). Alternatively or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

In some embodiments, the isolated antibody, or antigen-binding fragment thereof, comprises a VH that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 1, SEQ ID NO: 26, SEQ ID NO: 39 or SEQ ID NO: 44.

In some embodiments, the isolated antibody, or antigen-binding fragment thereof comprises a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 11, SEQ ID NO: 30, SEQ ID NO: 36 or SEQ ID NO: 11.

In some embodiments, the isolated antibody, or antigen-binding fragment thereof, comprises a VH that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 26, and a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 30 or SEQ ID NO: 36.

In some embodiments, the isolated antibody, or antigen-binding fragment thereof, comprises a VH that comprises the amino acid sequence of SEQ ID NO: 26 and a VL that comprises the amino acid sequence of SEQ ID NO: 36.

In some embodiments, the isolated antibody, or antigen-binding fragment thereof, comprises a VH that comprises the amino acid sequence of SEQ ID NO: 26 and a VL that comprises the amino acid sequence of SEQ ID NO: 30.

In some embodiments, the isolated antibody, or antigen-binding fragment thereof, comprises a VH that comprises the amino acid sequence of SEQ ID NO: 39 and a VL that comprises the amino acid sequence of SEQ ID NO: 36.

In some embodiments, the isolated antibody, or antigen-binding fragment thereof, comprises a VH that comprises the amino acid sequence of SEQ ID NO: 44 and a VL that comprises the amino acid sequence of SEQ ID NO: 11.

In some embodiments, the isolated antibody, or antigen-binding fragment thereof, comprises a VH that comprises the amino acid sequence of SEQ ID NO: 1 and a VL that comprises the amino acid sequence of SEQ ID NO: 11.

Any combination of these VH and VL sequences is also encompassed by the invention.

In certain embodiments, the antibody, or antigen-binding fragment thereof, described herein comprises an Fc domain. The Fc domain can be derived from IgA (e.g., IgA$_1$ or IgA$_2$), IgG, IgE, or IgG (e.g., IgG$_1$, IgG$_2$, IgG$_3$, or IgG$_4$). In some embodiments, the Fc domain comprises wild type sequence of an Fc domain. In some embodiments, the Fc domain comprises one or more mutations resulting in altered biological activity. For example, mutations may be introduced into the Fc domain to increase the homogeneity during the production of the recombinant protein. In some embodiments, the Fc domain is the Fc domain of human IgG1. In some embodiments, the lysine located in the C-terminal position of the Fc domain is deleted to increase the homogeneity during the production of the recombinant protein. In some embodiments, the lysine located in the C-terminal position of the Fc domain is present.

In some embodiments, the isolated antibody, or antigen-binding fragment thereof, comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 10, 29, 41 or 46.

In some embodiments, the isolated antibody, or antigen-binding fragment thereof, comprises a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 17, 32, or 37.

In some embodiments, the isolated antibody, or antigen-binding fragment thereof, comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 29 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 32 or SEQ ID NO: 37.

In some embodiments, the isolated antibody, or antigen-binding fragment thereof, comprises a heavy chain that comprises the amino acid sequence of SEQ ID NO: 29 and a light chain that comprises the amino acid sequence of SEQ ID NO: 37 (referred to herein as antibody "CP13E10-54HC-89LCv1").

In some embodiments, the isolated antibody, or antigen-binding fragment thereof, comprises a heavy chain that comprises the amino acid sequence of SEQ ID NO: 29 and a light chain that comprises the amino acid sequence of SEQ ID NO: 32 (referred to herein as antibody "CP13E10-54HC-89LC").

In some embodiments, the isolated antibody, or antigen-binding fragment thereof, comprises a heavy chain that comprises the amino acid sequence of SEQ ID NO: 41 and a light chain that comprises the amino acid sequence of SEQ ID NO: 37 (referred to herein as antibody "CP13E10-54HCv13-89LCv1").

In some embodiments, the isolated antibody, or antigen-binding fragment thereof, comprises a heavy chain that comprises the amino acid sequence of SEQ ID NO: 46 and a light chain that comprises the amino acid sequence of SEQ ID NO: 17 (referred to herein as antibody "CP13E10-291").

In some embodiments, the isolated antibody, or antigen-binding fragment thereof, comprises a heavy chain that comprises the amino acid sequence of SEQ ID NO: 10 and a light chain that comprises the amino acid sequence of SEQ ID NO: 17 (referred to herein as antibody "CP13E10").

Crystal structure studies have shown that CDCP1 adopts a crescent shape, and the CDCP1 antibody CP13E10-54HC-89LC antibody is positioned on the inside of the crescent. Six CDCP1 residues interact with the antibody near the center of the interface. Accordingly, in some embodiments, the isolated antibody, or antigen-binding fragment thereof, binds an epitope on CDCP1, wherein the epitope comprises at least one amino acid residue selected from the group consisting of Thr124, Thr160, Ser162, Ala195, Leu196, and His197, according to the numbering of SEQ ID NO: 90.

In some embodiments, the epitope further comprises at least one amino acid residue selected from the group consisting of: Lys45, Leu46, Gly47, Thr48, Pro49, Thr50, Ala53, Pro55, Glu92, Arg173, and Glu242, according to the numbering of SEQ ID NO: 90. In some embodiments, the epitope further comprises at least one amino acid residue selected from the group consisting of: Thr56, Tyr57, Thr66, Met67, Ile126, Val171, Arg173, according to the numbering of SEQ ID NO: 90.

In some embodiments, the epitope further comprises a glycan attached to Asn122, according to the numbering of SEQ ID NO: 90.

Also provided by the invention is an antibody, or antigen-binding fragment thereof, that competes for binding to CDCP1 with any of the antibody, or antigen-binding fragment thereof, described herein, such as any one of the antibodies provided herein (or antigen-binding fragments thereof). For example, if the binding of an antibody, or an antigen-binding portion thereof, to CDCP1 hinders the subsequent binding to CDCP1 by CP13E10-54HC-89LCv1, the antibody or an antigen-binding portion thereof competes with CP13E10-54HC-89LCv1 for CDCP1 binding.

Also provided by the invention is an antibody, or antigen-binding fragment thereof, that binds to the same CDCP1 epitope as any of the antibody, or antigen-binding fragment thereof, described herein, such as any one of the antibodies provided herein or antigen-binding fragment thereof. For example, antibody competition assay (and overlapping epitope analysis) can be assessed by surface plasmon resonance (SPR) or bio-layer interferometry (BLI), as described in detail herein.

The antibodies and antigen-binding fragments provided by the invention include monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion, domain antibodies (dAbs), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a human antibody. In certain embodiments, the antibody is a humanized antibody.

The binding affinity of an antibody can be expressed as an equilibrium dissociation constant ($K_D$) value, which refers to the dissociation rate of a particular antigen-antibody interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ (dissociation/association) and is expressed as a molar concentration (M), and the smaller the $K_D$, the stronger the affinity of binding. $K_D$ values for antibodies can be determined using methods well established in the art. Unless otherwise specified, "binding affinity" refers to monovalent interactions (intrinsic activity; e.g., binding of an antibody to an antigen through a monovalent interaction).

In certain embodiments, the antibody, or antigen-binding fragment thereof, of the invention has an affinity ($K_D$) value of or less than about 350 nM, about 325 nM, about 323.10 nM, about 300 nM, about 286.44 nM, about 275 nM, about 250 nM, about 232.13 nM, about 225 nM, about 219.13 nM, about 200 nM, about 195.54 nM, about 175 nM, about 158 nM, about 150 nM, about 125 nM, or about 100 nM.

In some embodiments, the antibody, or antigen-binding fragment thereof, binds CDCP1 with a $K_D$ value of or less than about 95 nM, about 90 nM, about 80 nM, about 79.89 nM, about 75 nM, about 70 nM, about 69.50 nM, about 65 nM, about 63.44 nM, about 60 nM, about 55 nM, about 52.88 nM, about 50 nM, about 45 nM, about 44.50 nM, about 41.99 nM, about 40 nM, about 35 nM, about 30 nM, about 25 nM, about 20 nM, about 10 nM, about 5 nM, or about 1 nM.

In some embodiments, the antibody, or antigen-binding fragment thereof, binds CDCP1 with a $K_D$ value of or less than about 5 nM, about 4.5 nM, about 4 nM, about 3.5 nM, about 3.12 nM, about 3 nM, about 2.90 nM, about 2.5 nM, about 2 nM, about 1.5 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

The value of $K_D$ can be determined directly by well-known methods, and can be computed even for complex mixtures by methods such as those, for example, set forth in Caceci et al., (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein.

One exemplary method for measuring binding affinity ($K_D$) value is surface plasmon resonance (SPR), typically using a biosensor system such as a BIACORE® system. SPR refers to an optical phenomenon that allows for the analysis of real-time biospecific interactions by detection of alterations in protein concentrations within a biosensor matrix, for example using the BIACORE® system. BIAcore kinetic analysis comprises analyzing the binding and dissociation of an antigen from a chip with an immobilized molecule (e.g., a molecule comprising an antigen-binding domain), on their surface; or the dissociation of an antibody, or antigen-binding fragment thereof, from a chip with an immobilized antigen.

In certain embodiments, the SPR measurement is conducted using a BIACORE® T100 or T200 instrument. For example, a standard assay condition for surface plasmon resonance can be based on antibody immobilization of approximately 100-500 Response Units (RU) of IgG on the SPR chip. Purified target proteins are diluted in buffer to a range of final concentrations and injected at a requisite flow rate (e.g., 10-100 µl/min) to allow the calculation of Ka. Dissociation is allowed to proceed to establish off-rate, followed by 3 M MgCl$_2$ (or 20 mM NaOH) for regeneration of the chip surface. Sensorgrams are then analyzed using a kinetics evaluation software package. In an exemplary embodiment, the SPR assay is according to the conditions as set forth in the Examples.

In certain embodiments, the binding affinity ($K_D$) value is measured using solution-based kinetic exclusion assay (KinExA™). In a particular embodiment, the KinExA measurement is conducted using a KinExA™ 3200 instrument (Sapidyne). The Kinetic Exclusion Assay (KinExA™) is a general purpose immunoassay platform (basically a flow spectrofluorimeter) that is capable of measuring equilibrium dissociation constants, and association and dissociation rate constants for antigen/antibody interactions. Since KinExA™ is performed after equilibrium has been obtained it is an advantageous technique to use for measuring the $K_D$ of high affinity interactions where the off-rate of the interaction may be very slow. The KinExA™ methodology can be conducted generally as described in Drake et al., (2004) Analytical Biochem. 328, 35-43.

Another method for determining the $K_D$ of an antibody is by using Bio-Layer Interferometry (BLI), typically using OCTET® technology (e.g., Octet QKe system) from ForteBio. In certain embodiments, the BLI measurement is conducted according to the following: sensor tips coated with a proprietary anti-human antibody (ForteBio) undergo BLI signal stabilization by dipping in running buffer (such as 10 mM Hepes Buffered Saline (HBS) containing 0.05% tween-20) for 120 s. The antibody is then captured by dipping the sensors into a running buffer solution (buffer may contain 1-10 ug/mL of the antibody) for 300 s. The signal is then stabilized by dipping the sensor tips back into running buffer for 120 s. The tips are then transferred into solution containing the cognate antigen. The binding of antibody-antigen is measured over 180 s prior to the sensor tips being transferred to running buffer in order to monitor receptor dissociation over 180 s. In case of CDCP1, typically a 7-point dose response of the antigen (may range from 1-2 nM in doubling dilutions) is measured. Additionally, sensor tips with no antibody captured are exposed to the antigen in order to monitor non-specific binding of the receptors to the sensor tips. A $2^{nd}$ reference type also includes a tip with antibody captured upon on it but with subsequent exposure to running buffer only with no antigen. This allows for double-referencing to eliminate both non-specific binding as well as system noise and the underlying baseline drift attributed to the antibody dissociating from the anti-human Fc sensor tip. The raw under goes double reference subtraction and is then fit to a 1:1 Langmuir type binding model to determine affinity and kinetic parameters.

In some embodiments, the CDCP1 is a human CDCP1, cyno CDCP1 or mouse CDCP1. In general, an anti-CDCP1 antibody should bind to CDCP1 with high affinity. It is desirable that the anti-CDCP1 antibody have binding affinities ($K_D$) to human CDCP1 in low nanomolar range, such as about 40 nM or lower. In some embodiments, the CDCP1 is a human CDCP1 and the $K_D$ value is about 40 nM, about 45 nM or about 50 nM. In some embodiments, the CDCP1 is a cyno CDCP1 and the $K_D$ value is about 62 nM, about 64 nM, about 66 nm, about 68 nM, or about 70 nM.

Antibody-Drug Conjugates

Antibody-drug conjugates or ADCs are an important class of highly potent biopharmaceutical drugs designed as a targeted therapy for the treatment of people with cancer. Unlike chemotherapy, ADCs are intended to target and kill only the cancer cells and spare healthy cells. ADCs are complex molecules composed of an antibody linked to a biologically active cytotoxic (anticancer) payload or drug. "Antibody-drug conjugate" as used herein, refer to an antibody, or a portion of an antibody, covalently linked to a cytotoxic or cytostatic drug/agent where the drug/agent is also referred to herein as a "payload".

The term prodrug refers to a precursor or derivative form of a pharmaceutically active substance that is less cytotoxic to tumor cells compared to the parent drug and is capable of being enzymatically activated or converted into the more active parent form. The prodrugs of this disclosure include, but are not limited to, phosphate-containing prodrugs, thiophosphate-containing prodrugs, sulfate-containing prodrugs, peptide-containing prodrugs, D-amino acid-modified pro drugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this disclosure include, but are not limited to, those chemotherapeutic agents.

The antibody and the drug may be directly linked or they may be linked via a moiety referred to as a linker. Linker or link refers to a chemical moiety comprising a covalent bond or a chain of atoms that covalently attaches an antibody to a drug moiety. In various embodiments, a linker is specified as L. Linkers include a divalent radical such as an alkylene, an arylene, a heteroarylene, moieties such as: —(CR2) nO(CR2)n—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

Anti-CDCP1 Antibodies and Conjugation Sites

In some aspects, the present invention provides a conjugate (or immunoconjugate) of the CDCP1 antibody as described herein, or of the antigen binding fragment thereof, wherein the antibody or the antigen binding fragment is conjugated to a drug (also referred to herein as payload) for targeted immunotherapy (e.g., antibody-drug conjugates also referred to as ADCs) either directly or indirectly via a linker. For example, a drug (e.g., a cytotoxic agent, which encompasses anti-tumor agents, among others) can be linked or conjugated to the CDCP1 antibody or the antigen binding fragment thereof as described herein for targeted local delivery of the drug moiety to a cell expressing CDCP1 on the cell surface (e.g., CDCP1 expressing tumors).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in international applications WO2012/059882 and WO2015/015448, each of which is incorporated herein by reference in its entirety.

In some aspects, CDCP1 ADCs may be generated using site-specific conjugation of linker-payload moieties though one or more reactive cysteine residues engineered into an anti-CDCP1 antibody constant domain (see, for example, WO2013/093809, US2014/0127211, US 2017/0216452 and WO 2017/093844, each of which is incorporated herein by reference in its entirety). One or more amino acid residues of an anti-CDCP1 antibody heavy chain may be substituted to another amino acid, such as a cysteine residue, for the purpose of conjugation to a drug or payload. In one aspect, the invention provides an anti-CDCP1 antibody, or antigen binding fragment thereof, comprising an antibody heavy chain constant region comprising an engineered cysteine residue at position: 118 (114 according to Kabat), 246, 249, 265, 267, 270, 276, 278, 283, 290, 292, 293, 294, 300, 302, 303, 314, 315, 318, 320, 327, 332, 333, 334, 336, 345, 347, 354, 355, 358, 360, 362, 370, 373, 375, 376, 378, 380, 382, 386, 388, 390, 392, 393, 401, 404, 411, 413, 414, 416, 418, 419, 421, 428, 431, 432, 437, 438, 439, 443 or 444, or any combination thereof, according to the numbering of the Eu index of Kabat). In particular, positions 118 (114 according to Kabat), 290, 334, 347, 373, 375, 380, 388, 392, 421, 443, or any combination thereof may be used. Additional cysteine substitutions may be introduced.

In another aspect, the invention provides an anti-CDCP1 antibody, or antigen binding fragment thereof, comprising a heavy chain constant domain comprising an engineered cysteine residue at position 290 (K290C), according to the numbering of the Eu index of Kabat.

One or more amino acid residues of an anti-CDCP1 antibody light chain constant domain may be substituted to another amino acid, such as a cysteine residue, for the purpose of conjugation to a drug or payload (see, for example, WO2013/093809, US2014/0127211, US 2017/0216452 and WO 2017/093844, each of which is incorporated herein by reference in its entirety). In one aspect, the invention provides an anti-CDCP1 antibody, or antigen binding fragment thereof, comprising an antibody light chain constant region comprising an engineered cysteine residue at position 110, 111, 125, 149, 155, 158, 161, 183, 185, 188, 189, 191, 197, 205, 207, 208 or 210, or any combination thereof, according to the numbering of Kabat. Additional cysteine substitutions may be introduced.

In another aspect, the invention provides an anti-CDCP1 antibody, or antigen binding fragment thereof, comprising a light chain constant domain comprising an engineered cysteine residue at position 183 (κK183C), according, to the numbering of Kabat.

In some aspects, the present invention provides for an antibody-drug conjugate comprising an antibody, or antigen binding fragment, having a heavy chain and/or light chain constant region comprising an engineered cysteine residue for site-specific conjugation. In some aspects, an antibody-drug conjugate has a heavy chain constant region comprising an engineered cysteine residue at positon 290 (K290C), according to the numbering of the Eu index of Kabat. In some aspects, an antibody-drug conjugate has a light chain constant region comprising an engineered cysteine residue at positon 183 (κK183C), according to the numbering of Kabat. In some aspects, an antibody-drug conjugate has a heavy chain constant region comprising an engineered cysteine residue at positon 290 (K290C), according to the numbering of the EU index of Kabat, and a light chain constant region comprises an engineered cysteine residue at positon 183 (κK183C), according to the numbering of Kabat.

In some embodiments, the isolated antibody, or antigen-binding fragment thereof, comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 19, 33, or 42.

In some embodiments, the isolated antibody, or antigen-binding fragment thereof, comprises a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 21, 34, or 38.

In some embodiments, the isolated antibody, or antigen-binding fragment thereof, of any one of E46-E56, comprising a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 33 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 34 or SEQ ID NO: 38.

In some embodiments, the isolated antibody, or antigen-binding fragment thereof, of any one of E46-E57, comprising a heavy chain that comprises the amino acid sequence of SEQ ID NO: 33 and a light chain that comprises the amino acid sequence of SEQ ID NO: 38.

In some embodiments, the isolated antibody, or antigen-binding fragment thereof, comprises a heavy chain that comprises the amino acid sequence of SEQ ID NO: 33 and a light chain that comprises the amino acid sequence of SEQ ID NO: 34.

In some embodiments, the isolated antibody, or antigen-binding fragment thereof, of any one of E46-E56, comprising a heavy chain that comprises the amino acid sequence of SEQ ID NO: 42 and a light chain that comprises the amino acid sequence of SEQ ID NO: 38.

In some embodiments, the isolated antibody, or antigen-binding fragment thereof, comprises a heavy chain that comprises the amino acid sequence of SEQ ID NO: 19 and a light chain that comprises the amino acid sequence of SEQ ID NO: 21.

In another aspect, CDCP1 ADCs may be generated using site-specific conjugation technology though one or more engineered acyl donor glutamine-containing tags or endogenous glutamine residues made reactive in an anti-CDCP1 antibody constant region. Methods of preparing antibodies for site-specific conjugation via acyl donor glutamine-containing tags or glutamine residues are described in PCT International Publication No. WO2012/059882 and WO2015/015448, each of which is incorporated herein by reference in its entirety.

In some aspects, the acyl donor glutamine-containing tag comprises at least one glutamine (Q) and may be attached to a specific position of the heavy and/or light chain (i.e., at the N-terminus, C-terminus or internally). In another aspect, the acyl donor glutamine-containing tag may comprise an amino acid sequence selected from: LLQG (SEQ ID NO: 91). In some aspects, an acyl donor glutamine-containing tag is inserted into at a specific position of the heavy and/or light chain (i.e., at the N-terminus, C-terminus or internally). In some aspects, an anti-CDCP1 antibody may comprise an acyl glutamine-containing tag having the amino acid sequence LLQG (SEQ ID NO: 91) that is inserted after position 135 and before position 136 according to the numbering of the Eu index of Kabat of the heavy chain.

In some embodiments, the antibody, or antigen-binding fragment thereof, comprises one or more substitutions selected from the group consisting of: N297A and K222R, according to the numbering of the Eu index of Kabat. In some embodiments, the antibody, or antigen-binding fragment thereof, comprises both substitutions, N297A and K222R, according to the numbering of the Eu index of Kabat.

In some embodiments, the isolated antibody, or antigen-binding fragment thereof, comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 25, 35, or 43.

In some embodiments, the isolated antibody, or antigen-binding fragment thereof, comprises a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NOs: 17, 32, or 37.

In some embodiments, the isolated antibody, or antigen-binding fragment thereof, comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 35 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 32 or SEQ ID NO: 37.

In some embodiments, the isolated antibody, or antigen-binding fragment thereof, comprises a heavy chain that comprises the amino acid sequence of SEQ ID NO: 35 and a light chain that comprises the amino acid sequence of SEQ ID NO: 37.

In some embodiments, the isolated antibody, or antigen-binding fragment thereof, comprises a heavy chain that comprises the amino acid sequence of SEQ ID NO: 35 and a light chain that comprises the amino acid sequence of SEQ ID NO: 32.

In some embodiments, the isolated antibody, or antigen-binding fragment thereof, comprises a heavy chain that comprises the amino acid sequence of SEQ ID NO: 43 and a light chain that comprises the amino acid sequence of SEQ ID NO: 37.

In some embodiments, the isolated antibody, or antigen-binding fragment thereof, comprises a heavy chain that comprises the amino acid sequence of SEQ ID NO: 25 and a light chain that comprises the amino acid sequence of SEQ ID NO: 17.

Nucleic Acids, Vectors and Host Cells

The invention also provides polynucleotides encoding any of the antibodies, including antibody fragments and modified antibodies described herein. The invention also provides a method of making any of the polynucleotides described herein. Polynucleotides can be made and expressed by procedures known in the art.

The sequence of a desired antibody, defined antibody fragment, or antigen-binding fragment thereof, and nucleic acid encoding such antibody, or fragment thereof, can be determined using standard sequencing techniques. A nucleic acid sequence encoding a desired antibody, defined antibody fragment, or antigen-binding fragment thereof, may be inserted into various vectors (such as cloning and expression vectors) for recombinant production and characterization. A nucleic acid encoding the heavy chain, defined antibody fragment, or an antigen-binding fragment of the heavy chain, and a nucleic acid encoding the light chain, defined antibody fragment, or an antigen-binding fragment of the light chain, can be cloned into the same vector, or different vectors.

In one aspect, the invention provides polynucleotides encoding the amino acid sequences of any of the following CDCP1 antibodies and antigen-binding fragments thereof: CP13E10, CP13E10-183/290, CP13E10-H7C-K222R-N297A, CP13E10-54HC-89LC, CP13E10-54HC-89LC-183/290, CP13E10-54HC-89LC-H7C-K222R-N297A, CP13E10-54HC-89LCv1, CP13E10-54HC-89LCv1-183/290, CP13E10-54HC-89LCv1-H7C-K222R-N297A, CP13E10-54HCv13-89LCv1, CP13E10-54HCv13-89LCv1-183/290, CP13E10-54HCv13-89LCv1-H7C-K222R-N297A, CP13E10-291, antibody 23, antibody 24 and antibody 76. The polynucleotide encoding the amino acid sequences above, encodes an amino acid sequence at least 91%, 92%, 93%, 94%, 95%, 96%, 97%, 98%, or 99%, and more preferably identical to, the amino acid sequence of the antibodies, or antigen-binding fragment thereof, of the present invention as disclosed herein.

The invention provides polynucleotides encoding the amino acid sequences an antibody, or antigen-binding fragment thereof, that binds substantial the same epitope as an antibody selected from the group consisting of: CP13E10, CP13E10-183/290, CP13E10-H7C-K222R-N297A, CP13E10-54HC-89LC, CP13E10-54HC-89LC-183/290, CP13E10-54HC-89LC-H7C-K222R-N297A, CP13E10-54HC-89LCv1, CP13E10-54HC-89LCv1-183/290, CP13E10-54HC-89LCv1-H7C-K222R-N297A, CP13E10-54HCv13-89LCv1, CP13E10-54HCv13-89LCv1-183/290, CP13E10-54HCv13-89LCv1-H7C-K222R-N297A, CP13E10-291, antibody 23, antibody 24 and antibody 76.

The invention provides polynucleotides encoding the amino acid sequences of an antibody, or antigen-binding fragment thereof, that competes for binding to CXCR5 with an antibody selected from the group consisting of: CP13E10, CP13E10-183/290, CP13E10-H7C-K222R-N297A, CP13E10-54HC-89LC, CP13E10-54HC-89LC-183/290, CP13E10-54HC-89LC-H7C-K222R-N297A, CP13E10-54HC-89LCv1, CP13E10-54HC-89LCv1-183/290, CP13E10-54HC-89LCv1-H7C-K222R-N297A, CP13E10-54HCv13-89LCv1, CP13E10-54HCv13-89LCv1-183/290, CP13E10-54HCv13-89LCv1-H7C-K222R-N297A, CP13E10-291, antibody 23, antibody 24 and antibody 76.

The invention provides polynucleotides encoding one or more proteins comprising the amino acid sequence selected from the group consisting of: SEQ ID NOs:1-74.

In some embodiments, an isolated nucleic acid comprises the nucleotide sequence of SEQ ID NO: 75. In some embodiments, an isolated nucleic acid comprises the nucleotide sequence of SEQ ID NO: 76. In some embodiments, an isolated nucleic acid comprises the nucleotide sequence of SEQ ID NO: 77. In some embodiments, an isolated nucleic acid comprises the nucleotide sequence of SEQ ID NO: 78. In some embodiments, an isolated nucleic acid comprises the nucleotide sequence of SEQ ID NO: 79. In some embodiments, an isolated nucleic acid comprises the nucleotide sequence of SEQ ID NO: 80. In some embodiments, an isolated nucleic acid comprises the nucleotide sequence of SEQ ID NO: 81. In some embodiments, an isolated nucleic acid comprises the nucleotide sequence of SEQ ID NO: 82. In some embodiments, an isolated nucleic acid comprises the nucleotide sequence of SEQ ID NO: 83. In some embodiments, an isolated nucleic acid comprises the nucleotide sequence of SEQ ID NO: 84.

The invention provides cells comprising one or more nucleic acid molecules as set forth in one or more of SEQ ID NOs: 75-84. The invention provides cells comprising one or more nucleic acid molecules as set forth in SEQ ID NOs: 85 and 86.

In another aspect, the invention provides polynucleotides and variants thereof encoding an anti-CDCP1 antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. These amounts are not meant to be limiting, and increments between the recited percentages are specifically envisioned as part of the disclosure.

The invention provides polypeptides encoded by the nucleic acid molecules described herein.

In one embodiment, the VH and VL domains, or antigen-binding fragment thereof, or full length HC or LC, are encoded by separate polynucleotides. Alternatively, both VH and VL, or antigen-binding fragment thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a portion thereof. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5× SSC, 0.5% SDS, 1.0 mM EDTA (pH 8.0); hybridizing at 50° C.-65° C., 5× SSC, overnight; followed by washing twice at 65° C. for 20 minutes with each of 2×, 0.5× and 0.2× SSC containing 0.1% SDS.

As used herein, "highly stringent conditions" or "high stringency conditions" are those that: (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5× SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2× SSC (sodium chloride/sodium citrate) and 50% formamide at 55° C., followed by a high-stringency wash consisting of 0.1× SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al., eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

Vectors

In some embodiments, a vector is selected that is optimized for expression of polypeptides in CHO or CHO-derived cells, or in NSO cells. Exemplary vectors are described, e.g., in Running Deer et al., Biotechnol. Prog. 20:880-889 (2004).

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen. Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Host Cells

The antibody, or antigen-binding fragment thereof, may be made recombinantly using a suitable host cell. A nucleic acid encoding the antibody or antigen-binding fragment thereof can be cloned into an expression vector, which can then be introduced into a host cell, such as *E. coli* cell, a yeast cell, an insect cell, a simian COS cell, a Chinese hamster ovary (CHO) cell, or a myeloma cell where the cell does not otherwise produce an immunoglobulin protein, to obtain the synthesis of an antibody in the recombinant host cell. Preferred host cells include a CHO cell, a Human embryonic kidney HEK-293 cell, or an Sp2.0 cell, among many cells well-known in the art. An antibody fragment can be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

In various embodiments, anti-CDCP1 heavy chains and/or anti-CDCP1 light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, anti-CDCP1 heavy chains and/or anti-CDCP1 light chains may be expressed in yeast. See, e.g., U.S. Publication No. US 2006/0270045 A1. In some embodiments, a particular eukaryotic host cell is selected based on its ability to make desired post-translational modifications to the anti-CDCP1 heavy chains and/or anti-CDCP1 light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

Anti-CXCR5 antibodies may be purified by any suitable method. Such methods include, but are not limited to, the use of affinity matrices or hydrophobic interaction chromatography. Suitable affinity ligands include the CDCP1 ECD and ligands that bind antibody constant regions. For example, a Protein A, Protein G, Protein A/G, or an antibody affinity column may be used to bind the constant region and to purify an anti-CXCR5 antibody. Hydrophobic interactive chromatography, for example, a butyl or phenyl column, may also suitable for purifying some polypeptides. Many methods of purifying polypeptides are known in the art. 4 In some embodiments, an anti-CDCP1 antibody is produced in a cell-free system. Non-limiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Drugs

Drugs useful in preparation of the disclosed CDCP1 ADCs include any substance having biological or detectable activity, for example, therapeutic agents, detectable labels, binding agents, etc., and prodrugs, which are metabolized to an active agent in vivo. A drug may also be a drug derivative, wherein a drug has been functionalized to enable conjugation with an antibody of the invention.

A therapeutic agent is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulating agents. A cytotoxic effect refers to the depletion, elimination and/or the killing of a target cell(s). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells. A chemotherapeutic agent refers to an agent that is a chemical compound useful in the treatment of cancer. An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious.

In accordance with the disclosed methods, the CDCP1 ADCs may be produced or generated having (a) an antibody, or antigen binding fragment thereof, that binds to CDCP1; (b) a linker and (c) a drug. The drug-to-antibody ratio (DAR) or drug loading indicates the number of drug (D) molecules that are conjugated per antibody. The number of linker-drug moieties attached to an antibody can be any number preferred for development of an ADC. In some aspects, the number of linker-drug moieties per antibody is 4. In other aspects, the number of linker-drug moieties per antibody is 3. In another aspect, the number of linker-drug moieties per antibody is 2. In another aspect, the number of linker-drug moieties per antibody is 1. In other aspects, the number of linker-drug moieties per antibody is greater than 4, such as 5, 6, 7, 8, 9, 10, 11, 12 or greater than 12 linker-drug moieties per antibody. DAR can be determined by various conventional means such as UV spectroscopy, mass spectroscopy, ELISA assay, radiometric methods, hydrophobic interaction chromatography (HIC), electrophoresis and HPLC.

Examples of cytotoxic agents include, but are not limited to an anthracycline, an auristatin, CC-1065, a dolastatin, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof. Plant toxins, other bioactive proteins, enzymes (i.e., ADEPT), radioisotopes, photosensitizers (i.e., for photodynamic therapy) may also be used.

The anthracyclines are derived from bacteria Strepomyces and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, (1998). Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB).

In some aspects, the drug/payload is an auristatin. Auristatins inhibit cell proliferation by inhibiting the formation of microtubules during mitosis through inhibition of tubulin polymerization. PCT International Publication No. WO 2013/072813, which is incorporated herein by reference in its entirety, discloses auristatins that are useful in the CDCP1 ADCs of the present invention and provides methods of producing the auristatins. Non-limiting examples of auristatins include: payload 0101 (designated as #54 in WO 2013/072813) having the structure:

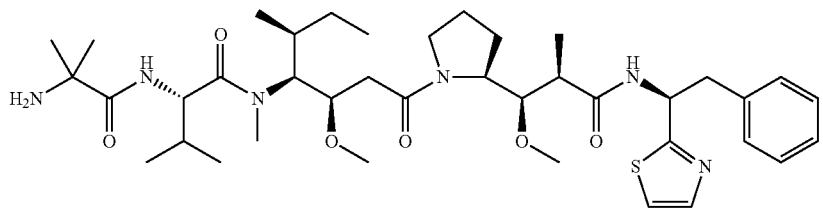 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

(2-methylalanyl-/V-[(3 4S,5S)-3-methoxy-1-{(2S)-2-[(1 2)-1-methoxy-2-methyl-3-oxo-3-{[(1 S)-2-phenyl-1-(1,3-thiazol-2-yl)ethyl]amino}propyl]pyrrolidin-1-yl}-5-methyl-1-oxoheptan-4-yl]-/V-methyl-L-valinamide), 3377 (N,2-dimethylalanyl-N-{(1 S,2R)-4-{(2S)-2-[(1R,2R)-3-{[(1 S)-1-carboxyl-2-phenylethyl]amino}-1-methoxy-2-methyl-3-oxopropyl]pyrrolidin-1-yl}-2-methoxy-1-[(1 S)-1-methylpropyl]-4-oxobutyl}-N-methyl-L-valinamide), and payload 0131 (designated as #118 in WO 2013/072813) having the structure

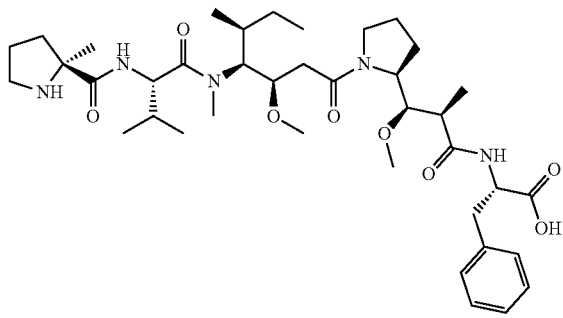 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

(2-methyl-L-proly-N-[(3R,4S,5S)-1-{(2S)-2-[(1R,2R)-3-{[(1 S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide).

Duocarmycin and CC-1065 are CPI-based monomers that act as DNA alkylating agents with cytotoxic potency. See Boger and Johnson, *PNAS* 92:3642-3649, 1995. Exemplary dolastatins include, but are not limited to, (+)-docarmycin A and (+)-duocarmycin SA, and (+)-CC-1065.

In some aspects, the drug/payload is a CPI or CBI dimer. CPI dimers induce inter-strand DNA crosslinking and potent cytotoxicity. PCT International Publication No. WO2015/110935, which is incorporated herein by reference in its entirety, discloses CPI and CBI dimers that are useful in generating the CDCP1 ADCs of the present invention and provides methods of producing the CPI and CBI dimers. A non-limiting example of CPI dimer includes: payload CPI-8314 dimer having the structure:

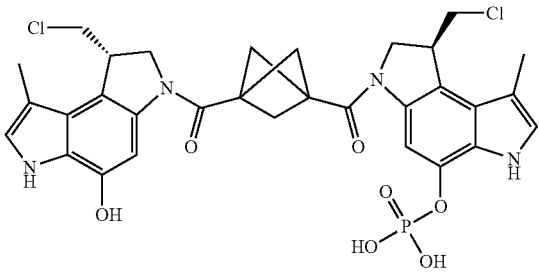 [SMILES: Cc1c[nH]c2c(O)cc3c(c12)[C@H](CCl)CN3C(=O)C12CC(C(=O)N3C[C@@H](CCl)c4c3cc(OP(=O)(O)O)c3[nH]cc(C)c43)(C1)C2]

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin. Calicheamicin, also called the LL-E33288 complex, for example, β-calicheamicin, 7-calicheamicin or N-acetyl-γ-calicheamicin (gamma-calicheamicin ($\gamma_1$)), is an enediyne antibiotic that was originally isolated as a natural product from the soil organism *Micromonospora echinospora* ssp. calichensis (Zein et al., Science 27;240(4856):1198-1201, 1988); it generates double-strand DNA breaks and subsequently induces apoptosis in target cells (Zein et al., Science 27;240(4856):1198-1201, 1988; Nicolaou et al., Chem. Biol. Sep;1(1):57-66, 1994; Prokop et al., Oncogene 22:9107-9120, 2003). The disulfide analog is N-acetyl-γ-calicheamicin dimethyl hydrazide.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., Science 189:1002-1005, 1975. Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some aspects of the invention, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, xanthines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin, or a combination thereof.

Immunomodulatory agents useful in the invention also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Representative immunosuppressive agents include 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

In some aspects of the invention, the drug is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, *Staphylococcal* enterotoxin-A, pokeweed antiviral protein, gelonin, diphtherin toxin, *Phytolaca americana* proteins (PAPI, PAPII, and PAP-S), *Momordica charantia* inhibitor, curcin, crotin, *Sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

Examples of hormones include, but are not limited to, estrogens, androgens, progestins and corticosteroids.

In some aspects of the invention, the drug is an oligonucleotide, such as anti-sense oligonucleotides.

Additional drugs useful in the invention include anti-angiogenic agents that inhibit blood vessel formation, for example, farnesyltransferase inhibitors, COX-2 inhibitors, VEGF inhibitors, bFGF inhibitors, steroid sulphatase inhibitors (e.g., 2-methoxyoestradiol bis-sulphamate (2-MeOE2bisMATE)), interleukin-24, thrombospondin, metallospondin proteins, class I interferons, interleukin 12, protamine, angiostatin, laminin, endostatin, and prolactin fragments.

Anti-proliferative agents and pro-apoptotic agents include activators of PPAR-gamma (e.g., cyclopentenone prostaglandins (cyPGs)), retinoids, triterpinoids (e.g., cycloartane, lupane, ursane, oleanane, friedelane, dammarane, cucurbitacin, and limonoid triterpenoids), inhibitors of EGF receptor (e.g., HER4), rampamycin, CALCITRIOL® (1,25-dihydroxycholecalciferol (vitamin D)), aromatase inhibitors (FEMARA® (letrozone)), telomerase inhibitors, iron chelators (e.g., 3-aminopyridine-2-carboxaldehyde thiosemicarbazone (Triapine)), apoptin (viral protein 3-VP3 from chicken aneamia virus), inhibitors of Bcl-2 and Bcl-X(L), TNF-alpha, FAS ligand, TNF-related apoptosis-inducing ligand (TRAIL/Apo2L), activators of TNF-alpha/FAS ligand/TNF-related apoptosis-inducing ligand (TRAIL/Apo2L) signaling, and inhibitors of PI3K-Akt survival pathway signaling (e.g., UCN-01 and geldanamycin).

Representative chemotherapeutic agents include alkylating agents such as thiotepa and cyclosphosphamide; alkyl sulfonates such as busulfan, improsulfan and piposulfan; aziidines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechiorethamine, mechiorethamine oxide hydrochloride, melphalan, novembichin, phenesterine, prednimustine, trofosfarnide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-EU; androgens such as calusterone, dromostanolone propionate, epitiostanol, mepitiostane, testolactone; anti-adrenal such as arninoglutethimide, mitotane, trilostane; folic acid replenisher such as frolinic acid; aceglatone; aldophospharnide glycoside; arninolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel (TAXOL®, Bristol-Myers Squibb Oncology of Princeton, N.J.) and doxetaxel (TAXOTERE®, Rhone-Poulenc Rorer of Antony, France); chiorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aininopterin; xeloda; ibandronate; CPT-11; topoisomerase inhibitor RFS 2000; difluoromethylornithine (DMFO); retinoic acid; esperamicins; and capecitabine.

Additional therapeutic agents that may be used in accordance with the present invention include photosensitizing agents, such as U.S. Publication No. 20020197262 and U.S. Pat. No. 5,952,329, which are incorporated herein by reference in its entirety, for photodynamic therapy; magnetic particles for thermotherapy, such as U.S. Publication No. 20030032995, which is incorporated herein by reference in its entirety; binding agents, such as peptides, ligands, cell adhesion ligands, etc., and prodrugs such as phosphate-containing prodrugs, thiophosphate-containing prodrugs, sulfate containing prodrugs, peptide containing prodrugs, β-lactam-containing prodrugs, substituted phenoxyacetamide-containing prodrugs or substituted phenylacetamide-containing prodrugs, 5-fluorocytosine and other 5-fluorouridine prodrugs that may be converted to the more active cytotoxic free drug.

For diagnostic methods using anti-CDCP1 antibodies, a drug may include a detectable label used to detect the presence of CDCP1-expressing tumor cells in vitro or in vivo. Radioisotopes that are detectable in vivo, such as those labels that are detectable using scintigraphy, magnetic resonance imaging, or ultrasound, may be used in clinical diagnostic applications. Useful scintigraphic labels include positron emitters and γ-emitters. Representative contrast agents for magnetic source imaging are paramagnetic or superparamagnetic ions (e.g., iron, copper, manganese, chromium, erbium, europium, dysprosium, holmium and gadolinium), iron oxide particles, and water soluble contrast agents. For ultrasonic detection, gases or liquids may be entrapped in porous inorganic particles that are released as microbubble contrast agents. For in vitro detection, useful detectable labels include fluorophores, detectable epitopes or binding agents, and radioactive labels.

Thus, in some aspects of the invention, the drug is an imaging agent (e.g., a fluorophore or a PET (Positron Emission Tomography) label, SPECT (Single-Photon Emission Computed Tomography) label), or MRI (Magnetic Resonance Imaging) label.

The term "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123, I-125, Y-90, Re-188, Re-186, At-211, Cu-67, Bi-212, and Pd-109. The label might also be a non-detectable entity such as a toxin.

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5-TAMRA), tetramethylrhodamine (TMR), and sulforhodamine (SR) (e.g., SR101).

Therapeutic or diagnostic radioisotopes or other labels (e.g., PET or SPECT labels) can be incorporated in the agent for conjugation to the anti-CDCP1 antibodies as described herein. The isotope may be directly bound to the antibody, for example, at a cysteine residue present in the antibody, or a chelator may be used to mediate the binding of the antibody and the radioisotope. Radioisotopes suitable for radiotherapy include but are not limited to α-emitters, β-emitters, and auger electrons. For diagnostic applications, useful radioisotopes include positron emitters and γ-emitters. An anti-CDCP1 antibody of the invention may further be iodinated, for example, on a tyrosine residue of the antibody, to facilitate detection or therapeutic effect of the antibody.

Examples of a radioisotope or other labels include, but are not limited to, $^{3}$H, $^{11}$C, $^{13}$N, $^{14}$C, $^{15}$N, $^{15}$O, $^{35}$S, $^{18}$F, $^{32}$P, $^{33}$P, $^{47}$Sc, $^{51}$Cr, $^{57}$Co, $^{58}$Co, $^{59}$Fe, $^{62}$Cu, $^{64}$Cu, $^{67}$Cu, $^{67}$Ga, $^{68}$Ga, $^{75}$Se, $^{76}$Br, $^{77}$Br, $^{86}$Y, $^{89}$Zr, $^{90}$Y, $^{94}$Tc, $^{95}$Ru, $^{97}$Ru, $^{99}$Tc, $^{103}$Ru, $^{105}$Rh, $^{105}$Ru, $^{107}$Hg, $^{109}$Pd, $^{111}$Ag, $^{111}$In, $^{113}$In, $^{121}$Te, $^{122}$Te, $^{123}$I, $^{124}$I, $^{125}$I, $^{125}$Te, $^{126}$I, $^{131}$I, $^{131}$In, $^{133}$I $^{142}$Pr, $^{143}$Pr, $^{153}$Pb, $^{153}$Sm, $^{161}$Tb, $^{165}$Tm, $^{166}$Dy, $^{166}$H, $^{167}$Tm, $^{168}$Tm, $^{169}$Yb, $^{177}$Lu, $^{186}$Re, $^{188}$Re, $^{189}$Re, $^{197}$Pt, $^{198}$Au, $^{199}$Au, $^{201}$Tl, $^{203}$Hg, $^{211}$At, $^{212}$Bi, $^{212}$Pb, $^{213}$Bi, $^{223}$Ra, $^{224}$Ac, and $^{225}$Ac.

Linkers

CDCP1 ADCs of the present invention may be prepared using a linker to directly or indirectly link or conjugate a drug to an antibody. A linker is a bifunctional compound that links a drug and an antibody to form an ADC. Such ADCs allow the selective delivery of drugs via antibodies that bind to specific antigens or proteins. Suitable linkers include, for example, cleavable and non-cleavable linkers. A cleavable linker is typically susceptible to cleavage and release of drug by specific intracellular and extracellular conditions. Major mechanisms by which a conjugated drug may be cleaved from an antibody intracellularly include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. A conjugated drug may be cleaved from an antibody extracellularly by proteases in a tumor microenvironment (TME), such as cathepsins. As a result of these varying mechanisms for cleavage, mechanisms of linking the drug to the antibody also vary widely and any suitable linker can be used.

Suitable linkers may include any cleavable linker. In some aspects, suitable linkers include a valine-citrulline (val-cit) linker, a phenylalanine-lysine (phe-lys) linker, a maleimidocaproyl-valine-citrulline-p-aminobenzyloxycarbonyl linker, or a 6-maleimidocaproyl-valine-citrulline-p-aminobenzylcarbamate (mc-val-cit-PABC or vc) linker, or contain a dipeptide attached to additional immolation elements, such as N~2~-acetyl-L-lysyl-L-valyl-L-citrulline-p-aminobenzyloxycarbonyl-N,N'-dimethylaminoethyl-CO-linker, suitable for transglutaminase-based conjugation technology. In another aspect, suitable linkers include disulfide linkers, such as sulfanyl pyridine (diS) linker and 2-(pyridin-2-yldisulfanyl)ethyl carbamoyl (diS-C$_2$OCO) linker. In another aspect, the linker may be a non-cleavable linker, such as maleimidocaproyl (mc), maleimido-heptanoyl (me) and maleimido-Peg6C2 (MalPeg6C2). In other aspects, suitable linkers include linkers hydrolyzable at a specific pH or a pH range, such as a hydrazone linker.

The linker may be covalently bound to the antibody through a thioester linkage, for instance by reaction of a maleimide or haloacetamide, present on the linker with a native or engineered cysteine residue present on the antibody. In another aspect, the linker may be covalently bound to the antibody through amide linkages to lysine residues present on the antibody, for instance by reaction of an N-hydroxy-succinimide activated carboxylic acid present on the linker with a free amine of a lysine residue. In another aspect, the linker may be covalently bound to the antibody through amide linkages to the side chains of glutamine residues present or engineered into the antibody, for instance by enzymatic reaction catalyzed by a transglutaminase enzyme that creates a new amide linkage from a primary amine present on the linker with a side chain amide of a glutamine residue.

In some aspects, the linker is selected from the group consisting of: valine-citrulline (val-cit), 6-maleimidocaproyl (mc), methoxy-polyethylene glycol maleimide 6 (MalPeg6), p-aminobenzylcarbamate (PABC), dimethylaminoethanol (DMAE), maleimidopropanoyl (MP), hydrolyzed Peg-maleimides, alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1carboxylate (SMCC), N-Succinimidyl (4-iodo-acetyl) aminobenzoate (SIAB), 6-maleimidocaproyl-valine-citrulline-p-aminobenzyloxycarbonyl (mc-val-cit-PAB), and 6-maleimidocaproyl-valine-citrulline-p-aminobenzylcarbamate (mc-val-cit-PABC or vc).

In some aspects, the linker is the linker is selected from the group consisting of: Ac-Lys-Gly (acetyl-lysine-glycine), aminocaproic acid, Ac-Lys-p-Ala (acetyl-lysine-p-alanine), amino-PEG2 (polyethylene glycol)-C2, amino-PEG3-C2, amino-PEG6-C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine.

In some embodiments, the linker is:
"mc-val-cit-PABC" or "vc" linker having the structure:

comprises the amino acid sequence of SEQ ID NO: 34, and wherein the linker-drug moiety is mc-val-cit-PABC-0101.

In some embodiments, the antibody drug conjugate comprises an anti-CDCP1 antibody described herein, wherein the antibody is conjugated to the linker-drug using an acyl donor glutamine-containing tag engineered at a specific site on the antibody. The linker may be selected from any of the linkers described herein. In some embodiments, the linker is selected from the group consisting of: Ac-Lys-Gly (acetyl-lysine-glycine), aminocaproic acid, Ac-Lys-p-Ala (acetyl-lysine-p-alanine), amino-PEG2 (polyethylene glycol)-C2,

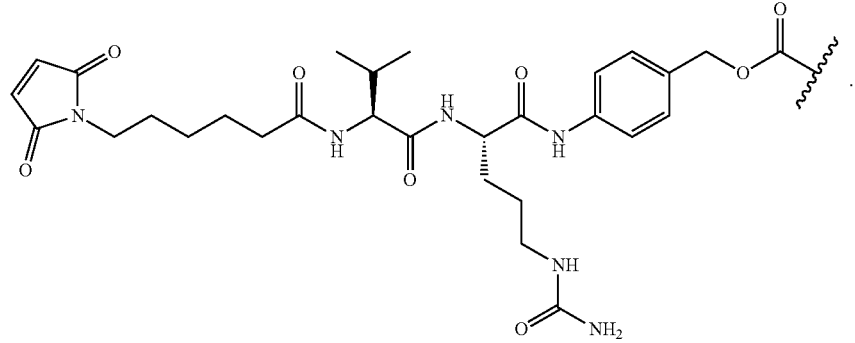 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

In some embodiments, the linker is amino-PEG6-C2 (or amino PEG6-propionyl).

In some embodiments, the antibody drug conjugate comprises an anti-CDCP1 antibody described herein, wherein the antibody is conjugated to the linker-drug moiety via one or more engineered cysteine residues on the antibody. The linker may be selected from any of the linkers described herein. In some embodiments, the linker is selected from the group consisting of: valine-citrulline (val-cit), 6-maleimidocaproyl (mc), methoxy-polyethylene glycol maleimide 6 (MalPeg6), p-aminobenzylcarbamate (PABC), dimethylaminoethanol (DMAE), maleimidopropanoyl (MP), hydrolyzed Peg-maleimides, alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1carboxylate (SMCC), N-Succinimidyl (4-iodo-acetyl) aminobenzoate (SIAB), 6-maleimidocaproyl-valine-citrulline-p-aminobenzyloxycarbonyl (mc-val-cit-PAB), and 6-maleimidocaproyl-valine-citrulline-p-aminobenzylcarbamate (mc-val-cit-PABC or vc). In some embodiments, the linker is mc-val-cit-PABC. In some embodiments, the drug moiety is an auristatin. In some embodiments, the drug moiety is 0101 or 0131.

In some aspects the present invention provides an antibody drug conjugate comprising an antibody, or antigen-binding fragment thereof, conjugated to a linker-drug moiety via one or more engineered cysteine residues on the antibody, wherein the antibody, or antigen-binding fragment thereof, comprises a heavy chain that comprises the amino acid sequence of SEQ ID NO: 33 and a light chain that comprises the amino acid sequence of SEQ ID NO: 38, and wherein the linker-drug moiety is mc-val-cit-PABC-0101.

In some aspects, the present invention provides an antibody drug conjugate comprising an antibody, or antigen-binding fragment thereof, conjugated to a linker-drug moiety via one or more engineered cysteine residues on the antibody, wherein the antibody, or antigen-binding fragment thereof, comprises a heavy chain that comprises the amino acid sequence of SEQ ID NO: 33 and a light chain that amino-PEG3-C2, amino-PEG6-C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC,
putrescine, and Ac-Lys-putrescine. In some embodiments, the linker is amino PEG6-propionyl (i.e., amino-PEG6-C2 or AMPeg6C2). In some embodiments, the drug moiety is an auristatin. In some embodiments, the drug moiety is 0101 or 0131.

In some aspects the present invention provides an antibody drug conjugate comprising an antibody, or antigen-binding fragment thereof, conjugated to a linker-drug moiety using an acyl donor glutamine-containing tag engineered at a specific site on the antibody, wherein the antibody, or antigen-binding fragment thereof, comprises a heavy chain that comprises the amino acid sequence of SEQ ID NO: 35 and a light chain that comprises the amino acid sequence of SEQ ID NO: 37, and wherein the linker-drug moiety is amino PEG6-propionyl-0131 (i.e., AmPeg6C2-0131).

In some aspects the present invention provides an antibody drug conjugate comprising an antibody, or antigen-binding fragment thereof, conjugated to a linker-drug moiety via one or more engineered cysteine residues on the antibody, wherein the antibody, or antigen-binding fragment thereof, comprises a heavy chain that comprises the amino acid sequence of SEQ ID NO: 35 and a light chain that comprises the amino acid sequence of SEQ ID NO: 32, and wherein the linker-drug moiety is amino PEG6-propionyl-0131 (i.e., AmPeg6C2-0131).

Optimal reaction conditions for the generation of ADCs may be empirically determined by a variation of reaction variables such as temperature, pH, linker-payload moiety input, and additive concentration. Conditions suitable for conjugation of other drugs may be determined by those skilled in the art without undue experimentation. Representative methods for conjugating and characterizing CDCP1 ADCs are described in Examples 17 and 18.

Following conjugation, the conjugates may be separated, purified from unconjugated reactants and/or aggregated forms of the conjugates, and characterized by conventional methods. This includes processes such as, but not limited to, mass spectrometry, size exclusion chromatography (SEC), ultrafiltration/diafiltration, ion exchange chromatography (IEC), chromatofocusing (CF), site-directed mutagenesis, fluorescence-labeling, X-ray crystallography, high performance liquid chromatography (HPLC), fast protein liquid chromatography (FPLC), Sephacryl S-200 chromatography or hydrophobic interaction chromatography (HIC). Suitable HIC media includes, but is not limited to, Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

In some embodiments, the antibody drug conjugate as described herein has a melting transition temperature greater than at least 60° C., at least 65° C., at least 70° C., at least 75° C., at least 80° C., at least 85° C. or at least 90° C. In some embodiments, the antibody drug conjugate has a melting transition temperature greater than about 65° C.

In some embodiments, the antibody drug conjugate as described herein binds CDCP1 at pH 7.4 with a $K_D$ value of or less than about 50 nM, about 48 nM, about 46 nM, about 45 nM, about 44 nM, about 42 nM, or about 40 nM. In some embodiments, the antibody drug conjugate binds CDCP1 at pH 6.8 with a $K_D$ value of or less than about 70 nM, about 68 nM, about 66 nM, about 65 nM, about 64 nM, about 62 nM, or about 60 nM.

In some embodiments, the antibody drug conjugate as described herein has a half maximal inhibitory concentration ($IC_{50}$) value of no more than about 20000 pM, about 15000 pM, about 10000 pM, about 9500 pM, 8000 pM, 7000 pM, 6000 pM, 5000 pM, 4000 pM, 3000 pM, 2000 pM, 1000 pM, 900 pM, 800 pM, 700 pM, 650 pM, 600 pM, 500 pM, 400 pM, 300 pM, 250 pM, 200 pM, or 100 pM. In some embodiments, the antibody drug conjugate as described herein has an $IC_{50}$ value of no more than about 100 pM, about 90 pM, about 80 pM, about 70 pM, about 60 pM, about 50 pM, about 40 µm, about 30 pM, about 20 pM, about 10 pM, about 9 pM, about 8 pM, about 7 pM, about 6 pM, about 5 pM, about 4 pM, about 3 pM, about 2 pM, or about 1 pM. In some embodiments, the IC50 values are determined in CDCP1 expressing cells.

In some embodiments, the antibody drug conjugate as described herein reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% as compared to mean tumor volume in untreated controls in a NSCLC PDX model. In some embodiments, the antibody drug conjugate reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% as compared to mean tumor volume in untreated controls in a head and neck cancer patient derived xenograft model.

Uses of CDCPJ Specific Antibodies and ADCs

The anti-CDCP1 antibodies and CDCP1 ADCs of the present invention are useful in various applications including, but not limited to, therapeutic treatment methods and diagnostic treatment methods.

In some aspects, the invention provides a method for treating a condition associated with CDCP1 expression in a subject. In some embodiments, the method of treating a condition associated with CDCP1 expression in a subject comprises administering to the subject in need thereof an effective amount of a composition (e.g., pharmaceutical composition) comprising the CDCP1 antibodies or the CDCP1 antibody conjugates as described herein. The conditions associated with CDCP1 expression include, but are not limited to, abnormal CDCP1 expression, altered or aberrant CDCP1 expression, malignant cells expressing CDCP1, and a proliferative disorder (e.g., cancer), an autoimmune disorder, an inflammatory disease, or an infectious disease.

Accordingly, in some aspects, the present invention provides methods of treating a cancer, an autoimmune disease, an inflammatory disease, or an infectious disease in a subject in need thereof comprising administering to the subject in need thereof an effective amount of a composition comprising the anti-CDCP1 antibodies or the CDCP1 antibody conjugates (or pharmaceutical compositions comprising the anti-CDCP1 antibodies or the CDCP1 antibody drug conjugates) as described herein.

The present invention provides methods of treating a tumor wherein the tumor cells express CDCP1 on the surface and wherein surrounding non-tumor tissues express less or no detectable cell surface CDCP1. The method comprises administering an antibody, or antigen binding fragment thereof, that specifically binds CDCP1 and is internalized by the cell. Preferably, the antibody, or antigen binding fragment thereof, is an antibody drug conjugate comprising a cytotoxic payload. Without wishing to be bound by any particular theory, the CDCP1 is activated in that it is phosphorylated at tyrosine 734 (P-734-tyr) and where the numbering is with reference to SEQ ID NO:90. Even more preferably, and without wishing to be bound by any particular theory, the method comprises treating a tumor within a hypoxic milieu such that CDCP1 is phosphorylated at Tyr734 at higher level than CDCP1 that is not in a tumor that is not in a hypoxic milieu. Such tumors include, among many others, lung cancer tumors and head and neck cancer tumors. The skilled artisan would appreciate, once provided with the teachings herein, that any tumor associated with a hypoxic milieu and/or greater level of P-tyr-734 than an otherwise identical tumor or tissue, can be treated using the antibodies and/or ADCs of the present invention.

Cancers

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micro metastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may, thus, be a metastatic breast cancer or a metastatic colon cancer, not liver cancer. The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

In some embodiments, knockdown of CDCP1 results in the upregulation of P38, Extracellular signal-regulated kinase 1 (ERK 1 and 2), Jun proto-oncogene (JUN isoforms 1, 2 and 3), AKT serine/threonine kinase 1 (AKT isoforms 1, 2 and 3), AMP-activated protein kinase (AMPK), signal transducer and activator of transcription (STAT2), STAT5 A/B, choline/ethanolamine kinase (CHK-2), and MET proto-oncogene, receptor tyrosine kinase (MET).

In one aspect, the disclosure provides a method for treating cancer in a patient in need thereof comprising: (a) evaluating a tumor sample for an amount of a mutant LKB1 and/or KRAS; and (b) administering an agent which binds to CDCP1 to the cancer patient if the amount of mutant LKB1 and/or KRAS is higher than a reference sample.

In one aspect, the disclosure provides a method of determining whether a tumor will respond to treatment with an agent which binds to CDCP1, comprising determining in a sample of said tumor the presence, absence, or amount of mutant LKB1 and/or KRAS protein or gene, whereby the presence of mutant LKB1 and/or KRAS or an increased amount of mutant LKB1 and/or KRAS protein or gene relative to a reference sample is indicative of a likelihood of responding to treatment with an agent which binds to CDCP1.

In one aspect, the disclosure provides a method for treating cancer in a patient in need thereof comprising: (a) selecting an agent which binds to CDCP1 on a target cell and is internalized when it contacts CDCP1 on the target cell; and (b) administering the agent to the cancer patient, wherein the agent which binds to CDCP1 is an antibody which activates CDCP1 and is conjugated to a PPP4R2 modulating agent.

In one aspect, the disclosure provides a method for treating cancer in a patient in need thereof comprising: (a) administering an agent which binds to CDCP1, wherein the agent which binds to CDCP1 is an antibody which does not activate CDCP1; and (b) administering an agent which modulates PARG.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the cancer is lung cancer. In some embodiments, the cancer subtype is SCLC, NSCLC, or mesothelioma. In one aspect, the disclosure provides a method of treating a lung cancer in a patient in need thereof, comprising administering an agent which binds to CDCP1 to the patient, wherein the lung cancer is characterized by AKT activation and the agent which binds to CDCP1 is a CDCP1 activating agent.

In some embodiments, the cancer is cancer of the prostate. In one aspect, the disclosure provides a method of treating a prostate cancer in a patient in need thereof, comprising administering an agent which binds to CDCP1 to the patient, wherein the prostate cancer is characterized by AKT activation and the agent which binds to CDCP1 is a CDCP1 activating agent.

In some embodiments, the cancer is cancer of the head and neck.

In some embodiments, the methods of the disclosure provide determining a prognosis of a subject having a proliferative disorder, for example, cancer (e.g., NSCLC, prostate cancer or a cancer of the head and neck). The prognosis may be, for example, a poor prognosis or a good prognosis, measured by a shortened survival or a prolonged survival, respectively. Further, the survival may be measured as an overall survival (OS), disease-free survival (DFS), or recurrence-free survival (RFS). The cancer may be primary or recurrent, and may be of any type (as described above), stage (e.g., Stage I, II, III, or IV or an equivalent of other staging system), and/or histology. The patient may be of any age, sex, performance status, and/or extent and duration of remission.

In some embodiments, knockdown of CDCP1 results in the downregulation of HCK proto-oncogene, Focal adhesion kinase (FAK), p70S6K, and phospholipase C gamma 1 (PLCγ1).

In some embodiments, the cancer is not bladder cancer.

Combination Therapies/Conjugation Agents

As described herein, the present invention relates to, in various embodiments, anti-tumor agents that may be a part of a conjugate of the invention or used in the context of various combination therapies encompassed by the present invention.

Combination therapy embraces the administration of an antibody-drug conjugate, and another therapeutic agent as part of a specific treatment regimen, optionally, including a maintenance phase, intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). Combination therapy generally is not intended to encompass the administration of two or more of these therapeutic agents as part of separate monotherapy regimens that incidentally and arbitrarily result in the combinations of the present invention.

Combination therapy embraces administration of these therapeutic agents in a sequential manner, that is, wherein each therapeutic agent is administered at a different time, as well as administration of these therapeutic agents, or at least two of the therapeutic agents, in a substantially simultaneous manner. Sequential or substantially simultaneous administration of each therapeutic agent can be effected by any appropriate route including, but not limited to, oral routes, intravenous routes, intramuscular, subcutaneous routes, and direct absorption through mucous membrane tissues. The therapeutic agents can be administered by the same route or by different routes. For example, a first therapeutic agent (e.g., a chemotherapeutic agent) can be administered orally, and a second agent (e.g., an ADC) can be administered intravenously. Further, a first therapeutic agent of the combination selected may be administered by intravenous injection while the other therapeutic agents of the combination may be administered orally. Alternatively, for example, both the therapeutic agents may be administered by intravenous or subcutaneous injection.

In the present disclosure the term sequential means, unless otherwise specified, characterized by a regular sequence or order, e.g., if a dosage regimen includes the administration of an ADC and a chemotherapeutic agent, a sequential dosage regimen could include administration of the ADC before, simultaneously, substantially simultaneously, or after administration of the chemotherapeutic agent, but both agents will be administered in a regular sequence or order. The term separate means, unless otherwise specified, to keep apart one from the other. The term simultaneously means, unless otherwise specified, happening or done at the same time, i.e., the compounds of the invention are administered at the same time. The term substantially simultaneously means that the compounds are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the ADC and the chemotherapeutic agent.

In some embodiments, the chemotherapeutic agent is selected from alkylating agents such as thiotepa and CYTOXAN cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel, ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above.

In some embodiments, the anti-tumor agent is a cytotoxic agent. In some embodiments, the cytotoxic agent is selected from methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin, doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine, and mixtures thereof.

In some embodiments, the cytotoxic agent is selected from paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, and mixtures thereof.

In some embodiments, the present compositions and methods find use in combination with checkpoint inhibitors—e.g., in the treatment of various cancers. For instance, the present compositions and methods may supplement checkpoint inhibitor-based cancer therapies, e.g., by improving patient response to the same (e.g., by converting non-responders to responders, and/or increasing the magnitude of therapeutic response, and/or reducing the dose or regimen needed for therapeutic response, and/or reducing one or more side effects of the checkpoint inhibitor-based cancer therapies).

In some embodiments, the checkpoint inhibitor is an agent that targets one of TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2.

In some embodiments, the immune checkpoint immunotherapy agent modulates PD-1) In some embodiments, the agent that targets PD-1 is an antibody or antigen-binding portion thereof that is specific for PD-1, optionally selected from nivolumab, pembrolizumab, and pidilizumab. In some embodiments, an antibody or antigen-binding portion thereof specific for PD-1 is Nivolumab and can be administered at 240 mg every 2 weeks. In some embodiments, an antibody or antigen-binding portion thereof that is specific for PD-1 is Pembrolizumab and can be administered at 200 mg every 3 weeks. In some embodiments, an antibody or antigen-binding portion thereof that is specific for PD-1 is Pidilizumab and can be administered at 200 mg every 3 weeks.

In some embodiments, the immune checkpoint immunotherapy agent modulates PD-L1. In some embodiments, the agent that modulates PD-L1 is an antibody or antigen-binding portion thereof that is specific for PD-LL. In some embodiments, the antibody or antigen-binding portion thereof that is specific for PD-L1 is selected from Atezolizumab, Avelumab, Durvalumab, and BMS-936559. In some embodiments, the antibody or antigen-binding portion thereof that is specific for PD-L1 is BMS-936559 and can be administered at 0.1 mg/kg every 2 weeks. In some embodiments, the antibody or antigen-binding portion thereof that is specific for PD-L1 is Atezolizumab and can be administered at 1200 mg every 3 weeks. In some embodiments, the antibody or antigen-binding portion thereof that is specific for PD-L1 is Avelumab and can be administered at 10 mg/kg every 2 weeks. In some embodiments, the antibody or antigen-binding portion thereof that is specific for PD-L1 is Durvalumab and can be administered at 10 mg/kg every 2 weeks.

In some embodiments, the agent that targets CTLA-4 is an antibody or antigen-binding portion thereof that is specific for CTLA-4, optionally selected from ipilimumab and tremelimumab. In some embodiments, the antibody or antigen-binding portion thereof that is specific for CTLA-4 is tremelimumab and can administered at 3 mg/kg, 6 mg/kg or 10 mg/kg. In some embodiments, the antibody or antigen-binding portion thereof that is specific for CTLA-4 is Ipilimumab and can be administered at 5 mg/mL 12 weeks.

CDCPJ and Hypoxia-Inducible Factor 2α (HIF-2α)

CDCP1 plays a critical role in the process of metastasis and in the survival of cells at distant sites of metastasis and demonstrates a unique role under conditions of oxygen deprivation (hypoxia). Hence, there is a biochemical pathway by which CDCP1 participates in the activation of Src-family members and the coupling of SFK activation to phosphorylation and regulation of protein kinase C delta (PKC-δ). Hypoxia triggers the elevation of hypoxia-inducible factors HIF-1α and HIF-2α by blocking von Hippel Lindau (VHL)-dependent HIF-α degradation. HIF is a heterodimer of two basic helix-loop-helix/PAS proteins, HIF-α and the aryl hydrocarbon nuclear translocator (ARNT or HIF-β). HIF-α and ARNT subunits are ubiquitously expressed; however, the α-subunit is labile under conditions of normal oxygen (5-21% O2). Under hypoxic conditions (0.5-5% O2) the HIF-α subunit is stabilized, dimerizes with ARNT, translocates to the nucleus, and subsequently binds to hypoxia response elements (HREs) within target genes. Among HIF transcription targets are genes involved in glucose metabolism, angiogenesis, and metastasis, thereby tightly linking HIF-mediated transcription to tumorigenesis. HIF-1α and HIF-2α are overexpressed in a number of primary and metastatic human cancers.

In some embodiments, the anti-tumor agent is a hypoxia-inducible factor-2 (HIF-2) inhibitor. In some embodiments, the HIF-2 inhibitor is selected from PT2385 and PT2977.

In some embodiments, the anti-tumor agent is not a Src inhibitor, optionally selected from KX2-391, bosutinib, saracatinib, and dasatinib. In some embodiments, the cancer is a tumor characterized by hypoxia.

Pharmaceutical Compositions

The present invention further provides pharmaceutical compositions including any of the anti-CDCP1 antibodies, antigen-binding fragments thereof, or CDCP1 ADCs disclosed herein, and a pharmaceutically acceptable carrier. Further, the compositions may include more than one anti-CDCP1 antibody and/or more than one CDCP1 ADC disclosed herein.

The composition of the present invention may further include pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). "Pharmaceutically acceptable salt" as used herein refers to pharmaceutically acceptable organic or inorganic salts of a molecule or macromolecule.

Another embodiment of the present disclosure is a pharmaceutical composition, or use of pharmaceutical composition, comprising an agent which binds to CDCP1 in a cancer patient if the amount of mutant LKB1 and/or KRAS is higher than a reference sample. In some embodiments, the pharmaceutical composition comprises an agent which binds to CDCP1 and is characterized by AKT activation or an agent that is a CDCP1 activating agent. In some embodiments, the pharmaceutical composition comprises an agent which activates CDCP1 and is conjugated to PPP4R2. In some embodiments, the pharmaceutical composition comprises an agent which binds to CDCP1 on a target cell and is internalized when it contacts CDCP1 on the target cell. Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In some embodiments, a pharmaceutical composition comprises the agents of the disclosure and a pharmaceutically acceptable carrier. An effective dose is an amount sufficient to affect a beneficial or desired clinical result.

A beneficial or desired clinical result may include, inter alia, a reduction in tumor size and/or tumor growth and/or a reduction of a cancer marker that is associated with the presence of cancer as compared to what is observed without administration of the small molecule or peptide agent. A beneficial or desired clinical result may also include, inter alia, an increased presence of a marker that is associated with a reduction of cancer as compared to what is observed without administration of the small molecule or peptide agent. Also included in a beneficial or desired clinical result is, inter alia, an increased amount of a gene comprising a marker linked to cancer etiology as compared to what is observed without administration of the inhibitor. The gene comprising a marker linked to cancer etiology may include, for example, an immune checkpoint gene, such as TIM-3, BTLA, PD-1, CTLA-4, B7-H4, GITR, galectin-9, HVEM, PD-L1, PD-L2, B7-H3, CD244, CD160, TIGIT, SIRPα, ICOS, CD172a, and TMIGD2.

The gene comprising a marker linked to cancer etiology may include, for example, a HIF-2 inhibitor.

Dosing and Administration

One will generally desire to employ appropriate salts and buffers to render delivery vehicles stable and allow for uptake by target cells. Aqueous compositions of the present invention comprise an effective amount of the delivery vehicle comprising an agent of the present invention (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present disclosure may include classic pharmaceutical preparations. Administration of these compositions according to the present invention may be via any common route so long as the target tissue is available via that route. This includes oral, nasal, or buccal. Alternatively, administration may be by intratumoral, intradermal, subcutaneous, intramuscular, intraperitoneal or intravenous injection, or by direct injection into cancer tissue. The agents disclosed herein may also be administered by catheter systems. Such compositions would normally be administered as pharmaceutically acceptable compositions as described herein.

Upon formulation, solutions may be administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic with, for example, sufficient saline or glucose. Such aqueous solutions may be used, for example, for intratumoral, intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pages 1035-1038 and 1570-1580, the contents of which are hereby incorporated by reference). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

In some embodiments, the first and second agents may be administered in either order (e.g., first then second or second then first) or concurrently.

In some embodiments, the present disclosure includes the agents described herein, and a second agent that is or comprises at least one other cancer biologic, therapeutic, chemotherapeutic or drug.

In some embodiments, the agents of the disclosure can be administered over any suitable period of time, such as a period from αβοντ 1 day to about 12 months. In some embodiments, for example, the period of administration can be from about 1 day to 90 days; from about 1 day to 60 days; from about 1 day to 30 days; from about 1 day to 20 days; from about 1 day to 10 days; from about 1 day to 7 days. In some embodiments, the period of administration can be from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks; from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

In some embodiments, the agents of the disclosure can be administered every day, every other day, every week, every 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or every 20 weeks, or every month.

In some embodiments, a therapeutically effective amount of a composition or agent of the present disclosure may be about 0.01 mg/kg per day to about 10 mg/kg per day. In some embodiments, dosages can range from about 0.1 mg/kg, 0.5 mg/kg, 1 mg/kg, 1.5 mg/kg, 3 mg/kg, 5 mg/kg, 6 mg/kg, 7.5 mg/kg, or about 10 mg/kg. In some embodiments, the dose will be in the range of about 0.1 mg/day to about 5 mg/kg; about 0.1 mg/day to about 10 mg/kg; about 0.1 mg/day to about 20 mg/kg; about 0.1 mg to about 30 mg/kg; or about 0.1 mg to about 40 mg/kg.

In some embodiments, a therapeutically effective amount of a composition or agent of the present disclosure may be about 0.1 mg to about 50 mg/kg or in single, divided, or continuous doses (which dose may be adjusted for the patient's weight in kg, body surface area in m², and age in years).

In some embodiments, a therapeutically effective amount of the composition or agent of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

In some embodiments, a therapeutically effective amount of a composition or agent of the present disclosure 0.01 mg/kg to about 500 mg/kg, for example, about 0.1 mg/kg to about 200 mg/kg (such as about 100 mg/kg), or about 0.1 mg/kg to about 10 mg/kg (such as about 0.1 mg/kg, 0.5 mg/kg, 1 mg/kg, 1.5 mg/kg, 3 mg/kg, 5 mg/kg, 6 mg/kg, 7.5 mg/kg, or about 10 mg/kg).

Kits of the Disclosure

The invention also provides kits that can simplify the administration of any agent described herein, such as an agent which binds to CDCP1 in a cancer patient if the amount of mutant LKB1 and/or KRAS is higher than a reference sample. In some embodiments, the agent binds to CDCP1 and is characterized by AKT activation or the agent is a CDCP1 activating agent. In some embodiments, the agent activates CDCP1 and is conjugated to a PPP4R2 modulating agent. In some embodiments, the agent binds to CDCP1 is conjugated to a PARG modulating agent.

An exemplary kit of the invention comprises any composition described herein in unit dosage form. In some embodiments, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can further comprise one or more additional agent, such as a biologic, therapeutic, chemotherapeutic or drug described herein. In some embodiments, the kit comprises a container containing an effective amount of a composition of the invention and an effective amount of another composition, such those described herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: CDCP1 Expression in Human Patient Tumors

CDCP1 expression was assessed by immunohistochemistry in human tumor microarrays. Tumor tissues were collected and analyzed in accordance with the informed consent documents signed by donors under Institutional Review Board approved procedures. Tumor cores (1.5 mm-2.0 mm diameter) were obtained from formalin-fixed, paraffin-embedded patient tumor samples and microarrays were constructed in paraffin blocks using standard methods. Sections were cut at 5 μm thickness, mounted to glass slides, and processed for immunohistochemistry. Slides were pre-treated with Epitope Retrieval Solution 2 (AR9640; Leica Biosystems, Buffalo Grove, IL) to expose antigenic sites, followed by labeling for CDCP1 using a modified Bond Polymer Refine (DS9800; Leica Biosystems, Buffalo Grove, IL) detection protocol including a peroxide block, a protein block to minimize non-specific antibody binding, a post-primary polymer reagent, DAB chromogen detection system, and hematoxylin counterstain. CDCP1 protein was detected on cell membranes using a rabbit anti-CDCP1 antibody (Cell Signaling Technologies, catalog #4115) diluted 1:100 in Leica Bond Primary Antibody Diluent (AR9352; Leica Biosystems, Buffalo Grove, IL).

Slides were evaluated for staining by a pathologist using light microscopy to determine a semi-quantitative H-score. The H-Score was calculated by multiplying the estimated percentage of tumor cells having membrane staining for each subjective staining intensity by that intensity value (0=negative, 1=low, 2=medium, 3=high) and then adding together all products for a summed score. For example, a tumor in which 50% of cells stained positive and were all of medium intensity while the other 50% were unstained would have an H-score of 100 ([50×0]+[0×1]+[50×2]+[0×3])=100). The higher the H-score value, the greater the membrane staining intensity and/or distribution of the target protein in that sample. For ease of interpretation, scores in the 201-300 range are arbitrarily considered high, in the 101-200 range, moderate, and in the 1-100 range, low, for target protein expression.

Table 1 shows the results of numerous tumors evaluated. CDCP1 expression was noted in all tumor types assayed. H-scores are given for numerous independent primary human tumors. Different patient samples are indicated by the given identifiers (Non-small cell lung cancer abbreviated as NSCLC). Average scores for tumors derived directly from patients tended to be lower than those from human tumors grown in immunocompromised mice (PDX tumors, see below). There are multiple possible explanations for this finding including different tumor growth rates between mouse and human, species differences in the tumor microenvironment, and differences in sample handling and processing. In spite of these differences, there is significant overlap between H-scores seen in both mouse cancer models and human tumors for the cancer types assayed.

TABLE 1

| Identifier | Cancer Type | H-score |
| --- | --- | --- |
| 36 | head-neck | 280 |
| S96-1568 | head-neck | 235 |
| 28 | head-neck | 230 |
| 39 | head-neck | 221 |
| 16 | head-neck | 220 |
| 38 | head-neck | 203 |
| 29 | head-neck | 201 |
| 34 | head-neck | 200 |
| 4 | head-neck | 195 |
| S96-1386 | head-neck | 195 |
| S99-26 | head-neck | 180 |
| 37 | head-neck | 175 |
| S96-3970 | head-neck | 165 |
| 45 | head-neck | 160 |
| CA4 | head-neck | 159 |
| 15 | head-neck | 158 |
| 3 | head-neck | 150 |
| CA3 | head-neck | 145 |
| S98-362 | head-neck | 140 |

TABLE 1-continued

| Identifier | Cancer Type | H-score |
| --- | --- | --- |
| 26 | head-neck | 130 |
| S96-1964 | head-neck | 125 |
| S96-3968 | head-neck | 120 |
| S96-3970 | head-neck | 115 |
| 21 | head-neck | 113 |
| S96-2045 | head-neck | 110 |
| 31 | head-neck | 103 |
| S96-1964 | head-neck | 95 |
| S96-3970 | head-neck | 95 |
| 48 | head-neck | 94 |
| 41 | head-neck | 90 |
| S96-3970 | head-neck | 90 |
| S96-1964 | head-neck | 80 |
| 24 | head-neck | 70 |
| 27 | head-neck | 70 |
| 42 | head-neck | 67 |
| 7 | head-neck | 50 |
| 44 | head-neck | 50 |
| 2 | head-neck | 44 |
| 35 | head-neck | 40 |
| 33 | head-neck | 30 |
| 25 | head-neck | 29 |
| CA1 | head-neck | 16 |
| 8 | head-neck | 10 |
| 22 | head-neck | 0 |
| P31-TC15 | lung-NSCLC | 215 |
| P471-TP13 | lung-NSCLC | 205 |
| P111-TP15 | lung-NSCLC | 201 |
| P106-TP16 | lung-NSCLC | 200 |
| P343-TP13 | lung-NSCLC | 200 |
| P122-TC16 | lung-NSCLC | 188 |
| P372-TP12 | lung-NSCLC | 180 |
| P381-TP11 | lung-NSCLC | 178 |
| P183-TP11 | lung-NSCLC | 165 |
| P37-TP13 | lung-NSCLC | 155 |
| P336-TC15 | lung-NSCLC | 150 |
| P300-TP12 | lung-NSCLC | 145 |
| P216-TP11 | lung-NSCLC | 145 |
| P450 Tp11 | lung-NSCLC | 135 |

TABLE 1-continued

| Identifier | Cancer Type | H-score |
|---|---|---|
| P207-TP11 | lung-NSCLC | 130 |
| P88-TP11 | lung-NSCLC | 129 |
| P299-TP11 | lung-NSCLC | 125 |
| P301-TP13 | lung-NSCLC | 124 |
| P116-TP11 | lung-NSCLC | 120 |
| P57 Tp15 | lung-NSCLC | 119 |
| P36-TC15 | lung-NSCLC | 115 |
| P149-TP11 | lung-NSCLC | 110 |
| P375-TP13 | lung-NSCLC | 109 |
| P34-TP11 | lung-NSCLC | 100 |
| P341-TP11 | lung-NSCLC | 90 |
| P319-TC15 | lung-NSCLC | 70 |
| P386-TP11 | lung-NSCLC | 69 |
| P241-TP13 | lung-NSCLC | 65 |
| P18-TC15 | lung-NSCLC | 60 |
| P374-TP13 | lung-NSCLC | 40 |
| P485-TP14 | lung-NSCLC | 40 |
| P108-TP11 | lung-NSCLC | 30 |
| P102-TC15 | lung-NSCLC | 25 |
| 1128152B | Breast | 181 |
| 1100452B | Breast | 173 |
| 1100513B | Breast | 155 |
| 29773 | Breast | 155 |
| 30063 | Breast | 136 |
| 1106582B | Breast | 125 |
| 29772 | Breast | 118 |
| 1100567B | Breast | 115 |
| 29961 | Breast | 112 |
| 29756 | Breast | 100 |
| 29754 | Breast | 100 |
| 1149262B | Breast | 90 |
| 29758 | Breast | 75 |
| 1142103B | Breast | 60 |
| 1148011B | Breast | 58 |
| 1099698B | Breast | 30 |
| 1100489B | Breast | 10 |
| 99-6854 | Ovarian | 220 |
| 01-2970 | Ovarian | 175 |
| ILS 31477 | Ovarian | 165 |
| ILS 31126 | Ovarian | 120 |
| 03-8026 | Ovarian | 95 |
| ILS 30202 | Ovarian | 92 |
| ILS 31680 | Ovarian | 75 |
| ILS 31680 | Ovarian | 40 |
| 03-4684 | Ovarian | 25 |
| ILS 30917 | Ovarian | 20 |
| ILS 26123 | Ovarian | 2 |
| ILS 30965 | Ovarian | 2 |
| ILS 31141 | Ovarian | 0 |
| ILS 26123 | Ovarian | 0 |
| ILS 29962 | Ovarian | 0 |
| ILS 29962 | Ovarian | 0 |
| ILS 28133 | Ovarian | 0 |

Example 2: CDCP1 Expression in Patient Derived Xenograft (PDX) Tumors

CDCP1 expression was surveyed by immunohistochemistry in Patient Derived Xenograft (PDX) tumors extracted from mice. Tumors were processed using standard methods for formalin-fixed paraffin embedded tissue. Sections were cut at 5 μm thickness, mounted to glass slides, and processed for immunohistochemistry. Slides were pretreated with Epitope Retrieval Solution 2 (AR9640; Leica Biosystems, Buffalo Grove, IL) to expose antigenic sites, followed by labeling for CDCP1 using a modified Bond Polymer Refine (DS9800; Leica Biosystems, Buffalo Grove, IL) detection protocol including a peroxide block, a protein block to minimize non-specific antibody binding, a post-primary polymer reagent, DAB chromogen detection system, and hematoxylin counterstain. CDCP1 protein was detected on cell membranes using a rabbit anti-CDCP1 antibody (Cell Signaling Technologies, catalog #4115) diluted 1:100 in Leica Bond Primary Antibody Diluent (AR9352; Leica Biosystems, Buffalo Grove, IL).

Slides were evaluated for staining by a pathologist using light microscopy to determine the H-score for each core in the microarray as described in Example 1. Table 2 shows the results of numerous PDX tumors assayed by the above method. H-scores are given for tumors from numerous independent PDX tumors. Different lines are indicated by PDX identifiers (Non-small cell lung cancer is abbreviated as NSCLC, while small cell lung cancer is abbreviated as SCLC). CDCP1 expression was noted in all tumor types assayed. The highest average score was associated with ovarian cancer models while the highest absolute scores were associated with ovarian and non-small cell lung cancers (NSCLC). Considered as a whole, 31.6% of models fell into the high expression category, 61.4% into moderate, and 7% into low. These data suggest a wide range of tumors that could be responsive to a drug specifically targeting CDCP1.

TABLE 2

| PDX identifier | Cancer type | H-score |
|---|---|---|
| PDX-HNX-24704 | head-neck | 222 |
| PDX-HNX-26755 | head-neck | 209 |
| PDX-HNX-24711 | head-neck | 208 |
| PDX-HNX-2471 | head-neck | 206 |
| PDX-HNX-24701 | head-neck | 185 |
| PDX-HNX-24712 | head-neck | 182 |
| PDX-HNX-26775 | head-neck | 176.5 |
| PDX-HNX-24709 | head-neck | 170 |
| PDX-HNX-24715 | head-neck | 161 |
| PDX-HNX-26771 | head-neck | 108 |
| PDX-HNX-24713 | head-neck | 105 |
| PDX-HNX-24708 | head-neck | 40 |
| PDX-NSX-26101 | lung-NSCLC | 260.5 |
| PDX-NSX-26115 | lung-NSCLC | 253 |
| PDX-NSX-26181 | lung-NSCLC | 246.5 |

TABLE 2-continued

| PDX identifier | Cancer type | H-score |
|---|---|---|
| PDX-NSX-26113 | lung-NSCLC | 227 |
| PDX-NSX-24107 | lung-NSCLC | 220 |
| PDX-NSX-26112 | lung-NSCLC | 218.3 |
| PDX-NSX-26109 | lung-NSCLC | 215 |
| PDX-NSX-24118 | lung-NSCLC | 215 |
| PDX-NSX-24101 | lung-NSCLC | 208 |
| PDX-NSX-15137 | lung-NSCLC | 196 |
| PDX-NSX-26184 | lung-NSCLC | 190 |
| PDX-NSX-12191 | lung-NSCLC | 185 |
| PDX-NSX-13120 | lung-NSCLC | 180 |
| PDX-NSX-26177 | lung-NSCLC | 179 |
| PDX-NSX-24106 | lung-NSCLC | 175 |
| PDX-NSX-11122 | lung-NSCLC | 175 |
| PDX-NSX-24106 | lung-NSCLC | 175 |
| PDX-NSX-13176 | lung-NSCLC | 170 |
| PDX-NSX-15187 | lung-NSCLC | 165 |
| PDX-NSX-24119 | lung-NSCLC | 145 |
| PDX-NSX-24114 | lung-NSCLC | 143 |
| PDX-NSX-26186 | lung-NSCLC | 89 |
| PDX-NSX-26186 | lung-NSCLC | 89 |
| PDX-NSX-26174 | lung-NSCLC | 86 |
| PDX-BRX-24312 | Breast | 230 |
| PDX-BRX-12351 | Breast | 200 |
| PDX-BRX-24307 | Breast | 196 |
| PDX-BRX-24304 | Breast | 191 |
| PDX-BRX-12377 | Breast | 185 |
| PDX-BRX-24302 | Breast | 185 |
| PDX-BRX-24309 | Breast | 172 |
| PDX-BRX-24308 | Breast | 170 |
| PDX-BRX-11380 | Breast | 147 |
| PDX-OVX-24413 | Ovarian | 268 |
| PDX-OVX-26466 | Ovarian | 237 |
| PDX-OVX-26402 | Ovarian | 206 |
| PDX-OVX-26401 | Ovarian | 195 |
| PDX-OVX-26404 | Ovarian | 185 |
| PDX-OVX-24412 | Ovarian | 105 |
| PDX-SCX-26872 | Lung-SCLC | 201 |
| PDX-SCX-26888 | Lung-SCLC | 173 |
| PDX-SCX-26881 | Lung-SCLC | 120 |
| PDX-BLA-26904 | Bladder | 183 |
| PDX-BLA-26903 | Bladder | 179 |
| PDX-BLA-26901 | Bladder | 120 | tocol. Adherent cells were dissociated using a non-enzymatic Cell Dissociation Buffer (Life Technologies #13150-016), washed in FACS buffer (Hanks Balanced Salt Solution, 2% FBS, 25 mM HEPES, 2 mM EDTA) and ultimately resuspended in a staining solution that contained 5 µg/mL of the Alexa 647 conjugated CP13E10-54HC-89LCv1 plus 7-AAD viability dye. For cells prepared as a background control, staining buffer omitted Alexa 647 conjugated CP13E10-54HC-89LCv1 and contained only the 7-AAD viability dye. Stained cells were washed and resuspended in FACS buffer and immediately acquired on a BD FACSAria instrument using BD FACSDiva™ Software. Dead cells positive for 7-AAD staining were gated out and the background subtracted geometric mean of fluorescence intensity (gMFI) of Alexa 647 positive cells in the APC channel was determined using FlowJo software.

CDCP1 levels were calculated from background subtracted gMFI through use of the Bangs Laboratories Quantum A647 MESF kit (catalog #647) following the manufacturer's recommended protocol. Briefly, blank beads and MESF (molecules of equivalent soluble fluorochrome) beads were respectively diluted into PBS, and run on the same day and at the same fluorescence settings as stained cells to establish a calibration curve using a quantitative analysis template (QuickCal) provided with the kit. The background subtracted gMFI value was identified on the calibration curve to determine MESF units for each cell line. MESF units were further divided by the F/P (fluorophore to protein) ratio of the Alexa 647 conjugated CP13E10-54HC-89LCv1 antibody to calculate the number of CDCP1 molecules per cell (surface exposed molecules only). Cell lines assayed by this method showed a range of expression from a low of 12814 molecules/cell (HuAoSMC) to a high of 233567 molecules/cell (PC3) (Table 3).

TABLE 3

| Cell line | PC3 | H1299 | SCC-25 | H2009 | PE/CA-PJ-49 | HuAoSMC |
|---|---|---|---|---|---|---|
| Cell type | Prostate cancer | NSCLC | Head and neck cancer | Lung adenocarcinoma | Oral squamous cell carcinoma | Primary human Aortic smooth muscle |
| CDCP1 (Molecules/cell) | 233567 | 69008 | 51810 | 48857 | 24501 | 12814 |

Example 3: Expression of CDCP1 on Human Cancer Cell Lines and Primary Cells

CDCP1 protein expression was characterized on the surface of a broad range of human cancer and normal cell lines including, PC3 (prostate cancer), H1299 (Non-Small Cell Lung Cancer), SCC-25 (head and neck cancer), H2009 (lung adenocarcinoma), PE/CA-PJ-49 (oral squamous cell carcinoma), and primary human aortic smooth muscle cell (HuAoSMC) by quantitative fluorescence flow cytometry. To accomplish this, anti-CDCP1 antibody, CP13E10-54HC-89LCv1, was used as a detection reagent by directly conjugating it with the fluorochrome, Alexa 647 using the Alexa Fluor 647 Antibody Labeling Kit (ThermoFisher Scientific #A20186) following the manufacturer's recommended pro- Example 4: Involvement of CDCP1 Expression and Phosphorylation in Multiple Cancers The transmembrane protein CDCP1 associates with Src and PKCS and all three proteins display increases in tyrosine phosphorylation when CDCP1 is activated. Tyr-734 has been identified as the site that is phosphorylated by Src and Src Family Kinases. Bioinformatics analyses of CDCP1 expression shows the involvement of CDCP1 in cancer metastasis and decreased patient survival, including the following, CDCP1 expression levels in multiple tumor types (breast, colon, pancreas, bladder, kidney, ovarian, lung) are higher than in the corresponding normal tissue, high levels of CDCP1 expression are predictive of shorter patient survival in lung adenocarcinomas, high levels of CDCP1 are associated with increases in the rate of 5-year recurrence of colorectal cancer; and CDCP1 tyrosine phosphorylation is higher in triple-negative breast cancers, which are known to have poor outcomes in metastatic settings. In addition, varying levels of CDCP1 expression have been measured in patients with clear cell renal cell carcinoma, and determined that the survival rate (Kaplan-Meier plots) of patients with high levels of CDCP1 expression was shorter than those with low levels of CDCP1. Tyrosine phosphorylation of CDCP1 in lung cancer cells has been shown to be greater than that found in normal tissue was described in previous studies. A correlation analysis of tyrosine phosphorylation of proteins in human lung cancer tumor samples has previously been shown, and it was found that there was a strong positive correlation between the tyrosine phosphorylation of CDCP1 and multiple SFKs. Similarly, human non-small cell lung cancer (NSCLC) cell lines and mice with activated KRAS and/or inactivated LKB1 tumor mutations displayed high levels of phosphorylated CDCP1 and SFKs.

HIF-2α and CDCP1 expression may play critical roles in promoting tumor metastasis in cells exposed to low oxygen levels, as CDCP1 is a target gene of Hypoxia-Inducible Factor 2c (HIF-2α). Hypoxia triggers the expression of HIF-2α and the activation of CDCP1 and Src, and stable knockdown of HIF-2α blocks the tyrosine phosphorylation of CDCP1 and Src by hypoxia. The injection of HIF-2α-overexpressing A375 cancer cells into mice has been shown to produce the formation of larger tumors than control A375 cells, and tumors with high levels of HIF-2α also contain enhanced CDCP1 protein expression. Notably, HIF-2α and CDCP1 expression displays a strong correlation with the Epidermal Growth Factor Receptor (EGFR) and the Met Hepatocyte Growth Factor Receptors, which are known to be regulated by hypoxia and are HIF-2α target genes.

Figure 1:
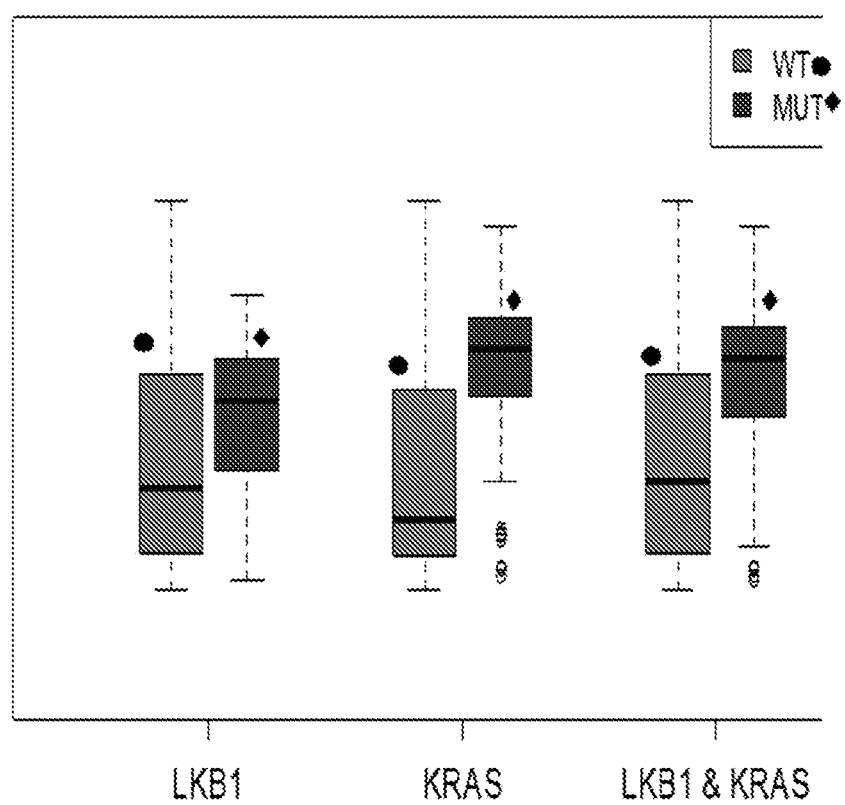
FIG. 1 is a box plot of bioinformatic analysis of expression microarray data from 790 cancer cell lines in the Sanger Cell Line Project showing that CDCP1 Expression is Increased in Cells Expressing Oncogenic KRAS and/or LKB1 Compared to Wild Type.

The expression of CDCP1 was compared in wild-type and mutant cells across the 45 most common tumor suppressor genes and oncogenes in profiles of 790 cancer cell lines in the Sanger project. The two genes that showed significantly higher CDCP1 expression in mutant compared to wild-type cells were KRAS and LKB1 (FIG. 1). The strong correlation in KRAS suggested that the overexpression of CDCP1 might be triggered by oncogenic KRAS. Human clinical data indicates that KRAS+LKB1 mutant tumors have much higher rates of metastasis than tumors with mutant KRAS alone, and patients with KRAS+LKB1 mutant tumors is the subgroup that has the worst clinical outcome.

Example 5: Validation of CDCP1 as a Therapeutic Target in Cancer

The particular focus in documenting a role for CDCP1 in lung cancer, informed the initial steps in the development of an anti-CDCP1 therapeutic agent. Therefore, as a first step to validate CDCP1 as a therapeutic target in metastatic tumors and to derive information relevant to a future precision medicine strategy, experiments were conducted to determine the effect of silencing CDCP1 in xenograft tumors of NSCLC cells in mice.

To obtain better clinical relevance, an orthotopic xenograft model of metastatic lung cancer was established. Tumors were first initiated in mice by the subcutaneous inoculation of A549 cells (with luciferase and shRNAs). Small pieces of the tumors were harvested and placed into the lungs of other mice, which then were treated with doxycycline. Lung tumors developed in mice that had A549 cells with control shRNA, but tumor growth was blocked when CDCP1 was silenced in A549 cells containing CDCP1-specific shRNA.

Figure 2:
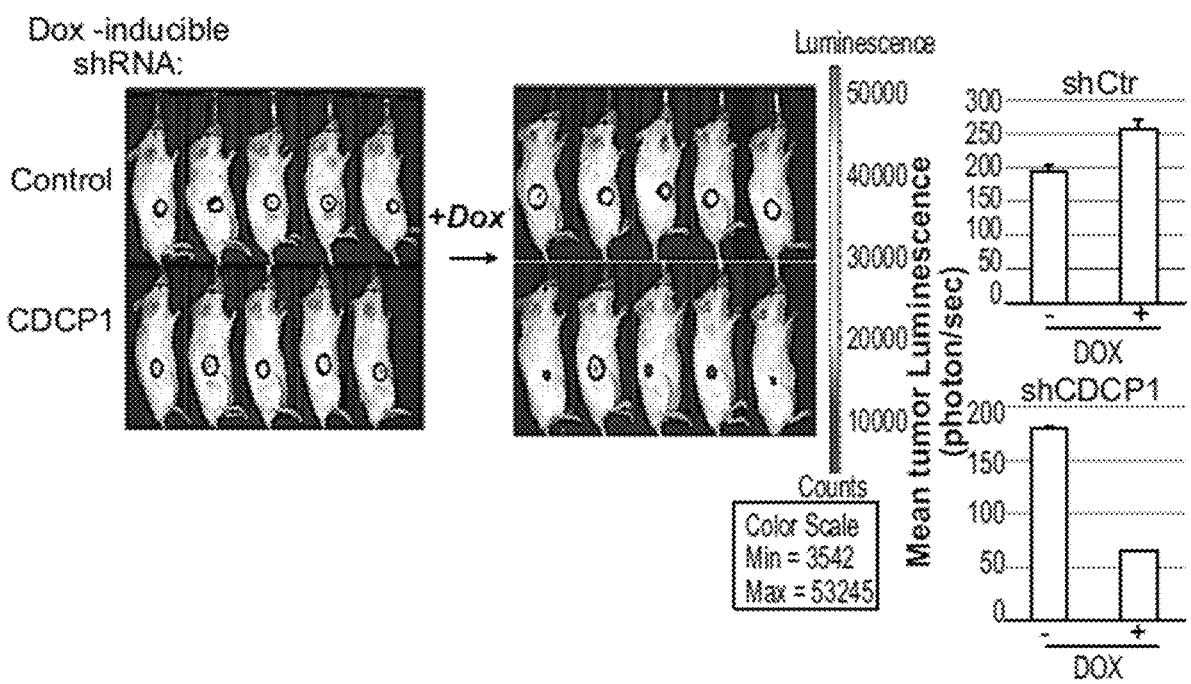
FIG. 2 shows that silencing CDCP1 Shrinks Established H2009 NSCLC tumors.

In another experiment H2009 NSCLC cells were inoculated with luciferase and shRNAs subcutaneously into mice (FIG. 2). No treatments were initiated until the tumors were established (~100 cm$^3$), after which the mice were fed doxycycline chow. After 3-4 weeks there was a substantial reduction in tumor size and weight in doxycycline-treated mice inoculated with cells having the CDCP1-specific shRNA but not in mice inoculated with cells containing control shRNA. These studies demonstrated that the silencing of CDCP1 expression could reduce the size of established tumors. These in vivo experiments established that CDCP1 promotes the growth and survival of metastasized tumors, and validated CDCP1 as a therapeutic target to reduce tumor growth and the size of established tumors.

Example 6: Selection of Anti-CDCP1 Antibodies

Anti-CDCP1 scFvs were selected from a phagemid-based human scFv naïve antibody library, displayed on M13 bacteriophage. Selection was based on phage binding to biotinylated human and mouse CDCP1 extracellular domains (ECDs; Human, RefSeq NP_073753.3, amino acids 1-663; Mouse, RefSeq NP_598735.2, amino acids 1-667) immobilized on streptavidin-coated magnetic beads. Human, mouse, and cynomolgus monkey CDCP1 ECDs (cyno; RefSeq XP_005546930.1, amino acids 30-663) were fused on their N-termini with a 6-histidine purification tag, expressed transiently in HEK293 mammalian cell culture, purified by Ni-NTA affinity chromatography, and chemically biotinylated with EZ-Link NHS-PEG4-Biotin (Thermo Pierce).

Three rounds of phage-display selections, followed by amplification of selected phage pools, were conducted, using either human CDCP1 ECD in all 3 rounds or alternating human-mouse-human (HmH) CDCP1 ECD. After the third round, 2400 individual colony-derived cultures were grown, and the culture supernatant or a periplasmic bacterial extract was screened for human, mouse and cyno CDCP1 ECD binding by an enzyme-linked immunosorbent assay (ELISA). There were 285 positive ELISA clones, 261 bound to human CDCP1 ECD, 184 bound to mouse CDCP1 ECD and 228 bound to cyno CDCP1 ECD. ELISA positive clones were further characterized by a flow cytometry assay that assessed binding to the human tumor cell line, H1299, which expresses CDCP1 on its cell surface. For all binders identified in this assay, the scFv region of phagemid DNA was sequenced to determine unique clones. Sequencing identified 82 unique scFv sequences, 48 of which bound cyno, mouse and human CDCP1 ECDs. These clones were reformatted to human IgG1 and prioritized based on human tumor cell in vitro toxicity (using an anti-human antibody toxin conjugate as a secondary reagent) and cell-based and biochemical binding assays. This process identified a candidate known as CP13E10 that was selected for further optimization by rational engineering as described herein.

The CP13E10 antibody heavy and light chain variable domains are set forth in SEQ ID NOS. 1 and 11, respectively, and the heavy and light chains are set forth in SEQ ID NOS. 10 and 17, respectively. Additional candidates identified by this process of evaluation are antibody 23, antibody 24 and antibody 76. The antibody 23 heavy and light chain variable domains are set forth in SEQ ID NOS. 47 and 52, respectively, and the heavy and light chains are set forth in SEQ ID NOS. 51 and 58, respectively. The antibody 24 heavy and light chain variable domains are set forth in SEQ ID NOS. 59 and 65, respectively, and the heavy and light chains are set forth in SEQ ID NOS. 64 and 70, respectively. The antibody 76 heavy and light chain variable domains are set forth in SEQ ID NOS. 47 and 71, respectively, and the heavy and light chains are set forth in SEQ ID NOS. 51 and 74, respectively.

Example 7: Optimization of Anti-CDCP1 Antibodies

Multi-parametric optimization of anti-CDCP1 antibody CP13E10 was facilitated using rational design engineering. The structure of CP13E10 Fab in complex with CDCP1-ECD was solved with 1.9 Å resolution and used to design rational phage display libraries to enable identification of CP13E10 variants with improved biophysical properties while maintaining CDCP1 binding properties. CP13E10 antibody hydrophobicity was reduced to facilitate efficient conjugation processes for producing antibody drug conjugates (ADCs) by incorporating three point mutations (Y(H100)H, W(H100C)H, Y(H100H)H) into CP13E10 CDRH3 (CP13E10-34 variant). Protein for characterization was generated by transiently transfecting DNA encoding the anti-CP13E10-34 antibody variant and parental CP13E10 antibody into HEK-293 cells and the resultant protein was Protein-A affinity purified and buffer exchanged into PBS-CMF pH7.2 using G-25 columns. The resultant CP13E10-34 antibody variant harboring Y(H100)H, W(H100C)H, Y(H100H)H exhibited significantly reduced hydrophobicity as detected by an analytical Hydrophobic Interaction Chromatography (HIC) method that utilizes a TSKgel Butyl-NPR chromatography column with a 1.5 M to 0 M ammonium sulfate gradient elution which allows for relative hydrophobicity ranking based on elution time. CP13E10 antibody eluted outside the human IgG pool elution envelope control with an elution time of 48.63 minutes that correlates with high hydrophobicity, while CP13E10 harboring the three CDRH3 point mutations (Y(H100)H, W(H100C)H, Y(H100H)H) had an elution time of 28.42 minutes that was within the human IgG pool elution envelope control profile (FIG. 3-4).

Although CP13E10-34 variant is significantly less hydrophobic than the parental CP13E10 antibody, incorporation of these CDRH3 mutations resulted in >7-fold lower binding to CDCP1 expressed on the surface of prostate cancer (PC3) cells assessed by using a competition fluorescence-activated cell sorting (FACS) assay with biotinylated CP13E10 antibody as the reporter antibody (FIG. 5). Specifically, CDCP1 binding properties were assessed for the CP13E10 antibody variants using a competition FACS assay with biotinylated CP13E10 antibody as the reporter antibody to determine if the CP13E10 variants could effectively compete with this wild type CP13E10 antibody for binding to CDCP1 antigen expressed on PC3 cells. For this competition FACS assay, the parental anti-CDCP1 CP13E10 reporter antibody was biotinylated using EZ-link Sulfo-NHS-Biotin Sulfosuccinimidobiotin (Thermo/Pierce, catalog number 21217) at a molar coupling ratio of 20:1 according to the manufacturer's protocols. Protein for this assay was generated by transiently transfecting DNA encoding the anti-CDCP1 CP13E10 variants and parental CP13E10 antibody into HEK-293 cells and resultant protein was Protein-A affinity purified and buffer exchanged into PBS-CMF pH 7.2 using G-25 columns. For this competition FACS assay procedure, PC3 cells were detached from flasks using cell dissociation buffer (Gibco, catalog number 13151-014), washed once with ice-cold FACS buffer (PBS-CMF pH 7.2+3% FBS+0.1% sodium azide) and $2.5 \times 10^5$ cells in 50 µl buffer were added to each well in 96-well V-bottom plates (Corning catalog number 3894). Biotinylated CP13E10 antibody diluted to 1.5 µg/mL in FACS buffer was mixed with varying concentrations of the anti-CDCP1 CP13E10 variants or parental (WT) CP13E10 antibody as the positive control, and the samples were added to the plate containing cells and incubated on ice for one hour. Next, the cells were washed twice with FACS buffer. Streptavidin-PE (Invitrogen/eBioscience catalog number 12-4317-87) diluted 1:200 was added and incubated for 30 minutes at room temperature. The cells were washed twice with FACS buffer and were fixed on ice for 15 minutes by adding 100 µl of BD Cytofix (BD Biosciences catalog number 554655) to each well. The cells were washed twice with FACS buffer. Fluorescence intensity was determined using BD FACS CANTO II and the results are shown in FIG. 5. Incorporation of the CDRH3 point mutation V(H97)E into the CP13E10-34 variant harboring Y(H100) H, W(H100C)H, Y(H100H)H restored CDCP1 binding properties of this variant CP13E10-54 to that of the parental CP13E10 antibody (FIG. 5). These data demonstrate that incorporation of V(H97)E into heavy chain CDR3 restored CDCP1 binding properties of this variant CP13E10-54 to that of the parental wild-type CP13E10 antibody. That is, CP13E10-54 variant equally competed with the biotinylated reporter anti-CDCP1 CP13E10 antibody for binding to CDCP1.

The CDRL3 mutations N(L93)Q and V(L94)E were then introduced into the CP13E10-54 variant to generate CP13E10-54HC-89LC and binding kinetics for recombinant CDCP1 extra-cellular domain (ECD) protein was determined by surface plasmon resonance. Specifically, the binding kinetics of anti-CDCP1 antibodies against recombinant human, cynomologus monkey and mouse CDCP1-ECD were determined using surface plasmon resonance (SPR) and a Biacore T200 instrument (GE Healthcare). An anti-human IgG antibody was amine coupled onto a CM5 carboxymethylated dextran sensor chip surface (GE Healthcare), using the manufacturer's recommendations, to densities of approximately 10,000-13,000 response units (RU). Each anti-CDCP1 antibody was diluted to 0.5 pg/mL in 10 mM HEPES pH 7.4, 0.15 M NaCl, 3 mM EDTA, 0.05% P-20 (HBS-EP+) and captured for about 20-23 seconds at a flow rate of 10 µL/min. Four 3-fold dilutions of CDCP1-ECD, ranging from 1,800 nM to 66.7 nM, were injected at a flow rate of 50 µLs/minute, associated for 54 seconds, and dissociated for 90 seconds. The sensorchip surface was regenerated with three 30 second pulses of 3M $MgCl_2$ at a flow rate of 50 µL/minute. All injections used HBS-EP+ as both the running and sample buffer and were performed at 25° C. with a data collection rate of 1 Hz. Sensorgrams were double referenced by using both a control surface and buffer injections. Rate constants were determined by fitting the data to a 1:1 model with Biacore T200 evaluation software v3.0 and the equation $K_D=k_d/k_a$. CP13E10-54HC-89LC antibody exhibited 4-fold and 3-fold higher affinity to human and cynomolgus monkey CDCP1-ECD, respectively, relative to parental CP13E10 antibody and >11-fold higher affinity to human CDCP1 versus the CP13E10-34 variant (FIG. 6). Further, the affinity of CP13E10-54HC-89LC for mouse CDCP1-ECD marginally increased (~1.6-fold) relative to the parental CP13E10 antibody and significantly increased (20-fold) versus the CP13E10-34 variant FIG. 6. That is, in addition to V(H97)E amino acid change that augments binding to CDCP1, incorporation of N(L93)Q and V(L94)E into CP13E10-54 CDRL3 to generate CP13E10-54HC-89LC further increased affinity to human, cynomolgus monkey and mouse CDCP1. Furthermore, the favorable hydrophobicity reduction observed via incorporation of Y(H100)H, W(H100C)H, Y(H100H)H) into mutations into CP13E10-WT antibody was maintained for CP13E10-54HC-89LC (FIG. 3-4).

The CP13E10-54HC-89LC antibody heavy and light chain variable domains are set forth in SEQ ID NOS. 26 and 30, respectively, and the heavy and light chains are set forth in SEQ ID NOS. 29 and 32, respectively. In another instance, V(H97)E, H(H100C)Q, L(H100D)V, L(H100E)Y, D(H100F)N mutations were incorporated into CP13E10-34 antibody to generate CP13E10-291 that resulted in this variant exhibiting a significant >200-fold increase in affinity to human CDCP1 and 14-fold increase to mouse CDCP1 relative to CP13E10-34 as determined by SPR (FIG. 6). Additionally, CP13E10-291 variant displays >70-fold increase in binding to cynomolgus monkey CDCP1 relative to CP13E10-WT antibody as shown in FIG. 6. The CP13E10-291 antibody heavy and light chain variable domains are set forth in SEQ ID NOS. 44 and 11, respectively, and the heavy and light chains are set forth in SEQ ID NOS. 46 and 17, respectively.

CP13E10-54HC-89LC antibody heavy chain variable region (VH) is completely IGHV1-46*01 (DP-7) germline with exclusion of CDRH3, however the light chain variable region (VL) contains three non-germline framework residues. To reduce risk of immunogenicity, IGKV146 (DPK23) was selected for germlining the VL frameworks. Furthermore, using the IGKV146 (IGKV3D-7*01, DPK23) germline substitutions removes an in silico predicted T-cell epitope in the VL framework 3 by incorporating the E(L79)Q germline change. The three substitutions based on IGKV146 germline (L(L4)M, R(L39)K, E(L79)Q) were incorporated into CP13E10-54HC-89LC to generate the CP13E10-54HC-89LCv1 antibody. CP13E10-54HC-89LCv1 retains equivalent CDCP1 binding properties relative to CP13E10-54HC-89LC as demonstrated by results obtained using a competition ELISA assay.

Specifically, CDCP1 binding properties were assessed for the germlined antibody variant CP13E10-54HC-89LCv1 using a competition ELISA with biotinylated CP13E10-54HC-89LC antibody as the reporter antibody to determine if the germlined variant could effectively compete with CP13E10-54HC-89LC antibody for binding to CDCP1 antigen. For this competition ELISA assay, the CP13E10-54HC-89LC reporter antibody was biotinylated using EZ-link Sulfo-NHS-Biotin Sulfosuccinimidobiotin (Thermo/Pierce, catalog number 21217) at a molar coupling ratio of 20:1 according to the manufacturer's protocols. Protein for this assay was generated by transiently transfecting DNA encoding the anti-CP13E10 variants into HEK-293 cells and resultant protein was Protein-A affinity purified and buffer exchanged into PBS-CMF pH 7.2 using G-25 columns. For this competition ELISA procedure, a 96-well plate (Costar catalog #3590) was coated with human extracellular domain recombinant human CDCP1 protein (CDCP1-ECD). The CDCP1-ECD protein was diluted to 1 μg/ml in PBS-CMF pH 7.2, 100 μl was added to each well of the plate, and the plate was incubated overnight at 4° C. The contents of the plate were discarded and then the plate was blocked with PBS-CMF pH7.2+0.02% casein for 3 hours at room temperature. Biotinylated CP13E10-54HC-89LC antibody at 20 ng/mL in PBS+0.5% BSA+0.02% tween-20 was mixed with varying concentrations of the anti-CDCP1 CP13E10 variants or parental (WT) CP13E10 antibody as the positive control, and the samples were added to the CDCP1 coated and blocked plate and incubated at room temperature for 2 hours. The wells were washed four times with PBS-CMF pH7.2+0.03% tween-20. Streptavidin-HRP (catalog #7100-05, Southern Biotech, (Birmingham, Alabama) diluted 1:10,000 was added and incubated for 30 minutes at room temperature. The wells were washed four times with PBS-CMF pH 7.2+0.03% tween-20 and then TMB (BioFx) was added. The reaction developed for 5 to 10 minutes and was then quenched with 0.18 N $H_2SO_4$. The absorbance at 450 nm was determined and the results are shown in FIG. 7.

Incorporating three amino acid substitutions based on IGKV146 germline (L(L4)M, R(L39)K, E(L79)Q) into the CP13E10-54HC-89LC variable light chain framework region resulted in CP13E10-54HC-89LCv1 and this variant completely retains human CDCP1 binding properties as detected in the completion ELISA analysis (FIG. 7). Additionally, the binding kinetics of germlined CP13E10-54HC-89LCv1 against recombinant human, cynomologus monkey and mouse CDCP1-ECD were determined using the surface plasmon resonance (SPR) method previously described and they were identical to the CP13E10-54HC-89LC variant further demonstrating that VL germline substitutions did not alter CDCP1 binding properties (FIG. 6).

Binding of CP13E10-54HC-89LCv1 to CDCP1 expressed on the surface of PC3 prostate cancer cells was evaluated using fluorescence-activated cell sorting (FACS). For this method, PC3 cells were detached from flasks using cell dissociation buffer (Gibco, catalog number 13151-014), washed once with ice-cold FACS buffer (PBS-CMF supplemented with 3% FBS and 0.1% w/v $NaN_3$, ice-cold) and $2.5 \times 10^5$ cells in 50 μl FACS buffer were added to each well in 96-well V-bottom plates (Corning catalog number 3894). Anti-CDCP1 antibodies were serially diluted in FACS buffer and 50 μL was added to each well containing PC3 cells and incubated on ice for 1 hour. Next, the 96-well plates were centrifuged at 1300 rpm for 4 minutes, supernatants discarded, and cells were washed twice with 150 μL/well FACS buffer. The secondary detection antibody R-PE-conjugated goat anti-human IgG Fc (Jackson Immuno Research Labs, Catalog #109-115-098) was diluted 1:200 in FACS buffer and 100 μL was added to each well and incubated for 30 minutes on ice. Cells were washed twice as specified above, 100 μL BD Cytofix (BD Biosciences #554655) was added to each well, and cells were incubated on ice for 15 minutes. Cells were washed twice as noted above and then resuspended in 100 μL FACS buffer and fluorescence intensity was determined using BD FACS CANTO II. These results demonstrate that germlined CP13E10-54HC-89LCv1 binding to CDCP1 expressed on the surface of PC3 prostate cancer cells using fluorescence-activated cell sorting (FACS) is indistinguishable from CP13E10-54HC-89LC (FIG. 8). The CP13E10-54HC-89LCv1 antibody heavy and light chain variable domains are set forth in SEQ ID NOS. 26 and 36, respectively, and the heavy and light chains are set forth in SEQ ID NOS. 29 and 37, respectively.

CP13E10-54HC-89LCv1 antibody contains a putative isomerization sequence liability in CDRH3, specifically D(H95)-G(H96). Incorporation of the G(H96)A mutation into CP13E10-54HC-89LCv1 generated variant CP13E10-54HCv13-89LCv1 that removes the potential isomerization sequence liability but retains CDCP1 binding properties in the competition ELISA relative to CP13E10-54HC-89LCv1 (FIG. 9).

Example 8: Engineering Antibodies to Enable Site-Specific Conjugation of Linker-Payloads Conjugation Via Cysteine Methods for preparing anti-CDCP1 antibodies for site-specific conjugation to various linker-payloads through reactive cysteine residues were generally performed as described in PCT International Publication No. WO2013/093809. One or more residues on either the heavy chain, such as position 290 according to the EU numbering of Kabat, or the light chain, such as 183 according to the numbering of Kabat, or were altered to a cysteine (C) residue by site directed mutagenesis. In some aspects, position K290 (EU numbering of Kabat or 307 using numbering of Kabat) in the human IgG1 heavy chain constant region of the anti-CDCP1 antibody variants were substituted with a reactive cysteine (C) to enable site-specific conjugation: CP13E10-183/290 HC (SEQ ID NO. 19), CP13E10-54HC-89LC-183/290 HC (SEQ ID NO. 33) and CP13E10-54HCv13-89LCv1-183/290 HC (SEQ ID NO. 42). In other aspects, residue K183 in the human Kappa light chain constant region was substituted to a reactive cysteine (C) to enable site-specific conjugation: CP13E10-183/290 LC (SEQ ID NO. 21), CP13E10-54HC-89LC-183/290 LC (SEQ ID NO. 34) and CP13E10-54HC-89LCv1-183/290 LC (SEQ ID NO. 38). Proteins for conjugation were produced by stable transfection of CHO-K1 SV 10E9 host cells with vectors encoding antibodies engineered with reactive cysteines. The resulting stable CHO pools were cultured, 11% DTNB (Ellman's Reagent, 5,5'-dithio-bis-[2-nitrobenzoic acid]) was added on day 10, and conditioned medium was harvested on day 12. The resultant conditioned medium was purified using a two column process: Protein-A MabSelect SuRe LX platform followed by TMAE (50 mM HEPES 65 mM NaCl pH 7.0) to remove HMMS process related impurities.

Conjugation Via Transglutaminase (TG)

Anti-CDCP1 antibodies were produced having human IgG1 constant regions engineered with an acyl donor glutamine-containing transglutaminase ("Q") tag inserted after threonine (T) position 135 and before serine (S) position 136 according to Eu numbering of Kabat for conjugation to various linker-payloads. Methods for preparing CDCP1 antibodies for site-specific conjugation through glutamine residues were generally performed as described in PCT International Publication WO2012/059882. In some aspects, an H7C-glutamine tag LLQG (SEQ ID NO: 91) was engineered into the anti-CDCP1 antibody after position T135 and before position S136 within the human $IgG_1$-$CH_1$ region in addition to substitution of N297A (EU numbering of Kabat) that allows for efficient transglutaminase mediated site-specific conjugation of endogenous glutamine (Q) at position 295 (EU numbering of Kabat) to enable a DAR 4 site specifically conjugated ADC. The antibodies were further altered to increase specificity of transglutaminase mediated conjugation to the engineered H7C-glutamine tag and endogenous glutamine (Q) at position 295 by substituting the lysine (K) amino acid at position 222 (EU numbering of Kabat) on the heavy chain with an arginine (R). These H7C-LLQG glutamine tag, N297A and K222R engineered anti-CDCP1 heavy chains CP13E10-H7C-K222R-N297A HC, CP13E10-54HC-89LC-H7C-K222R-N297A HC and CP13E10-54HCv13-89LCv1-H7C-K222R-N297A HC are set forth in SEQ ID NOS. 25, 35 and 43, respectively. Proteins for conjugation were produced by stable transfection of CHO-K1 SV 10E9 host cells with vectors encoding antibodies engineered with glutamine-containing transglutaminase ("Q") tag and harboring the N297A and K222R mutations. The resulting stable CHO pools were cultured and conditioned medium was harvested on day 12. The resultant conditioned medium was purified using a two column process: Protein-A MabSelect SuRe LX platform followed by TMAE (50 mM HEPES 65 mM NaCl pH 7.0) to remove HMMS process related impurities.

Example 9: Crystalographic Identification of CDCP1 Epitope of Fab Fragment of Anti-CDCP1 Antibody CP13E10-54HC-89LC The complex of human CDCP1 extra-cellular domain (ECD) and antibody CP13E10-54HC-89LC Fab was formed using a molar ratio of 1:1.1, concentrated to 15.2 mg/mL, and crystallized at 18° C. using the hanging drop technique with a 1:1 well solution to protein solution ratio. The crystals were obtained using 20% PEG 6K, 200 mM Magnesium Chloride, 200 mM Sodium Chloride, 100 mM Sodium Acetate pH 5.0 as a precipitant. For data collection, crystals were cryo-protected in reservoir solution with 20% ethylene glycol. Crystallographic data to 2.5 Å resolution were collected using synchrotron light source at the APS in Argonne, IL. Crystals belonged to the P $2_1$ $2_1$ $2_1$ space group with unit-cell parameters a=3Neg Å b=130.3 Å c=169.9 Å. The data were processed and scaled using autoPROC. The structure was solved by molecular replacement, using the structure of a proprietary antibody whose structure is not disclosed herein. The model of the entire complex was rebuilt and refined using the COOT and autoBuster programs. The final refined model had Rwork and Rfree values of 20.4% and 21.6%, respectively.

Epitope and Paratope Analysis

Figure 10:
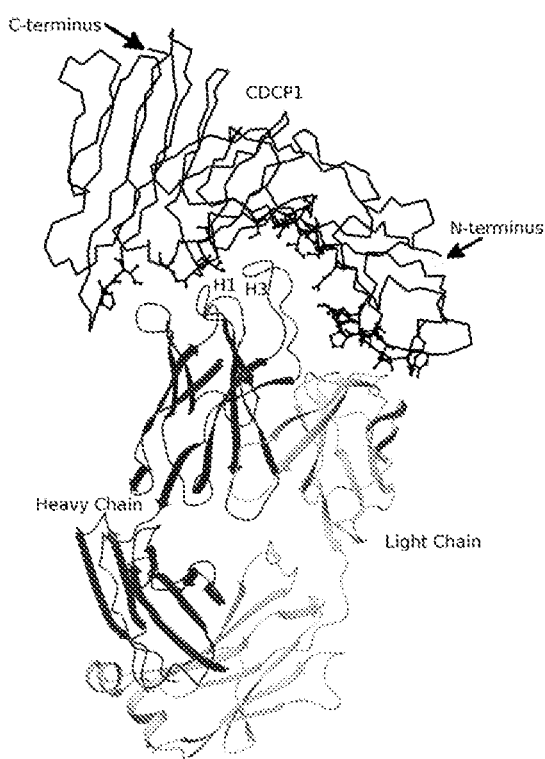
FIG. 10 provides an overview of the complex formed by the CDCP1 extracellular domain (ECD) and the Fab fragment of antibody CP13E10-54HC-89LC. The C-alpha trace at the top of the figure shows the position of CDCP1, with termini labeled. Ball and stick representation indicates antigen amino acid residues having at least one heavy atom (non-hydrogen) within 4 Å of a heavy atom of an amino acid residue of the antibody. Ribbon representation indicates the antibody, with black on the left showing the Fab heavy chain, and light gray on the right showing the Fab light chain. Labels indicate the position of the CDRH1 and CDRH3).
Figure 11:
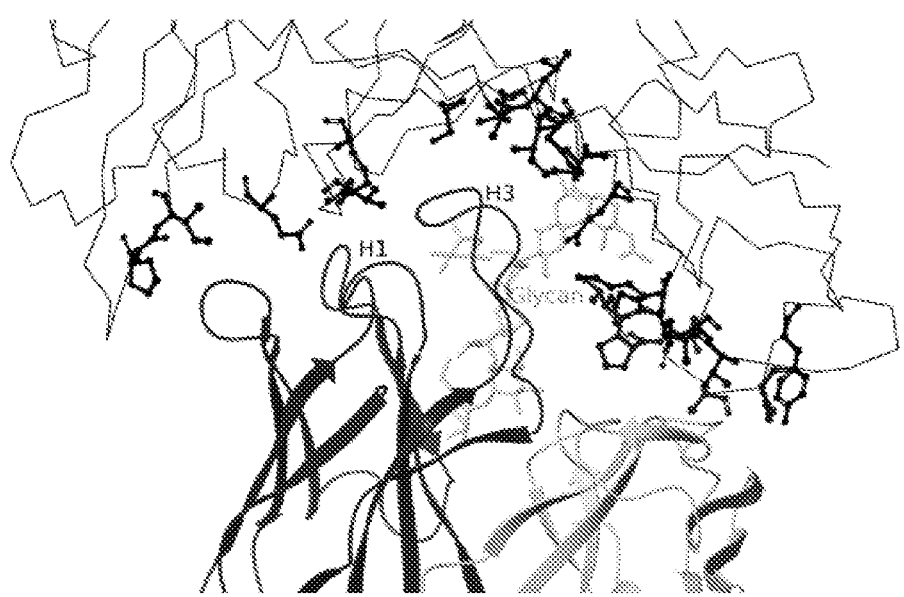
FIG. 11 is an antigen-centric close-up of the interface between CDCP1 ECD and the Fab fragment of antibody CP13E10-54HC-89LC. The orientation is the same as in FIG. 10. The light gray sticks indicate the glycan attached to Asn122 of CDCP1. Other renderings are the same as indicated in the description of FIG. 10.

The asymmetric unit contained a single copy of the Fab/antigen complex. FIG. 10-11 show renderings of the antigen and antibody residues making contacts of 4.0 Å or less. Tables 4-5 enumerate the corresponding epitope/paratope contacts involving the antibody complementarity determining regions (CDRs). Together, FIGS. 10-14 illustrate the positions of each CDR relative to the antigen; all six CDRs make antigen contacts. In addition, framework residues H71, H73, H74, L49, and L67 also contact CDCP1, with the first two having side chains that H-bond with the side chain of CDCP1 Glu242.

TABLE 4

Contacts <4.0 Å between CDCP1 ECD and light chain complementarity determining region (CDR) of Fab CP13E10-54HC-89LC

| Antibody Residue | Antigen Residue(s) | Primary Contact Type |
| --- | --- | --- |
| Ser(L28) | Ala53 | H-bond |
| Val(L29) | Ala53 | Van Der Waals |
| Gly (L30) | Ala53, Pro55 | Van Der Waals |
| Ser(L31) | Tyr57, Thr66 | Van Der Waals |
| Tyr(L32) | Thr48, Pro49, Thr50 | Van Der Waals |
| Asp(L50) | Leu46 | Van Der Waals |
| Asp(L50) | Thr66 | H-bond |
| Ser(L52) | Thr66 | H-bond |
| Asn(L53) | Thr66 | H-bond |
| Asn(L53) | Met67 | Van Der Waals |
| Arg(L91) | Leu46, Pro49 | Van Der Waals |
| Arg(L91) | Gly47 | H-bond |
| Ala(L92) | Pro49 | Van Der Waals |
| Gln(L94) | Asn122 glycan | Van Der Waals |

TABLE 5

Contacts <4.0 Å between CDCP1 ECD and heavy chain complementarity determining region (CDR) of Fab CP13E10-54HC-89LC

| Antibody Residue | Antigen Residue(s) | Main Contact Type |
|---|---|---|
| Thr(H28) | Val171 | Van Der Waals |
| Thr(H30) | Arg173 | Dipole-Dipole |
| Pro(H52A) | Glu242 | H-bond |
| Ser(H53) | Arg173 | H-bond |
| Ser(H53) | Glu242 | Van Der Waals |
| Gly(H54) | Glu242 | H-bond |
| Ser(H58) | Asn122 glycan | H-bond |
| Tyr(H59) | Asn122 glycan | H-bond |
| Gln(H61) | Asn122 glycan | Van Der Waals |
| Gln(H64) | Asn122 glycan | H-bond |
| Glu(H97) | Lys45 | H-bond |
| Glu(H97) | Glu92 | Van Der Waals |
| His(H100) | Glu92, Ser162 | H-bond |
| His(H100) | Ile126 | Van Der Waals |
| Phe(H100A) | Thr124, Thr160, Ser162, Ala195, Leu196, His197 | Van Der Waals |
| Asp(H100B) | Arg173 | H-bond |
| Leu(H100D) | Thr160, His197 | Van Der Waals |
| Leu(H100E) | Asn122 glycan | Van Der Waals |
| Asp(H100F) | Asn122 glycan | H-bond |
| Tyr(H100G) | Gly47, Thr48, Asn122 glycan | Van Der Waals |
| His(H100H) | Asn122 glycan | H-bond |

Figure 12:
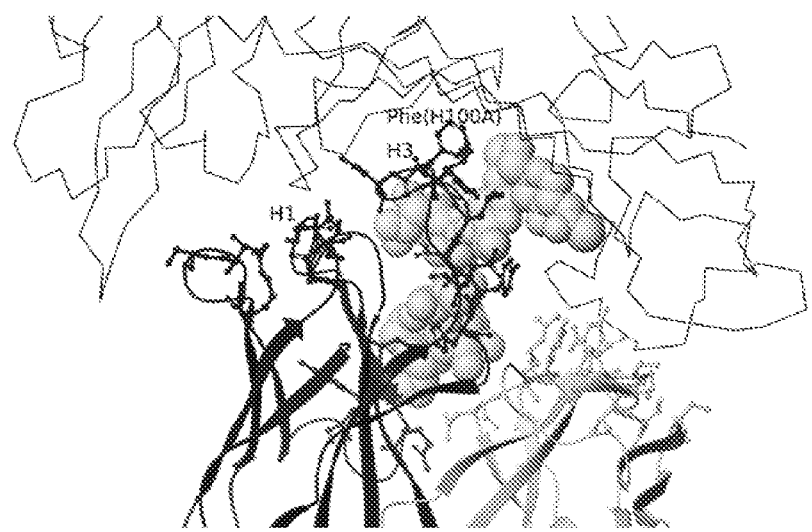
FIG. 12 shows an antibody-centric close-up of the interface between CDCP1 ECD and the Fab fragment of antibody CP13E10-54HC-89LC. The orientation is the same as in FIG. 10. The light gray space filling model indicates the glycan attached to Asn122 of CDCP1. The ball and stick renderings indicate antibody residues having at least one heavy atom within 4 Å of the heavy atom of an amino acid residue of CDCP1. Without wishing to be bound by any particular theory, the labeled residue Phe(H100A) appears to play a key role in making Van Der Waals contacts with six antigen residues (see Table 5).
Figure 13:
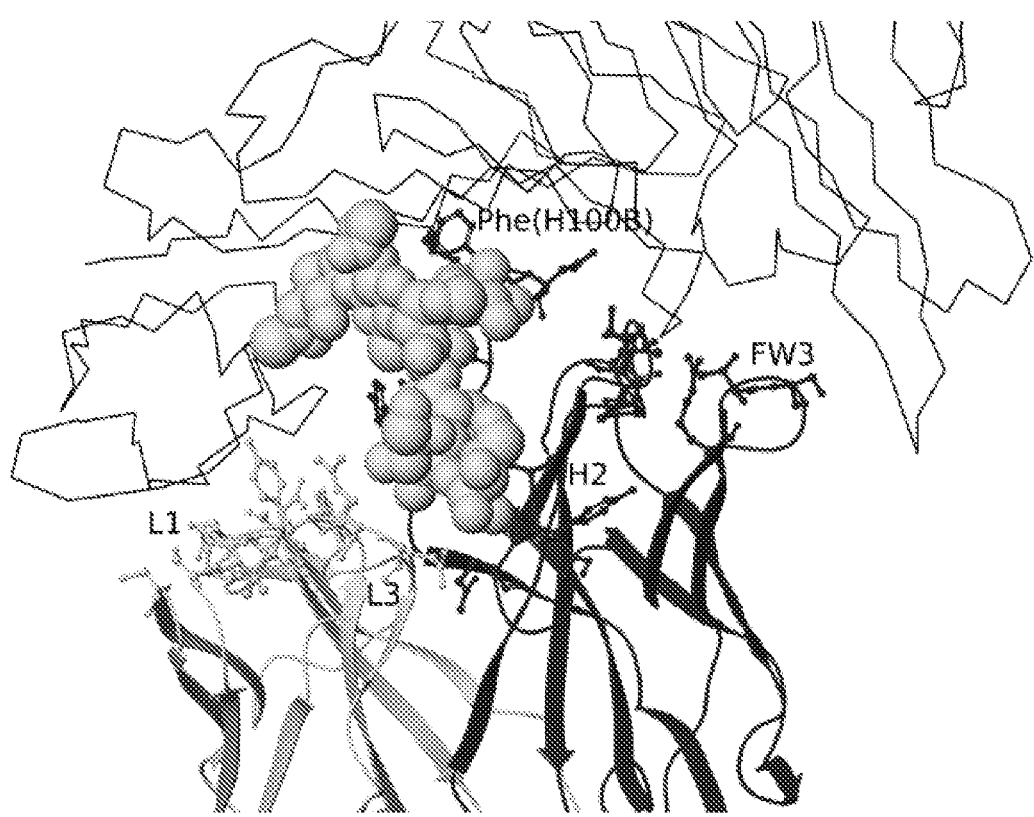
FIG. 13 shows a reverse close-up of the interface between CDCP1 ECD and the Fab fragment of antibody CP13E10-54HC-89LC. Relative to FIG. 12, this view reflects rotation of 180° about an axis parallel to the vertical page axis. Renderings are the same as in FIG. 12. The positions of CDRL1, CDRL3, and CDRH2 are labeled, as is a turn in framework 3 (FW3) of the heavy chain which makes contact with the antigen. CDRL2 is behind CDRL3 in this figure and so is not shown (see FIG. 14 for a different view showing CDRL2).
Figure 14:
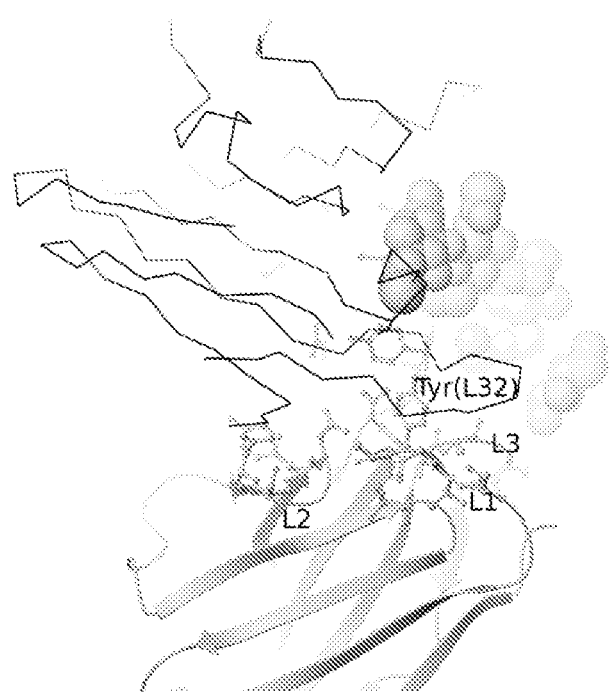
FIG. 14 depicts a reverse close-up of the interface between CDCP1 ECD and the VL of antibody CP13E10-54HC-89LC. Relative to FIG. 13, this view reflects rotation of 180° about an axis parallel to the vertical page axis. Renderings are the same as in FIG. 12. The positions of CDRL1, CDRL2, and CDRL3 are labeled. Amino acid residues 46-54 (numbered with reference to SEQ ID NO:90) of CDCP1 wrap around Tyr(L32) of CDRL1.
Figure 15A:
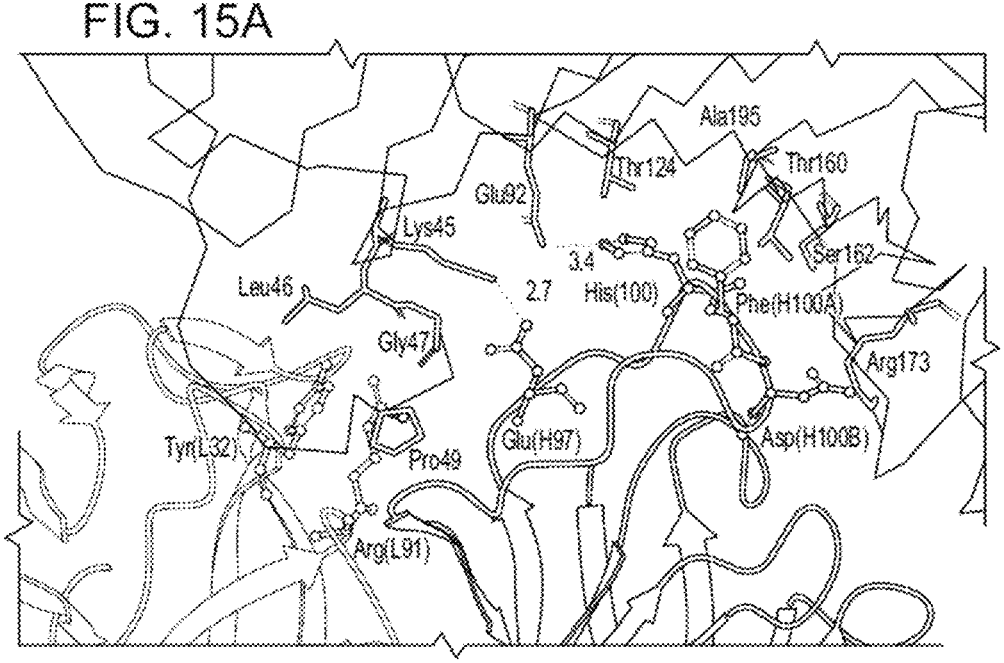
FIG. 15A shows a subset of interactions between CDCP1 ECD and a Fab of antibody CP13E10-54HC-89LC. The stick and C-alpha traces indicate CDCP1, and the ribbon and ball-and-stick representations indicate the antibody. Key amino acid residues are labeled, with only the antibody labels incorporating parentheses. Dotted lines indicate certain hydrogen bonds or salt bridges, with distance labels in Angstroms.
Figure 15B:
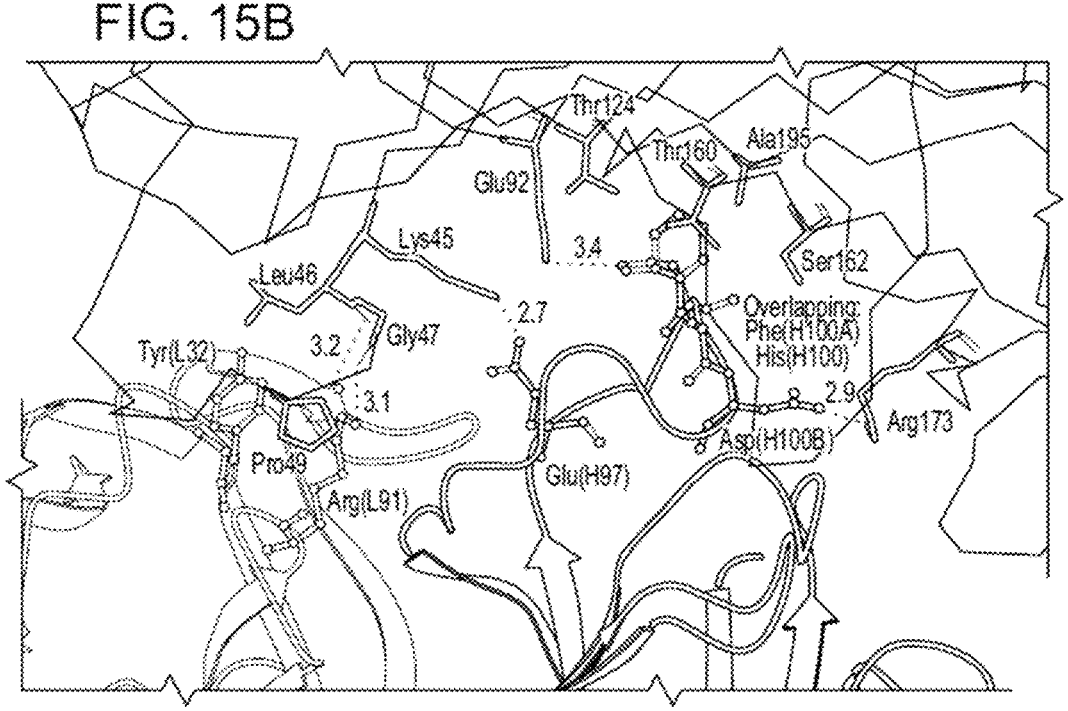
FIG. 15B shows a subset of interactions between CDCP1 ECD and a Fab of antibody CP13E10-54HC-89LC. This is an alternate view of the same model shown in FIG. 15A, with different distances indicated. Amino acid residues 46-54 (numbered with reference to SEQ ID NO:90) of CDCP1 wrap around Tyr(L32) of CDRL1.

The structure revealed an N-linked glycan attached to Asn122 of the antigen (see space filling representation in FIG. 12-13). Both antibody chains make contacts with the glycan. FIGS. 15A and 15B illustrate detailed features of the paratope/epitope interaction.

As is apparent in FIG. 10, the antigen adopts a crescent shape, and the antibody is positioned on the inside of the crescent. FIG. 12 shows that Phe(H100A) is near the center of the interface, making contacts with 6 CDCP1 residues (Table 5), more than any other CDR residue. The Phe side chain fills a pocket whose center is approximately identified by the backbone of CDCP1 Leu196, and whose border is approximately defined by the side chains of CDCP1 residues Thr124, Thr160, Ser162, Ala195, and His197. On either side of the Phe are charge interactions (see FIGS. 15A and 15B), such as between His(H100)/Glu92, Glu(H97)/Lys45, Asp (H100B)/Arg173, and Arg(H71)/Glu242. An additional residue making multiple close contacts is Tyr(L32), which has the Leu46-Pro55 region of CDCP1 wrapped around its phenol moiety. Arg(L91) interacts with the backbone of the same region. Binding of the antibody covers approximately 1800 Å$^2$ of the antigen surface (including the glycan attached to Asn122).

Example 10: Internalization of CP13E10-54HC-89LC

Antibody internalization is a critical characteristic for delivery of an ADC cytotoxic payload to the interior of a tumor cell. Therefore, an assessment of CDCP1 internalization induced by antibody CP13E10-54HC-89LC was conducted using the CDCP1-expressing human prostate cancer cell line, PC3.

To accomplish this, antibody CP13E10-54HC-89LC was conjugated to Alexa Fluor 647™ dye using the Invitrogen™ SAIVI™ Alexa Fluor™ 647 Antibody/Protein 1 mg-Labeling Kit (ThermoFisher Scientific) and purified according to manufacturer's instructions. PC3 cells in tissue culture plates at a density of ~0.2-0.5×10$^5$ cells/cm$^2$ were exposed to 2 μg/mL of purified AlexaFluor 647™-conjugated antibody CP13E10-54HC-89LC in growth medium (RPMI-1640 [Gibco], 10% heat-inactivated fetal bovine serum (Gibco) and incubated at 37° C. for intervals of time between 5 to 120 minutes. At the end incubation, plates were cooled on ice, medium was aspirated, and cells were washed with an excess of ice-cold phosphate buffer saline, Ca$^{2+}$Mg$^{2+}$ free (PBS [Gibco]). Cells were then detached with 0.25% Trypsin-EDTA (Gibco) followed by neutralization of trypsin with ice-cold growth medium. Detached cells were pelleted by centrifugation, rinsed once in ice-cold PBS, and a final pellet was collected and fixed in 4% paraformaldehyde (PFA) for 20 min at 4° C. After this incubation, PFA was removed by a washing with PBS.

Fixed samples were analyzed with an Amnis ImageStream® X Mark II (EMD Millipore) imaging cytometer, using the 40× objective at low speed/high sensitivity settings. The fluorescence signal of Alexa Fluor 647™ was detected in Ch11 with excitation/emission settings of the 642 nm laser. The raw image data were processed using IDEAS® software. Single cells were gated based on Area M01 (Brightfield) vs. Aspect ratio M01 (Brightfield) dot plot. Cells in focus were then gated based on Gradient RMS_Brightfield histogram. Digital masking for image segmentation of total, membrane, and internal compartments was employed to determine relative signal intensities of Alexa Fluor 647™ in each of those compartments for every analyzed cell, and expressed as medians for the cell population in a given sample. The quantitative data for each experiment were then exported to Microsoft® Excel and the ratios between the values for internal and membrane compartments were calculated and plotted versus time. The endocytic internalization rate constant, Ke, was determined based on published procedures (Wiley et al., 1982, J. Biol. Chem. 257: 4222-4229) using GraphPad Prism software to obtain the slope of the best fit linear regression line for the initial linear phase of internalization.

Figure 16:
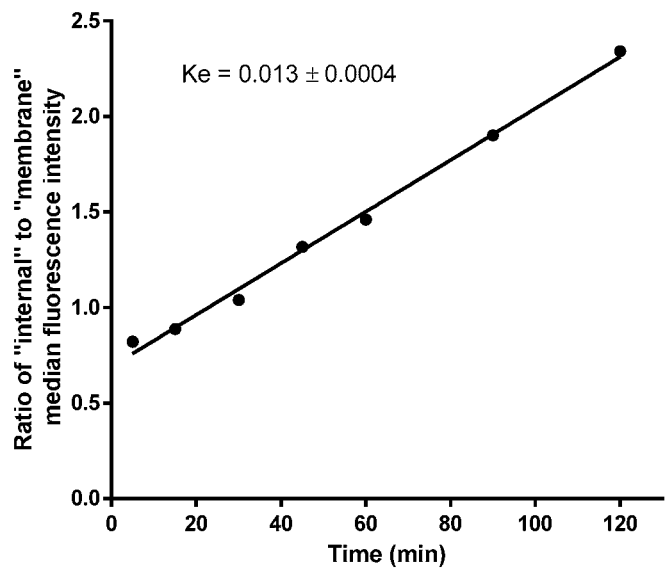
FIG. 16 shows a representative analysis of the time-dependent increase in the ratio of median fluorescence intensity values of the signal detected in "membrane" and "internal" cell compartments. The slope of the regression line represents the internalization rate (Ke).

As shown in FIG. 16, the CP13E10-54HC-89LC-induced target internalization rate (Ke) was 0.013±0.001 min$^{-1}$ in the PC3 cell line. The positive Ke indicates that the antibody was effectively internalized from the cell membrane into cells. Under these conditions neither antibody concentration nor relative cell density were found to have any affect the internalization rate.

Figure 17:
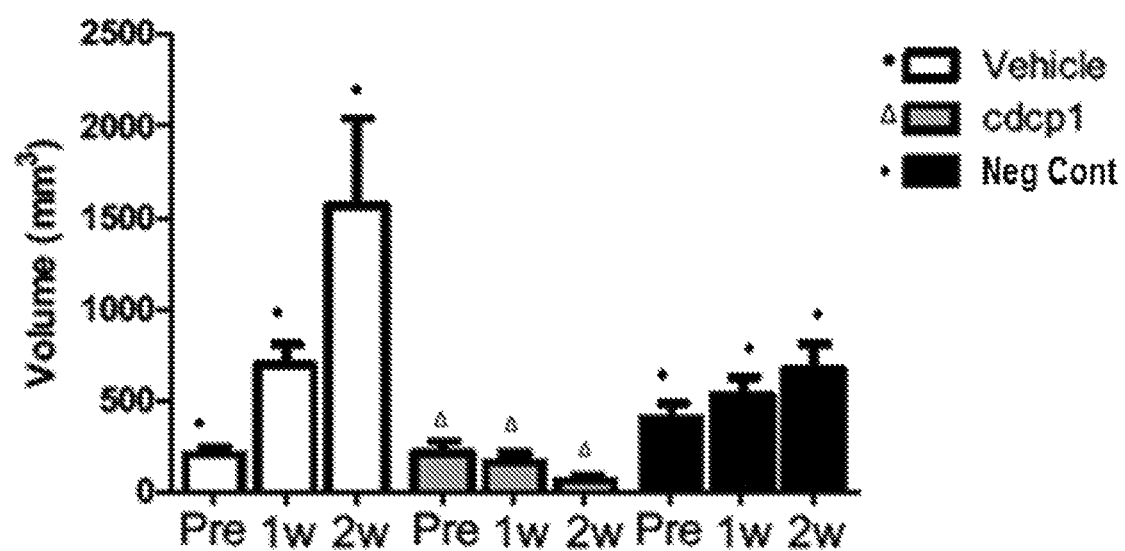
FIG. 17 shows a bar graph showing that CDCP1-ADC (CP13E10-SS3-LP15) blocked tumor growth in NSCLC PDX Model.

Example 11: Evaluation of CDCP1 Antibodies on CDCP1 Activity and Cellular Processes Since it was observed that there were high levels of CDCP1 protein expression and tyrosine phosphorylation in NSCLC cell lines and lung tissues, this informed the approach of using Patient-Derived Xenografts (PDX) of lung tumors to test the efficacy of CDCP1 ADCs. Lung tumors (<200 mm$^3$) of NSCLC cells were established in mice over a 21-day pre-treatment period, and these tumors had a high expression of CDCP1 protein. After 21 days, four treatments were delivered spaced four days apart. The tumor masses of vehicle-treated mice progressed steadily, reaching maximum size within 12 days (FIG. 17). In contrast, tumor growth was rapidly controlled by CDCP1-ADC (CP13E10-SS3-LP15) treatment, and there was no indication of detectable disease by day 32 of treatment. There was some efficacy with the negative ADC (linked to negative control antibody), which was not unexpected. The main finding was that the CDCP1-ADC successfully blocked the growth of the lung tumor, indicating along with other data that this antibody could be further refined as a lead candidate antibody. Thus, a variety of CDCP1-ADCs against multiple PDX tumor models were tested.

Figure 18A:
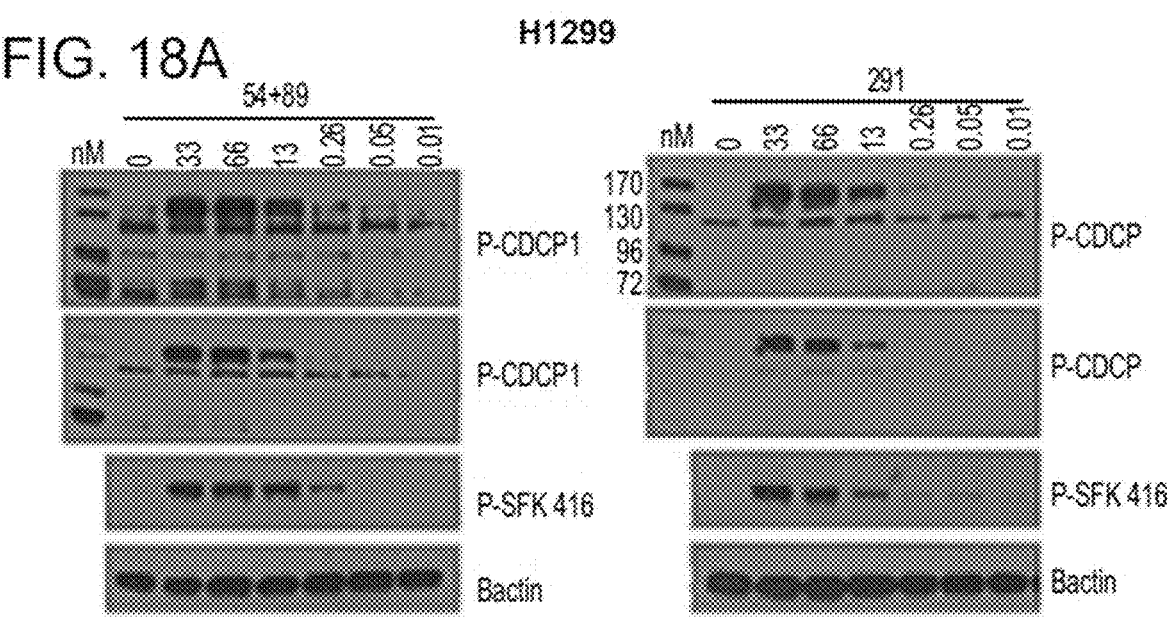
FIG. 18A-18C shows western blot images showing CDCP1 activation by short-term (5 min) treatment of cells with antibodies CP13E10-291 and CPE10-54HC-89LC in H1299 cells (FIG. 18A), MDA-MB-231 cells (FIG. 18B) and MCF10A cells (FIG. 18C).
Figure 18B:
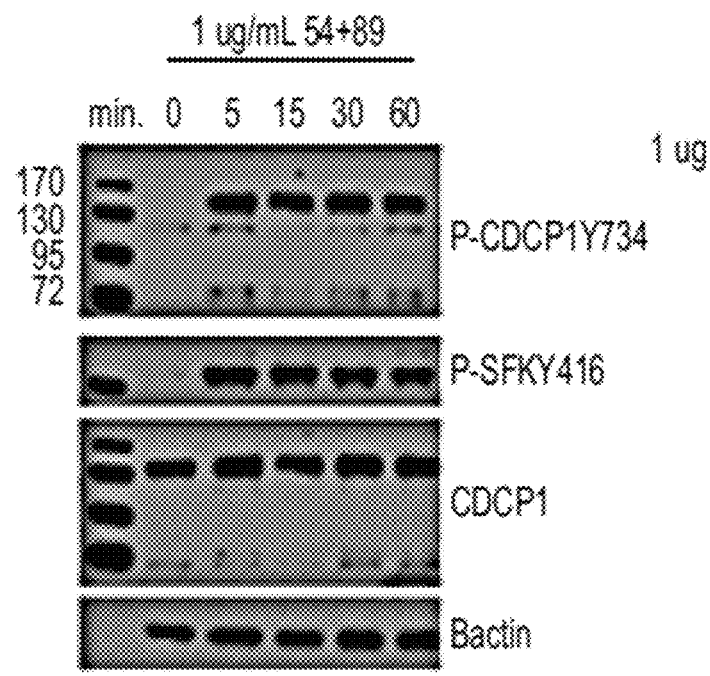
Figure 18C:
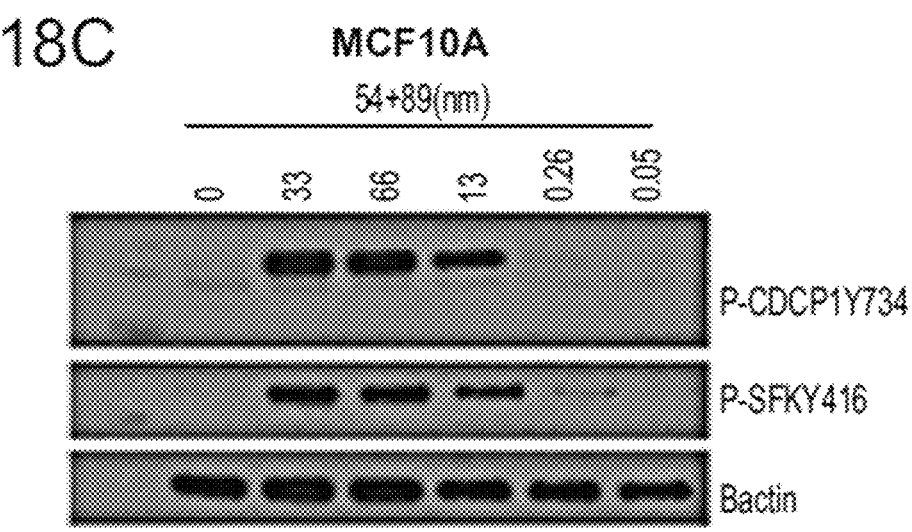
Figure 19A:
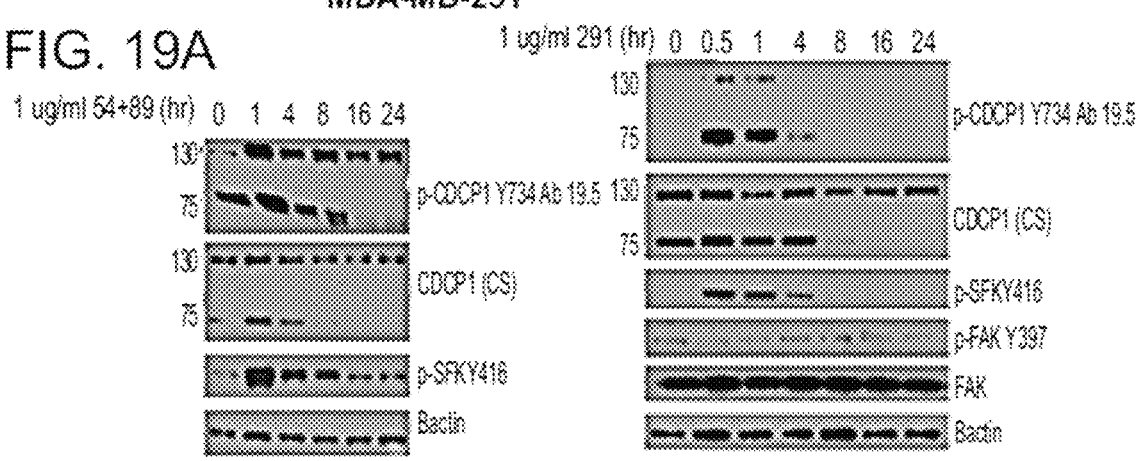
FIG. 19A-19B depicts western blot images showing CDCP1 degradation by prolonged treatment of breast cancer cells, MDA-MB-231 (FIG. 19A) and MDA-MB-468 (FIG. 19B) with antibodies CP13E10-291 and CPE10-54HC-89LC.
Figure 19B:
Figure 20:
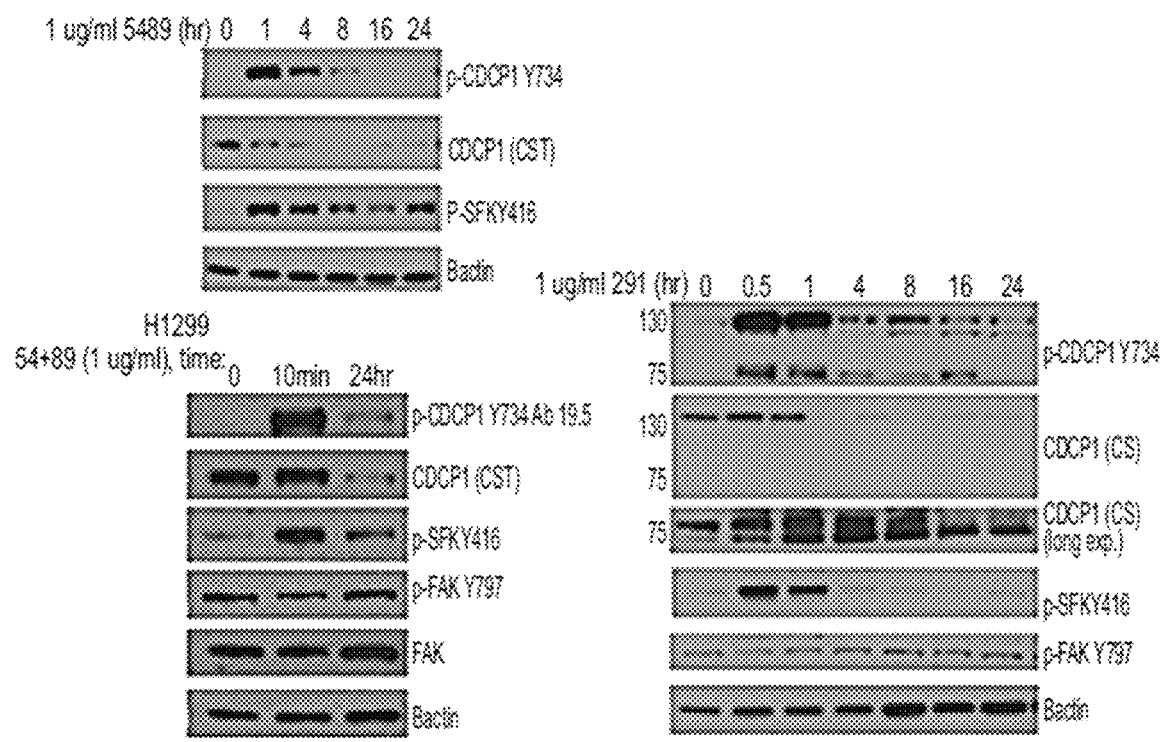
FIG. 20 shows western blot images showing CDCP1 degradation by prolonged treatment of H1299 cells with antibodies CP13E10-291 and CPE10-54HC-89LC, time-dependent decrease in CDCP1 expression and tyrosine phosphorylation, and loss of Src activation.

In a variety of experimental approaches, CDCP1 antibodies also were tested for their ability to activate CDCP1 and its downstream targets. Short-term treatment of cells with antibodies stimulated CDCP1 tyrosine phosphorylation as well as downstream phosphorylation of SFKs and PKCδ in several lung (H1299) and breast cancer (MDA-MB-231) cell lines and a normal breast epithelial (MCF10A) cell line (FIG. 18A-18C). In contrast, the prolonged treatment with CDCP1 antibodies caused a decrease in CDCP1 expression and phosphorylation, presumably due antibody-mediated internalization, and a reduction in downstream signaling, including a decrease in Src activation (FIGS. 19A-19B and FIG. 20).

Figure 21A:
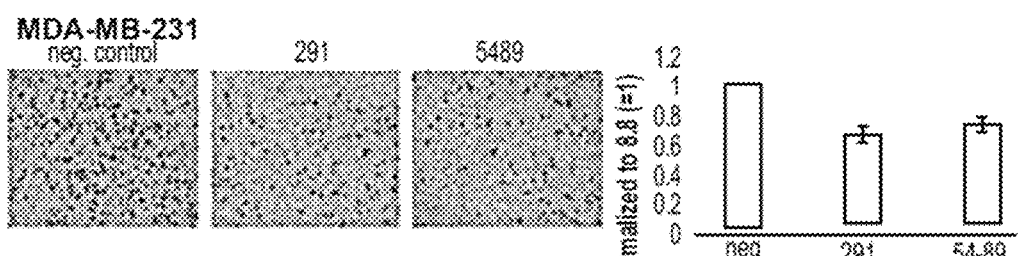
FIG. 21A-21B depicts immunohistochemical images and bar graphs showing that CDCP1 antibodies CP13E10-291 and CPE10-54HC-89LC reduce MDA-MB-231 cells (FIG. 21A) and H1299 cells (FIG. 21IB) migration.
Figure 21B:
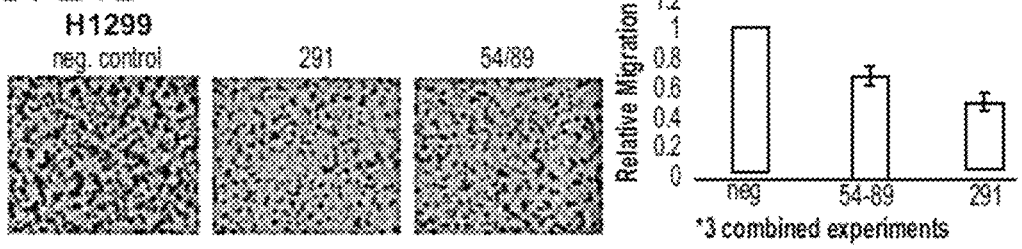

The effect of CDCP1 antibody treatment on cell migration and invasion was also tested due to the known positive role of CDCP1 in the regulation of these cellular processes. Surprisingly, the treatment of H1299 and MDA-MB-231 cells with several different CDCP1 antibodies produced a decrease in cell migration in a Transwell assay (FIG. 21A-21B) and a decrease in cell invasion in a three-dimensional tumor cell invasion assay (FIG. 22A-22B). These findings demonstrate CDCP1 activity and its downstream cellular processes.

The effect of CDCP1 antibody treatment on cell migration and invasion was also tested due to the known positive role of CDCP1 in the regulation of these cellular processes. Surprisingly, the treatment of H1299 and MDA-MB-231 cells with several different CDCP1 antibodies produced a decrease in cell migration in a Transwell assay and a decrease in cell invasion in a three-dimensional tumor cell invasion assay. The treatment of MDA-MB-231 cells with CDCP1 antibody also reduced spheroid size and invasion. In contrast, the treatment of MCF10A and DLD-1 cells with CDCP1 antibody produced an increase in cell migration. The opposite effects of CDCP1 antibodies on processes associated with tumor formation and growth may be due to the contrasting effects of CDCP1-activating antibodies on AKT activity in different cells, since AKT plays a positive role in migration in most cells. CDCP1-activating antibodies reduced the basal AKT phosphorylation (activity) in 1H1299 and H1373 cells, but had no effect on AKT in MCF10A, H1975, and HCT116 cells (FIG. 23A-23B). The contrasting effects of the antibodies on AKT activity in H1299 and MCF10A cells are consistent with their respective effects on cell invasion.

CDCP1 antibodies also reduced the basal AKT activity and AKT substrate phosphorylation in prostate cancer (PC3) cells (see FIG. 24A-24C). This inhibition was transient after an 80% reduction within 20 min, during prolonged antibody exposure the AKT phosphorylation returned towards the initial levels coincident with a reduction in the expression of CDCP1 protein expression. The reduction of AKT phosphorylation was blocked by the inhibition of Src, consistent with AKT inhibition being downstream of CDCP1 phosphorylation by Src. AKT activation downstream of G-protein-coupled receptor (IGF1, P2Y2, LPA, Muscarinic) activation was also blocked by CDCP1 activation.

Example 12: CDCP1 Signaling and Crosstalk with Other Proteins

To gain a greater understanding of the biological roles of CDCP1 and effects of CDCP1 antibody treatments, studies were performed to evaluate the involvement of CDCP1 on other downstream proteins and signaling pathways. FIG. 25 shows various western blot experiments of immunoprecipitation studies in which activating ("76") and non-activating ("24") antibodies were used to in the context of PC3 cells. Antibodies were added to intact cells (80 min, 4° C.). Negative control antibody and 24 (5 μg/ml); 76 (20 ng/m). Preferential CDCP1 partner binding was observed for: 76 mAb (activating): SRC, PPP4R2 and 24 mAb (non-activating): PARG1. Non-preferential binding to 76 and 24 was observed for β-Catenin, Transferrin Receptor, Importin-7.

Example 13: Binding of Antibodies CP13E10-54VH-89VL and CP13E10-54HC-89LCv1 to Human Cancer Cell Lines CP13E10-54HC-89LC and CP13E10-54HC-89LCv1 exhibited dose dependent binding to CDCP1 expressing cells as determined by flow cytometry. Binding was evaluated on three human cancer cell lines, PC3 (prostate cancer), H1299 (Non-small cell lung cancer), and H2009 (lung adenocarcinoma). To accomplish this, adherent cells were first dissociated with Cell Dissociation Buffer (Life Technologies #13150-016), pelleted by centrifugation, and resuspended by FACS buffer (PBS-CMF, 3% FBS, 0.1% weight/volume (w/v) sodium azide). Cells were then mixed with CP13E10-54HC-89LC or CP13E10-54HC-89LCv1 diluted in the same buffer to generate a 3-fold 12-point dilution series ranging from 100 nM to 0.565 pM final antibody concentration. Cells were maintained with antibody on ice for one hour, washed twice with ice-cold FACS buffer and then stained with anti-human IgG Fc conjugated with R-PE (Jackson ImmunoRsearch Labs #109-115-098). Following a thirty-minute incubation on ice in dark, the cells were washed twice, combined with eFluor 660 Fixable Viability Dye (eBioscience #65-0864-18), and fixed (BD Cytofix, BD Biosciences #554655). Stained cells were acquired on a LSR Fortessa instrument using BD FACSDiva Software. Background subtracted gMFI of viable cells was determined using FlowJo software and plotted using Graphpad Prism software to generate $EC_{50S}$ (FIGS. 26A and 26B). Values calculated for CP13E10-54HC-89LC ranged from 0.73-1.69 nM. The $EC_{50}$ of CP13E10-54HC-89LCv1, determined only for PC3 cells, was 4.06 nM (Table 6).

TABLE 6

| | | $EC_{50}$ (nM) | |
|---|---|---|---|
| Cell line | Cell type | CP13E10-54HC-89LC | CP13E10-54HC-89LCv1 |
| PC3 | Prostate cancer | 1.69 | 4.06 |
| H1299 | NSCLC | 0.73 | ND |
| H2009 | Lung adenocarcinoma | 0.77 | ND |

Example 14: Preparation of Anti-CDCP1 Antibodies, CP13E10-54HC-89LC and CP13E10-54HC-89LCv1 for Site Specific Conjugation of Linker-Cytotoxic Drug Payloads Methods of preparing CP13E10-54HC-89LC and CP13E10-54HC-89LCv1 derivatives for site specific conjugation through cysteine residues were generally performed as described in PCT Publication WO2013/093809 (which is incorporated herein in its entirety) and outlined in detail above. Methods of preparing CP13E10-54HC-89LC derivatives for site specific conjugation through glutamine residues were generally performed as described in PCT Publication WO2012/059882 and/or WO2016/166629 (which are incorporated herein in their entirety) and outlined in detail above.

To produce cysteine modified antibodies CP13E10-54HC-89LC-183/290 or CP13E10-54HC-89LCv1-183/290 or glutamine modified antibody CP13E10-54HC-89LC-H7C-K222R-N297A, CHO cells were transfected with DNA constructs encoding the respective antibodies and stable high production pools were isolated using standard procedures well-known in the art. A two column process was used to purify the antibodies from transfected cell conditioned medium. Briefly, antibodies were affinity purified using Protein-A (MabSelect SuRe LX platform) followed by purification using a TMAE column. In some cases, a final purification step using Phenyl Sepharose hydrophobic interaction chromatography (HIC) was employed.

The final purified products were analyzed by SoloVPE Slope Spectroscopy, SDS-PAGE, and analytical SEC (YMC-Pack Diol-200). Endotoxin was tested using Endosafe PTS RMPTS964 and Endosafe strip PTS-20 from Charles River Laboratories. The quantity of CHO host cell protein and Protein A impurities were assessed by Cygnus ELISA assays (catalog numbers F550 and F610, respectively). Preparations generally demonstrated endotoxin levels less than 1EU/mg, host cell protein contamination less than 100 ng/mg, Protein A contamination less than 10 ng/mg, and high molecular weight species less than 1% with the peak of interest containing 99% of the total protein.

Example 15: Generation of Cytotoxic Payload Drug Compounds

The auristatin drug compounds 0101 and 0131 were made according to the methods described in PCT Publication WO2013/072813 (which is incorporated herein in its entirety). In the published application, the auristatin compounds are indicated by the numbering system shown in the Table 7.

TABLE 7

| Auristatin Drug Compound | Designation in WO2013/072813 |
|---|---|
| 0101 | #54 |
| 0131 | #118 |

According to PCT Publication WO2013/072813 drug compound 0101 was made according to the following procedure.

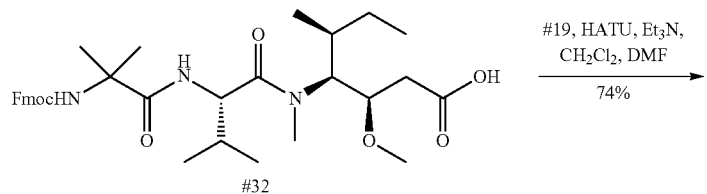

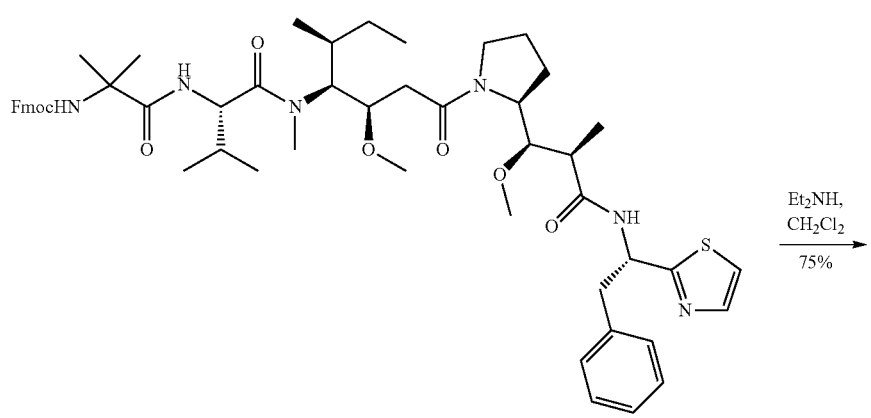

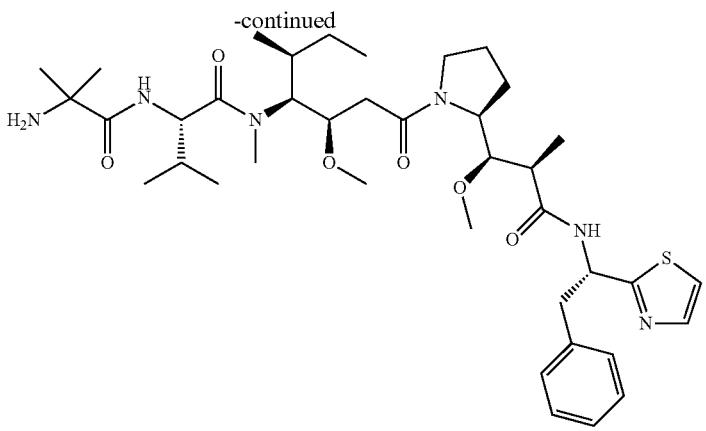

54

General Procedures as Described in WO 2013/072813, Incorporated Herein by Reference:

General Procedure A: 9-fluorenylmethyloxycarbonyl (FMOC) removal using diethylamine or piperidine. To a solution of the Fmoc-containing compound in dichloromethane or N,N-dimethylformamide (also referred to as DMF), was added an equal volume of diethylamine or piperidine. Reaction progress was monitored by LC-MS (or HPLC or TLC). Solvents were removed in vacuo, and in some cases the residue was azeotroped one to four times with heptane. Residue was usually diluted with dichloromethane and a small amount of methanol before being reduced down onto silica and purified by chromatography on silica gel, eluting with methanol in dichloromethane (or other appropriate mixture of solvents) to afford the desired material (or crude material was used as is).

General Procedure D: coupling with 0-(7-azabenzotriazol-1-yl)-N,N,N',N'-tetramethyluronium hexafluorophosphate (HATU). To a stirring solution of the amine (1.0 eq.) and acid (1.0-2.0 eq.) in dichloromethane, N,N-dimethylformamide (also referred to as DMF), or a mixture of both, HATU (1.0-2.0 eq.) was added followed by triethylamine (2.0-4.0 eq.) or diisopropylethylamine (2.0-4.0 eq., also referred to as Hunig's base). Reaction progress was monitored by LC-MS (or HPLC or TLC); the reaction was usually completed within three hours. Solvents were removed in vacuo. The residue was purified by silica gel or reverse phase chromatography or in some cases azeotroped three times with heptanes, diluted with a small amount of ethyl acetate before being reduced down onto silica or C18 bonded silica and purified by silica gel or reverse phase chromatography.

Step 1. Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53). According to general procedure D, from #32 (2.05 g, 2.83 mmol, 1 eq.) in dichloromethane (20 mL, 0.1 M) and N,N-dimethylformamide (3 mL), the amine #19 (2.5 g, 3.4 mmol, 1.2 eq.), HATU (1.29 g, 3.38 mmol, 1.2 eq.) and triethylamine (1.57 mL, 11.3 mmol, 4 eq.) was synthesized the crude desired material, which was purified by silica gel chromatography (Gradient: 0% to 55% acetone in heptane), producing #53 (2.42 g, 74%) as a solid. LC-MS: m/z 965.7 [M+H⁺], 987.6 [M+Na⁺], retention time=1.04 minutes; HPLC (Protocol A): m/z 965.4 [M+H⁺], retention time=11.344 minutes (purity >97%); ¹H NMR (400 MHz, DMSO-d₆), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24 (4 s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H].

Step 2. Synthesis of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (referred to herein as #54 or 0101). According to general procedure A, from #53 (701 mg, 0.726 mmol) in dichloromethane (10 mL, 0.07 M) was synthesized the crude desired material, which was purified by silica gel chromatography (Gradient: 0% to 10% methanol in dichloromethane). The residue was diluted with diethyl ether and heptane and was concentrated in vacuo to afford #54 (also referred to herein as 0101) (406 mg, 75%) as a white solid. LC-MS: m/z 743.6 [M+H⁺], retention time=0.70 minutes; HPLC (Protocol A): m/z 743.4 [M+H⁺], retention time=6.903 minutes, (purity >97%); ¹H NMR (400 MHz, DMSO-d6), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3 Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 11H], [4.49 (dd, J=9, 8 Hz) and 4.60 (dd, J=9, 7 Hz), total 1H], 3.16, 3.20, 3.21 and 3.25 (4 s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

In some embodiments, the drug 0101 is attached to linker 6-maleimidocaproyl-valine-citrulline-p-aminobenzylcarbamate (also referred to herein as "mc-val-cit-PABC", "mcValCitPABC" or "vc"). The linker-cytotoxic drug payload (LP), mc-val-cit-PABC-0101 (also referred to herein as "vc0101"), was made according to the methods described in PCT Publication WO2013/072813 (which is incorporated herein in its entirety).

According to PCT Publication WO2013/072813 drug compound 0131 was made according to the following procedure.

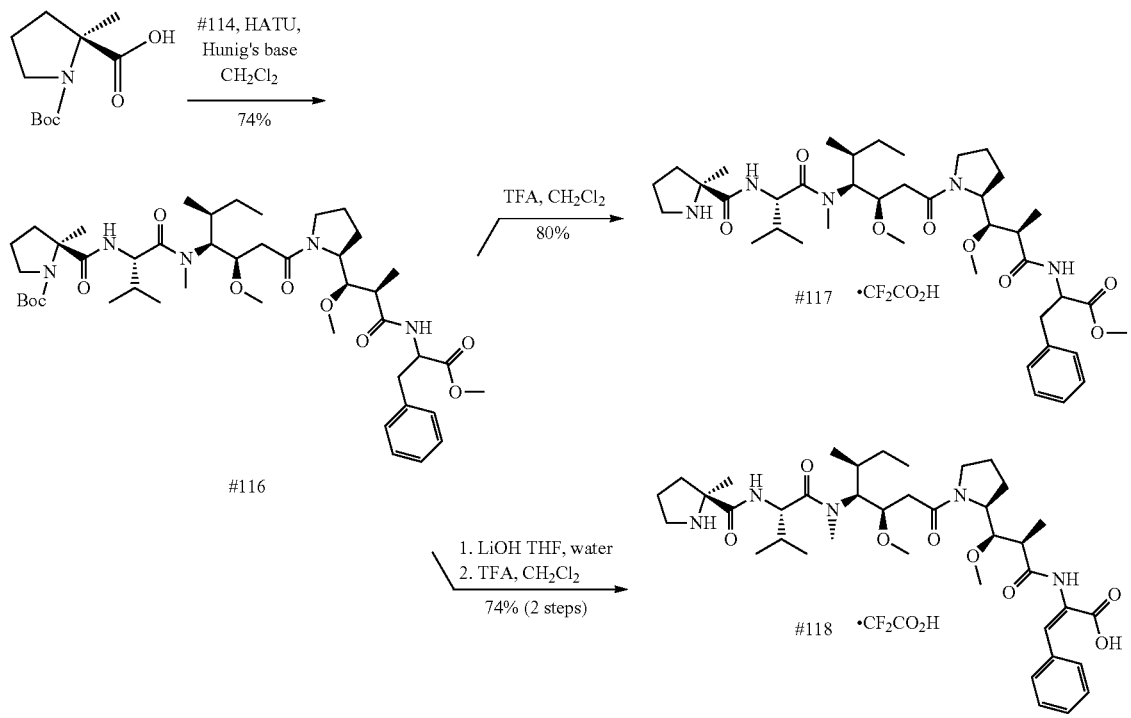

Step 1. Synthesis of 1-(tert-butoxycarbonyl)-2-methyl-L-prolyl-N-{(1S,2R)-4-{(2S)-2-[(1R,2R)-3-{[(1 S)-1-benzyl-2-methoxy-2-oxoethyl]amino}-1-methoxy-2-methyl-3-oxopropyl]pyrrolidin-1-yl}-2-methoxy-1-[(1 S)-1-inethylpropyl]4-oxobutyl}-N-methyl-L-valinamide(#116).

To a stirring solution of #114 (1.02 g, 1.61 mmol, 1.0 eq.) and 1-(tertbutoxycarbonyl)-2-methyl-L-proline (443 mg, 1.93 mmol, 1.2 eq.) in 12 mL of dichloromethane, HATU (735 mg, 1.93 mmol, 1.2 eq.) was added followed by Hunig's base (1.12 mL, 6.45 mmol, 4.0 eq.). The reaction was allowed to stir at room temperature for 2 hours. The reaction was reduced down, diluted with ethyl acetate before being washed with 0.5 N HCl and brine. Organics where then dried over sodium sulfate, reduced to a smaller volume, and then reduced down on silica. Silica chromatography was then performed (Gradient: 0%-45% acetone in heptanes) producing #116 (1.02 g, 74%) as a white solid. LC-MS (Protocol Q): m/z 844.3 [M+H+], 867.2 [M+Na+], retention time=2.15 minutes.

Step 2A. Synthesis of 2-methyl-L-prolyl-N-{(1 S,2R)-4-{(2S)-2-[(1R,2R)-3-{[(1 S)-1-benzyl-2-methoxy-2-oxoethyl]amino}-1-methoxy-2-methyl-3-oxopropyl]pyrrolidin-1-yl}-2-methoxy-1-[(1 S)-1-methylpropyl]-4-oxobutyl}-N-methyl-L-valinamide, trifluoroacetic acid salt (#117). To a stirring solution of #116 (450 mg, 0.533 mmol, 1.0 eq.) in 7 mL of dichloromethane at 0° C., TF A (3 mL, 40 mmol, 70 eq.) was added. The reaction was allowed to stir at 0° C. for 5 minutes and then allowed to warm to room temperature while stirring for 20 minutes. Reaction was reduced down, diluted with dichloromethane and a small amount of methanol before being reduced down onto silica. Silica chromatography was then performed (Gradient: 0%-20% methanol in ethyl acetate) producing #117 (396 mg, 89%) as a white solid. LC-MS (Protocol Q): m/z 744.5 [M+H+], 767.2 [M+Na+], retention time=1.40 minutes; HPLC (Protocol A at 45° C.): m/z 744.5 [M+H+], retention time=7.149 minutes (purity>91%). 1HNMR (400 MHz, DMSOd6), δ 8.73-9.14 (m), 8.66 (br d), 8.50 (d), 8.22 (d), 7.12-7.25 (m), 4.67-4.74 (m), 4.41-4.63 (m), 3.93-4.00 (m), 3.73 (dd), 3.63 (d), 3.46-3.57 (m), 3.38-3.45 (m), 3.26-3.23 (m), 3.22-3.25 (m), 3.06-3.22 (m), 2.99-3.05 (m), 2.93-2.97 (m), 2.80-2.89 (m), 2.75-2.78 (m), 2.64-2.67 (m), 2.46-2.50 (m), 2.27-2.43 (m), 2.00-2.26 (m), 1.85-1.99 (m), 1.70-1.83 (m), 1.52-1.69 (m), 1.33-1.51 (m), 1.18-1.31 (m), 0.98-1.07 (m), 0.93-0.97 (m), 0.82-0.92 (m), 0.71-0.78 (m).

Step 2B. Synthesis of 2-methyl-L-prolyl-N-[(3R,4S,5S)-1-{(2S)-2-[(1R,2R)-3-{[(1 S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#118). To a stirring solution of #116 (435 mg, 0.515 mmol), in 4 mL of THF under nitrogen, LiOH (24.7 mg, 1.03 mmol, 2.0 eq.) dissolved in 2 mL of water was added. The reaction was allowed to stir at room temperature until LC-MS indicated saponification of methyl ester. Reaction was concentrated in vacuo and then placed underneath vacuum. Reaction was diluted with dichloromethane and placed underneath nitrogen. To this stirring mixture TFA (3 mL, 40.5 mmol, 80 eq.) was added. Reaction was allowed to stir at room temperature for 30 minutes. Reaction was then reduced down. Residue was purified by medium pressure reverse phase C18 chromatography (Gradient: 5% to 60% acetonitrile in water with 0.02% TFA in each phase) #118 (396 mg, 89%) as a white solid. LC-MS (Protocol Q): m/z 730.2 [M+H+], retention time=1.18 minutes; HPLC (Protocol A at 45° C.): m/z 730.5 [M+H+], retention time=7.088 minutes (purity>98%). 1H NMR (400 MHz, DMSO-d6), δ 9.04-9.13 (m), 8.75-8.87 (m), 8.70 (d), 8.38 (d), 8.11(d), 7.10-7.24 (m), 4.66-4.74 (m), 4.48-4.64 (m), 4.37-4.47 (m), 3.91-3.99 (m), 3.77 (m), 3.47-3.56 (m), 3.33-3.47 (m), 3.08-3.30 (m), 2.93-3.07 (m), 2.75-2.86 (m), 2.63-2.69 (m), 2.45-2.50 (m), 2.28-2.44 (m), 2.03-2.27 (m), 1.88-2.02 (m), 1.68-1.86 (m), 1.55-1.67 (m), 1.30-1.47 (m), 1.17-1.29 (m), 0.98-1.05 (m), 0.93-0.97 (m), 0.83-0.92 (m), 0.71-0.79 (m).

According to PCT Publication WO2016/166629 (which is incorporated herein in its entirety) the auristatin compound 0131 (with the chemical name, 2-methyl-L-proly-N-[(3R,4S,5S)-1-{(2S)-2-[(1R,2R)-3-{[(1 S)-1-carboxy-2-phenyl-ethyl]amino}-1-methoxy-2-methyl-3-oxopropyl]pyrrolidin-1-yl}-3-methoxy-5-methyl-1-oxoheptan-4-yl]-N-methyl-L-valinamide) coupled to an amine donor linker that allows conjugation to an acyl donor antibody is referred to herein as amino-PEG6-C2-0131 and has the following structure:

The ADC, CP13E10-54HC-89LC-H7C-K222R-N297A-amino-PEG6-C2-0131 (i.e., CP13E10-54HC-89LC-H7C-K222R-N297A-AmPEG6C2-0131) was produced through chemical conjugation using the glutamine site specific transamidation method. In the transamidation reaction, the glutamine on the antibody acted as an acyl donor and the amine-containing compound on the linker-cytotoxic payload, amino-PEG6-C2-0131 (also referred to herein as amino PEG6-propionyl or AmPeg6C2-0131) having a structure described in PCT Publication WO2016/166629 (which is incorporated herein in its entirety), acted as an acyl acceptor (amine donor). Purified antibody CP13E10-54HC-89LC-117C (acyl donor) was incubated with a 10-25 molar excess of acyl acceptor, ranging between 1-2 mM of

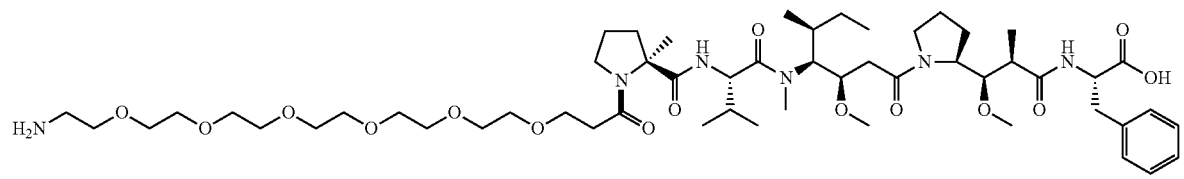

Example 16: Bioconjugation of CP13E10-54HC-89LC-183/290, CP13E10-54HC-89LCv1-183/290, and CP13E10-54HC-89LC-H7C-K222R-N297A Antibodies Antibodies of the present invention were conjugated to cytotoxic drug payloads via linkers to generate antibody-drug conjugates (ADCs). The conjugation method used was site specific (i.e., via particular cysteine residues or particular glutamine residues).

The ADCs, CP13E10-54HC-89LC-183/290-vc0101 and CP13E10-54HC-89LCv1-183/290-vc0101 were produced through chemical conjugation using the cysteine site specific methods. The linker-cytotoxic drug payload (LP), mc-Val-Cit-PABC-0101 (also referred to here as vc0101), was conjugated to anti-CDCP1 antibodies CP13E10-54HC-89LC-183/290 or CP13E10-54HC-89LCv1-183/290, prepared as described in Example 14, via their engineered cysteine residues. As a first step, the 5-thio-2-nitrobenzoic acid (TNB)-capped antibodies were reduced by 20-fold molar excess of tris (3-sulfonatophenyl) phosphine (TSPP) for 3 hours at 37° C. followed by desalting to remove excess TSPP. The reduced antibodies were incubated in 2-fold molar excess of dehydro ascorbic acid (DHA) for 0.5 hour at 25° C. to reform the inter-chain disulfide bonds. The LP was added to the reaction mixture at a LP/antibody molar ratio of 10 and reacted for an additional 1.5 hour at 25° C. in the presence of 15% (volume/volume) of dimethylacet-amide (DMA). After the incubation, 20-fold molar excess L-Cysteine was added to quench any unreacted LP.

The reaction mixture was then desalted to remove free LP and purified via hydrophobic interaction chromatography (HIC). The purified ADC was dialyzed into 20 mM histidine, 85 mg/mL sucrose, 20 pH 5.8 formulation buffer and stored at −80° C. The protein concentration was determined via UV spectrophotometer. The ADC was further characterized via SEC for purity; reverse phase (RP) UPLC and liquid chromatography electrospray ionization tandem mass spectrometry (LC-ESI MS) to calculate drug loading profile and drug-antibody ratio (DAR). Final ADC preparations generally had greater than 95% monomer purity with less than 5% high molecular weight species and a DAR of approximately 4.

AmPeg6C2-0131 (final concentration) in the presence of 0.75 units/mg antibody (final concentration) Streptoverticillium mobaraense transglutaminase in 200 mM sodium chloride and Tris HCl buffer at pH range 7.5-8.5. Following incubation at 25° C. for 14-20 hours, the antibody drug conjugate was purified by Butyl Sepharose HIC-FPLC (GE Healthcare, Piscataway, NJ) using standard chromatography methods known to persons skilled in the art.

The purified ADC was dialyzed into 20 mM histidine, 85 mg/mL sucrose, pH 5.8 formulation buffer and stored at −80° C. The protein concentration was determined via UV spectrophotometer. The ADC was further characterized via SEC for purity; reverse phase (RP) UPLC and liquid chromatography electrospray ionization tandem mass spectrometry (LC-ESI MS) to calculate drug loading profile and drug-antibody ratio (DAR). Final ADC preparations generally had greater than 95% monomer purity with less than 5% high molecular weight species and a DAR of approximately 4.

Example 17: Characterization of CP13E10-54HC-89LCv1-183/290-Vc0101 ADC

Post-conjugation (see Examples 16 and 17) the CP13E10-54HC-89LCv1-183/290-vc0101 ADC was formulated into 20 mM histidine, 85 mg/mL sucrose, pH 5.8 and at 3.27 mg/mL there was no apparent issue with solubility, viscosity or aggregate formation. CP13E10-54HC-89LCv1-183/290-vc0101 was characterized via size exclusion chromatography (SEC) for purity; reverse phase (RP) UPLC and liquid chromatography electrospray ionization tandem mass spectrometry (LC-ESI MS) to calculate drug loading profile and drug-antibody ratio (DAR). These results show that the overall yield of a DAR 4.0 ADC was 51% and free drug was below LOQ. To determine integrity of the CP13E10-54HC-89LCv1-183/290-vc0101 ADC, the percent purity was calculated using non-reducing and reducing capillary gel electrophoresis (cGE, Caliper LabChip GXII: Perkin Elmer Waltham, MA). CP13E10-54HC-89LCv1-183/290-vc0101 ADC displays excellent integrity and the preparation was shown to be virtually devoid of HMMS or LMMS at 99.47% intact ADC using non-reducing cGE and 99.91% presence of heavy and light chains under reducing conditions. Differential Scanning Calorimetry (DCS) was used to determine the thermal stability of the CP13E10-54HC-89LCv1-183/290-vc0101 ADC. For this analysis, the ADC formulated into 20 mM histidine, 8.5% sucrose, 0.005% EDTA, pH 5.8 was dispensed into the sample tray of a MicroCal VP-Capillary DSC with Autosampler (GE Healthcare Bio-Sciences, Piscataway, NJ), equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, MA) was used to fit the data to an MN2-State Model with an appropriate number of transitions. CP13E10-54HC-89LCv1-183/290-vc0101 ADC exhibited good thermal stability as demonstrated by the following melting transition points: Tm1=65.15° C., Tm2=78.97° C., Tm3=85.45° C. and apparent Fab Tm=79.2° C. Taken together these results demonstrate that that site-specific conjugation of Auristatin 0101 (also called #54) via a mc-val-cit-PABC (also referred to herein as "vc") linker to the engineered positions C290 (EU numbering of Kabat or 307 using numbering of Kabat) in the human IgG1 heavy chain constant region and C183 according to the numbering of Kabat in the Kappa constant region of the anti-CDCP1 CP13E10-54HC-89LCv1 antibody yielded a conjugate with excellent integrity and thermal stability.

The binding kinetics of anti-CDCP1 CP13E10-54HC-89LCv1-183/290 antibody and its respective site-specifically conjugated ADC, CP13E10-54HC-89LCv1-183/290-vc0101 against recombinant human, CDCP1-ECD were determined at pH7.4 and pH6.8 using surface plasmon resonance (SPR) and a Biacore T200 instrument (GE Healthcare) using the method described in Example 7. Comparison of the ADC binding to CDCP1-ECD at pH6.8 versus physiological pH7.4 was done to elucidate if the ADC is able to bind within the acidic tumor microenvironment. At pH7.4, both CP13E10-54HC-89LCv1-183/290 antibody and CP13E10-54HC-89LCv1-183/290-vc0101 ADC have similar $K_D$ values (FIG. 27). Further, the $K_D$ values CP13E10-54HC-89LCv1-183/290 antibody and its respective site-specifically conjugated ADC against human CDCP1 ECD at pH6.8 are similar to those calculated at pH7.4 (FIG. 27). These combined results suggest that the CP13E10-54HC-89LCv1-183/290-vc0101 ADC would bind CDCP1 within the acidic tumor microenvironment. Furthermore, the binding kinetic values obtained for CP13E10-54HC-89LCv1-183/290-vc0101 ADC demonstrate that site-specific conjugation of Auristatin 0101 (also called #54) via a mc-val-cit-PABC (also referred to herein as "vc") linker to the engineered positions C290 (EU numbering of Kabat or 307 using numbering of Kabat) in the human $IgG_1$ heavy chain constant region and C183 according to the numbering of Kabat in the Kappa constant region of the anti-CDCP1 CP13E10-54HC-89LCv1 antibody do not alter CDCP1 binding properties.

Example 18: Antibody-Dependent Cell-Mediated Cytotoxicity

Antibody-Dependent Cell-Mediated Cytotoxicity (ADCC) occurs through engagement of the Fc portion of an antibody bound to the surface of a target cell with the FCγRIIIa receptor on Natural Killer (NK) cells. Target-cell bound antibody interaction with FCγRIIIa induces signaling in effector NK cells that leads to the release of cytolytic molecules such as granzymes that kill the target cell. Anti-tumor activity of an antibody can be partially attributed to, or enhanced by ADCC. CDCP1 antibody CP13E10-54HC-89LCv1-183/290 and ADC CP13E10-54HC-89LCv1-183/290-vc0101 were evaluated for their ability to induce ADCC on target cells in vitro. In this example two methods were used, one flow cytometry based and one luciferase reporter based assay.

For the flow cytometry based method, target PC3 cells were plated overnight at 37° C., 5% $CO_2$. Cells were seeded at 10,000 cells/well in 96 well tissue culture plates in assay medium (RPMI-1640 (Gibco), 10% ultra-low IgG FBS (Gibco). Effector NK cells were isolated from healthy human donors by negative selection using a CD56+/CD16+ NK Cell Isolation Kit (Miltenyi Biotec). Target cells were fluorescently labeled with Cell Trace Far Red (ThermoFisher) and a dilution series of antibody CP13E10-54HC-89LCv1-183/290 or ADC CP13E10-54HC-89LCv1-183/290-vc0101 was subsequently added to the target cells. NK effector cells were then added at 70,000 cells per well for an effector to target ratio of 7:1. This co-culture was incubated for 4 hours at 37° C., 5% $CO_2$. Medium containing non-adherent cells was then collected and set aside for later use. Adherent cells were dissociated (Cell Dissociation Buffer, Gibco) and collected by centrifugation. Pelleted cells were combined with their corresponding medium containing non adherent cells and stained with LIVE/DEAD Violet Dead Cell Stain (ThermoFisher). Stained cells were run on an LSRFortessa flow cytometer (BD Biosciences) and target PC3 cells gated on CellTrace Far Red staining. The percentage of dead PC3 cells was determined by LIVE/DEAD Fixable Violet Dead Cell Stain positive cells in the PC3 gate. As shown in FIG. 28A, both CP13E10-54HC-89LCv1-183/290 and ADC CP13E10-54HC-89LCv1-183/290-vc0101 induce ADCC and therefore engage receptor FCγRIIIa on NK cells.

ADCC was also evaluated using a luciferase ADCC Reporter Bioassay (Promega). In this kit engineered ADCC reporter Jurkat cells (Bioassay Effector Cells) stably express FcγRIII high affinity V158 variant and an NFAT response element that drives expression of firefly luciferase after activation of FcγRIII by antibody Fc binding. PC3 target cells were plated overnight at 370 C, 5% C02 at 6250 cells per well in a 96 well tissue culture plate. The next day the plating medium (RPMI-1640 (Gibco), 10% ultra-low IgG FBS (Gibco) was removed and a serial dilution of antibody CP13E10-54HC-89LCv1-183/290 or ADC CP13E10-54HC-89LCv1-183/290-vc0101 was added and incubated at room temperature for 15 minutes. Bioassay Effector Cells were then added to the target cells at an effector to target ratio of 12:1 and incubated overnight at 370 C, 5% $CO_2$. The next day 75 μL of Bio-Glo Luciferase Assay Reagent was added to each well and luminescence in relative light units (RLU) was determined using an Envision plate reader (Perkin Elmer). As shown in FIG. 28B both CP13E10-54HC-89LCv1-183/290 and ADC CP13E10-54HC-89LCv1-183/290-vc0101 induce luciferase reporter expression and therefore engage receptor FCγRIIIa which is indicative of ADCC activity.

Example 19: In Vitro Cytotoxicity of CP13E10-54HC-89LC-183/290-Vc0101, CP13E10-54HC-89LCv1-183/290-vc0101, and CP13E10-54HC-89LC-H7C-K222R-N297-AmPEG6C2-0131

The cytotoxicity of the CDCP1 ADCs, CP13E10-54HC-89LC-183/290-vc0101, CP13E10-54HC-89LCv1-183/290-vc0101, and CP13E10-54HC-89LC-H7C-K222R-N297A-

AmPEG6C2-0131, was evaluated on a broad range of cell types; e.g., human prostate cancer PC3, Non-Small Cell Lung Cancer (NSCLC) H1299, head and neck cancer SCC-25, lung adenocarcinoma H2009, oral squamous cell carcinoma PE/CA-PJ-49, and primary human aortic smooth muscle cells (HuAoSMC). Cells were incubated in a 6-fold 9-point dilution series of respective ADCs ranging in concentration from 600 nM to 0.357225 pM. Cells were maintained in a standard tissue culture incubator for four days followed by viability analysis using the ATPlite reagent and following the manufacturer's suggested protocol (PerkinElmer #6016731). The mean of luminescence counts of triplicate samples were normalized to a medium only control (growth medium no ADC) to calculate percent viability. ADC $IC_{50s}$ (concentration at which cell viability inhibited 50%) were calculated using a logistic non-linear-regression analysis.

Table 8 shows $IC_{50s}$ of the test ADCs across cell lines. All three ADCs were cytotoxic to all cancer cell lines. However, non-tumorigenic primary aortic smooth muscle cells that expressed the least amount of CDCP1 were largely resistant to the cytotoxic effect of the ADCs (not different from negative control). Although there was not an absolute correlation between CDCP1 expression and cytotoxicity, the most sensitive cell type, PC3, expressed the highest levels of CDCP1 while decreased cytotoxicity was associated with lower expressers.

began in order to track tumor growth and estimate cell doubling time. Tumor volume was estimated using the equation $V=(A*B^2)/2$ where A is the long axis and B is the short axis. When tumors reached a volume of 500 mm$^3$ to 1,500 mm$^3$, they were harvested for study and for re-transplant in naïve mice as a PDX line. Tumors were mechanically dissociated into fragments for cryopreservation or additional passage in mice.

For efficacy studies, PDX tumors were aseptically harvested from passaging mice and minced into fragments approximately 2 mm in diameter. The PDX tumor fragments were transplanted into the right flank of naïve 7-10-week old NOD-SCID mice.

Tumor growth was initially followed by palpability with measurements beginning once tumor volumes reached about 30 mm$^3$. Studies were randomized based on tumor size once a cohort of tumor-bearing mice reached an average of 200 mm$^3$. Animals were then dosed by intravenous injection of test ADCs once every four days (day 1, 5, 9, and 13) for four total doses (q4d×4). For each tumor measurement taken at regular intervals the tumor volume was calculated and an average tumor size +/− the standard error of the mean (SEM) was derived per cohort of surviving animals to determine tumor growth rates. In some studies, a "waterfall plot" was derived by calculating the maximum observed percent difference in tumor volume from the starting volume post the final dose of ADC. Most PDX models were prescreened for

TABLE 8

| Cell line | Cell type | CP13E10-54HC-89LCv1-183/290-vc0101 $IC_{50}$ (pM) | CP13E10-54HC-89LC-183/290-vc0101 $IC_{50}$ (pM) | CP13E10-54HC-89LC-H7C-K222R-N297A-AmPEG6C2-0131 $IC_{50}$ (pM) | mAbNeg-183/290-vc0101 (neg con) $IC_{50}$ (pM) | Aur0101 (free payload) $IC_{50}$ (pM) |
|---|---|---|---|---|---|---|
| PC3 | Prostate cancer | 36.1 ± 14.9 | 44.2 ± 6.1 | 7.8 | 126723.3 ± 105006.4 | 63.6 |
| H1299 | NSCLC | 9475.0 ± 397.4 | 18280 ± 7297.3 | 36.6 | 254200 ± 12445.1 | 201.9 |
| SCC-25 | Head and neck cancer | 649.4 ± 175.8 | 649.8 ± 306.2 | 537.3 | 68936.7 ± 23083.2 | 47.0 |
| H2009 | Lung adenocarcinoma | 754.6 ± 284 | 1013.9 ± 400.9 | 242.9 | 148906.7 ± 85391.1 | 115.6 |
| PE/CA-PJ-49 | Oral squamous cell carcinoma | 4192.3 ± 2496.0 | 5604.3 ± 4011.4 | 2282 | 66466.7 ± 20109.0 | 37.3 |
| HuAoSMC | Primary Aortic smooth muscle | 269266.7 ± 37646.3 | 300233.3 ± 36077.2 | 4264000 | 301166.7 ± 37409.4 | 176.4 |

Example 20: In Vivo Efficacy of CP13E10-54HC-89LC-183/290-Vc0101, CP13E10-54HC-89LCv1-183/290-vc0101, and CP13E10-54HC-89LC-H7C-K222R-N297A-AmPEG6C2-0131 in Patient Derived Xenograft (PDX) Tumor Bearing Mice The effects of ADCs were evaluated on the in vivo growth of human tumor patient-derived xenografts (PDX) implanted into immunodeficient NOD/SCID mice. To establish initial PDX cell lines, primary human tumor resection samples were procured from clinical sites following Institutional Review Board for the Protection of Human Subjects approval and in accordance with HIPAA regulations. Tumor fragments were implanted subcutaneously in mice and animals were monitored for health status daily and for tumor growth by visual inspection twice per week. Once the tumors were palpable, measurements of tumor volume cell membrane CDCP1 expression using an immunohistochemical assay to assign an H-score as described in Example 1 above.

Two pancreatic cancer PDX models expressing substantial amounts of CDCP1 (PDX-PAX-24509, H-score 245 and PDX-PAX-24513, H-score 190) were evaluated for response to CP13E10-54HC-89LC-H7C-AmPEG6-0131 or CP13E10-54HC-89LC-183/290-vc0101 dosed at 0.3, 1, or 3 mg/kg on four occasions at four day intervals (q4d×4; cohort size n=10). In pancreatic tumor model PDX-PAX-24513, tumors progressed rapidly regardless of ADC or dose with all animals succumbing by day 15 (FIG. 29A-29B). Using the following RECIST criteria, the response in this model was classified as Progressive Disease (PD):

RECIST Criteria:
  Complete Response (CR): 100% decrease in tumor volume compared to starting volume Partial Response (PR): Regression in tumor volume greater than 30% but less than 100% compared to starting volume Stable Disease (SD) 30% regression in tumor volume up to a 20% increase from starting volume Progressive Disease (PD) Tumor growth greater than 20% compared to starting volume Objective Response Rate (ORR) defined as the summed percentage of CR and PR Measurements for RECIST determination recorded on the day of maximal response at least one day past the last dose of test compound Pancreatic cancer model PDX-PAX-24509 showed a similar response with both ADCs and was also classified as PD (FIG. 30A-30B). Although CP13E10-54HC-89LC-183/290-vc0101 treatment resulted in PD at all doses (FIG. 30B), there was a significant survival benefit associated with this ADC compared to CP13E10-54HC-89LC-H7C-AmPEG6-0131. Notably, CP13E10-54HC-89LC-183/290-vc0101 dosed at 3 mg/kg produced the longest survival time of all treatments as illustrated in FIG. 31 (mean±SE, 47.1±0.72 days). This survival was statistically significantly longer than animals dosed with PBS (mean±SE, 16.9±0.99 days; log-rank, p<0.0001) or 3 mg/kg of CP13E10-54HC-89LC-H7C-AmPEG6-0131 (mean±1 SE, 20.8±0.68 days; log-rank, p<0.0001).

The response to CP13E10-54HC-89LC-H7C-AmPEG6-0131 or CP13E10-54HC-89LC-183/290-vc0101 was also compared in non-small cell lung cancer (NSCLC) models. NSCLC tumors expanded rapidly when model PDX-NSX-26101 was dosed with 0.3, 1, or 3 mg/kg (cohort size n=10) CP13E10-54HC-89LC-H7C-AmPEG6-0131 classifying the response as PD (FIG. 32A). PDX-NSX-26101 also demonstrated PD when dosed with CP13E10-54HC-89LC-183/290-vc0101 at 0.3 and 1 mg/kg. However, CP13E10-54HC-89LC-183/290-vc0101 at 3 mg/kg showed a transient tumor regression leading to a Partial Response (PR) extending until at least two weeks beyond the final dose (FIG. 32B). Transient tumor regression and a PR was also seen in NSCLC model PDX-NSX-26113 (H-score 227; cohort size n=10) dosed at 3 mg/kg with either CP13E10-54HC-H7C-AmPEG6-0131 or CP13E10-54HC-89LC-183/290-vc0101 although the duration of regression was greater with CP13E10-54HC-89LC-183/290-vc0101 (FIGS. 33A and 33B).

Additional studies, in which PDX cohorts were dosed with ADCs and control compounds as described above, were conducted to determine the performance of CP13E10-54HC-89LC-183/290-vc0101 and CP13E10-54HC-89LCv1-183/290-vc0101 in comparison to the current standard of care (SOC) for NSCLC and H&N cancers. In NSCLC model PDX-NSX-15137 (cohort size n=10), CP13E10-54HC-89LCv1-183/290-vc0101 at 4.5 and 1.5 mg/kg yielded sustained tumor regression over 35 days (greater than 2 weeks post last treatment) at which time the average tumor size in the SOC cohort (Paclitaxel, 22.5 mg/kg) had doubled (FIG. 34A). At the 4.5 mg/kg dose, regression was maintained beyond day 42 at which time all mice in the paclitaxel cohort had been sacrificed due to excessive tumor growth. In H&N model PDX-HNX-24715 (H-score 161; cohort size n=10), CP13E10-54HC-89LCv1-183/290-vc0101 dosed at 1.5 mg/kg produced tumor regression at day 25 (greater than 1 week post last dose) at which time tumors in the SOC cohort (cisplatin, 5 mg/kg) had more than doubled in size (FIG. 34B). In the same model, CP13E10-54HC-89LCv1-183/290-vc0101 at 4.5 mg/kg and CP13E10-54HC-89LC-183/290-vc0101 and CP13E10-54HCv13-89LCv1-183/290-vc0101 (ADC with same antibody sequence as CP13E10-54HC-89LCv1-183/290-vc0101 except that the glycine residue at heavy chain amino acid position 96 was replaced by alanine) at 3 mg/kg, induced tumor regressions that exceeded 80 days in duration (9 weeks post last dose). PDX-NSX-15137 and PDX-HNX-24715 both demonstrated transient tumor regressions when dosed with negative control Neg-ADC at 3 mg/kg. However, the response to both CP13E10-54HC-89LCv1-183/290-vc0101 (4.5 mg/kg) and CP13E10-54HC-89LC-183/290-vc0101 (3 mg/kg) was superior to Neg-ADC. This non-specific effect of the negative control is presumed to occur due to cleavage of the protease sensitive linker in the tumor microenvironment.

In the PDX models described above, even when ADC treatment led to tumor regression, tumors were not completely eradicated and all eventually resumed growth. To investigate if renewed tumor growth was associated with the development of resistance to ADC treatment we first dosed CP13E10-54HC-89LC-183/290-vc0101 in PDX NSCLC model PDX-NSX-26113 intravenously at 0.3, 1, and 3 mg/kg four times each at four day intervals (cohort size n=10). We noted sustained tumor regression in the 3 mg/kg cohort that was superior to the negative control Neg-ADC response at day 42 (greater than 3 weeks post last dose) after which tumors expanded. On day 56 average tumor size had increased to approximately four times initial volume in the CP13E10-54HC-89LC-183/290-vc0101 3 mg/kg cohort (FIG. 35A). At that time tumors were excised from the 3 mg/kg cohort, combined, dissociated, and re-implanted into a cohort of naïve NOD/SCID mice. As in the previous cohort, tumors were allowed to expand until they reached an average volume of approximately 200 mm$^3$ at which time animals were randomly assigned to treatment groups (CP13E10-54HC-89LC-183/290-vc0101, 1, 3, 6 mg/kg; negative control Neg-ADC 3, 6 mg/kg, PBS; q4dx4; n=10 animals/cohort). We noted that treatment with CP13E10-54HC-89LC-183/290-vc0101 at 3 mg/kg induced tumor regression until approximately day 40. By day 40 all mice in the Neg-ADC 3 mg/kg control group had been terminated due to excessive tumor growth (FIG. 35B). In the 6 mg/kg CP13E10-54HC-89LC-183/290-vc0101 cohort, regression was seen past day 50 at which time all mice in the Neg-ADC 6 mg/kg control group had been terminated due to excessive tumor growth (FIG. 35B). These results indicate that although tumors regrow after CP13E10-54HC-89LC-183/290-vc0101 treatment in the original group, this regrowth was not associated with the development of resistance to this ADC. In fact, tumors in the naïve cohort appeared equally sensitive to treatment as in the original cohort.

Additional PDX studies using smaller cohorts of mice (n=4-5) were conducted with H&N and NSCLC models dosed with CP13E10-54HC-89LC-183/290-vc0101 q4dx4 at 3 mg/kg. Tumor growth was monitored as before and maximum average change (measured at least one day after the final dose for regression to stable disease or on day 21 [7-days post last dose] for progressive disease) in tumor size was determined. The volume of the maximal change was divided by the average pre-treatment starting volume and then subtracted by 100 to derive a percent change (e.g., tumor regression to 20 mm$^3$ from a starting value of 200 mm$^3$ would give (20/200)-100=−90% with the negative value indicating tumor regression). In this way, maximal changes across numerous independent PDX models were visualized in a "waterfall plot." Such a waterfall plot is shown for fourteen different PDX models in FIG. 36. Note that the data in this figure also includes the findings from the 3 mg/kg arms of some of the larger multi-dose studies described above (PDX-PAX-24513, PDX-PAX-24509, PDX-NSX-26113, PDX-NSX-26101, PDX-HNX-26755, PDX-NSX-15137) that had cohort sizes of ten. This analysis revealed a broad efficacy profile across numerous NSCLC and H&N PDX models. In total, one Complete Response and ten Partial Responses were seen giving an objective response rate (ORR) of 79% in this experimental series.

To gain a more comprehensive understanding of the breadth of efficacy of CP13E10-54HC-89LC-183/290-vc0101, a large panel of PDX models across numerous indications was assembled. Tumor types in this panel included, ovarian, breast, bladder, H&N, NSCLC, and small cell lung cancer. Expression of CDCP1 in most of these models was verified by IHC and an H-score was assigned to each. Subsequently, small tumor-bearing cohorts (n=4-5 mice) were established and dosed with CP13E10-54HC-89LCv1-183/290-vc0101 at 3 mg/kg to derive a waterfall plot (FIG. 37). Once again, a broad efficacy profile was seen across indications. Notably, 0/3 bladder cancer PDX models gave a Partial or Complete Response suggesting that bladder cancer may not be a viable indication for this ADC. Of the 40 total models analyzed in this series, 20% gave a Complete Response and an additional 43% gave a Partial Response for an Objective Response Rate of 63% across all indications.

TABLE 9

| Antibody | Heavy Chain (HC) | | | | | | | | | | Light Chain (LC) | | | | | | |
|---|---|---|---|---|---|---|---|---|---|---|---|---|---|---|---|---|---|
| | $V_H$ | HC CDR1 | HC CDR2 | HC CDR3 | JH | CH1 | HINGE | CH2 | CH3 | HC | $V_L$ | LC CDR1 | LC CDR2 | LC CDR3 | JK or JL | CL | LC |
| CP13E10 | 1 | 2 | 3 | 4 | 5 | 6 | 7 | 8 | 9 | 10 | 11 | 12 | 13 | 14 | 15 | 16 | 17 |
| CP13E10-183/290 | 1 | 2 | 3 | 4 | 5 | 6 | 7 | 18 | 9 | 19 | 11 | 12 | 13 | 14 | 15 | 20 | 21 |
| CP13E10-H7C-K222R-N297A | 1 | 2 | 3 | 4 | 5 | 22 | 23 | 24 | 9 | 25 | 11 | 12 | 13 | 14 | 15 | 16 | 17 |
| CP13E10-54HC-89LC | 26 | 2 | 3 | 27 | 28 | 6 | 7 | 8 | 9 | 29 | 30 | 12 | 13 | 31 | 15 | 16 | 32 |
| CP13E10-54HC-89LC-183/290 | 26 | 2 | 3 | 27 | 28 | 6 | 7 | 18 | 9 | 33 | 30 | 12 | 13 | 31 | 15 | 20 | 34 |
| CP13E10-54HC-89LC-H7C-K222R-N297A | 26 | 2 | 3 | 27 | 28 | 22 | 23 | 24 | 9 | 35 | 30 | 12 | 13 | 31 | 15 | 16 | 32 |
| CP13E10-54HC-89LCv1 | 26 | 2 | 3 | 27 | 28 | 6 | 7 | 8 | 9 | 29 | 36 | 12 | 13 | 31 | 15 | 16 | 37 |
| CP13E10-54HC-89LCv1-183/290 | 26 | 2 | 3 | 27 | 28 | 6 | 7 | 18 | 9 | 33 | 36 | 12 | 13 | 31 | 15 | 20 | 38 |
| CP13E10-54HC-89LCv1-H7C-K222R-N297A | 26 | 2 | 3 | 27 | 28 | 22 | 23 | 24 | 9 | 35 | 36 | 12 | 13 | 31 | 15 | 16 | 37 |
| CP13E10-54HCv13-89LCv1 | 39 | 2 | 3 | 40 | 28 | 6 | 7 | 8 | 9 | 41 | 36 | 12 | 13 | 31 | 15 | 16 | 37 |
| CP13E10-54HCv13-89LCv1-183/290 | 39 | 2 | 3 | 40 | 28 | 6 | 7 | 18 | 9 | 42 | 36 | 12 | 13 | 31 | 15 | 20 | 38 |
| CP13E10-54HCv13-89LCv1-H7C-K222R-N297A | 39 | 2 | 3 | 40 | 28 | 22 | 23 | 24 | 9 | 43 | 36 | 12 | 13 | 31 | 15 | 16 | 37 |
| CP13E10-291 | 44 | 2 | 3 | 45 | 28 | 6 | 7 | 8 | 9 | 46 | 11 | 12 | 13 | 14 | 15 | 16 | 17 |
| Antibody 23 | 47 | 48 | 49 | 50 | 5 | 6 | 7 | 8 | 9 | 51 | 52 | 53 | 54 | 55 | 56 | 57 | 58 |
| Antibody 24 | 59 | 60 | 61 | 62 | 63 | 6 | 7 | 8 | 9 | 64 | 65 | 66 | 67 | 68 | 69 | 16 | 70 |
| Antibody 76 | 47 | 48 | 49 | 50 | 5 | 6 | 7 | 8 | 9 | 51 | 71 | 72 | 54 | 73 | 56 | 57 | 74 |

TABLE 10

SEQUENCE LIST

| SEQ ID NO. | Description | Sequence |
|---|---|---|
| 1 | CP13E10 $V_H$ CDRs as defined by Kabat underlined | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGVLRYFDWLLDYYYYMDVWGKGTTVTSS |
| 2 | CP13E10 HC CDR1 | SYYMH |
| 3 | CP13E10 HC CDR2 | IINPSGGSTSYAQKFQG |
| 4 | CP13E10 HC CDR3 | DGVLRYFDWLLDYYYY |

TABLE 10-continued

SEQUENCE LIST

| SEQ ID NO. | Description | Sequence |
|---|---|---|
| 5 | CP13E10 JH | WGKGTTVTVSS |
| 6 | CP13E10 CH1 | ASTKGPSVFPLAPSSKSTSGGTAALGCLVKDYFPEPVTVSWNSG ALTSGVHTFPAVLQSSGLYSLSSVVTVPSSSLGTQTYICNVNHK PSNTKVDKKV |
| 7 | CP13E10 HINGE | EPKSCDKTHTCPPCP |
| 8 | CP13E10 CH2 | APELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAK |
| 9 | CP13E10 CH3 (K): Can be prepared +/- lysine | GQPREPQVYTLPPSREEMTKNQVSLTCLVKGFYPSDIAVEWESN GQPENNYKTTPPVLDSDGSFFLYSKLTVDKSRWQQGNVFSCSVM HEALHNHYTQKSLSLSPGK |
| 10 | CP13E10 HC (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGVLRYFDWLLDYYYYMDVWGKGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK |
| 11 | CP13E10 V_L CDRs as defined by Kabat underlined | EIVLTQSPATLSLSPGERATLSCRASQSVGSYLAWYQQRPGQAP RLLIYDASNRATGIPARFSGSGSGTDFTLTISSLEPEDFAVYYC QQRAMVFTFGQGTKVEIK |
| 12 | CP13E10 LC CDR1 | RASQSVGSYLA |
| 13 | CP13E10 LC CDR2 | DASNRAT |
| 14 | CP13E10 LC CDR3 | QQRANVFT |
| 15 | CP13E10 JK | FGQGTKVEIK |
| 16 | CP13E10 CL | (R)TVAAPSVFIFPPSDEQLKSGTASVVCLLNNFYPREAKVQWK VDNALQSGNSQESVTEQDSKDSTYSLSSTLTLSKADYEKHKVYA CEVTHQGLSSPVTKSFNRGEC |
| 17 | CP13E10 LC | EIVLTQSPATLSLSPGERATLSCRASQSVGSYLAWYQQRPGQAP RLLIYDASNRATGIPARFSGSGSGTDFTLTISSLEPEDFAVYYC QQRANVFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| 18 | CP13E10-183/290 CH2 | APELLGGPSVFLFPPKPKDTLMISRTPEVTCVVVDVSHEDPEVK FNWYVDGVEVHNAKTCPREEQYNSTYRVVSVLTVLHQDWLNGKE YKCKVSNKALPAPIEKTISKAK |
| 19 | CP13E10-183/290 HC (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGVLRYFDWLLDYYYYMDVWGKGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTCPREEQYN STYRVVSVLTVLHQDWLNGKEYKCKVSNKALPAPIEKTISKAKG QPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK |
| 20 | CP13E10-183/290 CL | (R)TVAAPSVFIFPPSDEQLKSGTASVVCLLNNFYPREAKVQWK VDNALQSGNSQESVTEQDSKDSTYSLSSTLTLSCADYEKHKVYA CEVTHQGLSSPVTKSFNRGEC |
| 21 | CP13E10-183/290 LC | EIVLTQSPATLSLSPGERATLSCRASQSVGSYLAWYQQRPGQAP RLLIYDASNRATGIPARFSGSGSGTDFTLTISSLEPEDFAVYYC QQRANVFTFGQGTKVEIKRTVAAPSVFIFPPSDEQLKSGTASVV CLLNNFYPREAKVQWKVDNALQSGNSQESVTEQDSKDSTYSLSS TLTLSCADYEKHKVYACEVTHQGLSSPVTKSFNRGEC |

TABLE 10-continued

SEQUENCE LIST

| SEQ ID NO. | Description | Sequence |
|---|---|---|
| 22 | CP13E10-H7C-K222R-N297A CH1 | ASTKGPSVFPLAPSSKTLLQGSGGTAALGCLVKDYFPEPVTVS WNSGALTSGVHTFPAVLQSSGLYSLSSVVTVPSSSLGTQTYICN VNHKPSNTKVDKKV |
| 23 | CP13E10-H7C-K222R-N297A HINGE | EPKSCDRTHTCPPCP |
| 24 | CP13E10-H7C-K222R-N297A CH2 | APELLGGPSVFLFPPKPKDTLMISRTPEVTCVVVDVSHEDPEVK FNWYVDGVEVHNAKTKPREEQYASTYRVVSVLTVLHQDWLNGKE YKCKVSNKALPAPIEKTISKAK |
| 25 | CP13E10-H7C-K222R-N297A HC LLQG: H7C Glutamine-containing transglutaminase ("Q") tag K222R and N297A substitutions included to increase ADC homogeneity (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGVLRYFDWLLDYYYMDVWGKGTTVTVSSASTK GPSVFPLAPSSKSTLLQGSGGTAALGCLVKDYFPEPVTVSWNSG ALTSGVHTFPAVLQSSGLYSLSSVVTVPSSSLGTQTYICNVNHK PSNTKVDKKVEPKSCDRTHTCPPCPAPELLGGPSVFLFPPKPKD TLMISRTPEVTCVVVDVSHEDPEVKFNWYVDGVEVHNAKTKPRE EQYASTYRVVSVLTVLHQDWLNGKEYKCKVSNKALPAPIEKTIS KAKGQPREPQVYTLPPSREEMTKNQVSLTCLVKGFYPSDIAVEW ESNGQPENNYKTTPPVLDSDGSFFLYSKLTVDKSRWQQGNVFSC SVMHEALHNHYTQKSLSLSPGK |
| 26 | CP13E10-54HC-89LC V_H | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGELRHFDHLLDYHYYMDVWGQGTTVTVSS |
| 27 | CP13E10-54HC-89LC HC CDR3 | DGELRHFDHLLDYHYY |
| 28 | CP13E10-54HC-89LC JH | WGQGTTVTVSS |
| 29 | CP13E10-54HC-89LC HC (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGELRHFDHLLDYHYYMDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK |
| 30 | CP13E10-54HC-89LC V_L | EIVLTQSPATLSLSPGERATLSCRASQSVGSYLAWYQQRPGQAP RLLIYDASNRATGIPARFSGSGSGTDFTLTISSLEPEDFAVYYC QQRAQEFTFGQGTKVEIK |
| 31 | CP13E10-54HC-89LC LC CDR3 | QQRAQEFT |
| 32 | CP13E10-54HC-89LC LC | EIVLTQSPATLSLSPGERATLSCRASQSVGSYLAWYQQRPGQAP RLLIYDASNRATGIPARFSGSGSGTDFTLTISSLEPEDFAVYYC QQRAQEFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| 33 | CP13E10-54HC-89LC-183/290 HC (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGELRHFDHLLDYHYYMDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTCPREEQYN STYRVVSVLTVLHQDWLNGKEYKCKVSNKALPAPIEKTISKAKG |

TABLE 10-continued

SEQUENCE LIST

| SEQ ID NO. | Description | Sequence |
|---|---|---|
| | | QPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK |
| 34 | CP13E10-54HC-89LC-183/290 LC | EIVLTQSPATLSLSPGERATLSCRASQSVGSYLAWYQQRPGQAP RLLIYDASNRATGIPARFSGSGSGTDFTLTISSLEPEDFAVYYC QQRAQEFTFGQGTKVEIKRTVAAPSVFIFPPSDEQLKSGTASVV CLLNNFYPREAKVQWKVDNALQSGNSQESVTEQDSKDSTYSLSS TLTLSCADYEKHKVYACEVTHQGLSSPVTKSFNRGEC |
| 35 | CP13E10-54HC-89LCH7C-K222R-N297A HC LLQG: H7C Glutamine-containing transglutaminase ("Q") tag K222R and N297A substitutions included to increase ADC homogeneity (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDGELRHFDHLLDYHYYMDVWGQGTTVTVSSASTK GPSVFPLAPSSKSTLLQGSGGTAALGCLVKDYFPEPVTVSWNSG ALTSGVHTFPAVLQSSGLYSLSSVVTVPSSSLGTQTYICNVNHK PSNTKVDKKVEPKSCDRTHTCPPCPAPELLGGPSVFLFPPKPKD TLMISRTPEVTCVVVDVSHEDPEVKFNWYVDGVEVHNAKTKPRE EQYASTYRVVSVLTVLHQDWLNGKEYKCKSNKALPAPIEKTIS KAKGQPREPQVYTLPPSREEMTKNQVSLTCLVKGFYPSDIAVEW ESNGQPENNYKTTPPVLDSDGSFFLYSKLTVDKSRWQQGNVFSC SVMHEALHNHYTQKSLSLSPGK |
| 36 | CP13E10-54HC-89LCv1 V$_L$ | EIVMTQSPATLSLSPGERATLSC<u>RASQSVGSYLA</u>WYQQKPGQAP RLLIY<u>DASNRATG</u>IPARFSGSGSGTDFTLTISSLQPEDFAVYYC <u>QQRAQEFT</u>FGQGTKVEIK |
| 37 | CP13E10-54HC-89LCv1 LC | EIVMTQSPATLSLSPGERATLSCRASQSVGSYLAWYQQKPGQAP RLLIYDASNRATGIPARFSGSGSGTDFTLTISSLQPEDFAVYYC QQRAQEFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| 38 | CP13E10-54HC-89LCv1-183/290 LC | EIVMTQSPATLSLSPGERATLSCRASQSVGSYLAWYQQKPGQAP RLLIYDASNRATGIPARFSGSGSGTDFTLTISSLQPEDFAVYYC QQRAQEFTFGQGTKVEIKRTVAAPSVFIFPPSDEQLKSGTASVV CLLNNFYPREAKVQWKVDNALQSGNSQESVTEQDSKDSTYSLSS TLTLSCADYEKHKVYACEVTHQGLSSPVTKSFNRGEC |
| 39 | CP13E10-54HCv13-89LCv1 V$_H$ | EVQLVQSGAEVKKPGASVKVSCKASGYTFT<u>SYYMH</u>WVRQAPGQG LEWMG<u>IINPSGGSTSYAQKFQG</u>RVTMTRDT<u>S</u>TSTVYMELSSLRS EDTAVYYCAR<u>DAELRHFDHLLDYHYYMDV</u>WGQGTTVTVSS |
| 40 | CP13E10-54HCv13-89LCv1 HC CDR3 | DAELRHFDHLLDYHYYMDV |
| 41 | CP13E10-54HCv13-89LCv1 HC (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDAELRHFDHLLDYHYYMDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK |
| 42 | CP13E10-54HCv13-89LCv1-183/290 HC (K): Can be prepared +/- lysine | EVQLVQSGAEVKKPGASVKVSCKASGYTFTSYYMHWVRQAPGQG LEWMGIINPSGGSTSYAQKFQGRVTMTRDTSTSTVYMELSSLRS EDTAVYYCARDAELRHFDHLLDYHYYMDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTCPREEQYN STYRVVSVLTVLHQDWLNGKEYKCKVSNKALPAPIEKTISKAKG QPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK |

TABLE 10-continued

SEQUENCE LIST

| SEQ ID NO. | Description | Sequence |
|---|---|---|
| 43 | CP13E10-54HCv13-89LCv1-H7C-K222R-N297A HC LLQG: H7C Glutamine-containing transglutaminase ("Q") tag K222R and N297A substitutions included to increase ADC homogeneity (K): Can be prepared +/- lysine | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDAELRHFDHLLDYHYYMDVWGQGTTVTVSSASTKGPSVFPLAPSSKTLLQGSGGTAALGCLVKDYFPEPVTVSWNSGALTSGVHTFPPAVLQSSGLYSLSSVVTVPSSSLGTQTYICNVNHKPSNTKVDKKVEPKSCDRTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 44 | CP13E10-291 V<sub>H</sub> CDRs as defined by Kabat underlined | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDGELRHFDQVYNYHYYMDVWGQGTTVTVSS |
| 45 | CP13E10-291 HC CDR3 V(H97)E, H(H100C)Q, L(H100D)V, L(H100E)Y, D(H100F)N mutations incorporated | DGELRHFDQVYNYHYYMDV |
| 46 | CP13E10-291 HC (K): Can be prepared +/- lysine | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDGELRHFDQVYNYHYYMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 47 | Antibody 23 V<sub>H</sub> CDRs as defined by Kabat underlined | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARDPTYFDWTRRGYYYMDVWGKGTTVTVSS |
| 48 | Antibody 23 HC CDR1 | SYAIS |
| 49 | Antibody 23 HC CDR2 | GIIPIFGTANYAQKFQG |
| 50 | Antibody 23 HC CDR3 | DPTYFDWTRRGYYYMDV |
| 51 | Antibody 23 HC | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARDPTYFDWTRRGYYYMDVWGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 52 | Antibody 23 V<sub>L</sub> CDRs as defined by Kabat underlined | SYELTQPPSVSVSPGQTARITCSGDALPKKYAYWYQQKSGQAPVLVIYEDSKRPSGIPERFSGSSSGTMATLTISGARVEDEADYYCYSTDSSDNHRKGFGGGTKLTVL |
| 53 | Antibody 23 LC CDR1 | SGDALPKKYAY |
| 54 | Antibody 23 LC CDR2 | EDSKRPS |
| 55 | Antibody 23 LC CDR3 | YSTDSSDNHRKG |
| 56 | Antibody 23 JL | FGGGTKLTVL |

TABLE 10-continued

SEQUENCE LIST

| SEQ ID NO. | Description | Sequence |
|---|---|---|
| 57 | Antibody 23 CL | GQPKAAPSVTLFPPSSEELQANKATLVCLISDFYPGAVTVAWKA DSSPVKAGVETTTPSKQSNNKYAASSYLSLTPEQWKSHRSYSCQ VTHEGSTVEKTVAPTECS |
| 58 | Antibody 23 LC | SYELTQPPSVSVSPGQTARITCSGDALPKKYAYWYQQKSGQAPV LVIYEDSKRPSGIPERFSGSSSGTMATLTISGARVEDEADYYCY STDSSDNHRKGFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |
| 59 | Antibody 24 $V_H$ CDRs as defined by Kabat underlined | QVQLVESGGGVVQPGRSLRLSCAASGFTFSSYGMHWVRQAPGKG LEWVAVISYDGSNKYYADSVKGRFTISRDNSKNTLYLQMNSLRA EDTAVYYCARGVGLPDIWGQGTMVTVSS |
| 60 | Antibody 24 HC CDR1 | SYGMH |
| 61 | Antibody 24 HC CDR2 | VISYDGSNKYYADSVKG |
| 62 | Antibody 24 HC CDR3 | GVGLPDI |
| 63 | Antibody 24 JH | WGQGTMVTVSS |
| 64 | Antibody 24 HC (K): Can be prepared +/- lysine | QVQLVESGGGVVQPGRSLRLSCAASGFTFSSYGMHWVRQAPGKG LEWVAVISYDGSNKYYADSVKGRFTISRDNSKNTLYLQMNSLRA EDTAVYYCARGVGLPDIWGQGTMVTVSSASTKGPSVFPLAPSSK STSGGTAALGCLVKDYFPEPVTVSWNSGALTSGVHTFPAVLQSS GLYSLSSVVTVPSSSLGTQTYICNVNHKPSNTKVDKKVEPKSCD KTHTCPPCPAPELLGGPSVFLFPPKPKDTLMISRTPEVTCVVVD VSHEDPEVKFNWYVDGVEVHNAKTKPREEQYNSTYRVVSVLTVL HQDWLNGKEYKCKVSNKALPAPIEKTISKAKGQPREPQVYTLPP SREEMTKNQVSLTCLVKGFYPSDIAVEWESNGQPENNYKTTPPV LDSDGSFFLYSKLTVDKSRWQQGNVFSCSVMHEALHNHYTQKSL SLSPGK |
| 65 | Antibody 24 $V_L$ CDRs as defined by Kabat underlined | EIVMTQSPDTLSLSPGERATLSCRASQKIYYSYLAWYQQKPGQA PRLLISGASTRASDISDRFSGGGSGTDFTLTINSLESEDAAVYY CQQYDSLPVTFGRGTKLEIK |
| 66 | Antibody 24 LC CDR1 | RASQKIYYSYLA |
| 67 | Antibody 24 LC CDR2 | GASTRAS |
| 68 | Antibody 24 LC CDR3 | QQYDSLPVT |
| 69 | Antibody 24 JK | FGRGTKLEIK |
| 70 | Antibody 24 LC | EIVMTQSPDTLSLSPGERATLSCRASQKIYYSYLAWYQQKPGQA PRLLISGASTRASDISDRFSGGGSGTDFTLTINSLESEDAAVYY CQQYDSLPVTFGRGTKLEIKRTVAAPSVFIFPPSDEQLKSGTAS VVCLLNNFYPREAKVQWKVDNALQSGNSQESVTEQDSKDSTYSL SSTLTLSKADYEKHKVYACEVTHQGLSSPVTKSFNRGEC |
| 71 | Antibody 76 $V_L$ CDRs as defined by Kabat underlined | SYELTQPPSVSVSPGQTARITCSGDALPKKYAFWYQQKSGQAPV LVIYEDSKRPSGIPEKFSGSSSGTMATLTISGAQVEDEADYYCY STDSSDNPRGVFGGGTKLTVL |
| 72 | Antibody 76 LC CDR1 | SGDALPKKYA |
| 73 | Antibody 76 LC CDR3 | YSTDSSDNPRGV |
| 74 | Antibody 76 LC | SYELTQPPSVSVSPGQTARITCSGDALPKKYAFWYQQKSGQAPV LVIYEDSKRPSGIPEKFSGSSSGTMATLTISGAQVEDEADYYCY STDSSDNPRGVFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |
| 75 | CP13E10 $V_H$ Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGTATTACG ATATTTTGACTGGTTATTAGACTACTACTACTACATGGACGTCT GGGGCAAAGGGACCACGGTCACCGTCTCGAGC |

TABLE 10-continued

SEQUENCE LIST

| SEQ ID NO. | Description | Sequence |
|---|---|---|
| 76 | CP13E10 HC Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGTATTACG ATATTTTGACTGGTTATTAGACTACTACTACATGGACGTCT GGGGCAAAGGGACCACGGTCACCGTCTCGAGCGCGTCGACCAAG GGCCCATCGGTCTTCCCCCTGGCACCCTCCTCCAAGAGCACCTC TGGGGGCACAGCGGCCCTGGGCTGCCTGGTCAAGGACTACTTCC CCGAACCGGTGACGGTGTCGTGGAACTCAGGCGCCCTGACCAGC GGCGTGCACACCTTCCCGGCTGTCCTACAGTCCTCAGGACTCTA CTCCCTCAGCAGCGTGGTGACCGTGCCCTCCAGCAGCTTGGGCA CCCAGACCTACATCTGCAACGTGAATCACAAGCCCAGCAACACC AAGGTGGACAAGAAAGTTGAGCCCAAATCTTGTGACAAAACTCA CACATGCCCACCGTGCCCAGCACCTGAACTCCTGGGGGGACCGT CAGTCTTCCTCTTCCCCCCAAAACCCAAGGACACCCTCATGATC TCCCGGACCCCTGAGGTCACATGCGTGGTGGTGGACGTGAGCCA CGAAGACCCTGAGGTCAAGTTCAACTGGTACGTGGACGGCGTGG AGGTGCATAATGCCAAGACAAAGCCGCGGGAGGAGCAGTACAAC AGCACGTACCGTGTGGTCAGCGTCCTCACCGTCCTGCACCAGGA CTGGCTGAATGGCAAGGAGTACAAGTGCAAGGTCTCCAACAAAG CCCTCCCAGCCCCCATCGAGAAAACCATCTCCAAAGCCAAAGGG CAGCCCCGAGAACCACAGGTGTACACCCTGCCCCCATCCCGGGA GGAGATGACCAAGAACCAGGTCAGCCTGACCTGCCTGGTCAAAG GCTTCTATCCCAGCGACATCGCCGTGGAGTGGGAGAGCAATGGG CAGCCGGAGAACAACTACAAGACCACGCCTCCCGTGCTGGACTC CGACGGCTCCTTCTTCCTCTATAGCAAGCTCACCGTGGACAAGA GCAGGTGGCAGCAGGGGAACGTCTTCTCATGCTCCGTGATGCAT GAGGCTCTGCACAACCACTACACGCAGAAGAGCCTCTCCCTGTC CCCGGGT(AAA) |
| 77 | CP13E10 $V_L$ Nucleotide sequence | GAAATTGTGTTGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAGACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTAGAGCCTGAAGATTTTGCGGTTTATTACTGT CAGCAGCGTGCCAACGTATTCACTTTTGGCCAGGGGACCAAGGT GGAAATCAAA |
| 78 | CP13E10 LC Nucleotide sequence | GAAATTGTGTTGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAGACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTAGAGCCTGAAGATTTTGCGGTTTATTACTGT CAGCAGCGTGCCAACGTATTCACTTTTGGCCAGGGGACCAAGGT GGAAATCAAACGAACTGTGGCTGCACCATCTGTCTTCATCTTCC CGCCATCTGATGAGCAGTTGAAATCTGGAACTGCCTCTGTTGTG TGCCTGCTGAATAACTTCTATCCCAGAGAGGCCAAAGTACAGTG GAAGGTGGATAACGCCCTCCAATCGGGTAACTCCCAGGAGAGTG TCACAGAGCAGGACAGCAAGGACAGCACCTACAGCCTCAGCAGC ACCCTGACGCTGAGCAAAGCAGACTACGAGAAACACAAAGTCTA CGCCTGCGAAGTCACCCATCAGGGCCTGAGCTCGCCCGTCACAA AGAGCTTCAACAGGGGAGAGTGT |
| 79 | CP13E10-54HC-89LC $V_H$ Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGAGTTACG ACACTTTGACCACTTATTAGACTACCACTACATGGACGTCT GGGGCAGGGGACCACGGTCACCGTCTCGAGC |
| 80 | CP13E10-54HC-89LC HC Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT |

TABLE 10-continued

SEQUENCE LIST

| SEQ ID NO. | Description | Sequence |
|---|---|---|
| | | GAGGACACGGCCGTGTATTACTGTGCGAGAGATGGCGAGTTACG ACACTTTGACCACTTATTAGACTACCACTACTACATGGACGTCT GGGGGCCAGGGGACCACGGTCACCGTCTCGAGCGCGTCGACCAAG GGCCCATCGGTCTTCCCCCTGGCACCCTCCTCCAAGAGCACCTC TGGGGGCACAGCGGCCCTGGGCTGCCTGGTCAAGGACTACTTCC CCGAACCGGTGACGGTGTCGTGGAACTCAGGCGCCCTGACCAGC GGCGTGCACACCTTCCCGGCTGTCCTACAGTCCTCAGGACTCTA CTCCCTCAGCAGCGTGGTGACCGTGCCCTCCAGCAGCTTGGGCA CCCAGACCTACATCTGCAACGTGAATCACAAGCCCAGCAACACC AAGGTGGACAAGAAAGTTGAGCCCAAATCTTGTGACAAAACTCA CACATGCCCACCGTGCCCAGCACCTGAACTCCTGGGGGGACCGT CAGTCTTCCTCTTCCCCCCAAAACCCAAGGACACCCTCATGATC TCCCGGACCCCTGAGGTCACATGCGTGGTGGTGGACGTGAGCCA CGAAGACCCTGAGGTCAAGTTCAACTGGTACGTGGACGGCGTGG AGGTGCATAATGCCAAGACAAAGCCGCGGGAGGAGCAGTACAAC AGCACGTACCGTGTGGTCAGCGTCCTCACCGTCCTGCACCAGGA CTGGCTGAATGGCAAGGAGTACAAGTGCAAGGTCTCCAACAAAG CCCTCCCAGCCCCCATCGAGAAAACCATCTCCAAAGCCAAAGGG CAGCCCCGAGAACCACAGGTGTACACCCTGCCCCCATCCCGGGA GGAGATGACCAAGAACCAGGTCAGCCTGACCTGCCTGGTCAAAG GCTTCTATCCCAGCGACATCGCCGTGGAGTGGGAGAGCAATGGG CAGCCGGAGAACAACTACAAGACCACGCCTCCCGTGCTGGACTC CGACGGCTCCTTCTTCCTCTATAGCAAGCTCACCGTGGACAAGA GCAGGTGGCAGCAGGGGAACGTCTTCTCATGCTCCGTGATGCAT GAGGCTCTGCACAACCACTACACGCAGAAGAGCCTCTCCCTGTC CCCGGGT(AAA) |
| 81 | CP13E10-54HC-89LC V<sub>L</sub> Nucleotide sequence | GAAATTGTGTTGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAGACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTAGAGCCTGAAGATTTTGCGGTTTATTACTGT CAGCAGCGTGCCCAAGAGTTCACTTTTGGCCAGGGGACCAAGGT GGAAATCAAA |
| 82 | CP13E10-54HC-89LC LC Nucleotide sequence | GAAATTGTGTTGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAGACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTAGAGCCTGAAGATTTTGCGGTTTATTACTGT CAGCAGCGTGCCCAAGAGTTCACTTTTGGCCAGGGGACCAAGGT GGAAATCAAACGAACTGTGGCTGCACCATCTGTCTTCATCTTCC CGCCATCTGATGAGCAGTTGAAATCTGGAACTGCCTCTGTTGTG TGCCTGCTGAATAACTTCTATCCCAGAGAGGCCAAAGTACAGTG GAAGGTGGATAACGCCCTCCAATCGGGTAACTCCCAGGAGAGTG TCACAGAGCAGGACAGCAAGGACAGCACCTACAGCCTCAGCAGC ACCCTGACGCTGAGCAAAGCAGACTACGAGAAACACAAAGTCTA CGCCTGCGAAGTCACCCATCAGGGCCTGAGCTCGCCCGTCACAA AGAGCTTCAACAGGGGAGAGTGT |
| 83 | CP13E10-54HC-89LCv1 V<sub>L</sub> Nucleotide sequence | GAAATTGTGATGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAAACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTACAGCCTGAAGATTTTGCGGTTTATTACTGT CAGCAGCGTGCCCAAGAGTTCACTTTTGGCCAGGGGACCAAGGT GGAAATCAAA |
| 84 | CP13E10-54HC-89LCv1 LC Nucleotide sequence | GAAATTGTGATGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAAACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTACAGCCTGAAGATTTTGCGGTTTATTACTGT CAGCAGCGTGCCCAAGAGTTCACTTTTGGCCAGGGGACCAAGGT GGAAATCAAACGAACTGTGGCTGCACCATCTGTCTTCATCTTCC CGCCATCTGATGAGCAGTTGAAATCTGGAACTGCCTCTGTTGTG TGCCTGCTGAATAACTTCTATCCCAGAGAGGCCAAAGTACAGTG GAAGGTGGATAACGCCCTCCAATCGGGTAACTCCCAGGAGAGTG TCACAGAGCAGGACAGCAAGGACAGCACCTACAGCCTCAGCAGC ACCCTGACGCTGAGCAAAGCAGACTACGAGAAACACAAAGTCTA |

TABLE 10-continued

SEQUENCE LIST

| SEQ ID NO. | Description | Sequence |
|---|---|---|
| | | CGCCTGCGAAGTCACCCATCAGGGCCTGAGCTCGCCCGTCACAA AGAGCTTCAACAGGGGAGAGTGT |
| 85 | CP13E10-54HC-89LCv1-183/290 HC Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGAGTTACG ACACTTTGACCACTTATTAGACTACCACTACTACATGGACGTCT GGGGCCAGGGGACCACGGTCACCGTCTCGAGCGCGTCGACCAAG GGCCCATCGGTCTTCCCCCTGGCACCCTCCTCCAAGAGCACCTC TGGGGGCACAGCGGCCCTGGGCTGCCTGGTCAAGGACTACTTCC CCGAACCGGTGACGGTGTCGTGGAACTCAGGCGCCCTGACCAGC GGCGTGCACACCTTCCCGGCTGTCCTACAGTCCTCAGGACTCTA CTCCCTCAGCAGCGTGGTGACCGTGCCCTCCAGCAGCTTGGGCA CCCAGACCTACATCTGCAACGTGAATCACAAGCCCAGCAACACC AAGGTGGACAAGAAAGTTGAGCCCAAATCTTGTGACAAAACTCA CACATGCCCACCGTGCCCAGCACCTGAACTCCTGGGGGGACCGT CAGTCTTCCTCTTCCCCCCAAAACCCAAGGACACCCTCATGATC TCCCGGACCCCTGAGGTCACATGCGTGGTGGTGGACGTGAGCCA CGAAGACCCTGAGGTCAAGTTCAACTGGTACGTGGACGGCGTGG AGGTGCATAATGCCAAGACATGCCCGCGGGAGGAGCAGTACAAC AGCACGTACCGTGTGGTCAGCGTCCTCACCGTCCTGCACCAGGA CTGGCTGAATGGCAAGGAGTACAAGTGCAAGGTCTCCAACAAAG CCCTCCCAGCCCCCATCGAGAAAACCATCTCCAAAGCCAAAGGG CAGCCCCGAGAACCACAGGTGTACACCCTGCCCCCATCCCGGGA GGAGATGACCAAGAACCAGGTCAGCCTGACCTGCCTGGTCAAAG GCTTCTATCCCAGCGACATCGCCGTGGAGTGGGAGAGCAATGGG CAGCCGGAGAACAACTACAAGACCACGCCTCCCGTGCTGGACTC CGACGGCTCCTTCTTCCTCTATAGCAAGCTCACCGTGGACAAGA GCAGGTGGCAGCAGGGGAACGTCTTCTCATGCTCCGTGATGCAT GAGGCTCTGCACAACCACTACACGCAGAAGAGCCTCTCCCTGTC CCCCGGA(AAA) |
| 86 | CP13E10-54HC-89LCv1-183/290 LC Nucleotide sequence | GAAATTGTGATGACACAGTCTCCAGCCACCCTGTCTTTGTCTCC AGGGGAGAGAGCCACCCTCTCCTGCAGGGCCAGTCAGAGTGTTG GCAGCTACTTGGCCTGGTACCAACAGAAACCTGGCCAGGCTCCC AGGCTCCTCATCTATGATGCTTCCAACAGGGCCACTGGCATCCC AGCCAGGTTCAGTGGCAGTGGGTCTGGGACAGACTTCACCCTCA CCATCAGCAGCCTACAGCCTGAAGATTTTGCGGTTTATTACTGT CAGCAGCGTGCCCAAGAGTTCACTTTTGGCCAGGGGACCAAGGT GGAAATCAAACGTACTGTGGCTGCACCATCTGTCTTCATCTTCC CGCCATCTGATGAGCAGTTGAAATCTGGAACTGCCTCTGTTGTG TGCCTGCTGAATAACTTCTATCCCAGAGAGGCCAAAGTACAGTG GAAGGTGGATAACGCCCTCCAATCGGGTAACTCCCAGGAGAGTG TCACAGAGCAGGACAGCAAGGACAGCACCTACAGCCTCAGCAGC ACCCTGACGCTGAGCTGCGCAGACTACGAGAAACACAAAGTCTA CGCCTGCGAAGTCACCCATCAGGGCCTGAGCTCGCCCGTCACAA AGAGCTTCAACAGGGGAGAGTGT |
| 87 | CP13E10-54HC-89LCv1-H7C-K222R-N297A HC Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGAGTTACG ACACTTTGACCACTTATTAGACTACCACTACTACATGGACGTCT GGGGCCAGGGGACCACGGTCACCGTCTCGAGCGCGTCGACCAAG GGCCCATCGGTCTTCCCCCTGGCACCCTCCTCCAAGAGCACCCT GCTGCAGGGGTCTGGGGGCACAGCGGCCCTGGGCTGCCTGGTCA AGGACTACTTCCCCGAACCGGTGACGGTGTCGTGGAACTCAGGC GCCCTGACCAGCGGCGTGCACACCTTCCCGGCTGTCCTACAGTC CTCAGGACTCTACTCCCTCAGCAGCGTAGTGACCGTGCCCTCCA GCAGCTTGGGCACCCAGACCTACATCTGCAACGTGAATCACAAG CCCAGCAACACCAAGGTGGACAAGAAAGTTGAGCCCAAATCTTG TGACCGTACTCACACATGCCCACCGTGCCCAGCACCTGAACTCC TGGGGGGACCGTCAGTCTTCCTCTTCCCCCCAAAACCCAAGGAC ACCCTCATGATCTCCCGGACCCCTGAGGTCACATGCGTGGTGGT GGACGTGAGCCACGAAGACCCTGAGGTCAAGTTCAACTGGTACG TGGACGGCGTGGAGGTGCATAATGCCAAGACAAAGCCGCGGGAG GAGCAGTACGCCAGCACGTACCGTGTGGTCAGCGTCCTCACCGT CCTGCACCAGGACTGGCTGAATGGCAAGGAGTACAAGTGCAAGG |

TABLE 10-continued

SEQUENCE LIST

| SEQ ID NO. | Description | Sequence |
|---|---|---|
| | | TCTCCAACAAAGCCCTCCCAGCCCCCATCGAGAAAACCATCTCC AAAGCCAAAGGGCAGCCCCGAGAACCACAGGTGTACACCCTGCC CCCATCCCGGGAGGAGATGACCAAGAACCAGGTCAGCCTGACCT GCCTGGTCAAAGGCTTCTATCCCAGCGACATCGCCGTGGAGTGG GAGAGCAATGGGCAGCCGGAGAACAACTACAAGACCACGCCTCC CGTGCTGGACTCCGACGGCTCCTTCTTCCTCTATAGCAAGCTCA CCGTGGACAAGAGCAGGTGGCAGCAGGGGAACGTCTTCTCATGC TCCGTGATGCATGAGGCTCTGCACAACCACTACACGCAGAAGAG CCTCTCCCTGTCCCCCGGA(AAA) |
| 88 | CP13E10-291 $V_H$ Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGAATTACG ACACTTTGACCAGGTATACAACTACCACTACTACATGGACGTCT GGGGCCAGGGGACCACGGTCACCGTCTCGAGC |
| 89 | CP13E10-291 HC Nucleotide sequence | GAGGTCCAGCTGGTGCAGTCTGGGGCTGAGGTGAAGAAGCCTGG GGCCTCAGTGAAGGTTTCCTGCAAGGCATCTGGATACACCTTCA CCAGCTACTATATGCACTGGGTGCGACAGGCCCCTGGACAAGGG CTTGAGTGGATGGGAATAATCAACCCTAGTGGTGGTAGCACAAG CTACGCACAGAAGTTCCAGGGCAGAGTCACCATGACCAGGGACA CGTCCACGAGCACAGTCTACATGGAGCTGAGCAGCCTGAGATCT GAGGACACGGCCGTGTATTACTGTGCGAGAGATGGCGAATTACG ACACTTTGACCAGGTATACAACTACCACTACTACATGGACGTCT GGGGCCAGGGGACCACGGTCACCGTCTCGAGCGCGTCGACCAAG GGCCCATCGGTCTTCCCCCTGGCACCCTCCTCCAAGAGCACCTC TGGGGGCACAGCGGCCCTGGGCTGCCTGGTCAAGGACTACTTCC CCGAACCGGTGACGGTGTCGTGGAACTCAGGCGCCCTGACCAGC GGCGTGCACACCTTCCCGGCTGTCCTACAGTCCTCAGGACTCTA CTCCCTCAGCAGCGTGGTGACCGTGCCCTCCAGCAGCTTGGGCA CCCAGACCTACATCTGCAACGTGAATCACAAGCCCAGCAACACC AAGGTGGACAAGAAAGTTGAGCCCAAATCTTGTGACAAAACTCA CACATGCCCACCGTGCCCAGCACCTGAACTCCTGGGGGGACCGT CAGTCTTCCTCTTCCCCCCAAAACCCAAGGACACCCTCATGATC TCCCGGACCCCTGAGGTCACATGCGTGGTGGTGGACGTGAGCCA CGAAGACCCTGAGGTCAAGTTCAACTGGTACGTGGACGGCGTGG AGGTGCATAATGCCAAGACAAAGCCGCGGGAGGAGCAGTACAAC AGCACGTACCGTGTGGTCAGCGTCCTCACCGTCCTGCACCAGGA CTGGCTGAATGGCAAGGAGTACAAGTGCAAGGTCTCCAACAAAG CCCTCCCAGCCCCCATCGAGAAAACCATCTCCAAAGCCAAAGGG CAGCCCCGAGAACCACAGGTGTACACCCTGCCCCCATCCCGGGA GGAGATGACCAAGAACCAGGTCAGCCTGACCTGCCTGGTCAAAG GCTTCTATCCCAGCGACATCGCCGTGGAGTGGGAGAGCAATGGG CAGCCGGAGAACAACTACAAGACCACGCCTCCCGTGCTGGACTC CGACGGCTCCTTCTTCCTCTATAGCAAGCTCACCGTGGACAAGA GCAGGTGGCAGCAGGGGAACGTCTTCTCATGCTCCGTGATGCAT GAGGCTCTGCACAACCACTACACGCAGAAGAGCCTCTCCCTGTC CCCGGGT(AAA) |
| 90 | CUB domain-containing protein 1 isoform 1 precursor [Homo sapiens] Reference: NP 073753.3 | MAGLNCGVSIALLGVLLLGAARLPRGAEAFEIALPRESNITVLI KLGTPTLLAKPCYIVISKRHITMLSIKSGERIVFTFSCQSPENH FVIEIQKNIDCMSGPCPFGEVQLQPSTSLLPTLNRTFIWDVKAH KSIGLELQFSIPRLRQIGPGESCPDGVTHSISGRIDATVVRIGT FCSNGTVSRIKMQEGVKMALHLPWFHPRNVSGFSIANRSSIKRL CIIESVFEGEGSATLMSANYPEGFPEDELMTWQFVVPAHLRASV SFLNFNLSNCERKEERVEYYIPGSTTNPEVFKLEDKQPGNMAGN FNLSLQGCDQDAQSPGILRLQFQVLVQHPQNESNKIYVVDLSNE RAMSLTIEPRPVKQSRKFVPGCFVCLESRTCSSNLTLTSGSKHK ISFLCDDLTRLWMNVEKTISCTDHRYCQRKSYSLQVPSDILHLP VELHDFSWKLLVPKDRLSLVLVPAQKLQQHTHEKPCNTSFSYLV ASAIPSQDLYFGSFCPGGSIKQIQVKQNISVTLRTFAPSFQQEA SRQGLTVSFIPYFKEEGVFTVTPDTKSKVYLRTPNWDRGLPSLT SVSWNISVPRDQVACLTFFKERSGVVCQTGRAFMIIQEQRTRAE EIFSLDEDVLPKPSFHHHSFWVNISNCSPTSGKQLDLLFSVTLT PRTVDLTVILIAAVGGGVLLLSALGLIICCVKKKKKKTNKGPAV GIYNDNINTEMPRQPKKFQKGRKDNDSHVYAVIEDTMVYGHLLQ DSSGSFLQPEVDTYRPFQGTMGVCPPSPPTICSRAPTAKLATEE PPPRSPPESESEPYTFSHPNNGDVSSKDTDIPLLNTQEPMEPAE |

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in anyway.

What is claimed is:

1. An isolated antibody, or antigen-binding fragment thereof, that specifically binds CDCP1, comprising:
   (i) a VH that comprises:
      (a) a CDRH1 comprising the amino acid sequence of SEQ ID NO:2,
      (b) a CDRH2 comprising the amino acid sequence of SEQ ID NO:3; and
      (c) a CDRH3 comprising the amino acid sequence of SEQ ID NO:27;
   and (ii) a VL that comprises:
      (a) a CDRL1 comprising the amino acid sequence of SEQ ID NO:12,
      (b) a CDRL2 comprising the amino acid sequence of SEQ ID NO:13; and
      (c) a CDRL3 comprising the amino acid sequence of SEQ ID NO:31.

2. An antibody drug conjugate comprising an antibody, or antigen-binding fragment thereof, that specifically binds CUB Domain-Containing Protein-1 (CDCP1), wherein the antibody is conjugated to a drug moiety, wherein the antibody, or antigen-binding fragment thereof, comprises:
   (i) a heavy chain variable region (VH) that comprises:
      (a) a VH complementarity determining region one (CDRH1) comprising the amino acid sequence of SEQ ID NO: 2,
      (b) a VH complementarity determining region two (CDRH2) comprising the amino acid sequence of SEQ ID NO: 3, and
      (c) a VH complementarity determining region three (CDRH3) comprising the amino acid sequence selected from the group consisting of SEQ ID NO: 27, SEQ ID NO: 4, SEQ ID NO: 40 and SEQ ID NO: 45,
   and (ii) a light chain variable region (VL) that comprises:
      (a) a VL complementarity determining region one (CDRL1) comprising the amino acid sequence of SEQ ID NO: 12,
      (b) a VL complementarity determining region two (CDRL2) comprising the amino acid sequence of SEQ ID NO: 13, and
      (c) a VL complementarity determining region three (CDRL3) comprising the amino acid sequence selected from the group consisting of SEQ ID NO: 31 and SEQ ID NO:14.

3. The antibody drug conjugate of claim 2, wherein the antibody comprises a VH that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 26, and a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 30.

4. The antibody drug conjugate of claim 2, wherein the antibody comprises a VH that comprises the amino acid sequence of SEQ ID NO: 26 and a VL that comprises an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 36.

5. The antibody drug conjugate of claim 2, wherein the antibody comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 29 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 37 or SEQ ID NO: 32.

6. The antibody drug conjugate of claim 5, wherein the antibody comprises a heavy chain that comprises the amino acid sequence of SEQ ID NO: 29 and a light chain that comprises the amino acid sequence of SEQ ID NO: 37.

7. The antibody drug conjugate of claim 2, wherein the antibody comprises a heavy chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID No: 33 and a light chain comprising an amino acid sequence at least 90%, at least 91%, at least 92%, at least 93%, at least 94%, at least 95%, at least 96%, at least 97%, at least 98%, at least 99%, or 100% identical to the amino acid sequence of SEQ ID NO: 38 or SEQ ID NO: 34.

8. The antibody drug conjugate of claim 7, wherein the antibody comprises a heavy chain that comprises the amino acid sequence of SEQ ID NO: 33 and a light chain that comprises the amino acid sequence of SEQ ID NO: 38.

* * * * *

SEQUENCE LISTING

<160> NUMBER OF SEQ ID NOS: 92

<210> SEQ ID NO 1
<211> LENGTH: 128
<212> TYPE: PRT
<213> ORGANISM: Artificial Sequence
<220> FEATURE:
<223> OTHER INFORMATION: Synthetic Sequence

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Val Leu Arg Tyr Phe Asp Trp Leu Leu Asp Tyr Tyr
            100                 105                 110

Tyr Tyr Met Asp Val Trp Gly Lys Gly Thr Thr Val Thr Val Ser Ser
        115                 120                 125

<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 2

Ser Tyr Tyr Met His
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 3

Ile Ile Asn Pro Ser Gly Gly Ser Thr Ser Tyr Ala Gln Lys Phe Gln
1               5                   10                  15

Gly

<210> SEQ ID NO 4
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 4

Asp Gly Val Leu Arg Tyr Phe Asp Trp Leu Leu Asp Tyr Tyr Tyr Tyr
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 5

Trp Gly Lys Gly Thr Thr Val Thr Val Ser Ser
1               5                   10

<210> SEQ ID NO 6
<211> LENGTH: 98
<212> TYPE: PRT
<213> ORGANISM: Artificial Sequence
<220> FEATURE:
<223> OTHER INFORMATION: Synthetic Sequence

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 7
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 7

Glu Pro Lys Ser Cys Asp Lys Thr His Thr Cys Pro Pro Cys Pro
1               5                   10                  15

<210> SEQ ID NO 8
<211> LENGTH: 110
<212> TYPE: PRT
<213> ORGANISM: Artificial Sequence
<220> FEATURE:
<223> OTHER INFORMATION: Synthetic Sequence -continued

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 9
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 9

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 10
<211> LENGTH: 458
<212> TYPE: PRT
<213> ORGANISM: Artificial Sequence
<220> FEATURE:
<223> OTHER INFORMATION: Synthetic Sequence

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Arg Asp Gly Val Leu Arg Tyr Phe Asp Trp Leu Leu Asp Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
450                 455

<210> SEQ ID NO 11
<211> LENGTH: 106
<212> TYPE: PRT
<213> ORGANISM: Artificial Sequence
<220> FEATURE:
```

<223> OTHER INFORMATION: Synthetic Sequence

<400> SEQUENCE: 11

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Gly Ser Tyr
            20                  25                  30
Leu Ala Trp Tyr Gln Gln Arg Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ala Asn Val Phe Thr
                85                  90                  95
Phe Gly Gln Gly Thr Lys Val Glu Ile Lys
            100                 105
```

<210> SEQ ID NO 12
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 12

```
Arg Ala Ser Gln Ser Val Gly Ser Tyr Leu Ala
1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 13

```
Asp Ala Ser Asn Arg Ala Thr
1               5
```

<210> SEQ ID NO 14
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 14

```
Gln Gln Arg Ala Asn Val Phe Thr
1               5
```

<210> SEQ ID NO 15
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 15

```
Phe Gly Gln Gly Thr Lys Val Glu Ile Lys
1               5                   10
```

<210> SEQ ID NO 16

<211> LENGTH: 106
<212> TYPE: PRT
<213> ORGANISM: Artificial Sequence
<220> FEATURE:
<223> OTHER INFORMATION: Synthetic Sequence

<400> SEQUENCE: 16

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 17
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 17

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Val Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
            195                 200                 205
Asn Arg Gly Glu Cys
        210

<210> SEQ ID NO 18
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 18

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Cys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 19
<211> LENGTH: 458
<212> TYPE: PRT
<213> ORGANISM: Artificial Sequence
<220> FEATURE:
<223> OTHER INFORMATION: Synthetic Sequence

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Val Leu Arg Tyr Phe Asp Trp Leu Leu Asp Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
            210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Cys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
            355                 360                 365

Met Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
    450                 455

<210> SEQ ID NO 20
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 20

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

```
Tyr Ser Leu Ser Ser Thr Leu Thr Leu Ser Cys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 21
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Val Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Cys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 22
<211> LENGTH: 102
<212> TYPE: PRT
<213> ORGANISM: Artificial Sequence
<220> FEATURE:
<223> OTHER INFORMATION: Synthetic Sequence

<400> SEQUENCE: 22

Ala Ser Thr Lys Gly Pro Ser Val Phe Pro Leu Ala Pro Ser Ser Lys
1               5                   10                  15

Ser Thr Leu Leu Gln Gly Ser Gly Gly Thr Ala Ala Leu Gly Cys Leu
            20                  25                  30
```

```
Val Lys Asp Tyr Phe Pro Glu Pro Val Thr Val Ser Trp Asn Ser Gly
            35                  40                  45

Ala Leu Thr Ser Gly Val His Thr Phe Pro Ala Val Leu Gln Ser Ser
         50                  55                  60

Gly Leu Tyr Ser Leu Ser Ser Val Val Thr Val Pro Ser Ser Ser Leu
 65                  70                  75                  80

Gly Thr Gln Thr Tyr Ile Cys Asn Val Asn His Lys Pro Ser Asn Thr
                 85                  90                  95

Lys Val Asp Lys Lys Val
            100

<210> SEQ ID NO 23
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 23

Glu Pro Lys Ser Cys Asp Arg Thr His Thr Cys Pro Pro Cys Pro
1               5                  10                  15

<210> SEQ ID NO 24
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 24

Ala Pro Glu Leu Leu Gly Gly Pro Ser Val Phe Leu Phe Pro Pro Lys
1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Ala Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 25
<211> LENGTH: 462
<212> TYPE: PRT
<213> ORGANISM: Artificial Sequence
<220> FEATURE:
<223> OTHER INFORMATION: Synthetic Sequence

<400> SEQUENCE: 25

Glu Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
         35                  40                  45
```

```
Gly Ile Ile Asn Pro Ser Gly Ser Thr Ser Tyr Ala Gln Lys Phe
     50                  55                  60

Gln Gly Arg Val Thr Met Thr Arg Asp Thr Ser Thr Ser Thr Val Tyr
 65              70                  75                      80

Met Glu Leu Ser Ser Leu Arg Ser Glu Asp Thr Ala Val Tyr Tyr Cys
                 85                  90                  95

Ala Arg Asp Gly Val Leu Arg Tyr Phe Asp Trp Leu Leu Asp Tyr Tyr
             100                 105                 110

Tyr Tyr Met Asp Val Trp Gly Lys Gly Thr Thr Val Thr Val Ser Ser
         115                 120                 125

Ala Ser Thr Lys Gly Pro Ser Val Phe Pro Leu Ala Pro Ser Ser Lys
    130                 135                 140

Ser Thr Leu Leu Gln Gly Ser Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Arg Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Ala Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

```
<210> SEQ ID NO 26
<211> LENGTH: 128
<212> TYPE: PRT
<213> ORGANISM: Artificial Sequence
<220> FEATURE:
<223> OTHER INFORMATION: Synthetic Sequence

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

<210> SEQ ID NO 27
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 27

Asp Gly Glu Leu Arg His Phe Asp His Leu Leu Asp Tyr His Tyr Tyr
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 28

Trp Gly Gln Gly Thr Thr Val Thr Val Ser Ser
1               5                   10

<210> SEQ ID NO 29
<211> LENGTH: 458
<212> TYPE: PRT
<213> ORGANISM: Artificial Sequence
<220> FEATURE:
<223> OTHER INFORMATION: Synthetic Sequence

<400> SEQUENCE: 29

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Leu Arg His Phe Asp His Leu Leu Asp Tyr His
                100                 105                 110

Tyr Tyr Met Asp Val Trp Gly Gln Gly Thr Thr Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 30
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 30

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Gln Glu Phe Thr
                85                  90                  95

Phe Gly Gln Gly Thr Lys Val Glu Ile Lys
            100                 105
```

<210> SEQ ID NO 31
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 31

```
Gln Gln Arg Ala Gln Glu Phe Thr
1               5
```

<210> SEQ ID NO 32
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 32

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Gln Glu Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125
```

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 33
<211> LENGTH: 458
<212> TYPE: PRT
<213> ORGANISM: Artificial Sequence
<220> FEATURE:
<223> OTHER INFORMATION: Synthetic Sequence

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Cys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
            355                 360                 365

Met Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 34
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Gln Glu Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Cys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 35
<211> LENGTH: 462
<212> TYPE: PRT
<213> ORGANISM: Artificial Sequence
<220> FEATURE:
<223> OTHER INFORMATION: Synthetic Sequence

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Leu Leu Gln Gly Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Arg Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Ala Ser Thr Tyr Arg Val Val Ser Val
305                 310                 315                 320

-continued

```
Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
450                 455                 460
```

<210> SEQ ID NO 36
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 36

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Ala Gln Glu Phe Thr
            85                  90                  95

Phe Gly Gln Gly Thr Lys Val Glu Ile Lys
            100                 105
```

<210> SEQ ID NO 37
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 37

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Arg Ala Gln Glu Phe Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 38
<211> LENGTH: 213
<212> TYPE: PRT
<213> ORGANISM: Artificial Sequence
<220> FEATURE:
<223> OTHER INFORMATION: Synthetic Sequence

<400> SEQUENCE: 38

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Gly Ser Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Arg Ala Gln Glu Phe Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Cys Ala Asp Tyr Glu Lys His Lys Val Tyr Ala
                180                 185                 190
```

Cys Glu Val Thr His Gln Gly Leu Ser Ser Pro Val Thr Lys Ser Phe
        195                 200                 205

Asn Arg Gly Glu Cys
    210

<210> SEQ ID NO 39
<211> LENGTH: 128
<212> TYPE: PRT
<213> ORGANISM: Artificial Sequence
<220> FEATURE:
<223> OTHER INFORMATION: Synthetic Sequence

<400> SEQUENCE: 39

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

<210> SEQ ID NO 40
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 40

Asp Ala Glu Leu Arg His Phe Asp His Leu Leu Asp Tyr His Tyr Tyr
1               5                   10                  15

Met Asp Val

<210> SEQ ID NO 41
<211> LENGTH: 458
<212> TYPE: PRT
<213> ORGANISM: Artificial Sequence
<220> FEATURE:
<223> OTHER INFORMATION: Synthetic Sequence

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Ala Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 42
<211> LENGTH: 458
```

```
<212> TYPE: PRT
<213> ORGANISM: Artificial Sequence
<220> FEATURE:
<223> OTHER INFORMATION: Synthetic Sequence

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Cys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380
```

-continued

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
    435                 440                 445

Gln Lys Ser Leu Ser Leu Ser Pro Gly Lys
    450                 455

<210> SEQ ID NO 43
<211> LENGTH: 462
<212> TYPE: PRT
<213> ORGANISM: Artificial Sequence
<220> FEATURE:
<223> OTHER INFORMATION: Synthetic Sequence

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Glu Leu Arg His Phe Asp His Leu Leu Asp Tyr His
            100                 105                 110

Tyr Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Leu Leu Gln Gly Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Arg Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285
```

```
Lys Phe Asn Trp Tyr Val Asp Gly Val Glu Val His Asn Ala Lys Thr
    290                 295                 300

Lys Pro Arg Glu Glu Gln Tyr Ala Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 44
<211> LENGTH: 128
<212> TYPE: PRT
<213> ORGANISM: Artificial Sequence
<220> FEATURE:
<223> OTHER INFORMATION: Synthetic Sequence

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Leu Arg His Phe Asp Gln Val Tyr Asn Tyr His
            100                 105                 110

Tyr Tyr Met Asp Val Trp Gly Gln Gly Thr Thr Val Thr Val Ser Ser
        115                 120                 125

<210> SEQ ID NO 45
<211> LENGTH: 19
<212> TYPE: PRT
<213> ORGANISM: Artificial Sequence
<220> FEATURE:
<223> OTHER INFORMATION: Synthetic Sequence
```

<400> SEQUENCE: 45

```
Asp Gly Glu Leu Arg His Phe Asp Gln Val Tyr Asn Tyr His Tyr Tyr
1               5                   10                  15

Met Asp Val
```

<210> SEQ ID NO 46
<211> LENGTH: 458
<212> TYPE: PRT
<213> ORGANISM: Artificial Sequence
<220> FEATURE:
<223> OTHER INFORMATION: Synthetic Sequence

<400> SEQUENCE: 46

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Glu Leu Arg His Phe Asp Gln Val Tyr Asn Tyr His
            100                 105                 110

Tyr Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320
```

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
            355                 360                 365

Met Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
        450                 455

<210> SEQ ID NO 47
<211> LENGTH: 126
<212> TYPE: PRT
<213> ORGANISM: Artificial Sequence
<220> FEATURE:
<223> OTHER INFORMATION: Synthetic Sequence

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Thr Tyr Phe Asp Trp Thr Arg Arg Gly Tyr Tyr Tyr
            100                 105                 110

Met Asp Val Trp Gly Lys Gly Thr Thr Val Thr Val Ser Ser
            115                 120                 125

<210> SEQ ID NO 48
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 48

Ser Tyr Ala Ile Ser
1               5

<210> SEQ ID NO 49
<211> LENGTH: 17
<212> TYPE: PRT

```
<213> ORGANISM: Artificial Sequence
<220> FEATURE:
<223> OTHER INFORMATION: Synthetic Sequence

<400> SEQUENCE: 49

Gly Ile Ile Pro Ile Phe Gly Thr Ala Asn Tyr Ala Gln Lys Phe Gln
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 50

Asp Pro Thr Tyr Phe Asp Trp Thr Arg Arg Gly Tyr Tyr Tyr Met Asp
1               5                   10                  15

Val

<210> SEQ ID NO 51
<211> LENGTH: 456
<212> TYPE: PRT
<213> ORGANISM: Artificial Sequence
<220> FEATURE:
<223> OTHER INFORMATION: Synthetic Sequence

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Thr Tyr Phe Asp Trp Thr Arg Arg Gly Tyr Tyr Tyr
            100                 105                 110

Met Asp Val Trp Gly Lys Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

-continued

```
Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Glu Glu Met Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
    450                 455

<210> SEQ ID NO 52
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 52

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Arg Val Glu
65                  70                  75                  80

Asp Glu Ala Asp Tyr Tyr Cys Tyr Ser Thr Asp Ser Ser Asp Asn His
            85                  90                  95

Arg Lys Gly Phe Gly Gly Gly Thr Lys Leu Thr Val Leu
        100                 105

<210> SEQ ID NO 53
```

```
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 53

Ser Gly Asp Ala Leu Pro Lys Lys Tyr Ala Tyr
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 54

Glu Asp Ser Lys Arg Pro Ser
1               5

<210> SEQ ID NO 55
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 55

Tyr Ser Thr Asp Ser Ser Asp Asn His Arg Lys Gly
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 56

Phe Gly Gly Gly Thr Lys Leu Thr Val Leu
1               5                   10

<210> SEQ ID NO 57
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 57

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95
```

```
Glu Lys Thr Val Ala Pro Thr Glu Cys Ser
            100                 105
```

<210> SEQ ID NO 58
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 58

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
50                  55                  60

Ser Ser Gly Thr Met Ala Thr Leu Thr Ile Ser Gly Ala Arg Val Glu
65                  70                  75                  80

Asp Glu Ala Asp Tyr Tyr Cys Tyr Ser Thr Asp Ser Ser Asp Asn His
                85                  90                  95

Arg Lys Gly Phe Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 59
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 59

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Val Gly Leu Pro Asp Ile Trp Gly Gln Gly Thr Met Val
            100                 105                 110

Thr Val Ser Ser
        115

<210> SEQ ID NO 60
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 60

Ser Tyr Gly Met His
1               5

<210> SEQ ID NO 61
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 61

Val Ile Ser Tyr Asp Gly Ser Asn Lys Tyr Tyr Ala Asp Ser Val Lys
1               5                   10                  15

Gly

<210> SEQ ID NO 62
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 62

Gly Val Gly Leu Pro Asp Ile
1               5

<210> SEQ ID NO 63
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 63

Trp Gly Gln Gly Thr Met Val Thr Val Ser Ser
1               5                   10

<210> SEQ ID NO 64
<211> LENGTH: 446
<212> TYPE: PRT
<213> ORGANISM: Artificial Sequence
<220> FEATURE:
<223> OTHER INFORMATION: Synthetic Sequence

<400> SEQUENCE: 64

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Gly Leu Pro Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys
            435                 440                 445

<210> SEQ ID NO 65
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 65

Glu Ile Val Met Thr Gln Ser Pro Asp Thr Leu Ser Leu Ser Pro Gly
1               5                   10                  15

Glu Arg Ala Thr Leu Ser Cys Arg Ala Ser Gln Lys Ile Tyr Tyr Ser
            20                  25                  30

Tyr Leu Ala Trp Tyr Gln Gln Lys Pro Gly Gln Ala Pro Arg Leu Leu
        35                  40                  45

Ile Ser Gly Ala Ser Thr Arg Ala Ser Asp Ile Ser Asp Arg Phe Ser
    50                  55                  60

Gly Gly Gly Ser Gly Thr Asp Phe Thr Leu Thr Ile Asn Ser Leu Glu
65                  70                  75                  80

Ser Glu Asp Ala Ala Val Tyr Tyr Cys Gln Gln Tyr Asp Ser Leu Pro
                85                  90                  95

Val Thr Phe Gly Arg Gly Thr Lys Leu Glu Ile Lys
            100                 105

<210> SEQ ID NO 66
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 66

Arg Ala Ser Gln Lys Ile Tyr Tyr Ser Tyr Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 67

Gly Ala Ser Thr Arg Ala Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 68

Gln Gln Tyr Asp Ser Leu Pro Val Thr
1               5

<210> SEQ ID NO 69
<211> LENGTH: 10
<212> TYPE: PRT
<213> ORGANISM: Artificial Sequence
<220> FEATURE:
```

<223> OTHER INFORMATION: Synthetic Sequence

<400> SEQUENCE: 69

Phe Gly Arg Gly Thr Lys Leu Glu Ile Lys
1               5                   10

<210> SEQ ID NO 70
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 70

Glu Ile Val Met Thr Gln Ser Pro Asp Thr Leu Ser Leu Ser Pro Gly
1               5                   10                  15

Glu Arg Ala Thr Leu Ser Cys Arg Ala Ser Gln Lys Ile Tyr Tyr Ser
            20                  25                  30

Tyr Leu Ala Trp Tyr Gln Gln Lys Pro Gly Gln Ala Pro Arg Leu Leu
        35                  40                  45

Ile Ser Gly Ala Ser Thr Arg Ala Ser Asp Ile Ser Asp Arg Phe Ser
    50                  55                  60

Gly Gly Gly Ser Gly Thr Asp Phe Thr Leu Thr Ile Asn Ser Leu Glu
65                  70                  75                  80

Ser Glu Asp Ala Ala Val Tyr Tyr Cys Gln Gln Tyr Asp Ser Leu Pro
                85                  90                  95

Val Thr Phe Gly Arg Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 71
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 71

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Phe Trp Tyr Gln Gln Lys Ser Gly Gln Ala Pro Val Leu Val Ile Tyr
        35                  40                  45

```
Glu Asp Ser Lys Arg Pro Ser Gly Ile Pro Glu Lys Phe Ser Gly Ser
            50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Asp Asn Pro
                 85                  90                  95

Arg Gly Val Phe Gly Gly Gly Thr Lys Leu Thr Val Leu
            100                 105
```

<210> SEQ ID NO 72
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 72

```
Ser Gly Asp Ala Leu Pro Lys Lys Tyr Ala
 1               5                  10
```

<210> SEQ ID NO 73
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 73

```
Tyr Ser Thr Asp Ser Ser Asp Asn Pro Arg Gly Val
 1               5                  10
```

<210> SEQ ID NO 74
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 74

```
Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
                 20                  25                  30

Phe Trp Tyr Gln Gln Lys Ser Gly Gln Ala Pro Val Leu Val Ile Tyr
             35                  40                  45

Glu Asp Ser Lys Arg Pro Ser Gly Ile Pro Glu Lys Phe Ser Gly Ser
            50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Asp Asn Pro
                 85                  90                  95

Arg Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160
```

```
Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 75
<211> LENGTH: 384
<212> TYPE: DNA
<213> ORGANISM: Artificial Sequence
<220> FEATURE:
<223> OTHER INFORMATION: Synthetic Sequence

<400> SEQUENCE: 75
gaggtccagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccctag tggtggtag cacaagctac      180 gcacagaagt tccagggcag agtcaccatg accaggaca cgtccacgag cacagtctac      240
atggagctga gcagcctgag atctgaggac acggccgtgt attactgtgc gagagatggc     300
gtattacgat attttgactg gttattagac tactactact acatggacgt ctggggcaaa    360
gggaccacgg tcaccgtctc gagc                                            384

<210> SEQ ID NO 76
<211> LENGTH: 1374
<212> TYPE: DNA
<213> ORGANISM: Artificial Sequence
<220> FEATURE:
<223> OTHER INFORMATION: Synthetic Sequence

<400> SEQUENCE: 76
gaggtccagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccctag tggtggtag cacaagctac      180 gcacagaagt tccagggcag agtcaccatg accaggaca cgtccacgag cacagtctac      240
atggagctga gcagcctgag atctgaggac acggccgtgt attactgtgc gagagatggc     300
gtattacgat attttgactg gttattagac tactactact acatggacgt ctggggcaaa    360
gggaccacgg tcaccgtctc gagcgcgtcg accaagggcc catcggtctt ccccctggca    420
ccctcctcca agagcacctc tgggggcaca gcggccctgg gctgcctggt caaggactac    480
ttccccgaac cggtgacggt gtcgtggaac tcaggcgccc tgaccagcgg cgtgcacacc    540
ttcccggctg tcctacagtc ctcaggactc tactccctca gcagcgtggt gaccgtgccc    600
tccagcagct tgggcaccca gacctacatc tgcaacgtga atcacaagcc cagcaacacc    660
aaggtggaca agaaagttga gcccaaatct tgtgacaaaa ctcacacatg cccaccgtgc    720
ccagcacctg aactcctggg gggaccgtca gtcttcctct ccccccaaa cccaaggac      780 accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
```

```
gcccccatcg agaaaaccat ctccaaagcc aaagggcagc ccgagaacc acaggtgtac    1080 accctgcccc catcccggga ggagatgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctatagcaag    1260
ctcaccgtgg acaagagcag gtggcagcag gggaacgtct tctcatgctc cgtgatgcat    1320
gaggctctgc acaaccacta cacgcagaag agcctctccc tgtccccggg taaa          1374
```

<210> SEQ ID NO 77

<400> SEQUENCE: 77

000

<210> SEQ ID NO 78
<211> LENGTH: 318
<212> TYPE: DNA
<213> ORGANISM: Artificial Sequence
<220> FEATURE:
<223> OTHER INFORMATION: Synthetic Sequence

<400> SEQUENCE: 78

```
gaaattgtgt tgacacagtc tccagccacc ctgtctttgt ctccagggga gagagccacc     60
ctctcctgca gggccagtca gagtgttggc agctacttgg cctggtacca acagagacct    120
ggccaggctc ccaggctcct catctatgat gcttccaaca gggccactgg catcccagcc    180
aggttcagtg gcagtgggtc tgggacagac ttcaccctca ccatcagcag cctagagcct    240
gaagattttg cggtttatta ctgtcagcag cgtgccaacg tattcacttt tggccagggg    300
accaaggtgg aaatcaaa                                                   318
```

<210> SEQ ID NO 79
<211> LENGTH: 639
<212> TYPE: DNA
<213> ORGANISM: Artificial Sequence
<220> FEATURE:
<223> OTHER INFORMATION: Synthetic Sequence

<400> SEQUENCE: 79

```
gaaattgtgt tgacacagtc tccagccacc ctgtctttgt ctccagggga gagagccacc     60
ctctcctgca gggccagtca gagtgttggc agctacttgg cctggtacca acagagacct    120
ggccaggctc ccaggctcct catctatgat gcttccaaca gggccactgg catcccagcc    180
aggttcagtg gcagtgggtc tgggacagac ttcaccctca ccatcagcag cctagagcct    240
gaagattttg cggtttatta ctgtcagcag cgtgccaacg tattcacttt tggccagggg    300
accaaggtgg aaatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                            639
```

<210> SEQ ID NO 80
<211> LENGTH: 384
<212> TYPE: DNA
<213> ORGANISM: Artificial Sequence

```
<220> FEATURE:
<223> OTHER INFORMATION: Synthetic Sequence

<400> SEQUENCE: 80
gaggtccagc tggtgcagtc tggggctgag gtgaagaagc ctggggcctc agtgaaggtt      60
tcctgcaagg catctggata cccttcacc agctactata tgcactgggt gcgacaggcc      120
cctggacaag ggcttgagtg gatgggaata tcaaccccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagagatggc     300
gagttacgac actttgacca cttattagac taccactact acatggacgt ctggggccag     360
gggaccacgg tcaccgtctc gagc                                            384

<210> SEQ ID NO 81
<211> LENGTH: 1374
<212> TYPE: DNA
<213> ORGANISM: Artificial Sequence
<220> FEATURE:
<223> OTHER INFORMATION: Synthetic Sequence

<400> SEQUENCE: 81
gaggtccagc tggtgcagtc tggggctgag gtgaagaagc ctggggcctc agtgaaggtt      60
tcctgcaagg catctggata cccttcacc agctactata tgcactgggt gcgacaggcc      120
cctggacaag ggcttgagtg gatgggaata tcaaccccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagagatggc     300
gagttacgac actttgacca cttattagac taccactact acatggacgt ctggggccag     360
gggaccacgg tcaccgtctc gagcgcgtcg accaagggcc catcggtctt ccccctggca     420
ccctcctcca agagcacctc tgggggcaca gcggccctgg gctgcctggt caaggactac     480
ttccccgaac cggtgacggt gtcgtggaac tcaggcgccc tgaccagcgg cgtgcacacc     540
ttcccggctg tcctacagtc ctcaggactc tactccctca gcagcgtggt gaccgtgccc     600
tccagcagct tgggcaccca gacctacatc tgcaacgtga atcacaagcc cagcaacacc     660
aaggtggaca gaaagttga gcccaaatct tgtgacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aagggcagc cccgagaacc acaggtgtac    1080
accctgcccc catcccggga ggagatgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctatagcaag    1260
ctcaccgtgg acaagagcag gtggcagcag gggaacgtct tctcatgctc cgtgatgcat    1320
gaggctctgc acaaccacta cacgcagaag agcctctccc tgtccccggg taaa          1374

<210> SEQ ID NO 82
<211> LENGTH: 318
<212> TYPE: DNA
```

<213> ORGANISM: Artificial Sequence
<220> FEATURE:
<223> OTHER INFORMATION: Synthetic Sequence

<400> SEQUENCE: 82

```
gaaattgtgt tgacacagtc tccagccacc ctgtctttgt ctccagggga gagagccacc      60
ctctcctgca gggccagtca gagtgttggc agctacttgg cctggtacca acagagacct     120
ggccaggctc ccaggctcct catctatgat gcttccaaca gggccactgg catcccagcc     180
aggttcagtg gcagtgggtc tgggacagac ttcaccctca ccatcagcag cctagagcct     240
gaagattttg cggtttatta ctgtcagcag cgtgcccaag agttcacttt tggccagggg     300
accaaggtgg aaatcaaa                                                    318
```

<210> SEQ ID NO 83
<211> LENGTH: 639
<212> TYPE: DNA
<213> ORGANISM: Artificial Sequence
<220> FEATURE:
<223> OTHER INFORMATION: Synthetic Sequence

<400> SEQUENCE: 83

```
gaaattgtgt tgacacagtc tccagccacc ctgtctttgt ctccagggga gagagccacc      60
ctctcctgca gggccagtca gagtgttggc agctacttgg cctggtacca acagagacct     120
ggccaggctc ccaggctcct catctatgat gcttccaaca gggccactgg catcccagcc     180
aggttcagtg gcagtgggtc tgggacagac ttcaccctca ccatcagcag cctagagcct     240
gaagattttg cggtttatta ctgtcagcag cgtgcccaag agttcacttt tggccagggg     300
accaaggtgg aaatcaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                             639
```

<210> SEQ ID NO 84
<211> LENGTH: 318
<212> TYPE: DNA
<213> ORGANISM: Artificial Sequence
<220> FEATURE:
<223> OTHER INFORMATION: Synthetic Sequence

<400> SEQUENCE: 84

```
gaaattgtga tgacacagtc tccagccacc ctgtctttgt ctccagggga gagagccacc      60
ctctcctgca gggccagtca gagtgttggc agctacttgg cctggtacca acagaaacct     120
ggccaggctc ccaggctcct catctatgat gcttccaaca gggccactgg catcccagcc     180
aggttcagtg gcagtgggtc tgggacagac ttcaccctca ccatcagcag cctacagcct     240
gaagattttg cggtttatta ctgtcagcag cgtgcccaag agttcacttt tggccagggg     300
accaaggtgg aaatcaaa                                                    318
```

<210> SEQ ID NO 85
<211> LENGTH: 639
<212> TYPE: DNA
<213> ORGANISM: Artificial Sequence
<220> FEATURE:
<223> OTHER INFORMATION: Synthetic Sequence

<400> SEQUENCE: 85

```
gaaattgtga tgacacagtc tccagccacc ctgtctttgt ctccagggga gagagccacc      60
ctctcctgca gggccagtca gagtgttggc agctacttgg cctggtacca acagaaacct     120
ggccaggctc ccaggctcct catctatgat gcttccaaca gggccactgg catcccagcc     180
aggttcagtg gcagtgggtc tgggacagac ttcaccctca ccatcagcag cctacagcct     240
gaagattttg cggtttatta ctgtcagcag cgtgcccaag agttcacttt tggccagggg     300
accaaggtgg aaatcaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639
```

<210> SEQ ID NO 86
<211> LENGTH: 1374
<212> TYPE: DNA
<213> ORGANISM: Artificial Sequence
<220> FEATURE:
<223> OTHER INFORMATION: Synthetic Sequence

<400> SEQUENCE: 86

```
gaggtccagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccta gtggtggtag cacaagctac     180
gcacagaagt tccagggcag agtcaccatg accaggga cgtccacgag cacagtctac     240
atggagctga gcagcctgag atctgaggac acggccgtgt attactgtgc gagagatggc     300
gagttacgac actttgacca cttattagac taccactact acatggacgt ctggggccag     360
gggaccacg tcaccgtctc gagcgcgtcg accaagggcc catcggtctt ccccctggca     420
ccctcctcca agagcacctc tgggggcaca gcggccctgg gctgcctggt caaggactac     480
ttccccgaac cggtgacggt gtcgtggaac tcaggcgccc tgaccagcgg cgtgcacacc     540
ttcccggctg tcctacagtc ctcaggactc tactccctca gcagcgtggt gaccgtgccc     600
tccagcagct tgggcaccca gacctacatc tgcaacgtga atcacaagcc cagcaacacc     660
aaggtggaca agaaagttga gcccaaatct tgtgacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
tgcccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aagggcagc cccgagaacc acaggtgtac    1080
accctgcccc catcccggga ggagatgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctatagcaag    1260
```

```
ctcaccgtgg acaagagcag gtggcagcag gggaacgtct tctcatgctc cgtgatgcat    1320
gaggctctgc acaaccacta cacgcagaag agcctctccc tgtccccgg aaaa           1374

<210> SEQ ID NO 87
<211> LENGTH: 639
<212> TYPE: DNA
<213> ORGANISM: Artificial Sequence
<220> FEATURE:
<223> OTHER INFORMATION: Synthetic Sequence

<400> SEQUENCE: 87
gaaattgtga tgacacagtc tccagccacc ctgtctttgt ctccagggga gagagccacc      60
ctctcctgca gggccagtca gagtgttggc agctacttgg cctggtacca acagaaacct     120
ggccaggctc ccaggctcct catctatgat gcttccaaca gggccactgg catcccagcc     180
aggttcagtg gcagtgggtc tgggacagac ttcaccctca ccatcagcag cctacagcct     240
gaagattttg cggtttatta ctgtcagcag cgtgcccaag agttcacttt tggccagggg     300
accaaggtgg aaatcaaacg tactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agctgcgcag actacgagaa acacaaagtc tacgcctgcg aagtcaccca tcagggcctg     600
agctcgcccg tcacaaagag cttcaacagg ggagagtgt                            639

<210> SEQ ID NO 88
<211> LENGTH: 1386
<212> TYPE: DNA
<213> ORGANISM: Artificial Sequence
<220> FEATURE:
<223> OTHER INFORMATION: Synthetic Sequence

<400> SEQUENCE: 88
gaggtccagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagagatggc     300
gagttacgac acttgacca cttattagac taccactact acatggacgt ctggggccag     360 ggaccacgg tcaccgtctc gagcgcgtcg accaagggcc catcggtctt ccccctggca     420
ccctcctcca agagcaccct gctgcagggg tctgggggca gcggccct gggctgcctg     480 gtcaaggact acttccccga accggtgacg gtgtcgtgga actcaggcgc cctgaccagc     540
ggcgtgcaca ccttcccggc tgtcctacag tcctcaggac tctactccct cagcagcgta     600
gtgaccgtgc cctccagcag cttgggcacc cagacctaca tctgcaacgt gaatcacaag     660
cccagcaaca ccaaggtgga caagaaagtt gagcccaaat cttgtgaccg tactcacaca     720
tgcccaccgt gcccagcacc tgaactcctg ggggaccgt cagtcttcct cttccccca     780 aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacgccagca cgtaccgtgt ggtcagcgtc     960
```

| | |
|---|---|
| ctcaccgtcc tgcaccagga ctggctgaat ggcaaggagt acaagtgcaa ggtctccaac | 1020 |
| aaagccctcc cagcccccat cgagaaaacc atctccaaag ccaagggca gccccgagaa | 1080 |
| ccacaggtgt acaccctgcc cccatcccgg gaggagatga ccaagaacca ggtcagcctg | 1140 |
| acctgcctgg tcaaaggctt ctatcccagc gacatcgccg tggagtggga gagcaatggg | 1200 |
| cagccggaga caactacaa gaccacgcct cccgtgctgg actccgacgg ctccttcttc | 1260 |
| ctctatagca agctcaccgt ggacaagagc aggtggcagc aggggaacgt cttctcatgc | 1320 |
| tccgtgatgc atgaggctct gcacaaccac tacacgcaga agagcctctc cctgtccccc | 1380 |
| ggaaaa | 1386 |

<210> SEQ ID NO 89
<211> LENGTH: 384
<212> TYPE: DNA
<213> ORGANISM: Artificial Sequence
<220> FEATURE:
<223> OTHER INFORMATION: Synthetic Sequence

<400> SEQUENCE: 89

| | |
|---|---|
| gaggtccagc tggtgcagtc tggggctgag gtgaagaagc ctggggcctc agtgaaggtt | 60 |
| tcctgcaagg catctggata caccttcacc agctactata tgcactgggt gcgacaggcc | 120 |
| cctggacaag gcttgagtg gatgggaata atcaaccta gtggtggtag cacaagctac | 180 |
| gcacagaagt tccagggcag agtcaccatg accaggaca cgtccacgag cacagtctac | 240 |
| atggagctga gcagcctgag atctgaggac acggccgtgt attactgtgc gagagatggc | 300 |
| gaattacgac actttgacca ggtatacaac taccactact acatggacgt ctggggccag | 360 |
| gggaccacgg tcaccgtctc gagc | 384 |

<210> SEQ ID NO 90
<211> LENGTH: 1374
<212> TYPE: DNA
<213> ORGANISM: Artificial Sequence
<220> FEATURE:
<223> OTHER INFORMATION: Synthetic Sequence

<400> SEQUENCE: 90

| | |
|---|---|
| gaggtccagc tggtgcagtc tggggctgag gtgaagaagc ctggggcctc agtgaaggtt | 60 |
| tcctgcaagg catctggata caccttcacc agctactata tgcactgggt gcgacaggcc | 120 |
| cctggacaag gcttgagtg gatgggaata atcaaccta gtggtggtag cacaagctac | 180 |
| gcacagaagt tccagggcag agtcaccatg accaggaca cgtccacgag cacagtctac | 240 |
| atggagctga gcagcctgag atctgaggac acggccgtgt attactgtgc gagagatggc | 300 |
| gaattacgac actttgacca ggtatacaac taccactact acatggacgt ctggggccag | 360 |
| gggaccacgg tcaccgtctc gagcgcgtcg accaagggcc catcggtctt ccccctggca | 420 |
| ccctcctcca agagcacctc tgggggcaca gcggccctgg gctgcctggt caaggactac | 480 |
| ttccccgaac cggtgacggt gtcgtggaac tcaggcgccc tgaccagcgg cgtgcacacc | 540 |
| ttcccggctg tcctacagtc ctcaggactc tactccctca gcagcgtggt gaccgtgccc | 600 |
| tccagcagct tgggcaccca gacctacatc tgcaacgtga atcacaagcc cagcaacacc | 660 |
| aaggtggaca agaaagttga gcccaaatct tgtgacaaaa ctcacacatg cccaccgtgc | 720 |
| ccagcacctg aactcctggg gggaccgtca gtcttcctct tccccccaaa acccaaggac | 780 |
| accctcatga tctcccggac ccctgaggtc acatgcgtgg tggtggacgt gagccacgaa | 840 |
| gaccctgagg tcaagttcaa ctggtacgtg gacggcgtgg aggtgcataa tgccaagaca | 900 |

-continued

```
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aagggcagc cccgagaacc acaggtgtac    1080
accctgcccc catcccggga ggagatgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctatagcaag   1260
ctcaccgtgg acaagagcag gtggcagcag gggaacgtct tctcatgctc cgtgatgcat   1320
gaggctctgc acaaccacta cacgcagaag agcctctccc tgtccccggg taaa         1374
```

<210> SEQ ID NO 91
<211> LENGTH: 836
<212> TYPE: PRT
<213> ORGANISM: Artificial Sequence
<220> FEATURE:
<223> OTHER INFORMATION: Synthetic Sequence

<400> SEQUENCE: 91

```
Met Ala Gly Leu Asn Cys Gly Val Ser Ile Ala Leu Leu Gly Val Leu
 1               5                  10                  15

Leu Leu Gly Ala Ala Arg Leu Pro Arg Gly Ala Glu Ala Phe Glu Ile
                20                  25                  30

Ala Leu Pro Arg Glu Ser Asn Ile Thr Val Leu Ile Lys Leu Gly Thr
            35                  40                  45

Pro Thr Leu Leu Ala Lys Pro Cys Tyr Ile Val Ile Ser Lys Arg His
        50                  55                  60

Ile Thr Met Leu Ser Ile Lys Ser Gly Glu Arg Ile Val Phe Thr Phe
65                  70                  75                  80

Ser Cys Gln Ser Pro Glu Asn His Phe Val Ile Glu Ile Gln Lys Asn
                85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
            180                 185                 190

Lys Met Ala Leu His Leu Pro Trp Phe His Pro Arg Asn Val Ser Gly
        195                 200                 205

Phe Ser Ile Ala Asn Arg Ser Ser Ile Lys Arg Leu Cys Ile Ile Glu
    210                 215                 220

Ser Val Phe Glu Gly Glu Gly Ser Ala Thr Leu Met Ser Ala Asn Tyr
225                 230                 235                 240

Pro Glu Gly Phe Pro Glu Asp Glu Leu Met Thr Trp Gln Phe Val Val
                245                 250                 255

Pro Ala His Leu Arg Ala Ser Val Ser Phe Leu Asn Phe Asn Leu Ser
            260                 265                 270
```

```
Asn Cys Glu Arg Lys Glu Arg Val Glu Tyr Tyr Ile Pro Gly Ser
        275                 280                 285

Thr Thr Asn Pro Glu Val Phe Lys Leu Glu Asp Lys Gln Pro Gly Asn
290                 295                 300

Met Ala Gly Asn Phe Asn Leu Ser Leu Gln Gly Cys Asp Gln Asp Ala
305                 310                 315                 320

Gln Ser Pro Gly Ile Leu Arg Leu Gln Phe Gln Val Leu Val Gln His
                325                 330                 335

Pro Gln Asn Glu Ser Asn Lys Ile Tyr Val Asp Leu Ser Asn Glu
                340                 345                 350

Arg Ala Met Ser Leu Thr Ile Glu Pro Arg Pro Val Lys Gln Ser Arg
                355                 360                 365

Lys Phe Val Pro Gly Cys Phe Val Cys Leu Glu Ser Arg Thr Cys Ser
        370                 375                 380

Ser Asn Leu Thr Leu Thr Ser Gly Ser Lys His Lys Ile Ser Phe Leu
385                 390                 395                 400

Cys Asp Asp Leu Thr Arg Leu Trp Met Asn Val Glu Lys Thr Ile Ser
                405                 410                 415

Cys Thr Asp His Arg Tyr Cys Gln Arg Lys Ser Tyr Ser Leu Gln Val
                420                 425                 430

Pro Ser Asp Ile Leu His Leu Pro Val Glu Leu His Asp Phe Ser Trp
        435                 440                 445

Lys Leu Leu Val Pro Lys Asp Arg Leu Ser Leu Val Leu Val Pro Ala
        450                 455                 460

Gln Lys Leu Gln Gln His Thr His Glu Lys Pro Cys Asn Thr Ser Phe
465                 470                 475                 480

Ser Tyr Leu Val Ala Ser Ala Ile Pro Ser Gln Asp Leu Tyr Phe Gly
                485                 490                 495

Ser Phe Cys Pro Gly Gly Ser Ile Lys Gln Ile Gln Val Lys Gln Asn
        500                 505                 510

Ile Ser Val Thr Leu Arg Thr Phe Ala Pro Ser Phe Gln Gln Glu Ala
        515                 520                 525

Ser Arg Gln Gly Leu Thr Val Ser Phe Ile Pro Tyr Phe Lys Glu Glu
        530                 535                 540

Gly Val Phe Thr Val Thr Pro Asp Thr Lys Ser Lys Val Tyr Leu Arg
545                 550                 555                 560

Thr Pro Asn Trp Asp Arg Gly Leu Pro Ser Leu Thr Ser Val Ser Trp
                565                 570                 575

Asn Ile Ser Val Pro Arg Asp Gln Val Ala Cys Leu Thr Phe Phe Lys
                580                 585                 590

Glu Arg Ser Gly Val Val Cys Gln Thr Gly Arg Ala Phe Met Ile Ile
                595                 600                 605

Gln Glu Gln Arg Thr Arg Ala Glu Glu Ile Phe Ser Leu Asp Glu Asp
610                 615                 620

Val Leu Pro Lys Pro Ser Phe His His His Ser Phe Trp Val Asn Ile
625                 630                 635                 640

Ser Asn Cys Ser Pro Thr Ser Gly Lys Gln Leu Asp Leu Leu Phe Ser
                645                 650                 655

Val Thr Leu Thr Pro Arg Thr Val Asp Leu Thr Val Ile Leu Ile Ala
                660                 665                 670

Ala Val Gly Gly Gly Val Leu Leu Leu Ser Ala Leu Gly Leu Ile Ile
                675                 680                 685
```

```
Cys Cys Val Lys Lys Lys Lys Lys Thr Asn Lys Gly Pro Ala Val
    690             695             700

Gly Ile Tyr Asn Asp Asn Ile Asn Thr Glu Met Pro Arg Gln Pro Lys
705             710             715                     720

Lys Phe Gln Lys Gly Arg Lys Asp Asn Asp Ser His Val Tyr Ala Val
            725             730                 735

Ile Glu Asp Thr Met Val Tyr Gly His Leu Leu Gln Asp Ser Ser Gly
                740             745             750

Ser Phe Leu Gln Pro Glu Val Asp Thr Tyr Arg Pro Phe Gln Gly Thr
        755             760             765

Met Gly Val Cys Pro Pro Ser Pro Pro Thr Ile Cys Ser Arg Ala Pro
770                 775             780

Thr Ala Lys Leu Ala Thr Glu Glu Pro Pro Pro Arg Ser Pro Pro Glu
785             790             795                     800

Ser Glu Ser Glu Pro Tyr Thr Phe Ser His Pro Asn Asn Gly Asp Val
                805             810                 815

Ser Ser Lys Asp Thr Asp Ile Pro Leu Leu Asn Thr Gln Glu Pro Met
            820             825             830

Glu Pro Ala Glu
        835

<210> SEQ ID NO 92
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 92

Leu Leu Gln Gly
1
```